United States Patent
Zhu et al.

(10) Patent No.: US 6,686,368 B1
(45) Date of Patent: Feb. 3, 2004

(54) INHIBITORS OF FACTOR XA

(75) Inventors: Bing-Yan Zhu, Belmont, CA (US); Zhaozhong Jon Jia, So. San Francisco, CA (US); Wenrong Huang, Cupertino, CA (US); Yonghong Song, Foster City, CA (US); James Kanter, So. San Francisco, CA (US); Robert M. Scarborough, Half Moon Bay, CA (US)

(73) Assignee: Millennium Pahrmaceuticals, Inc., Cambridge, MA (US)

( * ) Notice: Subject to any disclaimer, the term of this patent is extended or adjusted under 35 U.S.C. 154(b) by 5 days.

(21) Appl. No.: 10/387,927

(22) Filed: Mar. 12, 2003

Related U.S. Application Data

(62) Division of application No. 09/662,807, filed on Sep. 15, 2000
(60) Provisional application No. 60/154,332, filed on Sep. 17, 1999.

(51) Int. Cl.$^7$ .................... C07D 401/12; C07D 403/12; A61K 31/4155
(52) U.S. Cl. ............. 514/272; 514/252.05; 514/255.05; 514/341; 514/397; 514/406; 544/238; 544/331; 544/405; 546/275.4; 548/312.4; 548/364.1
(58) Field of Search ........................ 546/275.4; 544/238, 544/331, 405; 548/312.4, 364.1; 514/272, 341, 252.05, 255.05, 397, 406

(56) References Cited

U.S. PATENT DOCUMENTS

| | | | |
|---|---|---|---|
| 5,082,949 A | * | 1/1992 | Sohn et al. ................. 548/378 |
| 5,569,768 A | | 10/1996 | Boyd et al. | |

FOREIGN PATENT DOCUMENTS

| | | |
|---|---|---|
| JP | 11-302177 | 11/1999 |
| WO | 98/28269 | 7/1998 |
| WO | 98/28282 | 7/1998 |
| WO | 98/57934 | 12/1998 |
| WO | WO 98/57951 | * 12/1998 |
| WO | WO 99/00121 | 1/1999 |
| WO | WO 99/00126 | 1/1999 |
| WO | WO 99/00128 | 1/1999 |
| WO | WO 99/32477 | 7/1999 |

OTHER PUBLICATIONS

Suzuki, H., et al., "Selective Reduction with Lithium Aluminum Hydride/Diphosphorus Tetraiodide. A Mild Conversion of Aromatic Ketones to Parent Hydrocarbons," *Chemistry Letters*, pp. 909–910 (1983).

"Dictionary of Organic Compounds, 5th Ed., vol. 5", Chapman and Hall, New York, US, XP002161122 157909 compounds T–00160, T–00161, T–00162, p. 5119, (1982).

Chen, Qing–Yun and Li, Zhan–Ting, "Photo–induced electron–transfer reaction of aryl perfluoroalkanesulfonates with anilines," *Journal of Fluorine Chemistry*, 66, pp. 59–62 (1994).

Keumi, Takashi, et al., "2–(Trifluoromethylsulfonyloxy)pyridine as a Reagent for the Ketone Synthesis from Carboxylic Acids and Aromatic Hydrocarbons," *Bull. Chem. Soc. Jpn.*, 61, pp. 455–459 (1988).

Sipe, Herbert J., Jr., et al., "An Improved Synthesis of Aryl Sulfones," *Synthesis*, No. 3, pp. 283–284 (1984).

Rauch et al., PubMed Abstract (Ann Intern Med 134(3): 224–38), 2001.*

Van Aken et al., PubMed Abstract (Clin Appl Thromb Hemost 7(3): 195–204), 2001.*

Bing–Yan Zhu and Robert M. Scarborough, Factor Xa Inhibitors: Recent Advances in Anticoagulant Agents, *Annual Report in Medicinal Chemistry—35*, pp 83–102 (2000).

* cited by examiner

*Primary Examiner*—Deepak Rao
(74) *Attorney, Agent, or Firm*—Townsend and Townsend and Crew LLP

(57) ABSTRACT

Novel compounds, their salts and compositions related thereto having activity against mammalian factor Xa are disclosed. The compounds are useful in vitro or in vivo for preventing or treating coagulation disorders.

19 Claims, No Drawings

INHIBITORS OF FACTOR XA

CROSS REFERENCE TO RELATED APPLICATIONS

This application is a divisional of U.S. Ser. No. 09/662,807 filed Sep. 15, 2000 which claims benefit of priority under 35 U.S.C. §119(e) to U.S. Provisional Application No. 60/154,332 filed on Sep. 17, 1999, which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel non-amidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-mnolecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi-et al., Thromb. Res. 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as iin vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New. Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds are needed which selectively or preferentially bind to Factor Xa. Compounds with a higher affinity for binding to Factor Xa than to thrombin are desired, especially those compounds having good bioavailability or other pharmacologically desirable properties.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals characterized by undesired thrombosis which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In one embodiment, the present invention provides compounds comprising a five-membered heterocyclic ring structure having from 1–4 hetero, atoms selected from the group consisting of N, O and S or a bicyclic ring system comprising the 5-membered heterocyclic ring structure wherein the bicyclic ring structure may have 1–5 hetero atoms selected from the group consisting of N, O and S, and wherein the overall compound has an essentially neutral pH. Preferably, a pH of about pH 5–8, more preferably, about pH 6–7.5 and most preferably, about pH 7.0. The. compounds according to the invention are potent and selective inhibitors of factor Xa versus other proteases of the coagulation cascade (e.g. thrombin, etc.) or the fibrinolytic cascade, and are useful as diagnostic reagents as well as antithrombotic agents. Particular embodiments of the compounds of the present invention are set forth below as preferred embodiments and include all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is an aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, aminoloweralkyl, hydroxyloweralkyl, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in thering structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells. to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as.diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

PREFERRED EMBODIMENTS

The invention provides a compound of the formula (I):

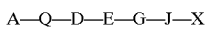

wherein:

A is selected from:
  (a) $C_1$–$C_6$-alkyl;
  (b) $C_3$–$C_8$-cycloalkyl;
  (c) —N($R^2$,$R^3$), —C(=N$R^2$)—$R^3$, —C(=N$R^2$)N($R^2$, $R^3$), —N($R^3$)—C(=N$R^2$)N($R^2$,$R^3$)—, and —N($R^2$)—C(=N$R^3$)—$R^2$
  (d) phenyl, which is independently substituted with 0–2 $R^1$ substituents;
  (e) naphthyl, which is independently substituted with 0–2 $R^1$ substituents; and
  (f) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:
  Halo, —CN, —C(=O)—N($R^2$,$R^3$), —NO$_2$, —SO$_2$N($R^2$,$R^3$), —SO$_2$$R^2$, —(CH$_2$)$_m$N$R^2$$R^3$, —(CH$_2$)$_m$—C(=N$R^3$)$R^2$, —(CH$_2$)$_m$—C(=N$R^2$)—N($R^2$,$R^3$), —(CH$_2$)$_m$—N($R^2$)—C(=N$R^2$)—N($R^2$,$R^3$), —(CH$_2$)$_m$N$R^2$—C$_{3-6}$heterocyclics, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CF$_3$, —O$R^2$, and a 5–6 membered heterocyclic system containing from 1–4 heteroatoms selected from N, O and S, wherein from 1–4 hydrogen atoms on the heterocyclic system may be independently replaced with a member selected from the group consisting of halo, C$_{1-4}$alkyl-CN, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl and —NO$_2$;

$R^2$ and $R^3$ are independently selected from the group consisting of:
  —H, O$R^a$, —N(—$R^a$,—$R^b$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl-CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$;

or $R^2$ and $R^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be. independently replaced with a member selected from the group consisting of halo, C$_{1-4}$alkyl-CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

$R^a$ and $R^b$ are independently selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, or $R^a$ and $R^b$ can be taken together with a nitrogen atom to which they are attached to form a 3–8 heterocyclic ring system containing 1–4 heteroatoms selected from N, O and S, wherein from 1–4 hydrogen atoms on the heterocyclic ring system may be independently replaced with a member selected from the group consisting of halo, —CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

m is an integer of 0–2;

Q is selected from the group consisting of:
  a direct link, divalent —C$_{1-4}$alkyl, divalent —C$_{2-4}$alkenyl, divalent —C$_{2-4}$alkynyl, —C(=O)—, —C(=NH)—, —C(=NMe)—, —N(—$R^4$)—, —N(—$R^4$)—CH$_2$—, —C(=O)—N(—$R^4$)—, —N(—$R^4$)—C(=O)—, —S(=O)$_2$—, —O—, —S(=O)$_2$—N(—$R^4$)— and —N(—$R^4$)—S(=O)$_2$—, wherein one or more hydrogens on each of the divalent C$_{1-4}$alkyl, divalent C$_{2-4}$alkenyl and divalent C$_{2-4}$alkynyl moieties can be replaced with a —$R^4$ group;

$R^4$ is selected from the group consisting of:
  —H, —CF$_3$, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, —CF$_3$, and —NO$_2$;

D is selected from the group consisting of:
  (a) a direct link;
  (b) phenyl, which is independently substituted with 0–2 $R^{1a}$ substituents;
  (c) naphthyl, which is independently substituted with 0–2 $R^{1a}$ substituents; and
  (d) monocyclic or fused bicyclic heterocyclic ring system having from 5 to 10 ring atoms, wherein 1–4 ring atoms of the ring system are selected from N, O and S, and wherein the ring system may be substituted from 0–2 $R^{1a}$ substituents;

$R^{1a}$ is selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, (CH$_2$)$_n$NR$^{2a}$R$^{3a}$, SO$_2$NR$^{2a}$R$^{3a}$, SO$_2$R$^{2a}$, CF$_3$, OR$^{2a}$, a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

$R^{2a}$ and $R^{3a}$ are independently selected from the group consisting of:
—H, $C_{1-4}$alkyl, $C_{2-4}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

n is an integer of 0–2;

E is selected from the group consisting of:
a direct link, —(CH$_2$)$_q$—C(=O), (CH$_2$)$_q$—N(R$^5$)—C(=O)—(CH$_2$)$_x$—, —(CH$_2$)$_q$—C(=O)—N(—R$^5$)—(CH$_2$)$_x$—, —(CH$_2$)$_q$—N(—R$^5$)—(CH$_2$)$_x$—, —(CH$_2$)$_q$—N(R$^5$)CO—NR$^6$(CH$_2$)$_x$— and —SO$_2$—;

q and x are independently an integer of 0–2;

$R^5$ and $R^6$ are independently selected from the group consisting of:
H, —$C_{1-6}$alkyl, —$C_{1-6}$alkyloxy, —$C_{2-6}$alkenyl, —$C_{2-6}$alkynyl, —$C_{3-8}$cycloalkyl, —$C_{0-6}$alkyl$C_{3-8}$cycloalkyl, —$C_{1-4}$alkyl-C(=O)—OH, —CO$_6$alkyl-(carbocyclic aryl), —$C_{0-4}$alkyl-(monocyclic heteroaryl) and —$C_{1-4}$alkyl-C(=O)—O—$C_{1-4}$alkyl, wherein from 0–4 hydrogen atoms on the ring atoms of the carbocyclic aryl moiety and the monocyclic heteroaryl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —S(=O)$_2$—OH, —CN, —CF$_3$ and —NO$_2$;

G is selected from the group consisting of:
phenyl, which is substituted with 0–2 $R^{1b}$ groups; and a 5–6 membered aromatic and non-aromatic heterocyclic ring containing 1–4 hetero atoms selected from N, O and S wherein the heterocyclic ring is substituted with 0–2 $R^{1b}$ groups;

$R^{1b}$ is independently selected from the group consisting of:
halo, —$C_{1-6}$alkyl, —$C_{2-6}$alkenyl, —$C_{2-6}$alkynyl, —$C_{3-8}$cycloalkyl, —$C_{0-6}$alkyl$C_{3-8}$cycloalkyl, —$C_{1-4}$alkyl-C(=O)—OH, —CN, —COOR$^{2b}$, —CONR$^{2b}$R$^{3b}$, —NO$_2$, —S(=O)$_2$—OH, —N(R$^{2b}$,—R$^{3b}$), —C(=O)—N(—R$^{2b}$,—R$^{3b}$), —S(=O)$_2$—N(—R$^{2b}$,—R$^{3b}$), —S(=O)$_2$—R$^{2b}$, —CF$_3$, —O—R$^{2b}$, —O—CH$_2$—CH$_2$—O—R$^{2b}$, —O—CH$_2$—O—R$^{2b}$, —N(—CH$_2$—CH$_2$—O—R$^{2b}$)$_2$, —N(—R$^{2b}$)—C(=O)—R$^{3b}$, —N(—R$^{2b}$)—S(=O)$_2$—R$^{3b}$, and a 5–6 membered heterocyclic ring containing 1–4 heteroatoms selected from N, O and S substituted with 0–4 $R^{1b'}$ groups;

alternatively, when two $R^{1b}$ may be present on adjacent ring atoms of G and combine to form a benzene ring substituted with 0–4 $R^{1b'}$ groups or a 5–6 membered aromatic or non-aromatic heterocyclic ring having 1–3 heteroatoms selected from N, O and S substituted with 0–4 $R^{1b'}$ groups;

in a second alternative, one of the $R^{1b}$ groups of G can cylize with the —N—R$^5$ group of E to form a 5–7 membered heterocyclic ring containing 1–4 heteroatoms selected from N, O and S, which is substituted with 0–4 $R^{1b'}$ groups, wherein two of the $R^{1b'}$ groups attached to the same ring carbon may form a (=O) group;

$R^{2b}$ and $R^{3b}$ are independently selected from the group consisting of:
—H, —$C_{1-6}$alkyl, —$C_{1-6}$alkyloxy, —$C_{2-6}$alkenyl, —$C_{2-6}$alkynyl, —$C_{3-8}$cycloalkyl, —$C_{0-6}$alkyl$C_{3-8}$cycloalkyl and —$C_{0-6}$alkyl-(carbocyclic aryl), wherein from 0–4 hydrogen atoms on the ring atoms of the carbocyclic aryl moiety may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —S(=O)$_2$—OH, —CN, —CF$_3$ and —NO$_2$;

$R^{1b'}$ is independently selected from the group consisting of:
halo, —$C_{1-6}$alkyl, —$C_{2-6}$alkenyl, —$C_{2-6}$alkynyl, —$C_{3-8}$cycloalkyl, —$C_{0-6}$alkyl$C_{3-8}$Cycloalkyl, —$C_{1-4}$alkyl-C(=O)—OH, —CN, —NO$_2$, —S(=O)$_2$—OH, —N(—R$^{2b'}$,—R$^{3b'}$), —C(=O)—N(—R$^{2b'}$,—R$^{3b'}$), —S(=O)$_2$—N(—R$^{2b'}$,—R$^{3b'}$), —S(=O)$_2$—R$^{2b'}$, —CF$_3$, —O—R$^{2b'}$, —O—CH$_2$—CH$_2$—O—R$^{2b'}$, —O—CH$_2$—C(=O)—O—R$^{2b'}$, —N(—R$^{2b'}$)—CH$_2$—CH$_2$—O—R$^{2b'}$, —N(—CH$_2$—CH$_2$—O—R$^{2b'}$)$_2$, —N(—R$^{2b'}$)—C(=O)—R$^{3b'}$ and —N(—R$^{2b'}$)—S(=O)$_2$—R$^{3b'}$;

$R^{2b'}$ and $R^{3b'}$ are independently selected from the group consisting of:
—H, —$C_{1-6}$alkyl, —$C_{1-6}$alkoxy, —$C_{2-6}$alkenyl, —$C_{2-6}$alkynyl, —$C_{3-8}$cycloalkyl, —$C_{0-6}$alkyl$C_{3-8}$cycloalkyl and —$C_{0-6}$alkyl-(carbocyclic aryl), wherein from 0–4 hydrogen atoms on the ring atoms of the carbocyclic aryl moiety may be independently replaced with a member selected from the group consisting of halo, —$C_{1-4}$alkyl, —$C_{2-6}$alkenyl, —$C_{2-6}$alkynyl, —$C_{3-8}$cycloakyl, —$C_{0-4}$alkyl$C_{3-8}$cycloalkyl, —S(=O)$_2$—OH, —CN, —CF$_3$ and —NO$_2$;

J is selected from the group consisting of:
a direct link, —S(=O)$_2$—, —C(=O)—, —N(—R$^7$)—S(=O)$_2$—, —C(=O)—N(—R$^7$)—S(=O)$_2$—, —C(=O)—N(—R$^7$)—(CH$_2$)$_y$—, —S(=O)$_2$—N(—R$^7$)—(CH$_2$)$_y$—, and —N(—R$^7$)—C(=O)—(CH$_2$)$_y$—;

y is an integer of 0–2;

$R^7$ is selected from the group consisting of:
—H, —$C_{2-4}$alkyl, —$C_{2-6}$alkenyl, —$C_{2-6}$alkynyl, —$C_{3-8}$cycloalkyl, —$C_{0-6}$alkyl$C_{3-8}$cycloalkyl, —$C_{1-6}$alkyl-C(=O)—OH, —$C_{1-6}$alkyl-OH, —$C_{1-6}$alkyl-O—$C_{1-4}$alkyl, —$C_{0-4}$alkyl-(carbocyclic aryl), —$C_{0-4}$alkyl-(monocyclic or bicyclic heterocyclic ring system having from 0–4 heteroatoms selected from the group consisting of N, O and S), —CH$_2$—C(=O)—O—C$_{1-4}$alkyl and —CH$_2$—C(=O)—O—C$_{1-4}$alkyl-(carbocyclic aryl), wherein from 0–4 hydrogen atoms on the ring atoms of the carbocyclic aryl moiety or the heterocyclic ring system may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —S(=O)$_2$—OH, —CN, —CF$_3$ and —NO$_2$;

X is selected from the group consisting of:
  phenyl, which is substituted with 0–3 R$^{1c}$ groups;
  naphthyl, which is substituted with 0–3 R$^{1c}$ groups;
  a 6-membered heteroaromatic ring containing from 1–2 nitrogen atoms, wherein the ring is substituted with 0–3 R$^{1c}$ groups; and
  a fused heterobicyclic ring system, wherein the ring system contains 1–3 heteroatoms selected from N, O and S and is substituted with 0–3 R$^{1c}$ groups;

R$^{1c}$ is independently selected from the group consisting of:
  halo, —CF$_3$, —C$_{1-6}$alkyl, —C$_{2-6}$alkenyl, —C$_{2-6}$alkynyl, —C$_{3-8}$cycloalkyl, —C$_{0-6}$alkylC$_{3-8}$cycloalkyl, —C$_{1-4}$alkyl-C(=O)—OH, —CF$_3$, —CN, —NO$_2$, —(CH$_2$)$_z$—N(—R$^{2c}$,—R$^{3c}$), —C(=O)—N(R$^{2c}$,—R$^{3c}$), —C(=NH)—N(—R$^{2c}$,—R$^{3c}$), —C(=NMe)—N(—R$^{2c}$,—R$^{3c}$), —S(=O)$_2$—N(—R$^{2c}$,—R$^{3c}$), —S(=O)$_2$—R$^{2c}$, —S(=O)$_2$OH, —CF$_3$, —O—R$^{2c}$, —O(—CH$_2$)$_z$—O—R$^{2c}$, —O(—CH$_2$)$_z$—C(=O)—O—R$^{2c}$, —N(—R$^{2c}$), —O(—CH$_2$)$_z$—O—R$^{2c}$, —N[(—CH$_2$)$_z$—O—R$^{2c}$]$_2$, —(CH$_2$)$_z$—N(—R$^{2c}$)—C(=O)R$^{3c}$, —(CH$_2$)$_z$—N(—R$^{2c}$)—S(=O)$_2$—R$^{3c}$, and a 5–6 membered heterocyclic ring containing 1–4 heteroatoms selected from N, O and S;

z is an integer of 0–4;

R$^{2c}$ and R$^{3c}$ are independently selected from the group consisting of:
  —H, —C$_{1-6}$alkyl, —C$_{1-6}$alkyloxy, —C$_{2-6}$alkenyl, —C$_{2-6}$alkynyl, —C$_{3-8}$cycloalkyl, —C$_{0-6}$alkylC$_{3-8}$cycloalkyl and —C$_{0-6}$alkyl-(carbocyclic aryl), wherein from 0–4 hydrogen atoms on the ring atoms of the carbocyclic aryl moiety may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —S(=O)$_2$—OH, —CN, —CF$_3$ and —NO$_2$;

and all pharmaceutically acceptable isomers, salts, hydrates, solvates and prodrug derivatives thereof.

The invention also provides a compound of the formula (I):

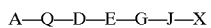

wherein:
A is selected from the group consisting of:
  —C$_{1-6}$alkyl and —C$_{3-8}$cycloalkyl;
  phenyl, which is substituted with 0–2 R$^1$ groups;
  naphthyl, which is substituted with 0–2 R$^1$ groups; and
  a 5–10 membered aromatic or non-aromatic heterocyclic ring system which may be a monocyclic ring system or a fused bicyclic ring system, wherein the heterocyclic ring system contains 1–4 heteroatoms selected from N, O and S and is substituted with 0–2 R$^1$ groups;

R$^1$ is independently selected from the group consisting of:
  halo, —C$_{1-4}$alkyl, —CN, —NO$_2$, —(CH$_2$)$_m$—N(—R$^2$,—R$^3$), —C(=O)—N(—R$^2$,—R$^3$), —S(=O)$_2$—N(—R$^2$,—R$^3$), —S(=O)$_2$—R$^2$, —(CH$_2$)$_m$—C(=NR$^3$)—R$^2$, (CH$_2$)$_m$—C(=NR$^2$)—N(R$^2$,—R$^3$), —(CH$_2$)$_m$—N(R$^2$)—C(=NR$^2$)—N(R$^2$,R$^3$), —CF$_3$, —(CH$_2$)$_m$—O—R$^2$ and a 5–6 membered aromatic heterocyclic ring containing 1–4 heteroatoms selected from N, O and S;

R$^2$ and R$^3$ are independently selected from the group consisting of:
  —H, —C$_{1-4}$alkyl,
or R$^2$ and R$^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, C$_1$–C$_4$-alkyl-CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

m is an integer of 0–2;

Q is selected from the group consisting of:
  a direct link, —C$_{1-4}$alkyl, —C$_{2-4}$alkenyl, —C$_{2-4}$alkynyl, —C(=O)—, —C(=NH)—, —C(=NMe)—, —N(—R$^4$)—, —N(—R$^4$)—CH$_2$—, —C(=O)—N(—R$^4$)—, —N(—R$^4$)—C(=O)—, —S(=O)$_2$—, —O—, —S(=O)$_2$—N(—R$^4$)— and —N(—R$^4$)—S(=O)$_2$—;

R$^4$ is selected from the group consisting of:
  —H, —CF$_3$, —C$_{1-4}$alkyl,

D is selected from the group consisting of:
  a direct link;
  phenyl, which is substituted with 0–2 R$^{1a}$ groups; and
  a 5–10 membered aromatic or non-aromatic heterocyclic ring system which may be a monocyclic ring system or a fused bicyclic ring system, wherein the heterocyclic ring system contains 1–4 heteroatoms selected from N, O and S and the ring system is substituted with 0–2 R$^{1a}$ groups;

R$^{1a}$ is independently selected from the group consisting of:
  halo, —C$_{1-4}$alkyl, —CN, —NO$_2$, —(CH$_2$)$_n$—N(—R$^{2a}$,—R$^{3a}$), —S(=O)$_2$—N(—R$^{2a}$,—R$^{3a}$), —S(=O)$_2$—R$^{2a}$, —CF$_3$, —(CH$_2$)$_n$—OR$^{2a}$, —C(=O)—O—R$^{2a}$, —C(=O)—N(—R$^{2a}$,—R$^{3a}$) and a 5–6 membered aromatic heterocyclic ring containing 1–4 heteroatoms selected from N, O and S;

n is an integer of 0–2;

R$^{2a}$ and R$^{3a}$ are independently selected from the group consisting of:
  —H, —CF$_3$ and —C$_{1-4}$alkyl, E is selected from the group consisting of:
  a direct link, —(CH$_2$)$_q$—C(=O)—, —(CH$_2$)$_q$—N(—R$^5$)—C(=O)—(CH$_2$)$_x$—, —(CH$_2$)$_q$—C(=O)—N(—R$^5$)—(CH$_2$)$_x$—, —(CH$_2$)$_q$—N(—R$^5$)—(CH$_2$)$_x$—, —(CH$_2$)$_q$—N(R$^5$)CO—NR$^6$(CH$_2$)$_x$— and —SO$_2$—;

R$^5$ and R$^6$ are each H, —C$_{1-4}$alkyl, —C$_{2-6}$alkenyl, —C$_{2-6}$alkynyl, —C$_{3-8}$cycloalkyl, or —C$_{0-4}$alkylC$_{3-8}$cycloalkyl;

q and x are independently an integer of 0–2;

G is selected from the group consisting of:

phenyl, which is substituted with 0–2 $R^{1b}$ groups; and a 5–6 membered aromatic and non-aromatic heterocyclic ring containing 1–4 hetero atoms selected from O, S and N, wherein the heterocyclic ring is substituted with 0–2 $R^{1b}$ groups;

$R^{1b}$ is independently selected from the group consisting of:
halo, —$C_{1-4}$alkyl, —CN, —$NO_2$, —N(—$R^{2b}$,—$R^{3b}$), —C(=O)—N(—$R^{2b}$,—$R^{3b}$), —S(=O)$_2$—N(—$R^{2b}$, —$R^{3b}$), —S(=O)$_2$—$R^{2b}$, —$CF_3$, —O—$R^{2b}$, —O—$CH_2$—$CH_2$—O—$R^{2b}$, —O—$CH_2$—C(=O)—O—$R^{2b}$, —N(—$R^{2b}$)—$CH_2$—$CH_2$—O—$R^{2b}$, —N(—$CH_2$—$CH_2$—O—$R^{2b}$)$_2$, —N(—$R^{2b}$)—C(=O)—$R^{3b}$, —N(—$R^{2b}$)—S(=O)$_2$—$R^{3b}$ and a 5–6 membered heterocyclic ring containing 1–4 heteroatoms selected from N, O and S;

alternatively, when two $R^{1b}$ may be present on adjacent ring atoms of G and combine to form a benzene ring substituted with 0–4 $R^{1b'}$ groups or a 5–6 membered aromatic or non-aromatic heterocyclic ring having 1–3 heteroatoms selected from N, O and S substituted with 0–4 $R^{1b'}$ groups;

in a second alternative, one of the $R^{1b}$ groups of G can cylize with the —N—$R^5$ group of E to form a 5–7 membered saturated, unsaturated or partially unsaturated heterocyclic ring containing 1–4 heteroatoms selected from N, O and S, which is substituted with 0–4 $R^{1b'}$ groups, wherein two of the $R^{1b'}$ groups attached to the same ring carbon may form a (=O) group;

$R^{2b}$ and $R^{3b}$ are independently selected from the group consisting of:
—H, —$CF_3$, —$C_{1-4}$alkyl and —$C_{1-4}$alkyl-(carbocyclic aryl);

$R^{1b'}$ is independently selected from the group consisting of:
halo, —$C_{1-4}$alkyl, —CN, —$NO_2$, —N(—$R^{2b'}$,—$R^{3b'}$), —C(=O)—N(—$R^{2b}$,—$R^{3b}$), —S(=O)$_2$—N(—$R^{2b'}$, —$R^{3b'}$), —S(=O)$_2$—$R^{2b'}$, —$CF_3$, O—$R^{2b'}$, —O—$CH_2$—$CH_2$—O—$R^{2b'}$, —O—$CH_2$—C(=O)—O—$R^{2b'}$, —N(—$R^{2b'}$)—$CH_2$—$CH_2$O—$R^{2b'}$, —N(—$CH_2$—$CH_2$—O—$R^{2b'}$)$_2$, —N(—$R^{2b'}$)—C(=O)—$R^{3b'}$, —N(—$R^{2b'}$)—S(=O)$_2$—$R^{3b'}$;

$R^{2b'}$ and $R^{3b'}$ are independently selected from the group consisting of:
—H, —$C_{1-4}$alkyl and —$C_{1-4}$alkyl-(carbocyclic aryl);

J is selected from the group consisting of:
a direct link, —S(=O)$_2$—, —C(=O)—, —N(—$R^7$)—S(=O)$_2$—, —C(=O)—N(—$R^7$)—S(=O)$_2$—, —C(=O)—N(—$R^7$)—(CH$_2$)$_y$—, —S(=O)$_2$—N(—$R^7$)—C(CH$_2$)$_y$— and —N(—$R^7$)—C(=O)—(CH$_2$)$_y$—;

y is an integer of 0–2;

$R^7$ is selected from the group consisting of:
—H, —$C_{1-4}$alkyl, —$C_{2-6}$alkenyl, —$C_{2-6}$alkynyl, —$C_{0-4}$alkyl-(carbocyclic aryl), —$C_{0-4}$alkyl-(heterocyclic ring system), —$CH_2$—C(=O)—O—$C_{1-4}$alkyl and —$CH_2$—C(=O)—O—$C_{1-4}$alkyl-(carbocyclic aryl);

X is selected from the group consisting of:
phenyl, which is substituted with 0–3 $R^{1c}$ groups;
naphthyl, which is substituted with 0–3 $R^{1c}$ groups;
a 6-membered heteroaromatic ring containing from 1–2 nitrogen atoms, wherein the ring is substituted with 0–3 $R^{1c}$ groups; and
a fused heterobicyclic ring system, wherein the ring system contains 1–3 heteroatoms selected from N, O and S and is substituted with 0–3 $R^{1c}$ groups;

$R^{1c}$ is independently selected from the group consisting of:
halo, —$C_{1-4}$alkyl, —CN, —$NO_2$, —(CH$_2$)$_z$—N(—$R^{2c}$,—$R^{3c}$), —C(=O)—N(—$R^{2c}$,—$R^{3c}$), —C(=NH)—N(—$R^{2c}$,—$R^{3c}$), —C(=NMe)—N(—$R^{2c}$,—$R^{3c}$), —S(=O)$_2$—N(—$R^{2c}$,—$R^{3c}$), —S(=O)$_2$—$R^{2c}$, —S(=O)$_2$—O$^-$, —$CF_3$, —O—$R^{2c}$, —O—$CH_2$—$CH_2$—O—$R^{2c}$, —O—$CH_2$—C(=O)—O—$R^{2c}$, —N(—$R^{2c}$)—$CH_2$—$CH_2$—O—$R^{2c}$, —N(—$CH_2$—$CH_2$—$R^{2c}$)$_2$, —(CH$_2$)$_z$—N(—$R^{2c}$)—C(=O)—$R^{3c}$, —(CH$_2$)$_z$—N(—$R^{2c}$)—S(=O)$_2$—$R^{3c}$, and a 5–6 membered heterocyclic ring containing 1–4 heteroatoms selected from N, O and S;

z is an integer of 0–2;

$R^{2c}$ and $R^{3c}$ are independently selected from the group consisting of:
—H, —$C_{1-4}$alkyl and —$C_{1-4}$alkyl-(carbocyclic aryl);

and all pharmaceutically acceptable isomers, salts, hydrates, solvates and prodrug derivatives, thereof.

The present invention also provides compounds of the formula (I):

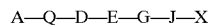

wherein:

A is selected from the group consisting of:

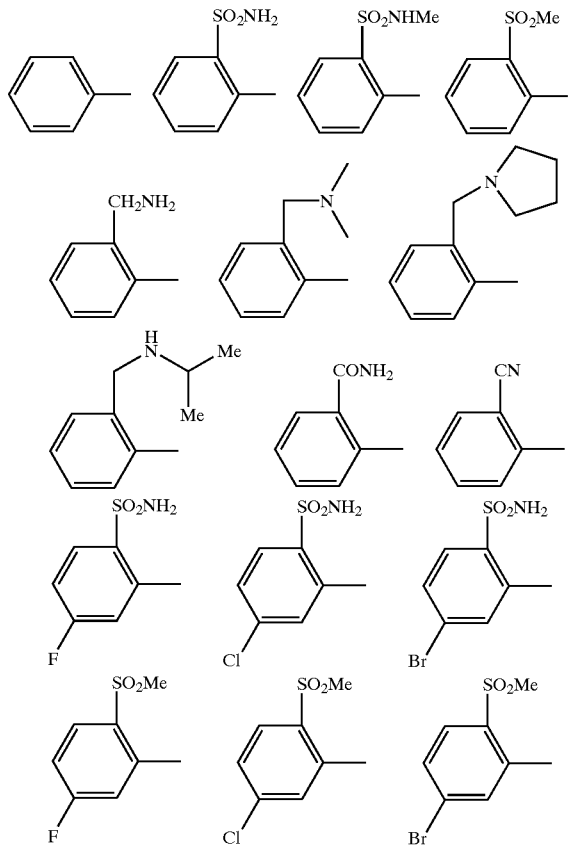

-continued
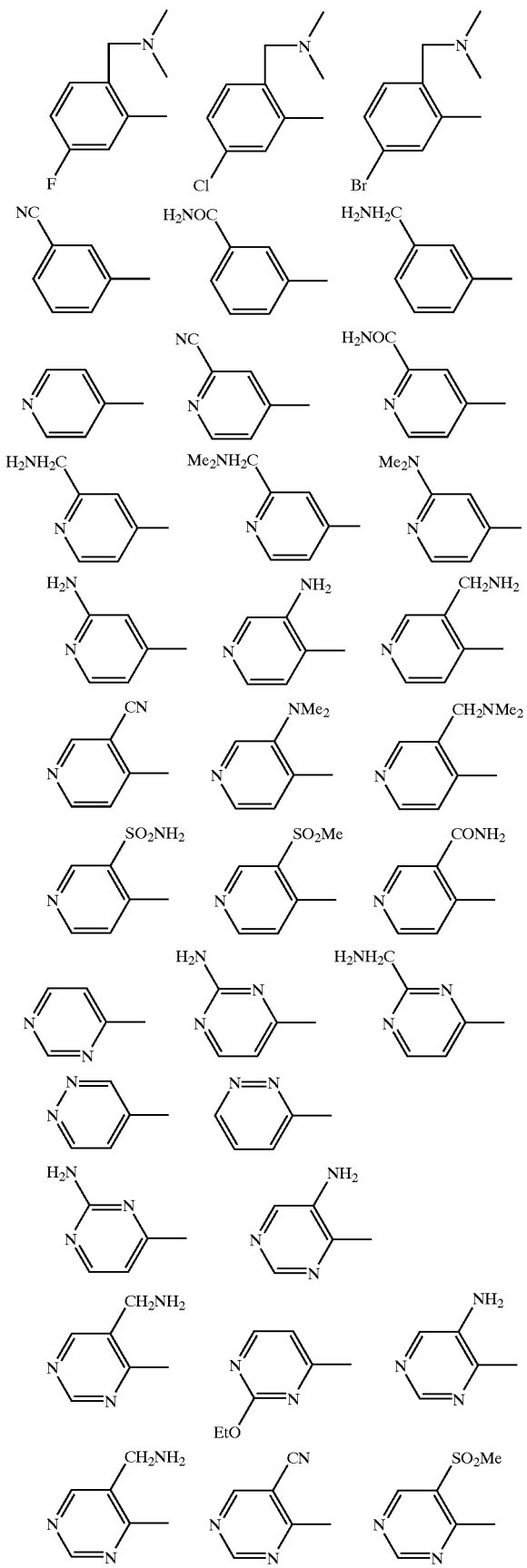
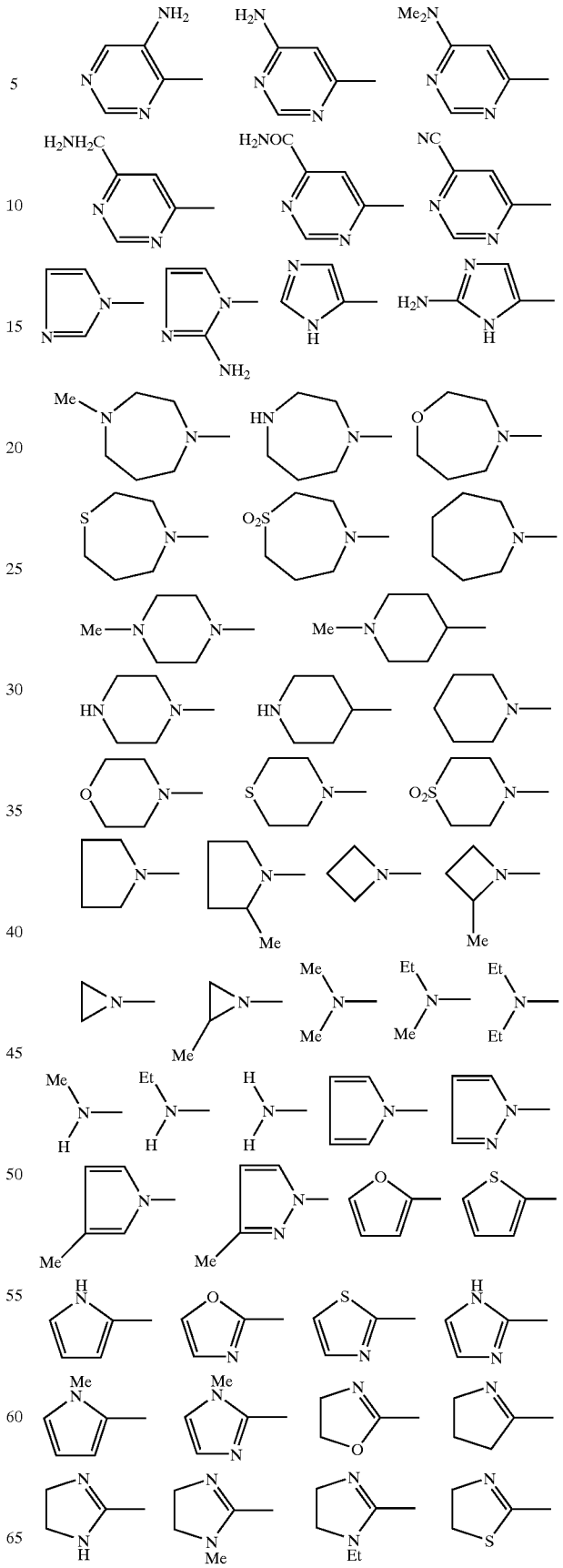

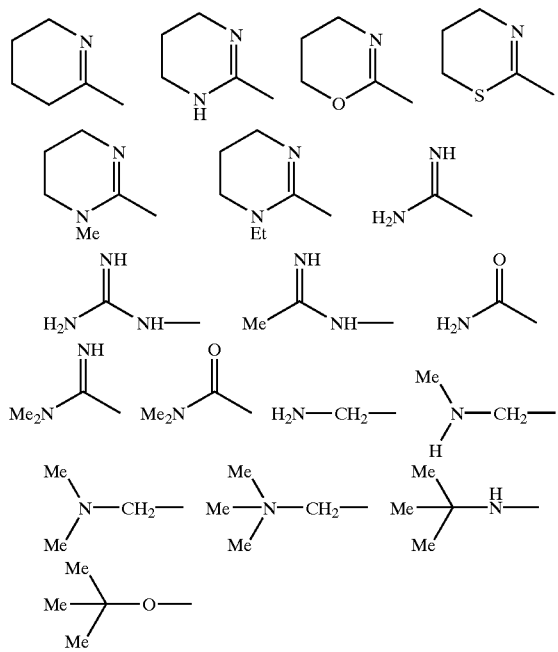
Q is selected from the group consisting of:
a direct link, —C(=NH), —C(=NMe)—, —C(=O)—, —CH₂—, —NH—, —N(—CH₃)—, —O—, —NH—CH₂—, —CH₂—NH—, —N(—CH₃)—CH₂—, and —CH₂—N(—CH₃)—;
D is selected from the group consisting of:
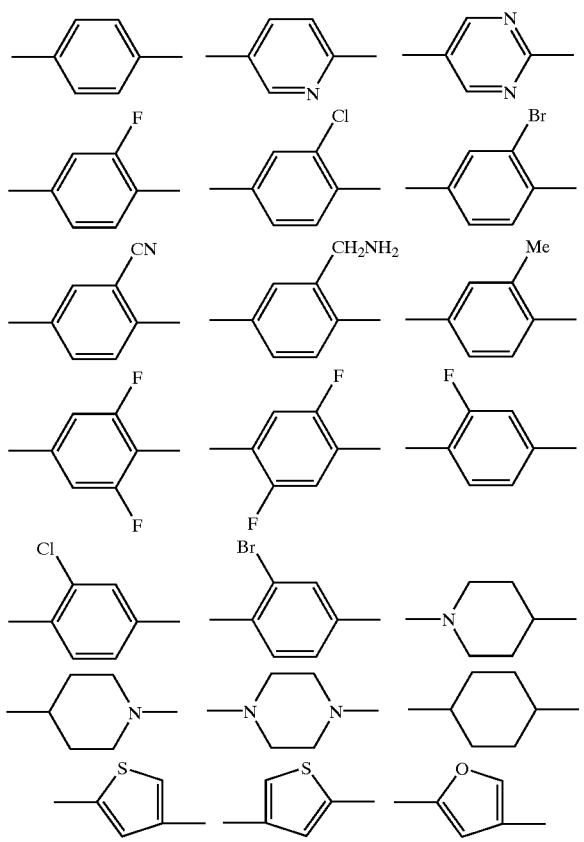
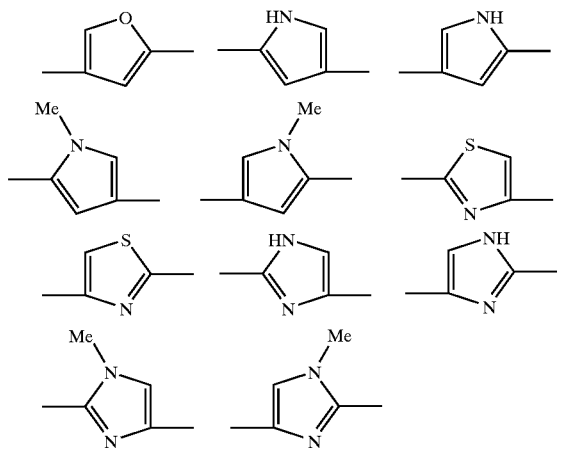
E is selected from the group consisting of:
a direct link, —NH—C(=O)—, —N(—CH₃)—C(=O)—, —N(—CH₂CO₂H)—C(=O)—, —C(=O)—NH—, —C(=O)—N(—CH₃)—, —NH—CH₂—and —CH₂—NH—;
G is selected from the group consisting of:
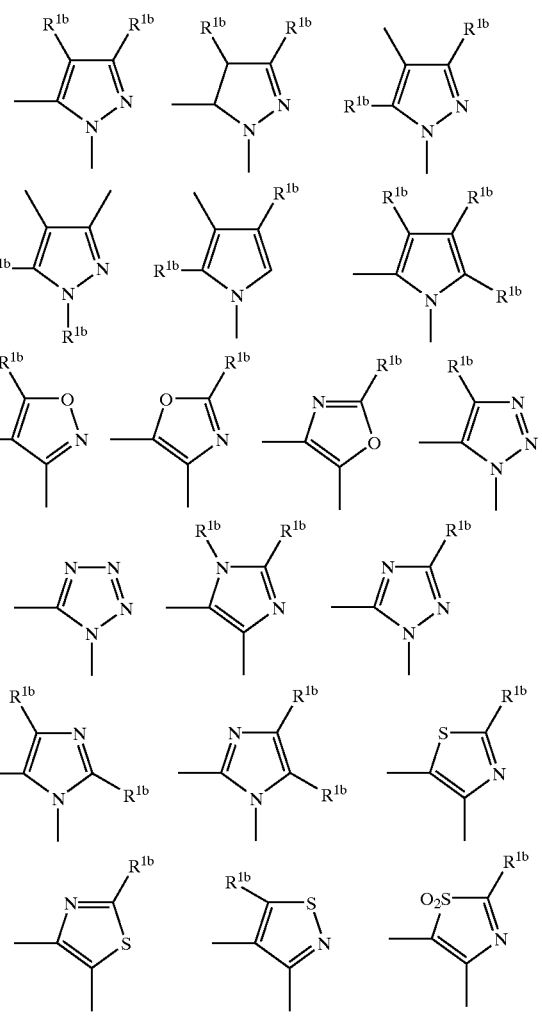

-continued
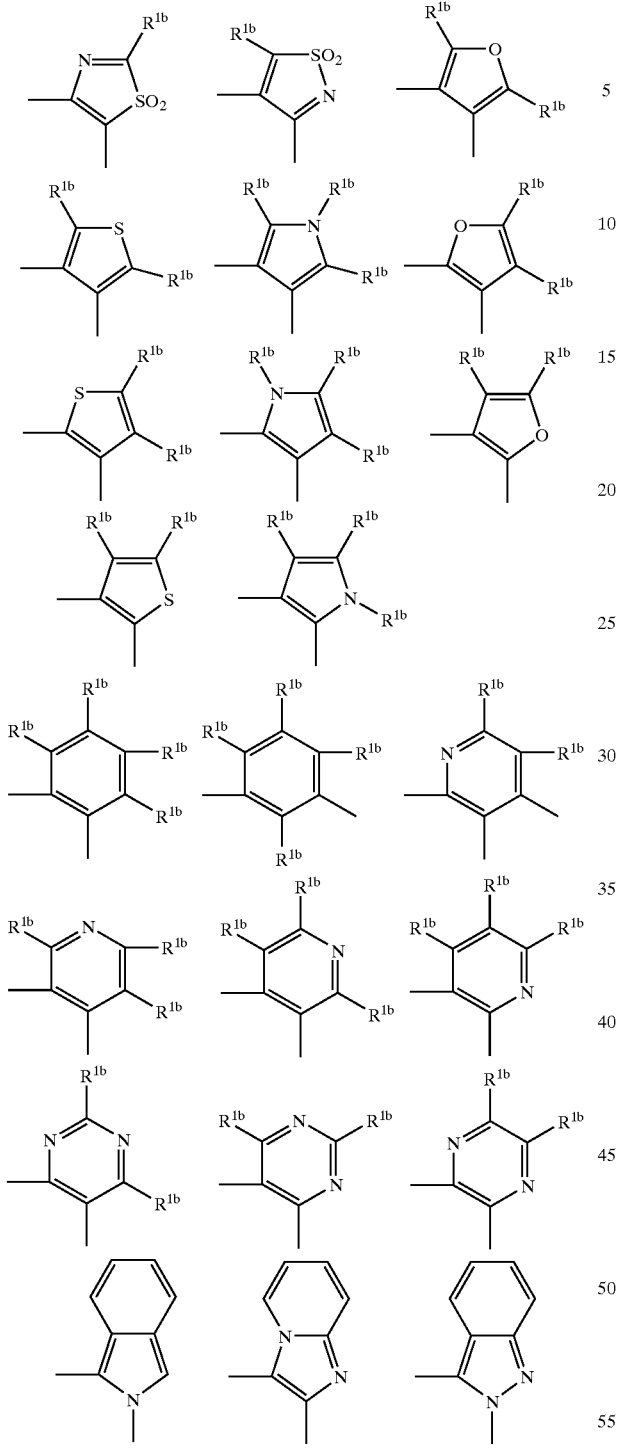
$R^{1b}$ is independently selected from the group consisting of:
—H, —Me, —CF$_3$, —F, —Cl, —Br, —SO$_2$Me, —CN, —CONH$_2$, —CONMe$_2$, —NH$_2$, —NO$_2$, —NHCOMe, —NHSO$_2$Me, —CR$_2$NH$_2$ and —CO$_2$H;
J is selected from the group consisting of:
a direct link, —NH—, —O—, —S(=O)$_2$—, —S(=O)$_2$—NH, —NH—S(=O)$_2$—, —C(=O)—, —NH—C(=O)— and —C(=O)—NH—;
X is selected from the group consisting of:
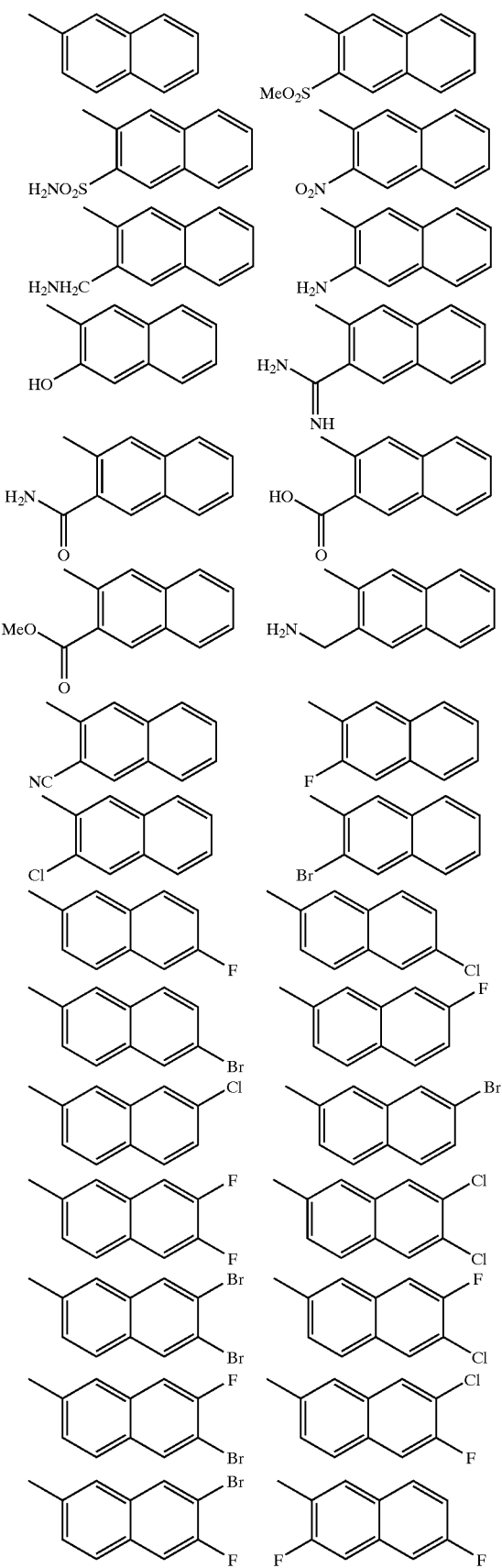

-continued
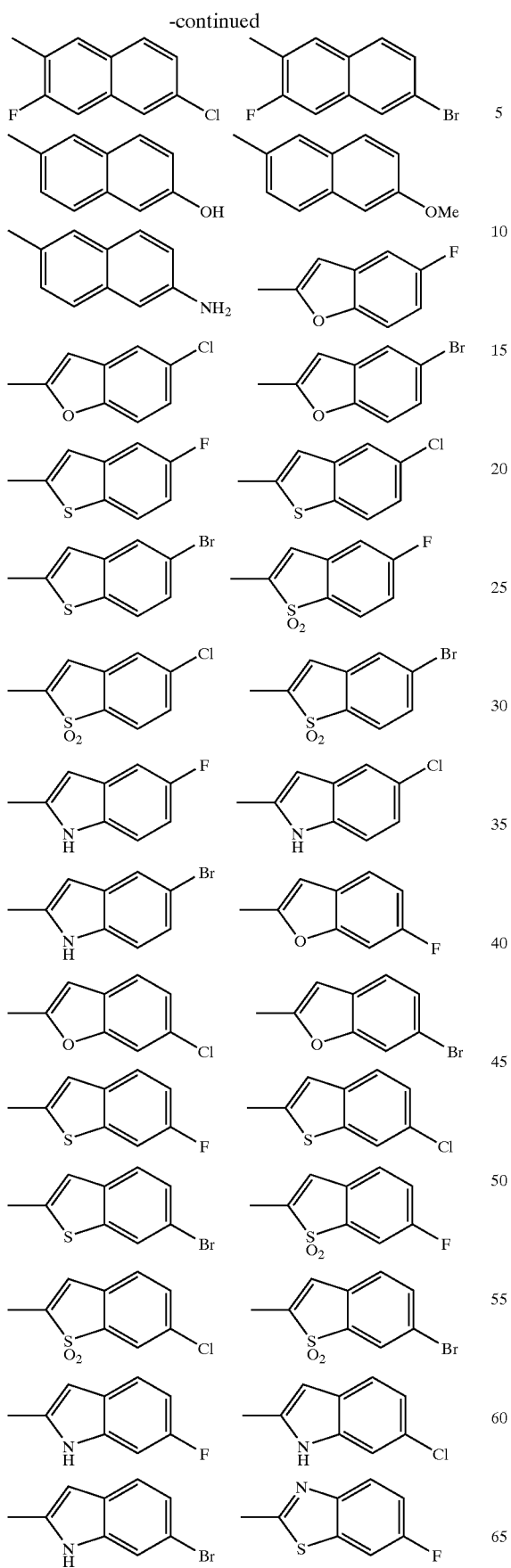
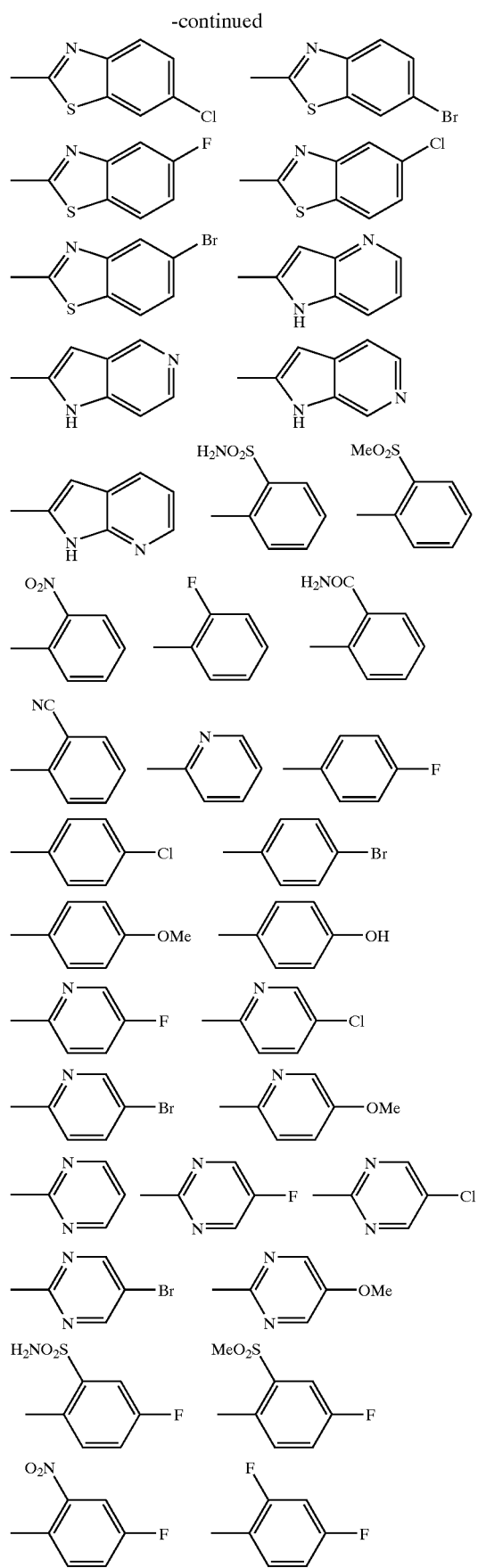

-continued
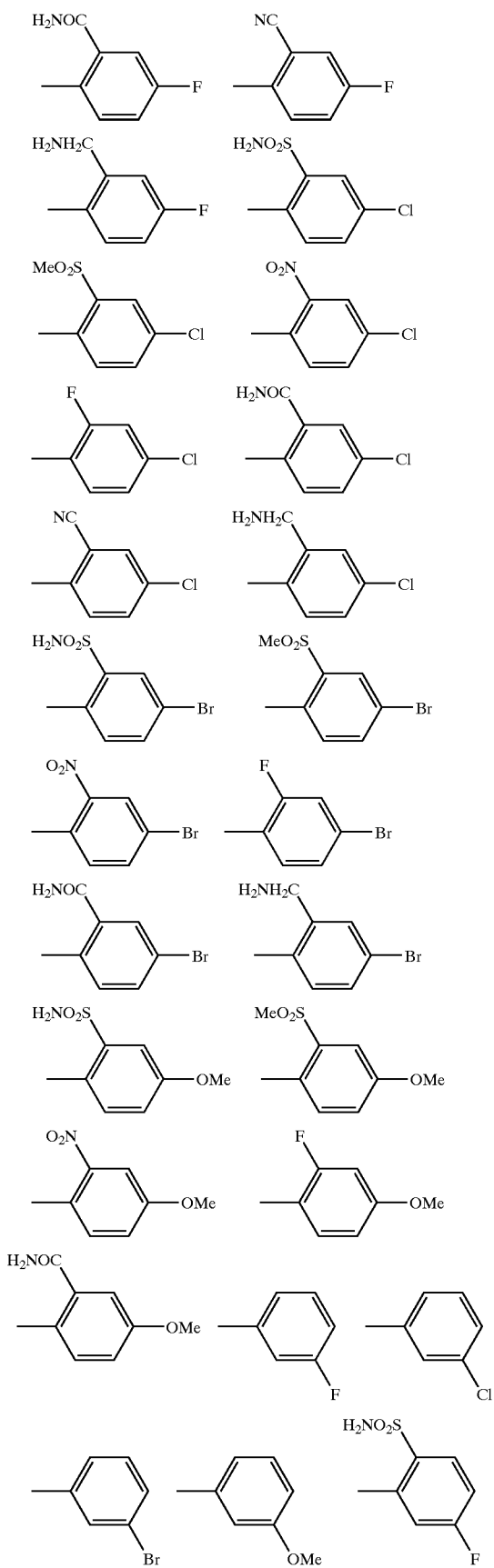
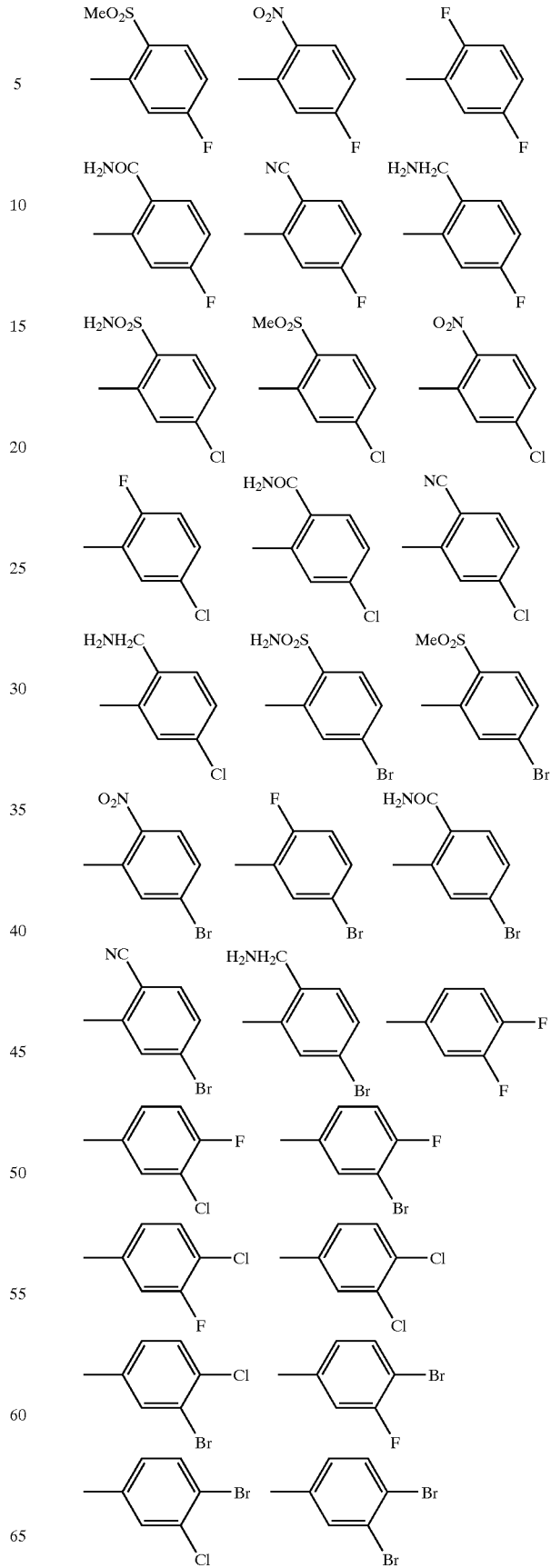

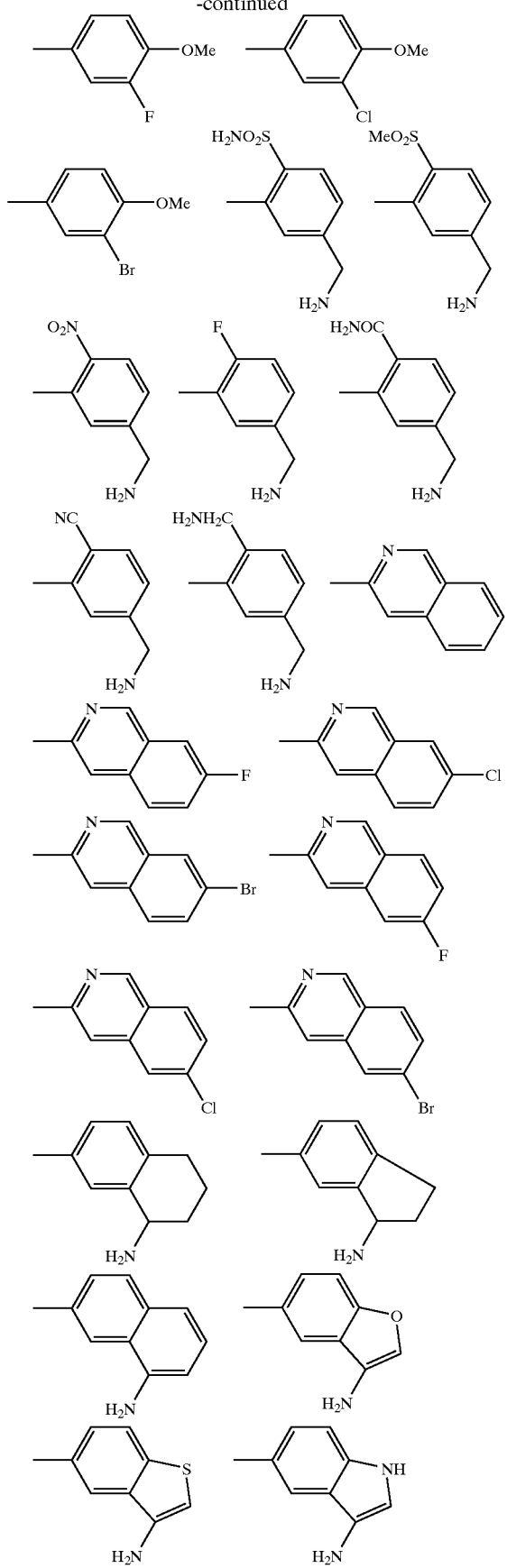
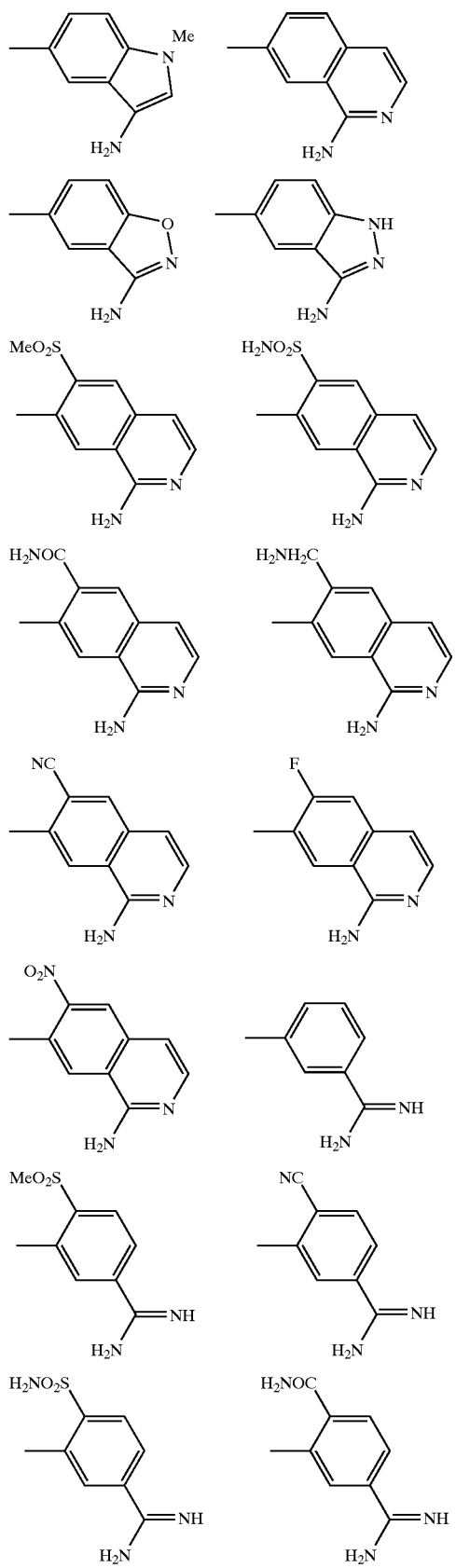

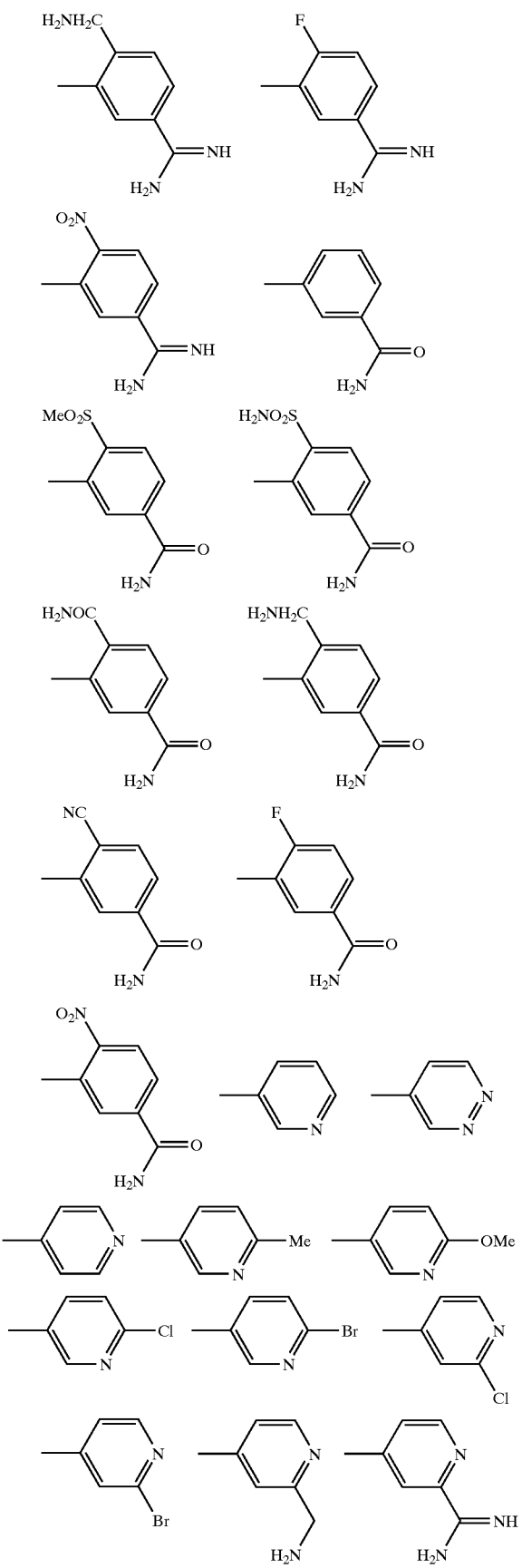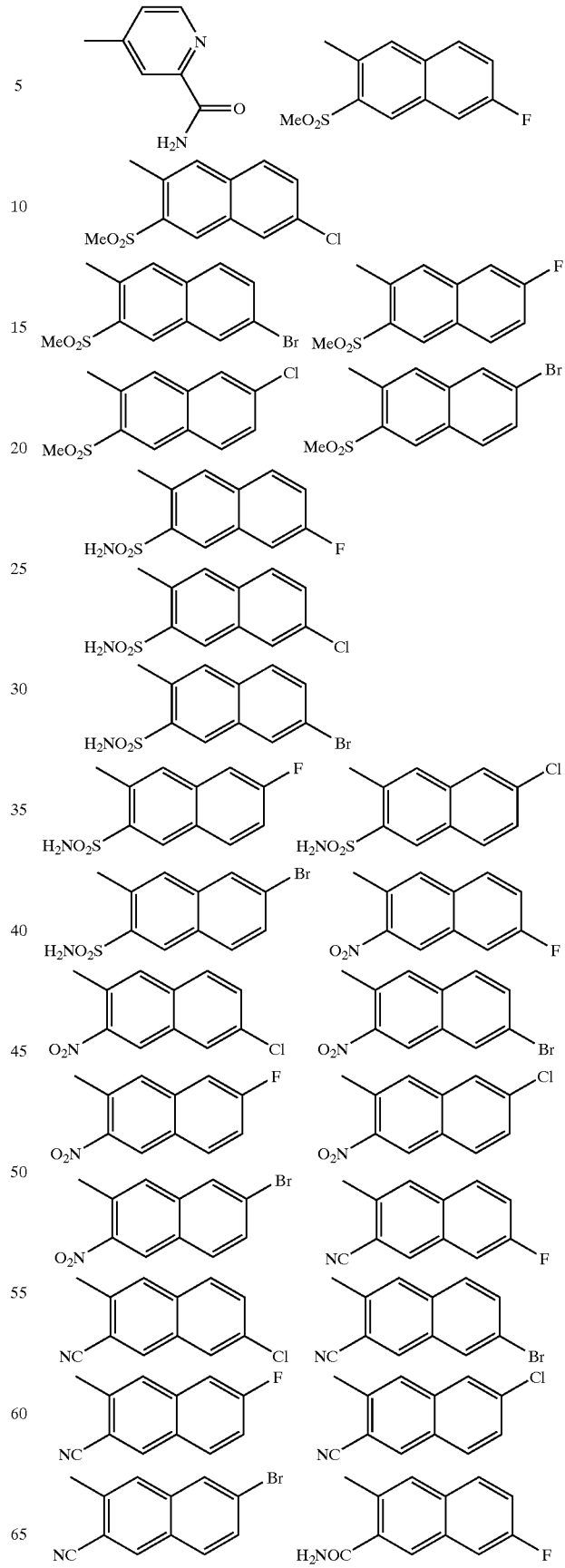

-continued
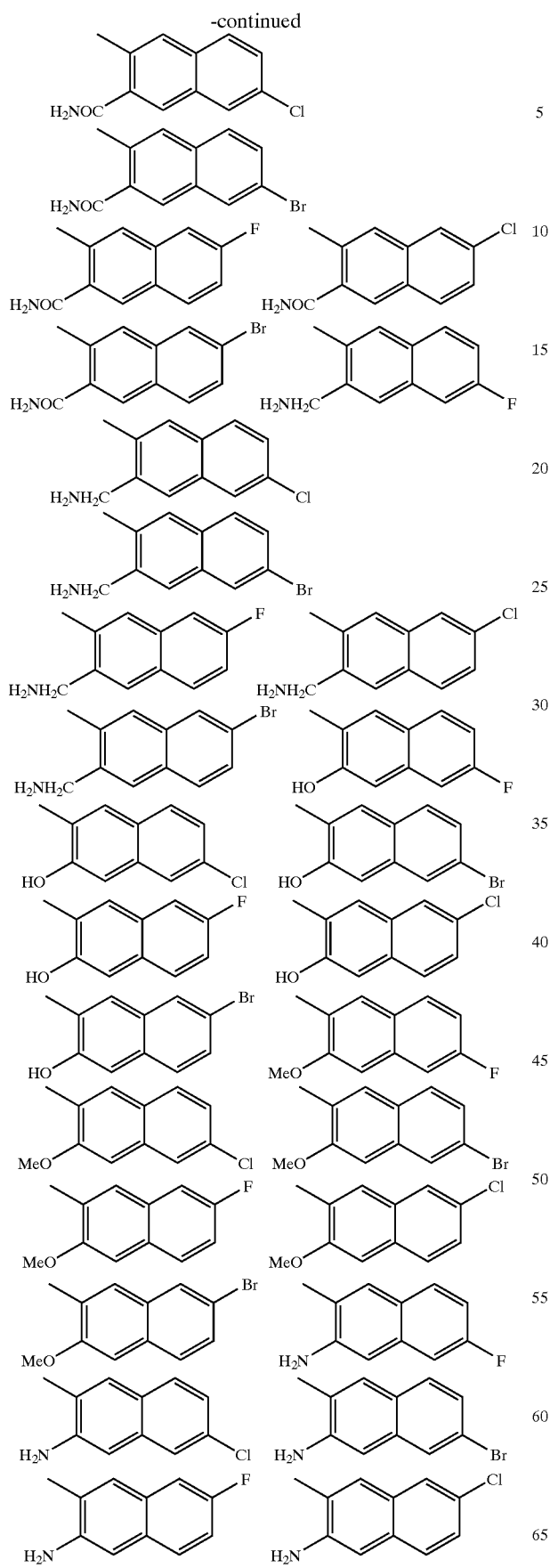
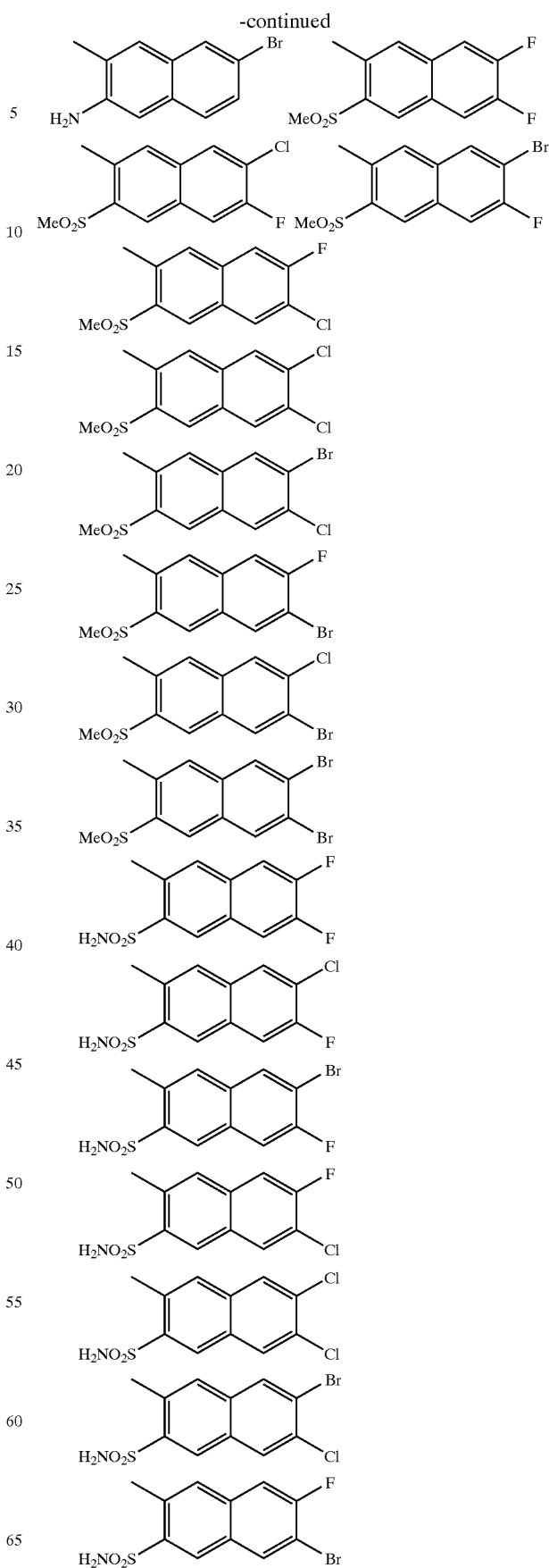

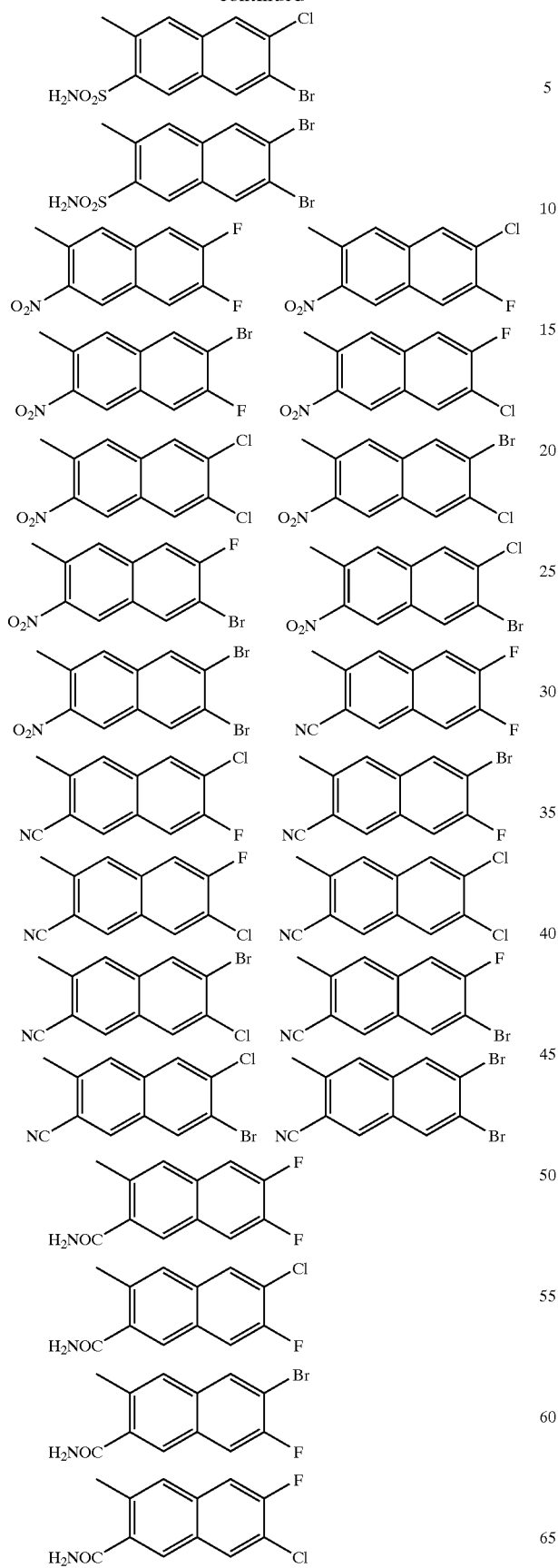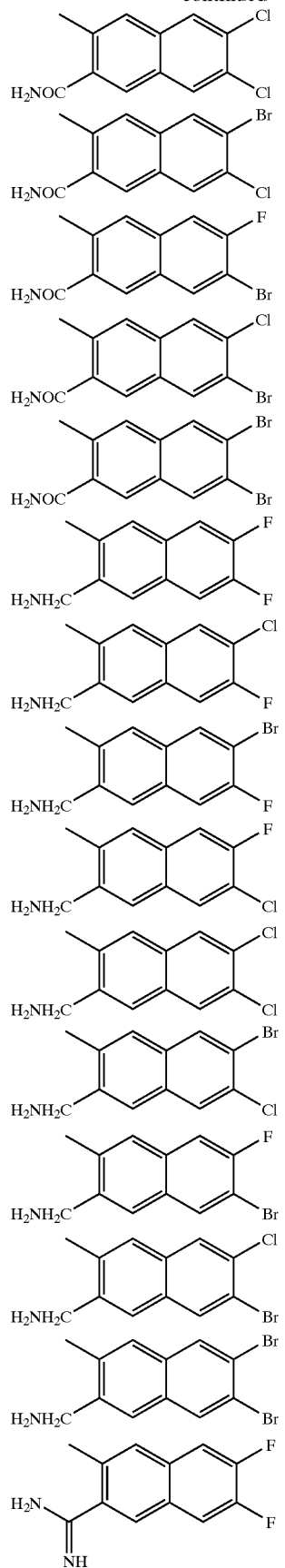

-continued
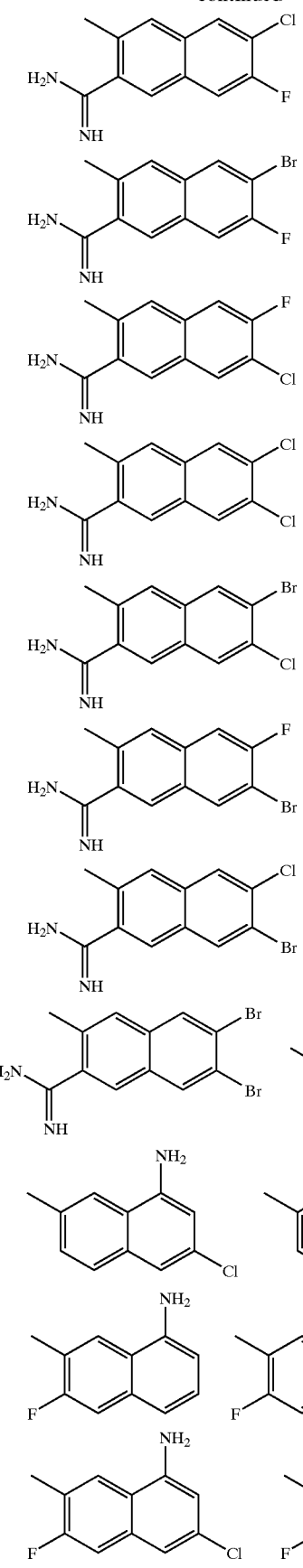
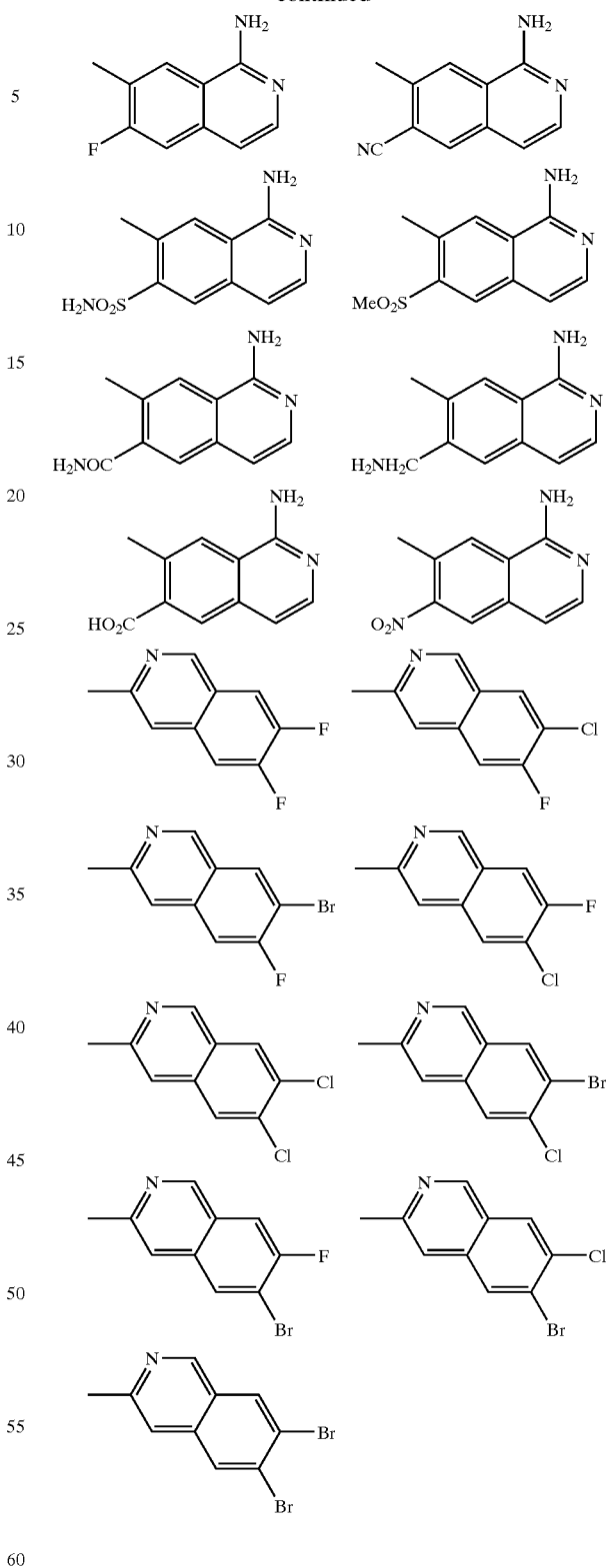
and all pharmaceutically acceptable isomers, salts, hydrates, solvates and prodrug derivatives, thereof.
The compounds listed in the following 53 tables are an embodiment of the present invention:

TABLE 1
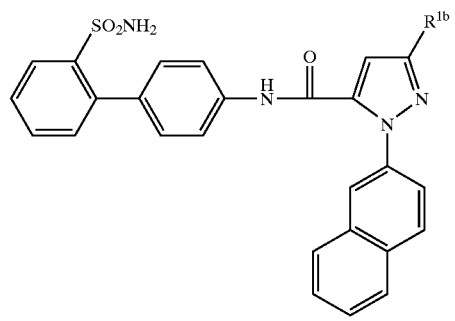
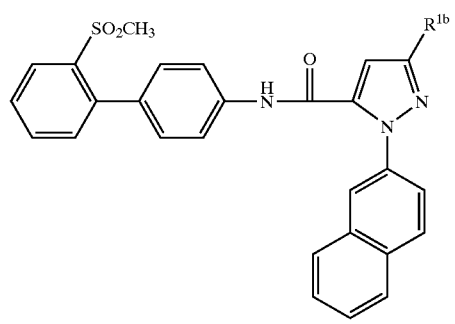
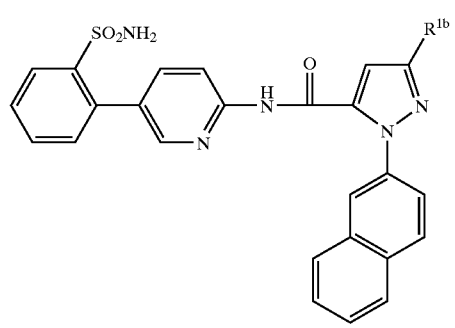
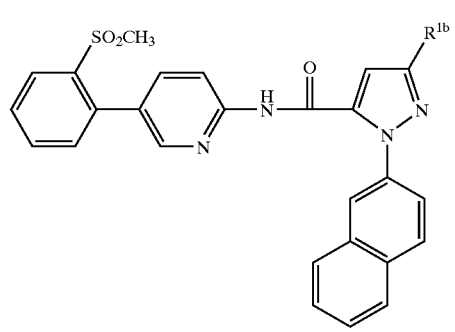
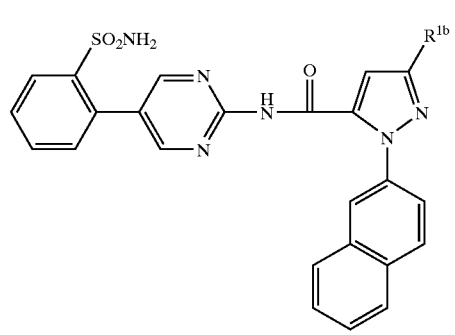
TABLE 1-continued
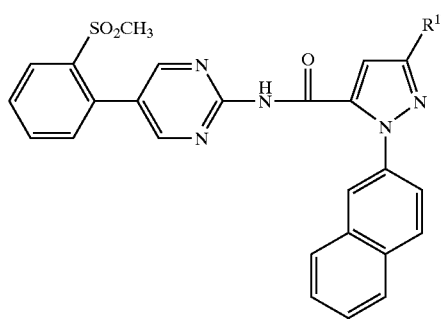
wherein:
$R^{1b}$ is selected from the group consisting of —H, —CH₃ and —CF₃.
TABLE 2
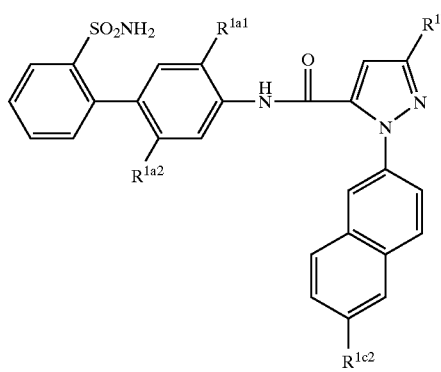
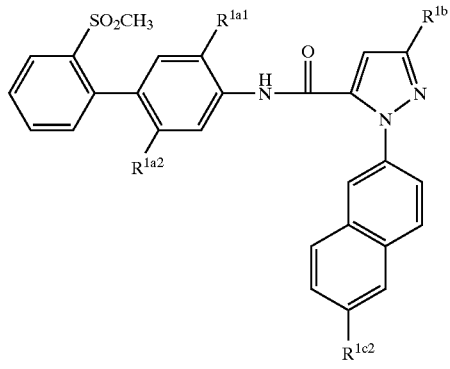
wherein:
$R^{1a1}$ and $R^{1a2}$ are independently selected from the group consisting of —H, —F, —Cl and —Br;
$R^{1b}$ is selected from the group consisting of —H, —CH₃ and CF₃; and
$R^{1c2}$ is selected from the group consisting of —H, —F, —Cl, —Br, —OH, —OCH₃ and —NH₂.

TABLE 3
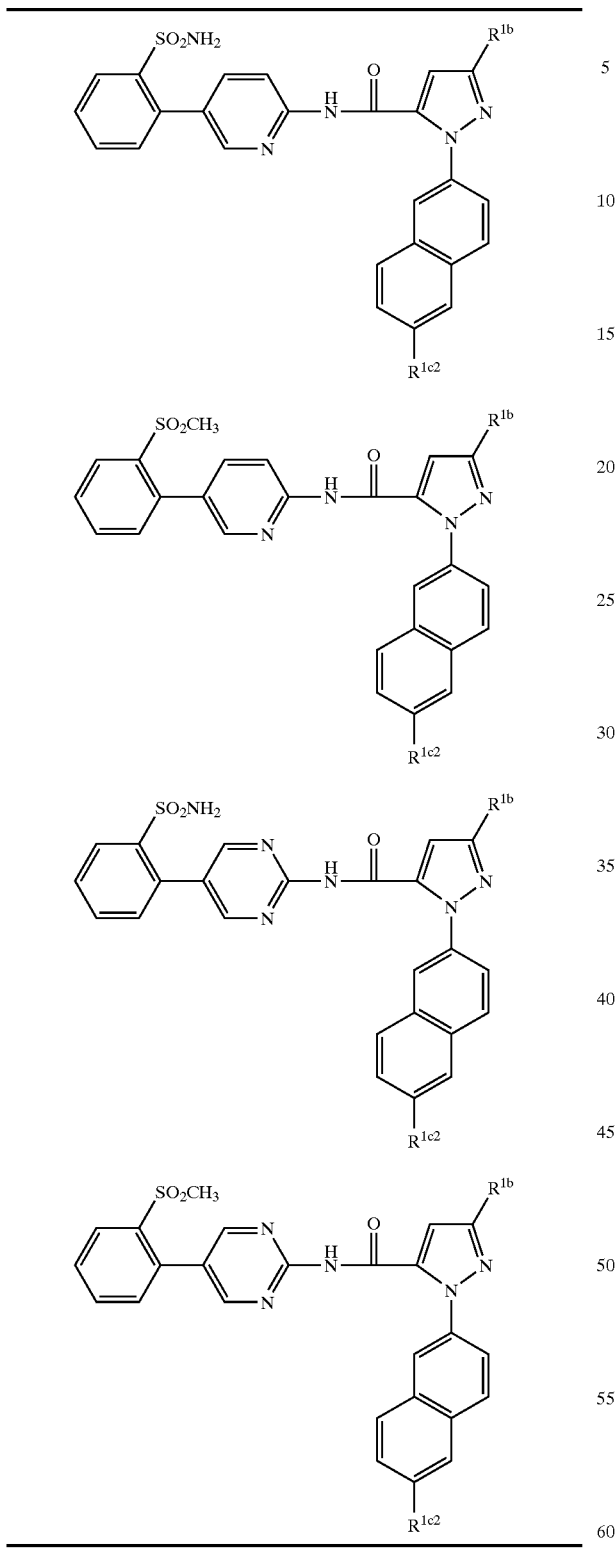
wherein:
$R^{1b}$ is selected from the group consisting of —H, —CH₃ and —CF₃; and
$R^{1c2}$ is selected from the group consisting of —H, —F, —Cl, —Br, —OH, —OCH₃ and —NH₂.
TABLE 4
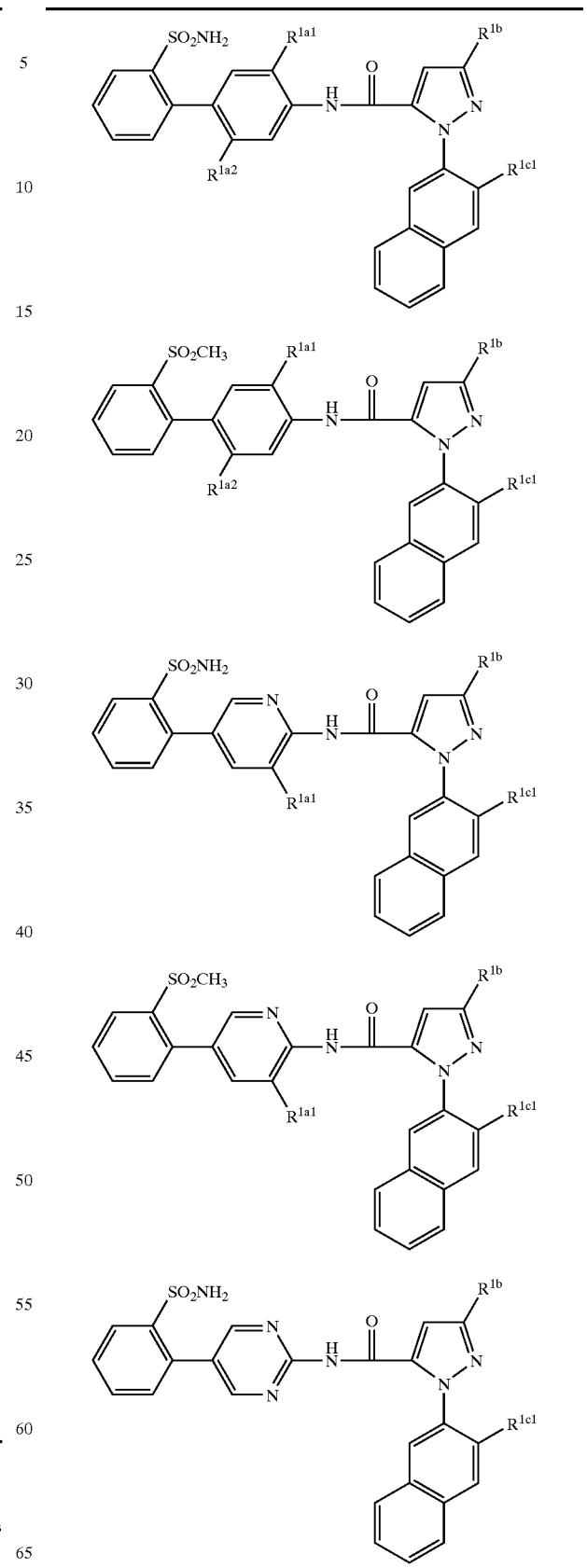

TABLE 4-continued

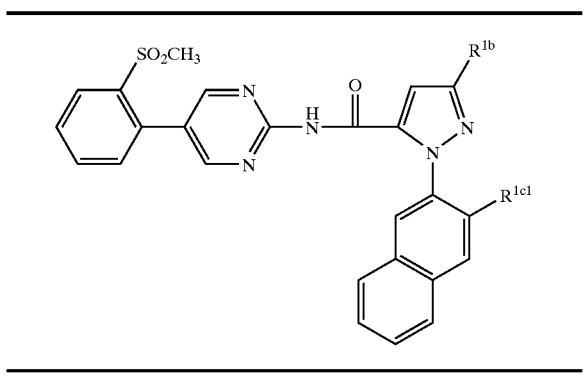

wherein:

$R^{1a1}$ and $R^{1a2}$ are independently selected from the group consisting of —H, —F, —Cl and —Br;

$R^{1b}$ is selected from the group consisting of —H, —CH$_3$ and —CF$_3$; and $R^{1c1}$ is selected from the group consisting of —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$.

TABLE 5

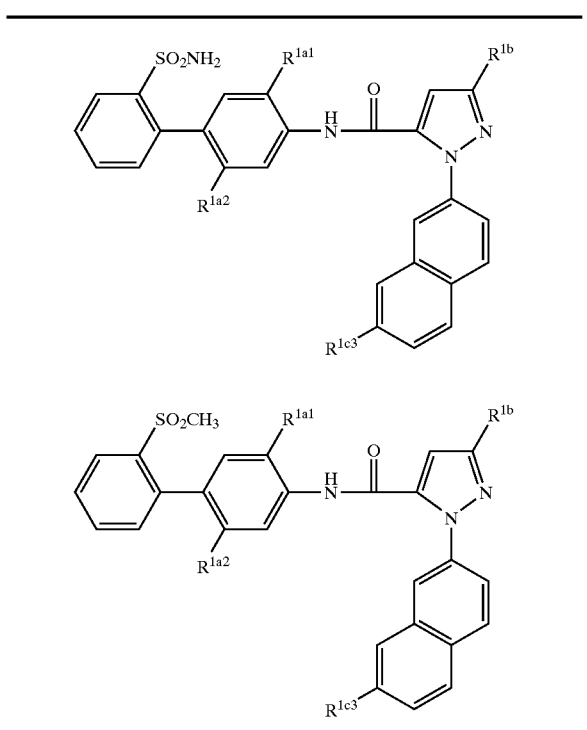

TABLE 5-continued

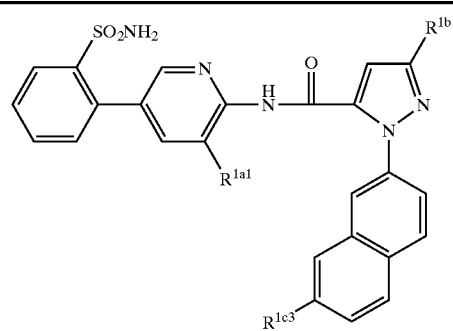

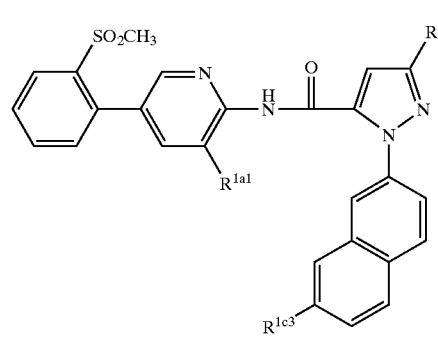

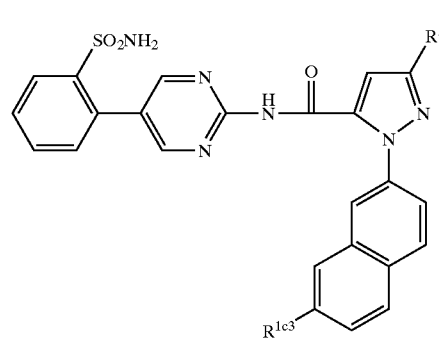

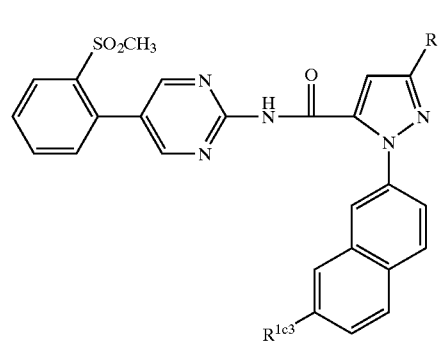

wherein:

$R^{1a1}$ and $R^{1a2}$ are independently selected from the group consisting of —H, —F, —Cl and —Br;

$R^{1b}$ selected from the group consisting of —H, —CH$_3$ and —CF$_3$; and $R^{1c3}$ is selected from the group consisting of —H, —F, —Cl, —Br, —OH, —OCH$_3$ and —NH$_2$.

TABLE 6

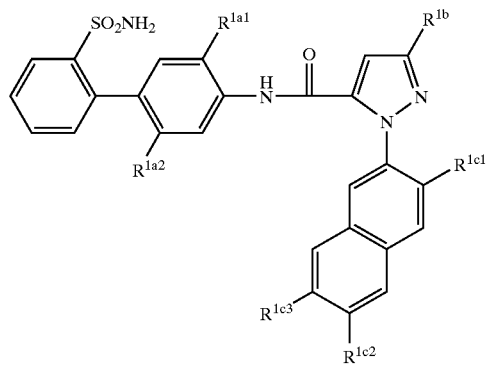

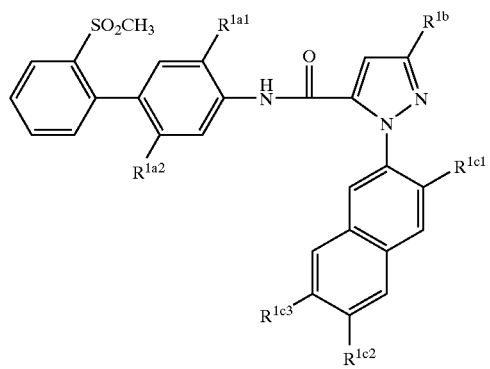

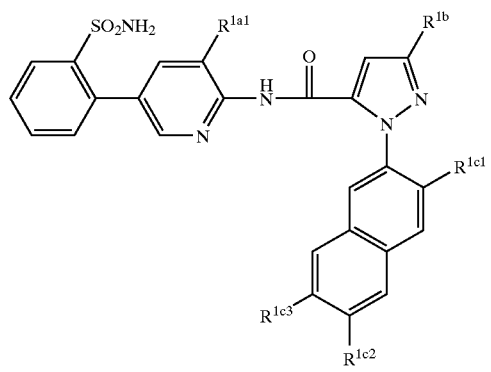

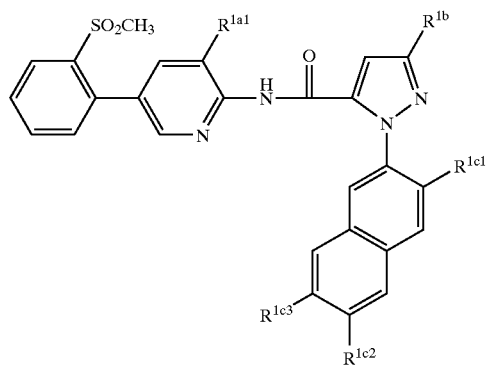

TABLE 6-continued

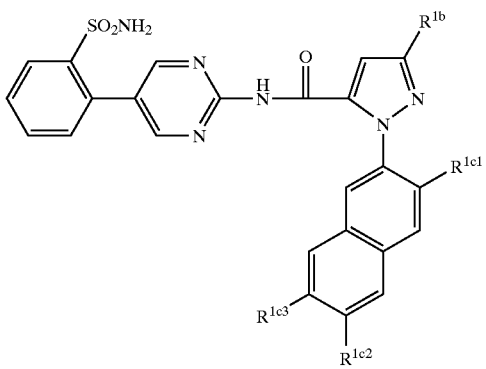

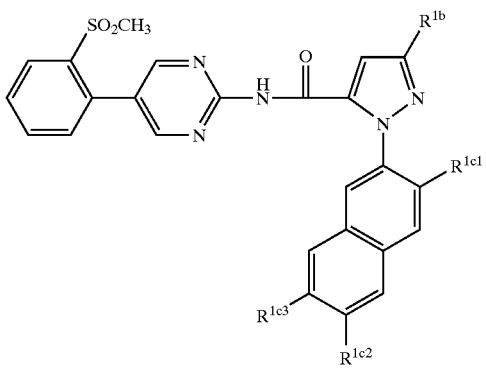

wherein:
$R^{1a1}$ and $R^{1a2}$ are independently selected from the group consisting of —H, —F, —Cl and —Br;
$R^{1b}$ is selected from the group consisting of —H, —CH₃, —CF₃, —CH₂CH₃, —CF₂CF₃, —CH₂NH₂, —CONH₂, —SO₂CH₃, —SO₂NH₂, —NH₂COCH₃ and —NH₂COCF₃;
$R^{1c1}$ is selected from the group consisting of —H, —F, —Cl, —Br, —CN, —CH₂NH₂, —CH₂OH, —CONH₂, —C(=NH)NH₂, —CO₂H, —CO₂Me, —SO₂Me, —SO₂NH₂, —OH, —NH₂, and —NO₂;
$R^{1c2}$ is selected from the group consisting of —H, —F, —Cl, —Br, —OH, —OCH₃, and —NH₂; and
$R^{1c3}$ is selected from the group consisting of —H, —F, —Cl, —Br, —OH, —OCH₃, and —NH₂.

TABLE 7

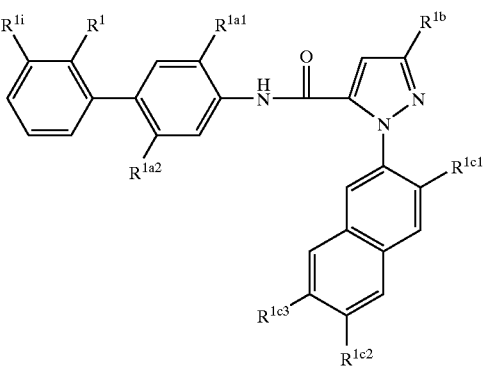

TABLE 7-continued

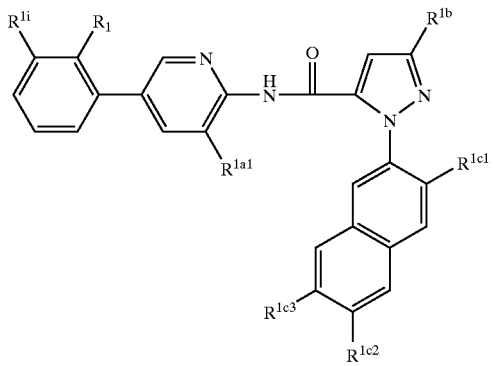

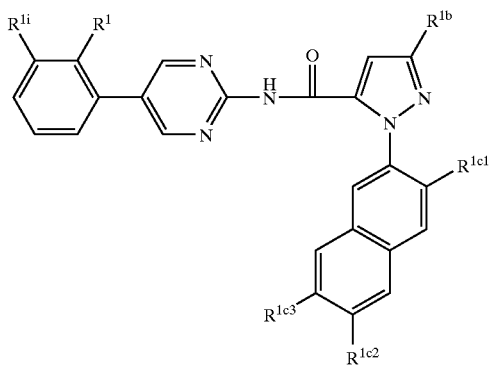

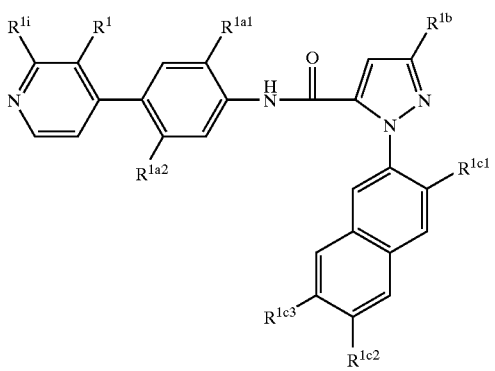

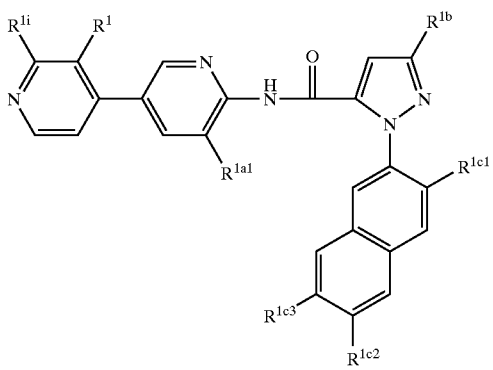

TABLE 7-continued

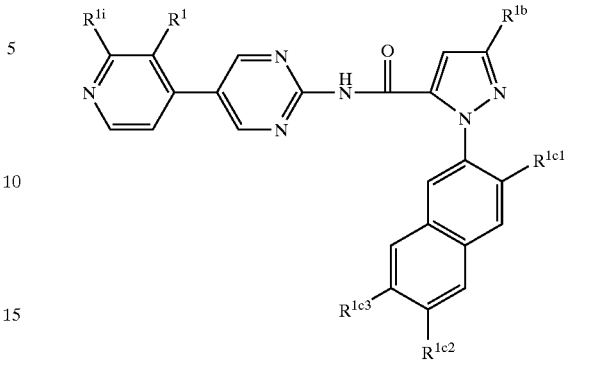

wherein:

$R^1$ is selected from the group consisting of —H, —NH$_2$, —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1i}$ is selected from the group consisting of —H, —NH$_2$, —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1a1}$ and $R^{1a2}$ are independently selected from the group consisting of —H, —F, —Cl and —Br;

$R^{1b}$ is selected from the group consisting of —H, —CH$_3$, —CF$_3$, —CH$_2$CH$_3$, —CF$_2$CF$_3$, —CH$_2$NH$_2$, —CONH$_2$, —SO$_2$CH$_3$, —SO$_2$NH$_2$, —NH$_2$COCH$_3$ and —NH$_2$COCF$_3$;

$R^{1c1}$ is selected from the group consisting of —H, —F, —Cl, —Br, —CN, —CH$_2$NH$_2$, —CH$_2$OH, —CONH$_2$—C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, —OH, —OCH$_3$, and —NH$_2$; and $R^{1c3}$ is selected from the group consisting of —H, —F, —Cl, —Br, —OH, —OCH$_3$, and —NH$_2$.

TABLE 8

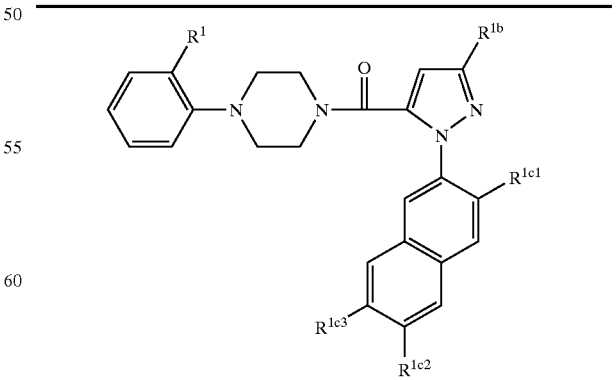

TABLE 8-continued

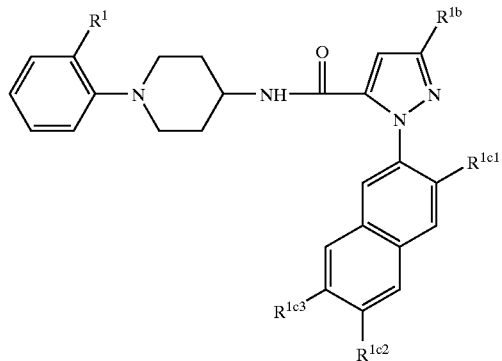

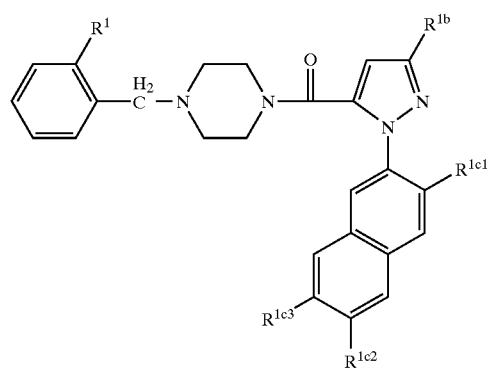

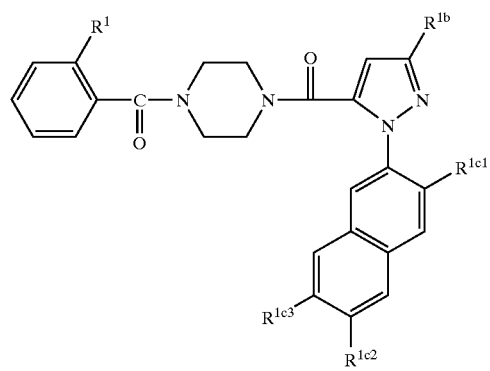

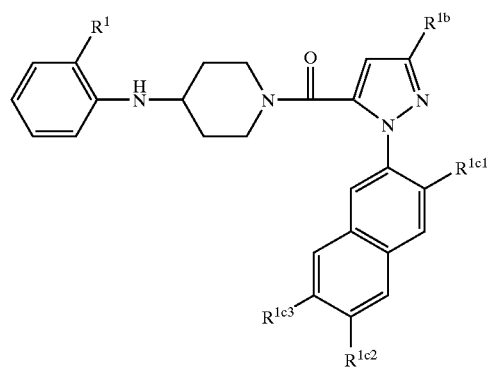

wherein:

R¹ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R$^{1b}$ is selected from the group consisting of —H, —CH$_3$ and —CF$_3$;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, —OH, —OCH$_3$, and —NH$_2$; and R$^{1c3}$ is selected from the group consisting of —H, —F, —Cl, —Br, —OH, —OCH$_3$, and —NH$_2$.

TABLE 9

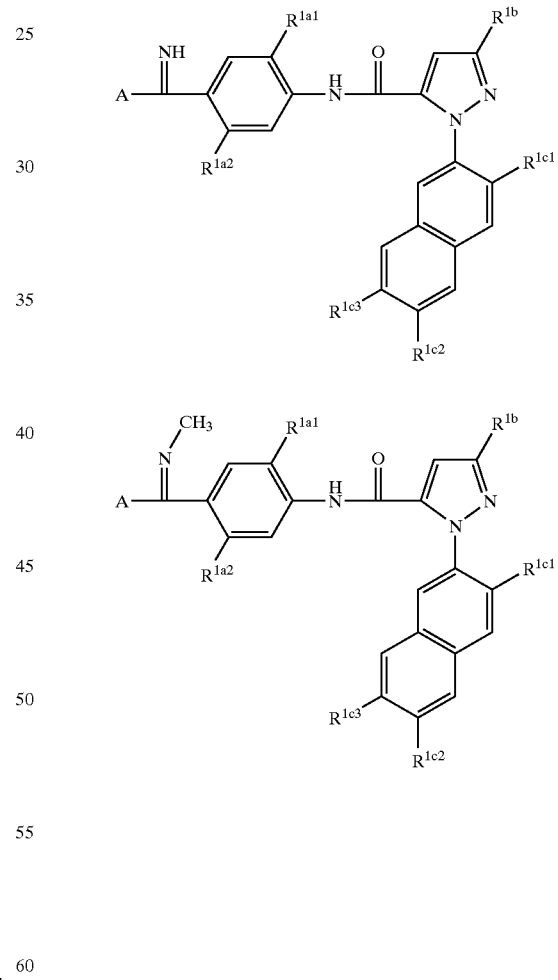

TABLE 9-continued
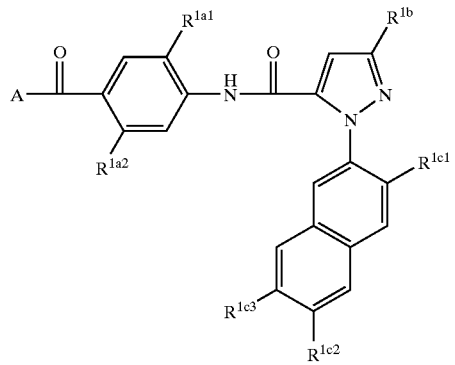
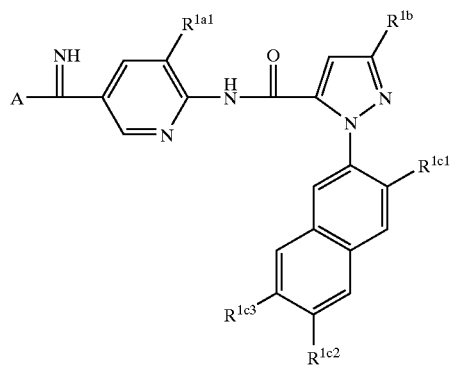
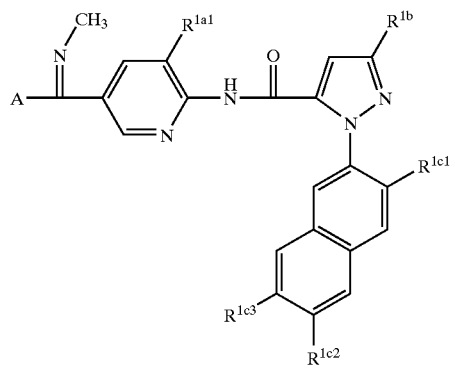
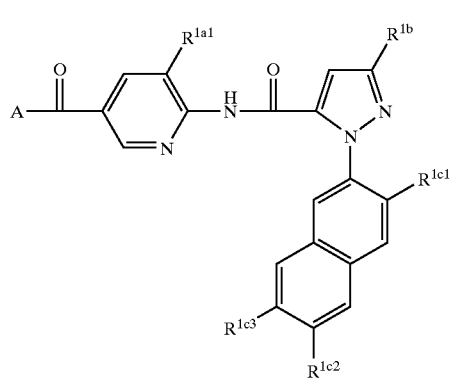
TABLE 9-continued
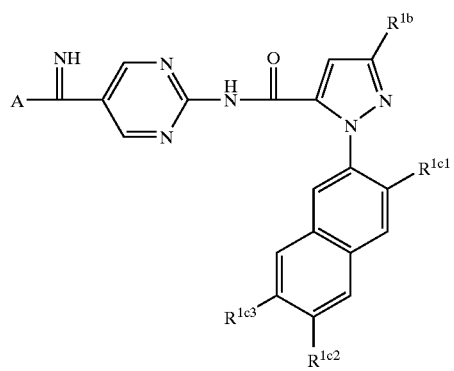
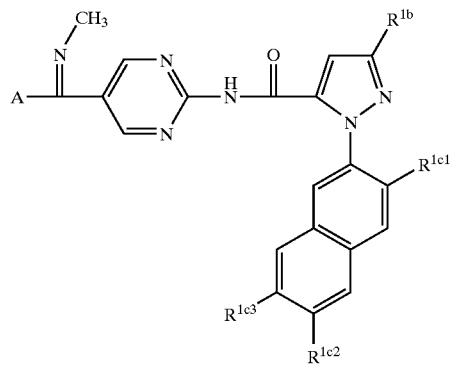
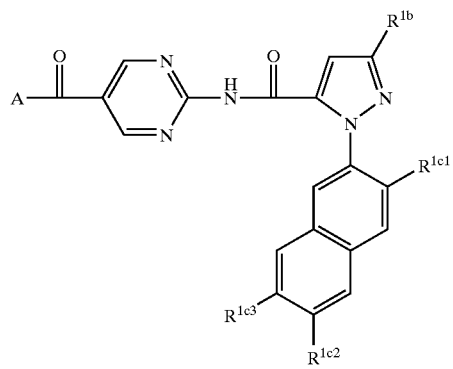
wherein:
A is selected from the group consisting of:
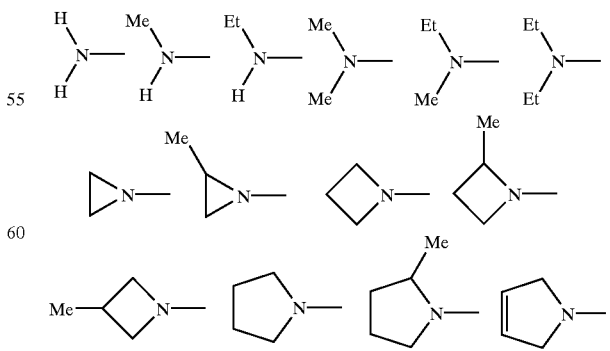

-continued

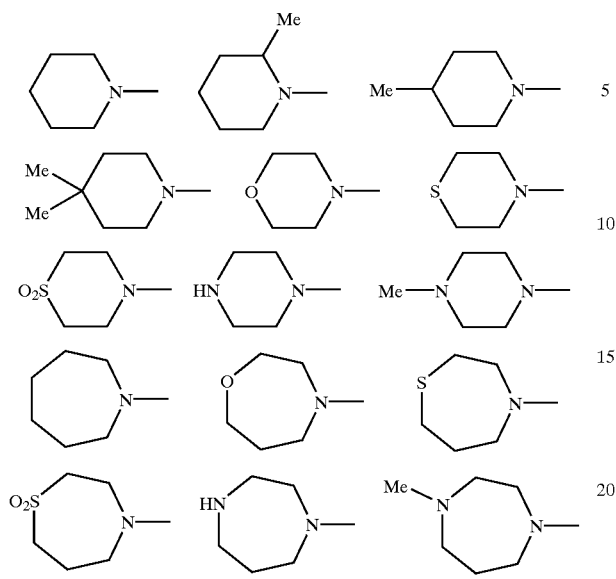

R$^{1a1}$ and R$^{1a2}$ are independently selected from the group consisting of —H, —F, —Cl and —Br;

R$^{1b}$ is selected from the group consisting of —H, —CH$_3$, —CF$_3$, —CH$_2$CH$_3$, —CF$_2$CF$_3$, —CH$_2$NH$_2$, —CONH$_2$, —SO$_2$CH$_3$, —SO$_2$NH$_2$, —NH$_2$COCH$_3$ and —NH$_2$COCF$_3$;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, —OH, —OCH$_3$, and —NH$_2$; and R$^{1c3}$ is selected from the group consisting of —H, —F, —Cl, —Br, —OH, —OCH$_3$, and —NH$_2$.

TABLE 10

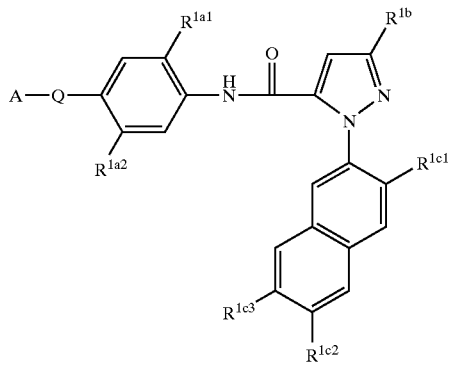

TABLE 10-continued

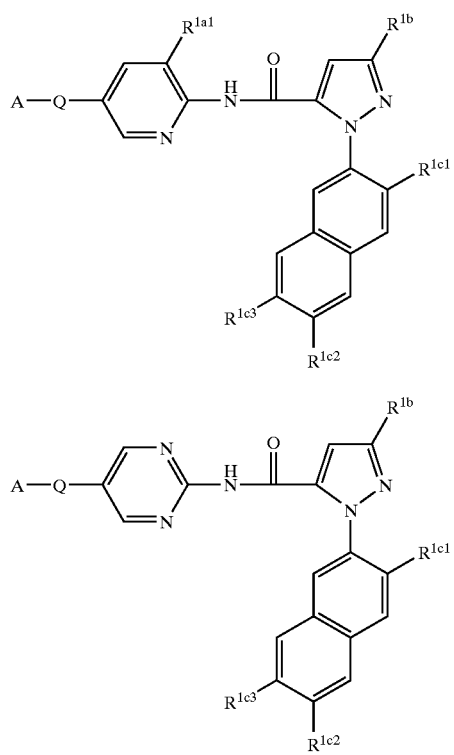

wherein:

A—Q is selected from the group consisting of:

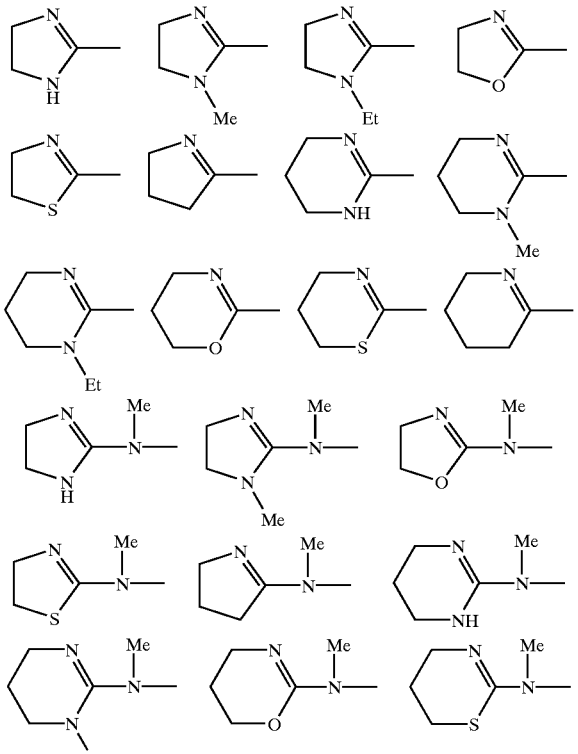

-continued

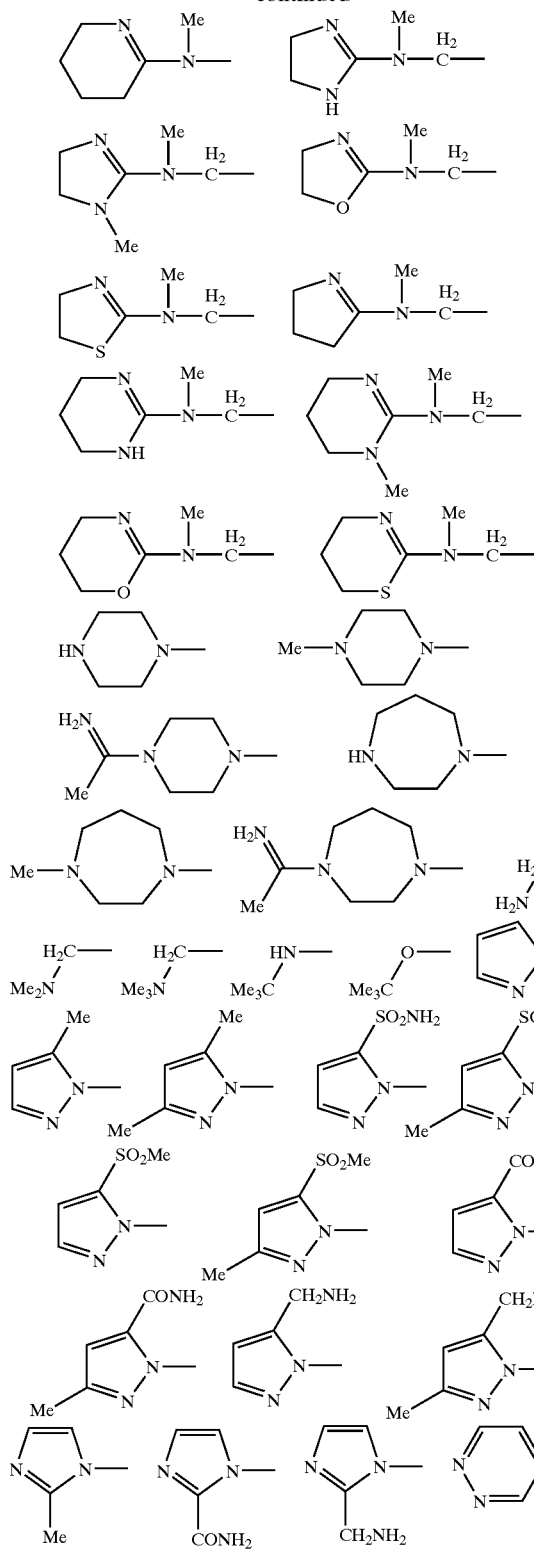

$R^{1a1}$ and $R^{1a2}$ are independently selected from the group consisting of —H, —F, —Cl and —Br;
$R^{1b}$ is selected from the group consisting of —H, —CH$_3$, —CF$_3$, —CH$_2$CH$_3$, —CF$_2$CF$_3$, —CH$_2$NH$_2$, —CONH$_2$, —SO$_2$CH$_3$, —S$_2$NH$_2$, —NH$_2$COCH$_3$ and —NH$_2$COCF$_3$;

$R^{1c1}$ is selected from the group consisting of —H, —F, —Cl, —Br, —CN, —CH$_2$NH$_2$, —CH$_2$OH, —CONH$_2$, —C(=NH$_2$), —CO$_2$H, —CO$_2$Me, —SO$_2$Me, —SO$_2$NH$_2$, —OH, —NH$_2$, and —NO$_2$;
$R^{1c2}$ is selected from the group consisting of —H, —F, —Cl, —Br, —OH, —OCH$_3$, and —NH$_2$; and
$R^{1c3}$ is selected from the group consisting of —H, —F, —Cl, —Br, —OH, —OCH$_3$, and —NH$_2$.

TABLE 11

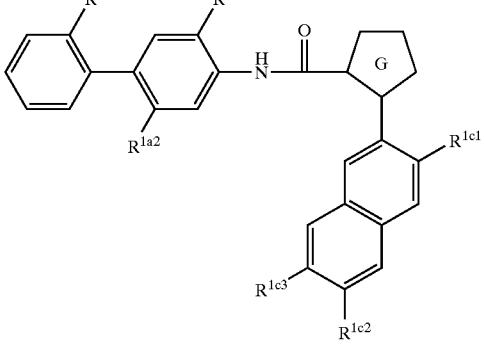

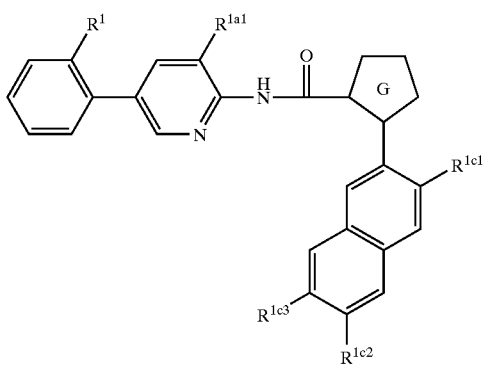

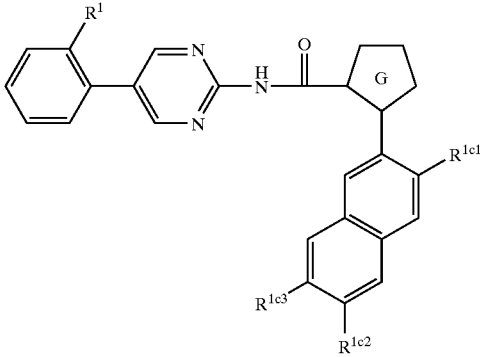

wherein:
$R^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;
$R^{1b}$ is selected from the group consisting of —H, —CH$_3$ and —CF$_3$;
$R^{1a1}$ and $R^{1a2}$ are independently selected from the group consisting of —H, —F, —Cl and —Br;
$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, —OH, —OCH$_3$, and —NH$_2$;
$R^{1c3}$ is selected from the group consisting of —H, —F, —Cl, —Br, —OH, —OCH$_3$, and —NH$_2$; and
G is selected from the group consisting of:
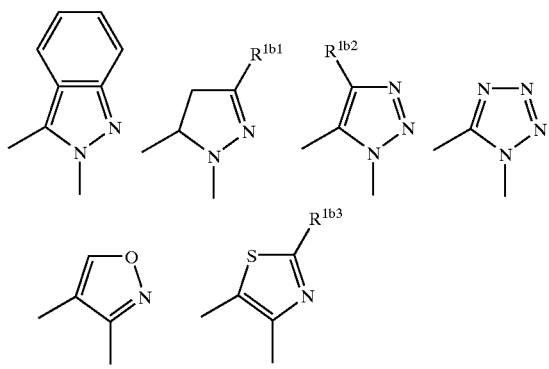
wherein:
$R^{1b1}$ is selected from the group consisting of —H, —CH$_3$ and —CF$_3$;
$R^{1b2}$ is selected from the group consisting of —H, —CH$_3$ and —CF$_3$; and
TABLE 12
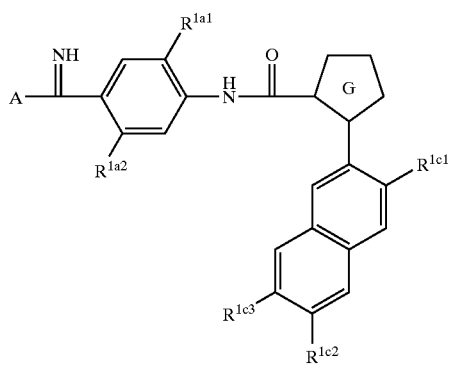
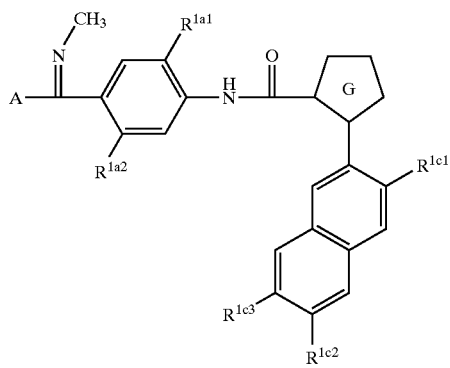
TABLE 12-continued
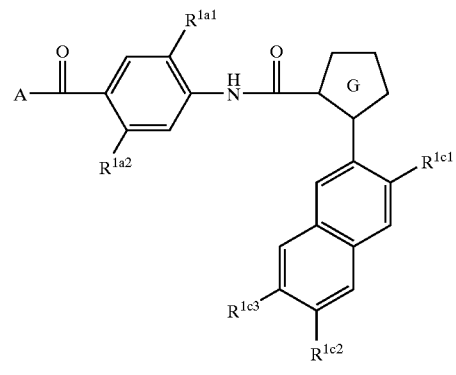
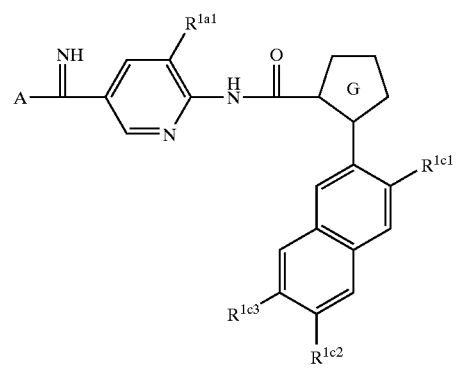

TABLE 12-continued

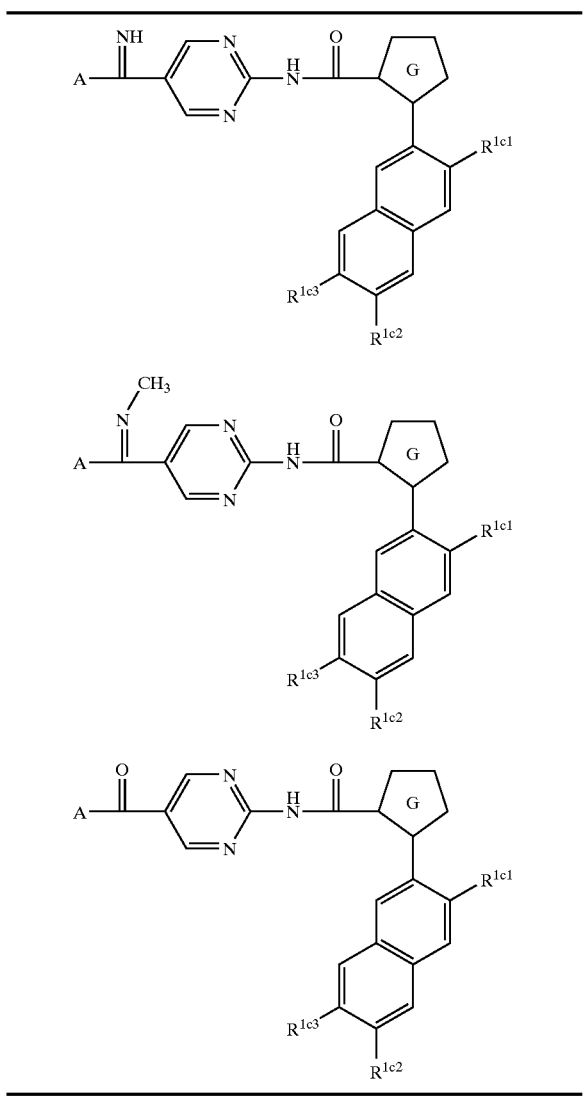

R$^{1b3}$ is selected from the group consisting of —Cl, —NH$_2$, —CH$_3$ and CF$_3$.

wherein:

A is selected from the group consisting of:

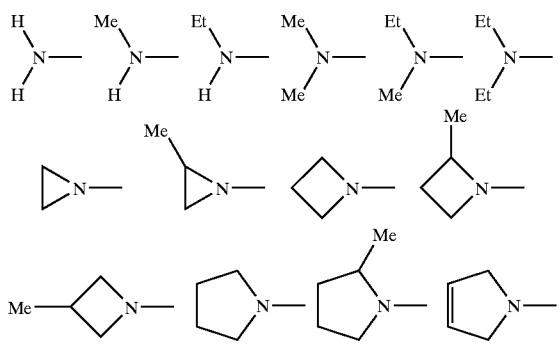

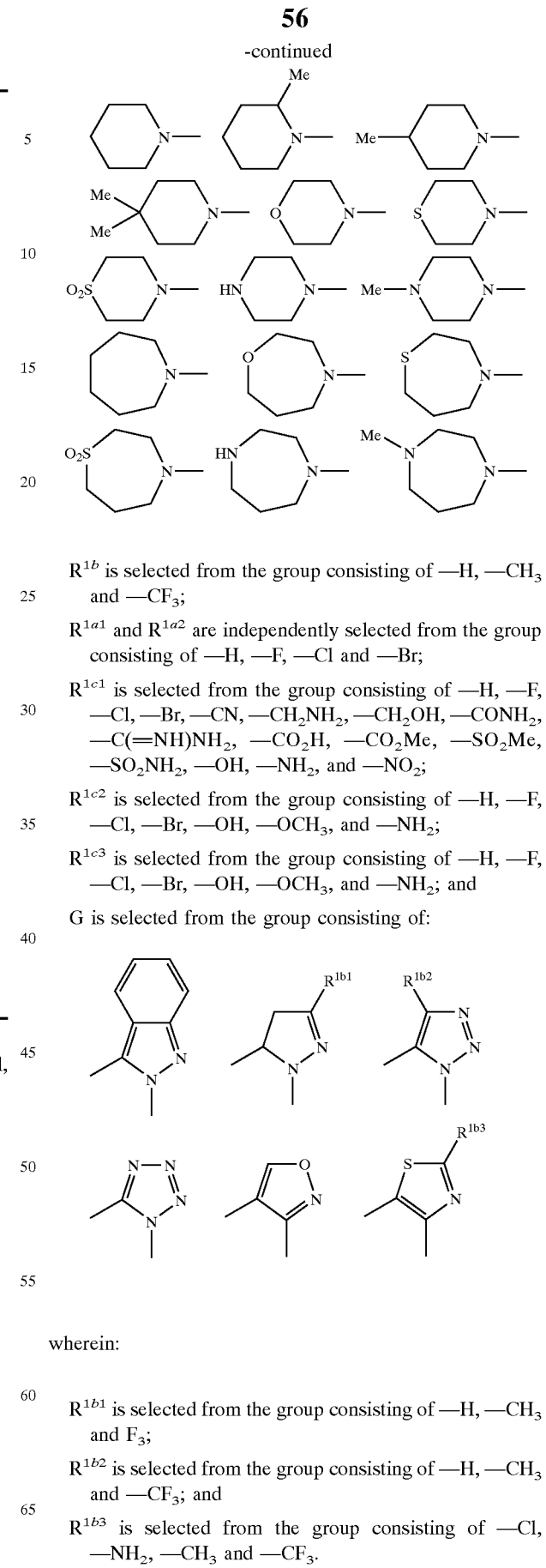

R$^{1b}$ is selected from the group consisting of —H, —CH$_3$ and —CF$_3$;

R$^{1a1}$ and R$^{1a2}$ are independently selected from the group consisting of —H, —F, —Cl and —Br;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, —OH, —OCH$_3$, and —NH$_2$;

R$^{1c3}$ is selected from the group consisting of —H, —F, —Cl, —Br, —OH, —OCH$_3$, and —NH$_2$; and G is selected from the group consisting of:

wherein:

R$^{1b1}$ is selected from the group consisting of —H, —CH$_3$ and F$_3$;

R$^{1b2}$ is selected from the group consisting of —H, —CH$_3$ and —CF$_3$; and

R$^{1b3}$ is selected from the group consisting of —Cl, —NH$_2$, —CH$_3$ and —CF$_3$.

TABLE 13
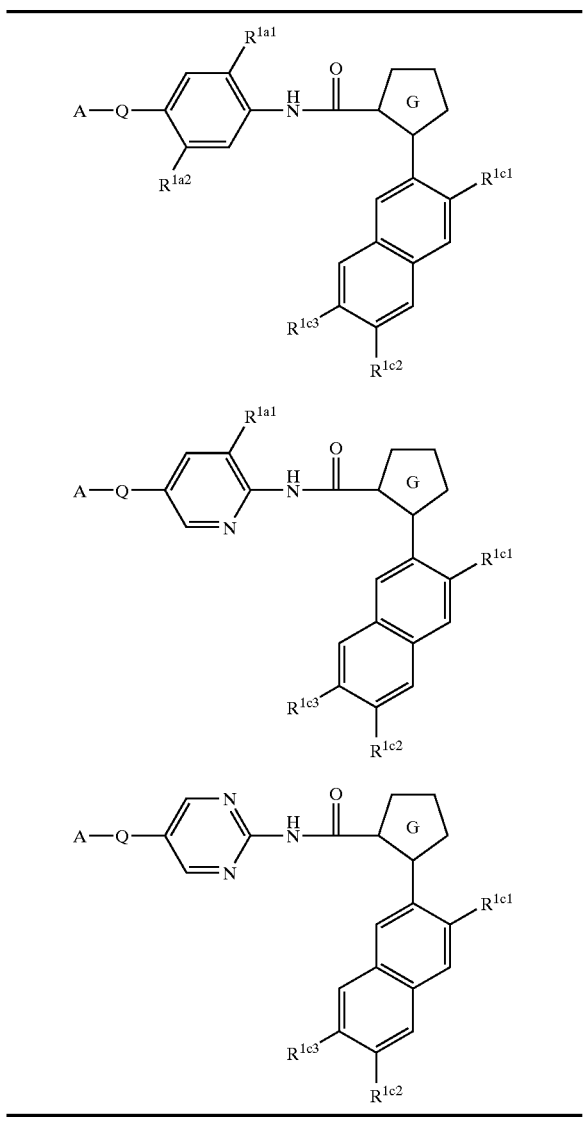
wherein:
A—Q is selected from the group consisting of:
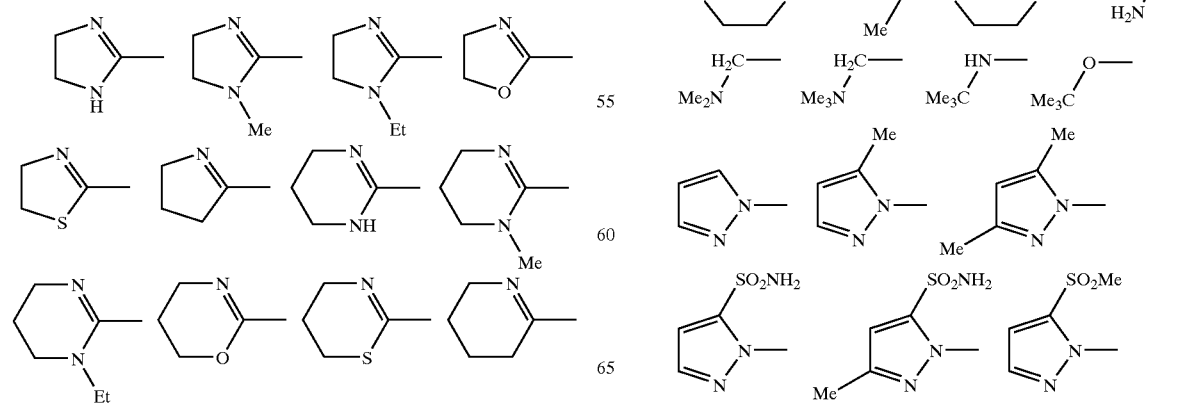

-continued

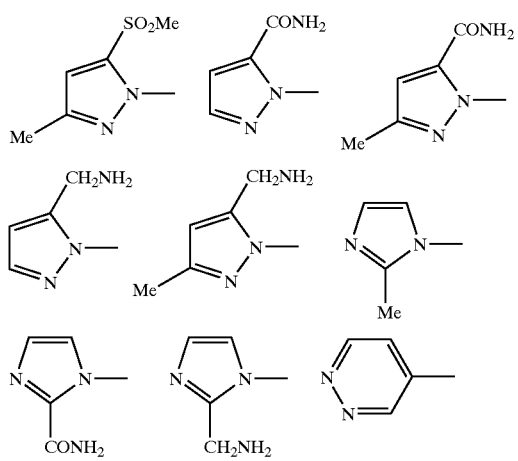

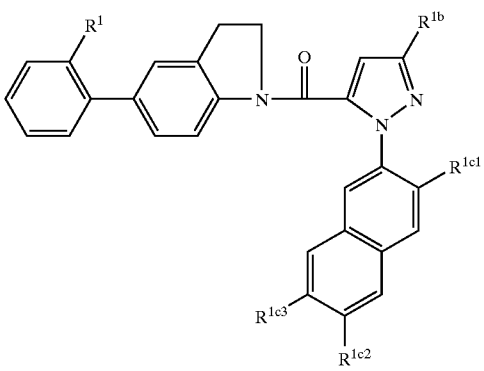

$R^{1b}$ is selected from the group consisting of —H, —CH₃ and —CF₃;

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH₂NH₂, —CH₂OH, —CONH₂, —C(=NH)NH₂, —CO₂H, —CO₂Me, —SO₂Me, —SO₂NH₂, —OH, —NH₂, and —NO₂;

$R^{1c2}$ is selected from the group consisting of —H, —F, —Cl, —Br, —OH, —OCH₃, and —NH₂;

$R^{1c3}$ is selected from the group consisting of —H, —F, —Cl, —Br, —OH, —OCH₃, and —NH₂; and G is selected from the group consisting of:

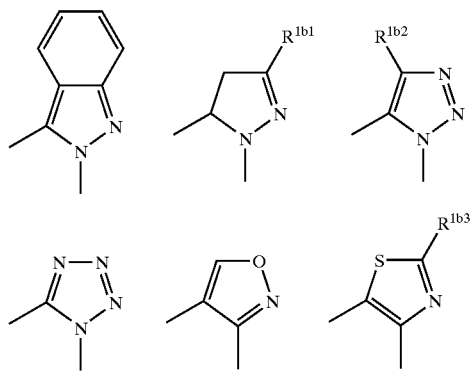

wherein:

$R^{1b1}$ is selected from the group consisting of —H, —CH₃ and —CF₃;

$R^{1b2}$ is selected from the group consisting of —H, —CH₃ and CF₃; and $R^{1b3}$ is selected from the group consisting of —Cl, —NH₂, —CH₃ and —CF₃.

TABLE 14

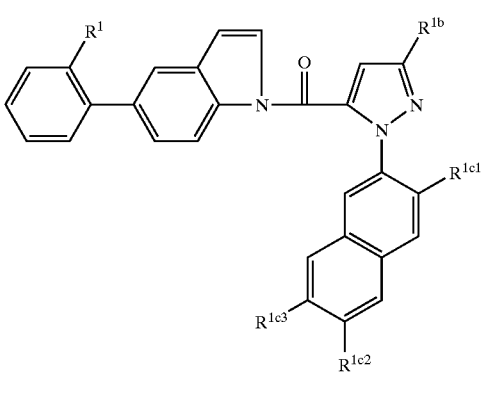

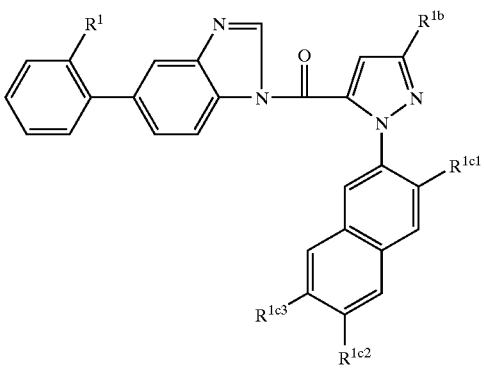

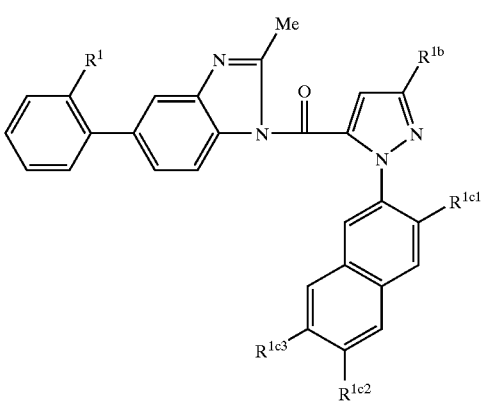

TABLE 14-continued

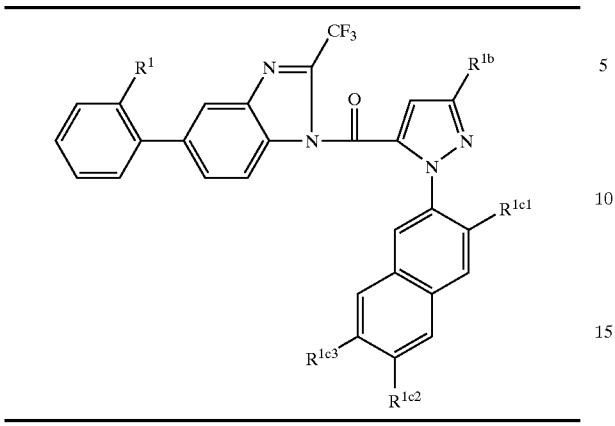

wherein:
R[1] is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;
R[1b] is selected from the group consisting of —H, —CH$_3$, —CF$_3$;
R[1c1] is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;
R[1c2] is selected from the group consisting of —H, —F, —Cl, —Br, —OH, —OCH$_3$, and —NH$_2$; and
R[1c3] is selected from the group consisting of —H, —F, —Cl, —Br, —OH, —OCH$_3$, and —NH$_2$.

TABLE 15

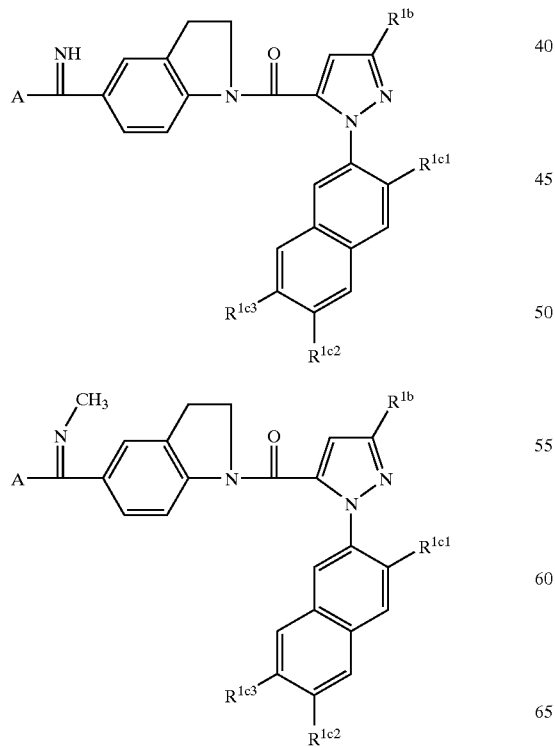

TABLE 15-continued

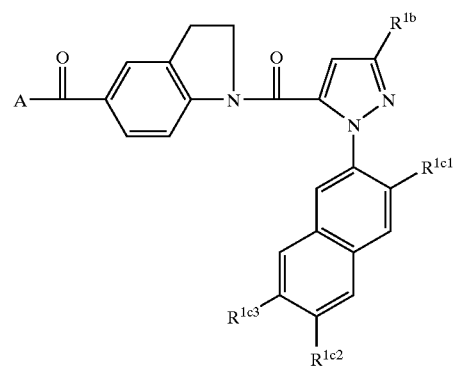

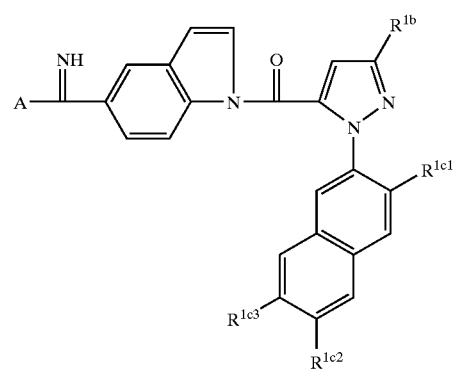

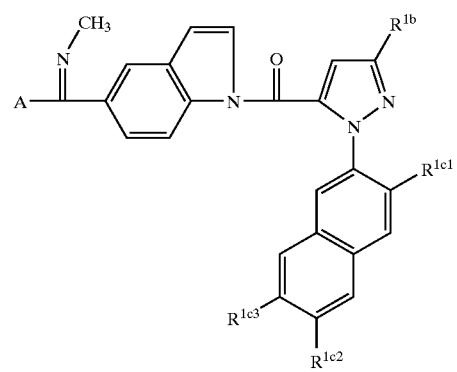

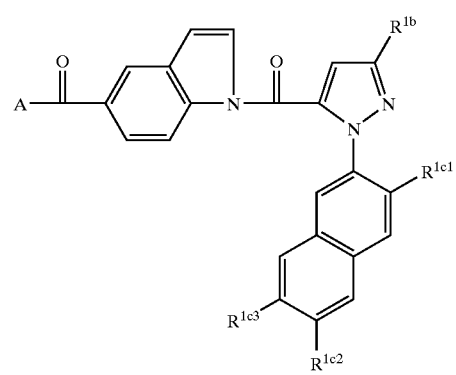

TABLE 15-continued
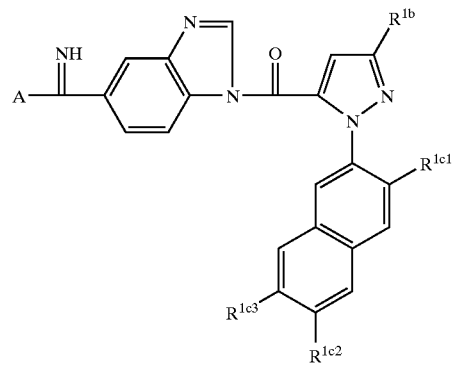
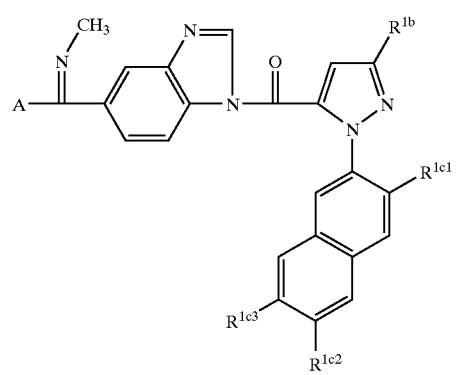
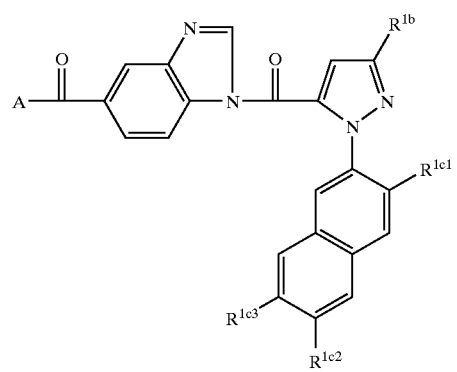
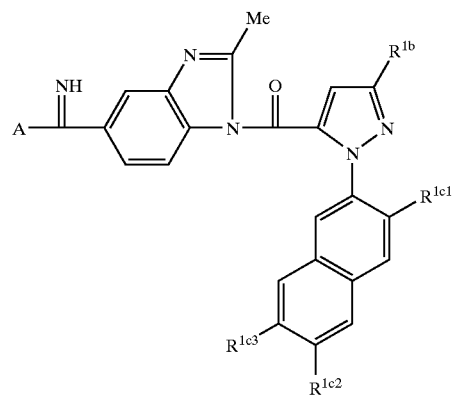
TABLE 15-continued
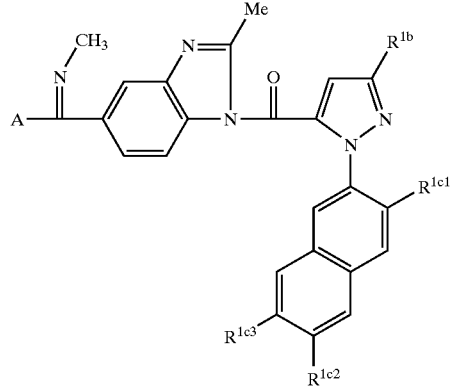
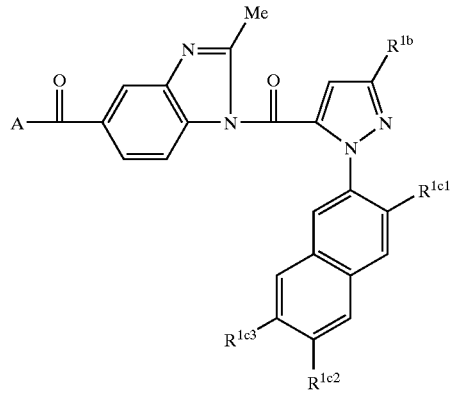
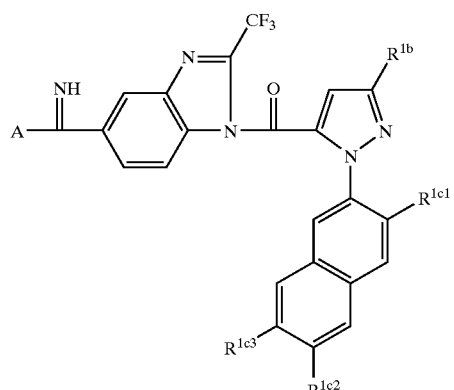
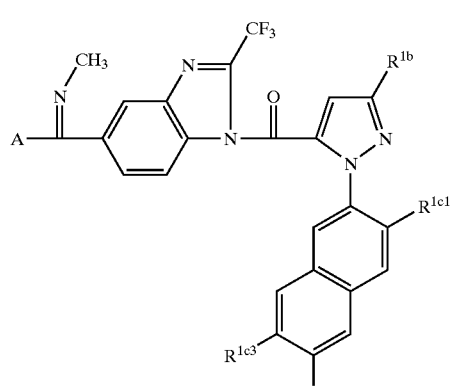

TABLE 15-continued

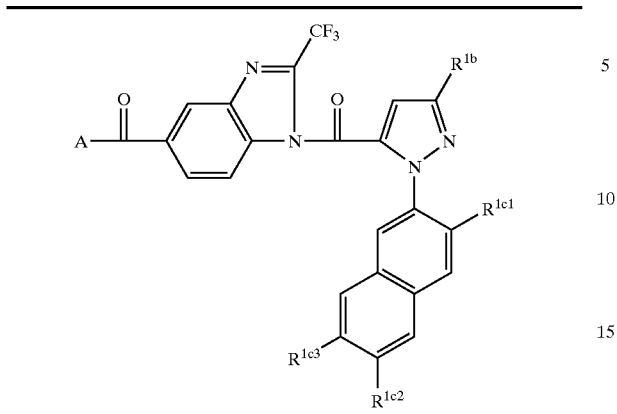

wherein:
A is selected from the group consisting of:

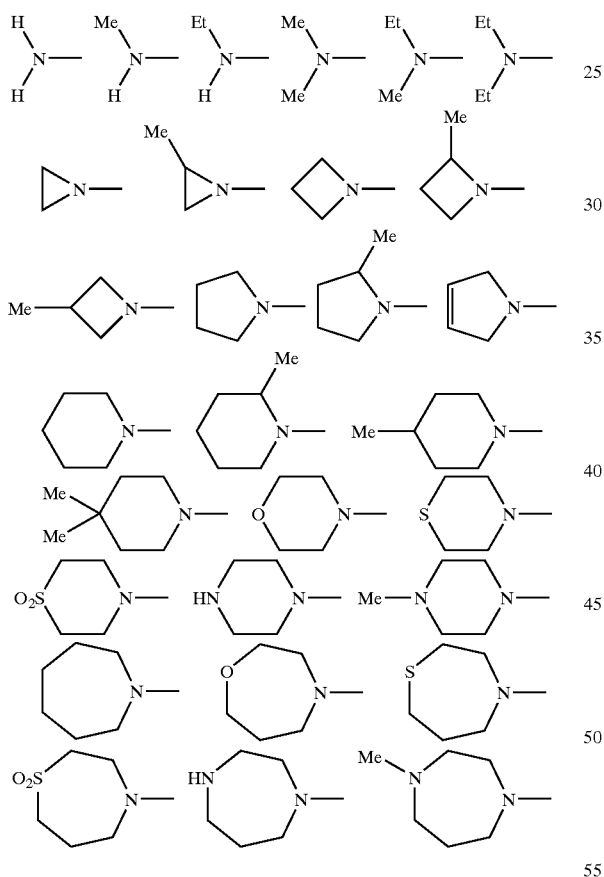

$R^{1b}$ is selected from the group consisting of —H, —CH$_3$ and —CF$_3$;
$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;
$R^{1c2}$ is selected from the group consisting of —H, —F, —Cl, —Br, —OH, —OCH$_3$, and —NH$_2$; and
$R^{1c3}$ is selected from the group consisting of —H, —F, —Cl, —Br, —OH, —OCH$_3$, and —NH$_2$.

TABLE 16

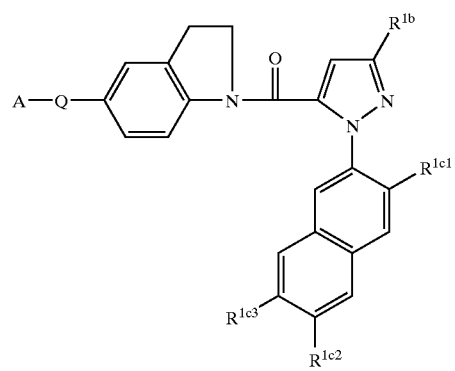

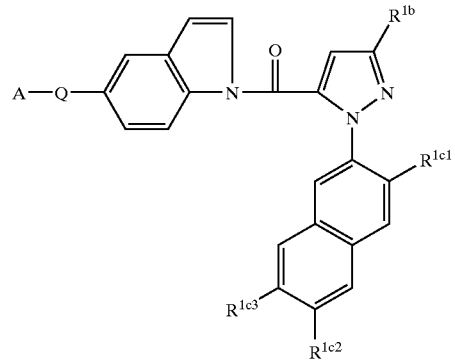

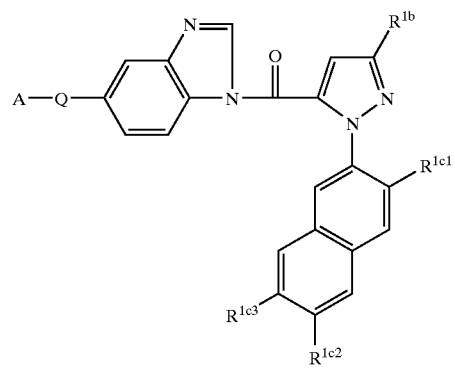

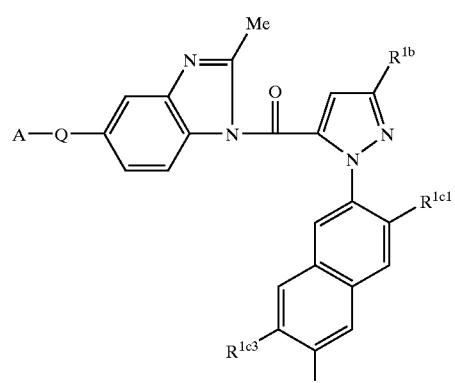

TABLE 16-continued

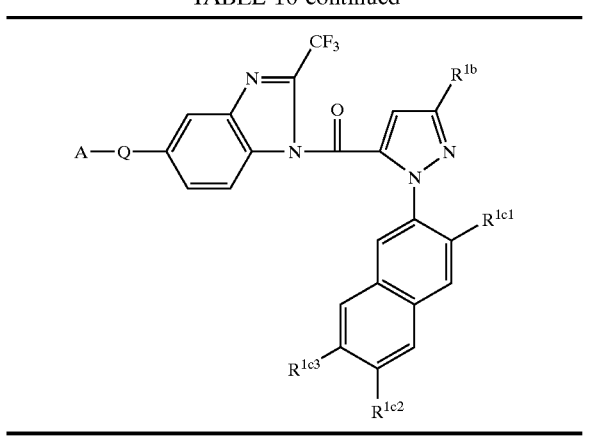

wherein:

A—Q is selected from the group consisting of:

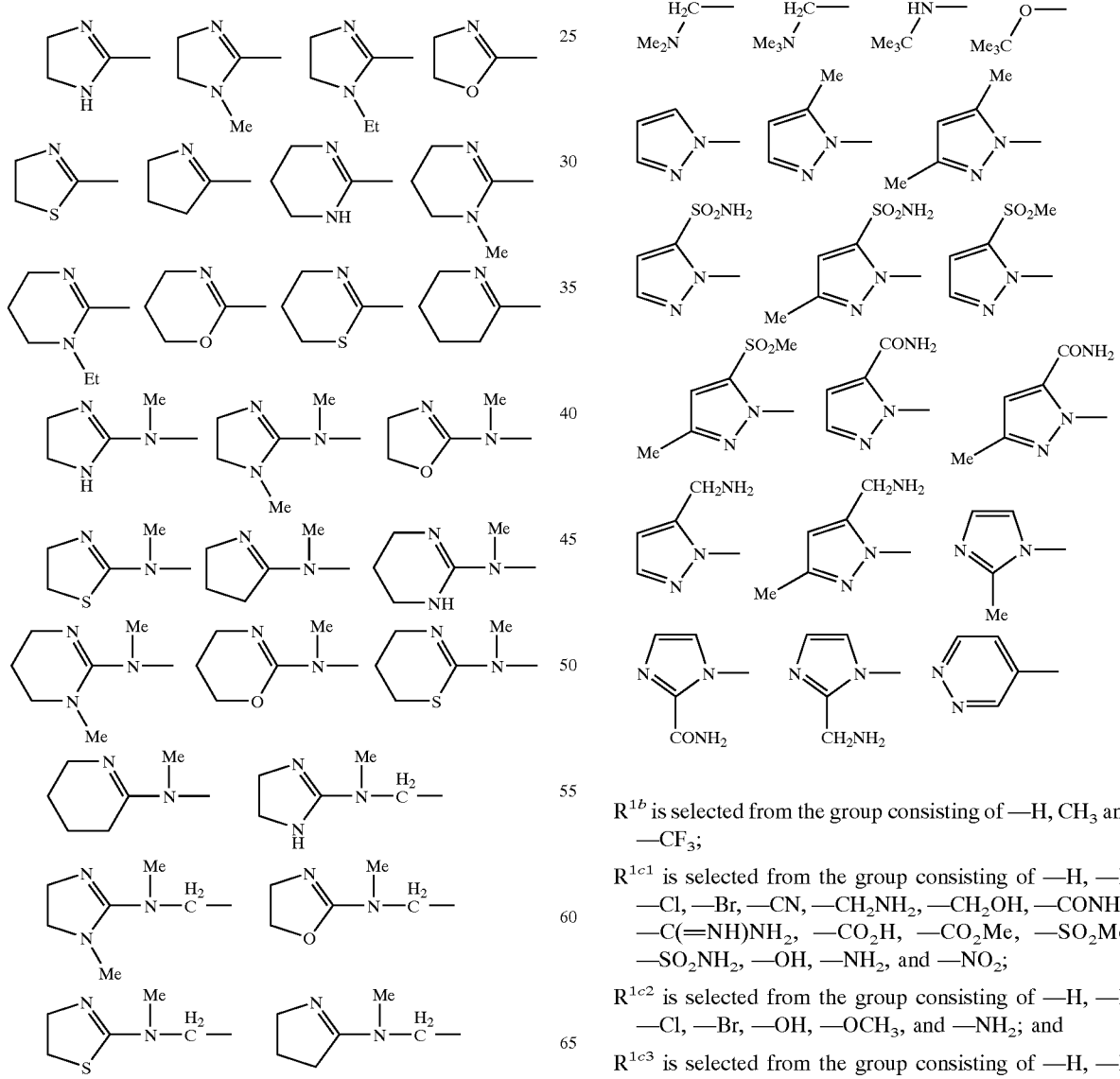

$R^{1b}$ is selected from the group consisting of —H, $CH_3$ and —$CF_3$;

$R^{1c1}$ is selected from the group consisting of —H, —F, —Cl, —Br, —CN, —$CH_2NH_2$, —$CH_2OH$, —$CONH_2$, —C(=NH)$NH_2$, —$CO_2H$, —$CO_2Me$, —$SO_2Me$, —$SO_2NH_2$, —OH, —$NH_2$, and —$NO_2$;

$R^{1c2}$ is selected from the group consisting of —H, —F, —Cl, —Br, —OH, —$OCH_3$, and —$NH_2$; and $R^{1c3}$ is selected from the group consisting of —H, —F, —C, —Br, —OH, —$OCH_3$, and —$NH_2$.

TABLE 17
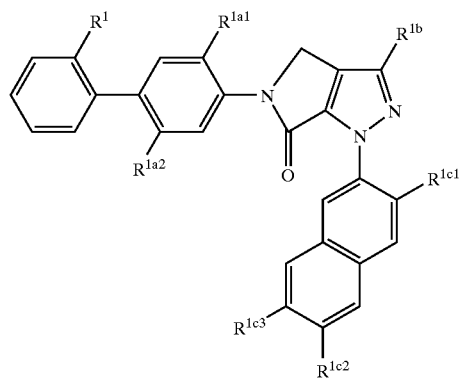
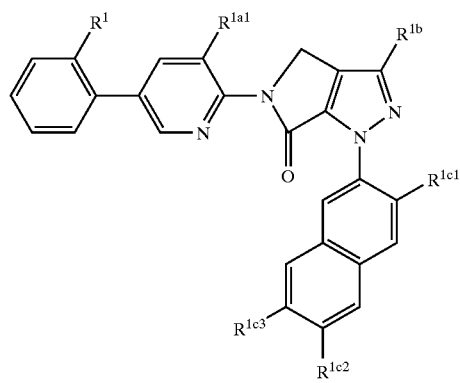
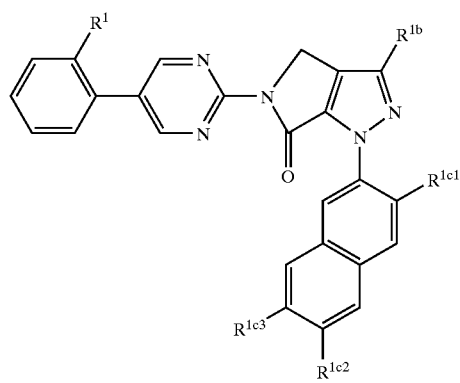
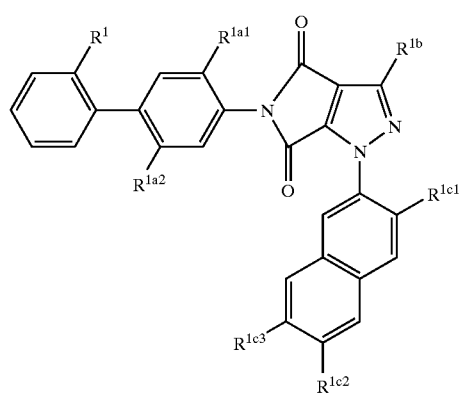
TABLE 17-continued
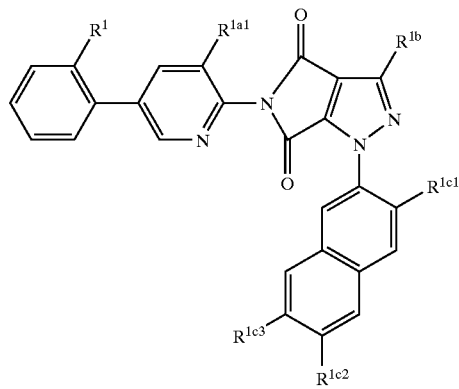
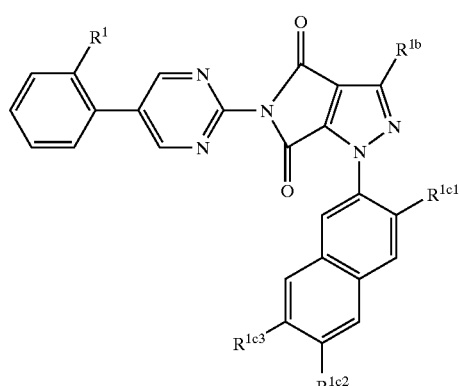
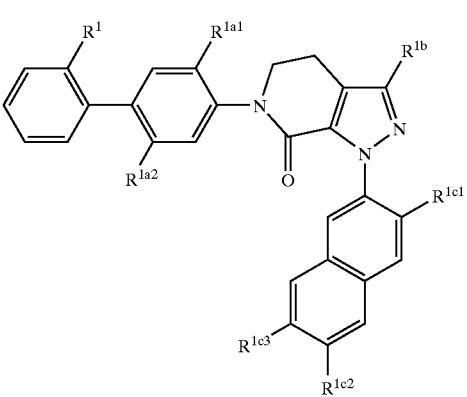
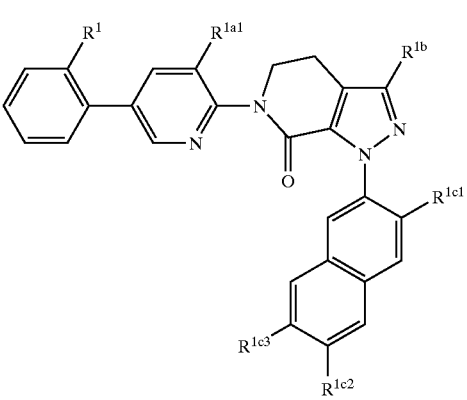

TABLE 17-continued
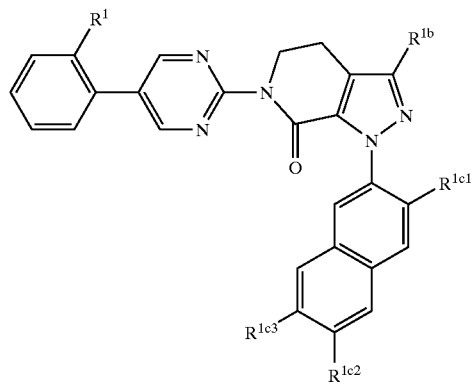
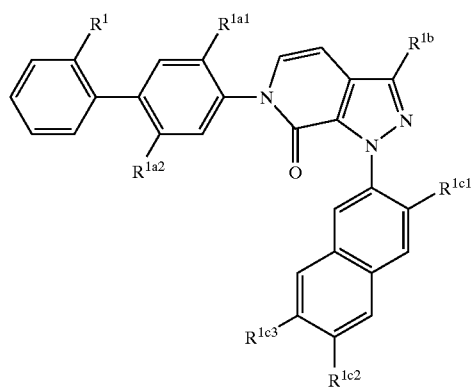
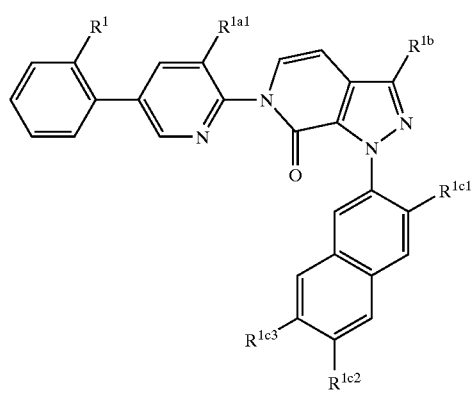
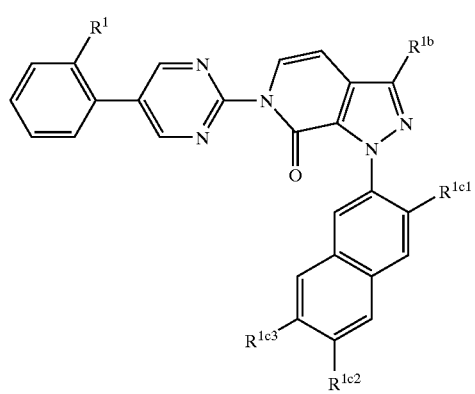
TABLE 17-continued
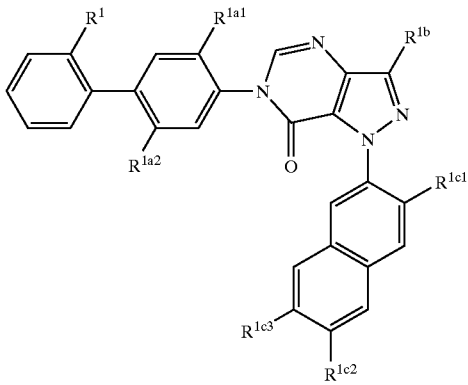
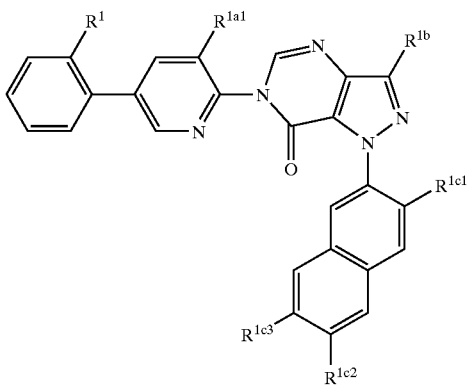
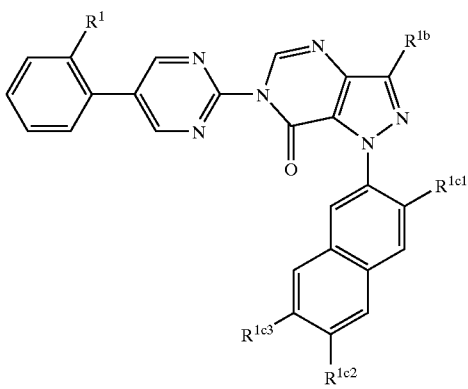
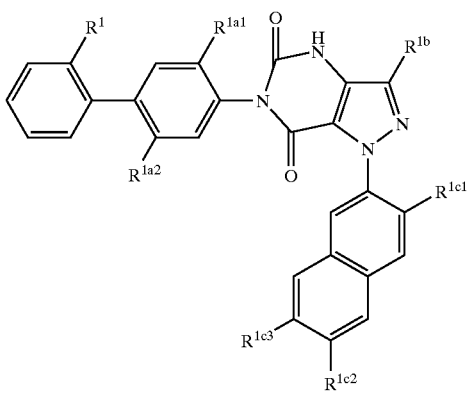

TABLE 17-continued

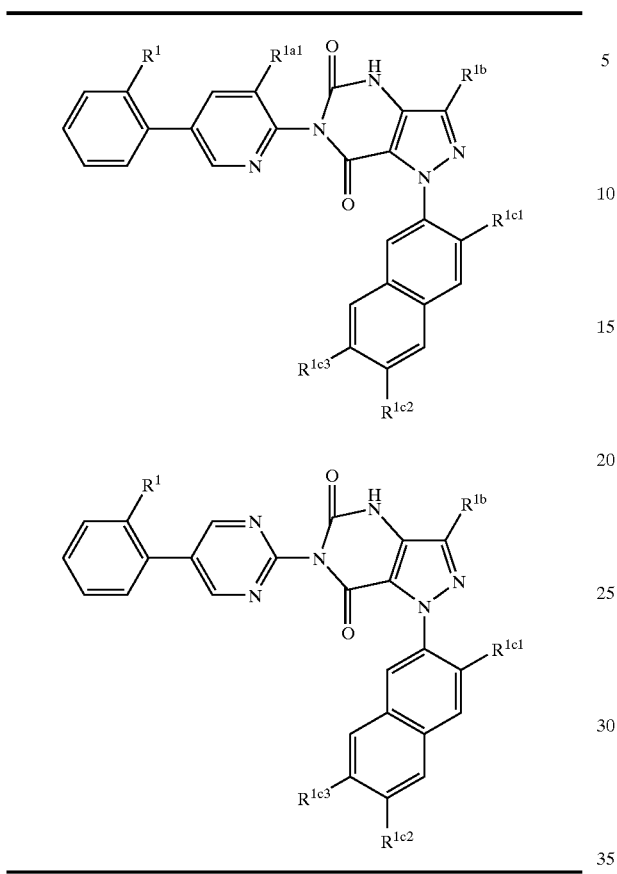

wherein:

R[1] is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R[1a1] and R[1a2] are independently selected from the group consisting of —H, —F, —Cl and Br;

R[1b] is selected from the group consisting of —H, —CH$_3$ and —CF$_3$;

R[1c1] is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R[1c2] is selected from the group consisting of —H, —F, —Cl, —Br, —OH, —OCH$_3$, and —NH$_2$; and R[1c3] is selected from the group consisting of —H, —F, —Cl, —Br, —OH, —OCH$_3$, and —NH$_2$.

TABLE 18

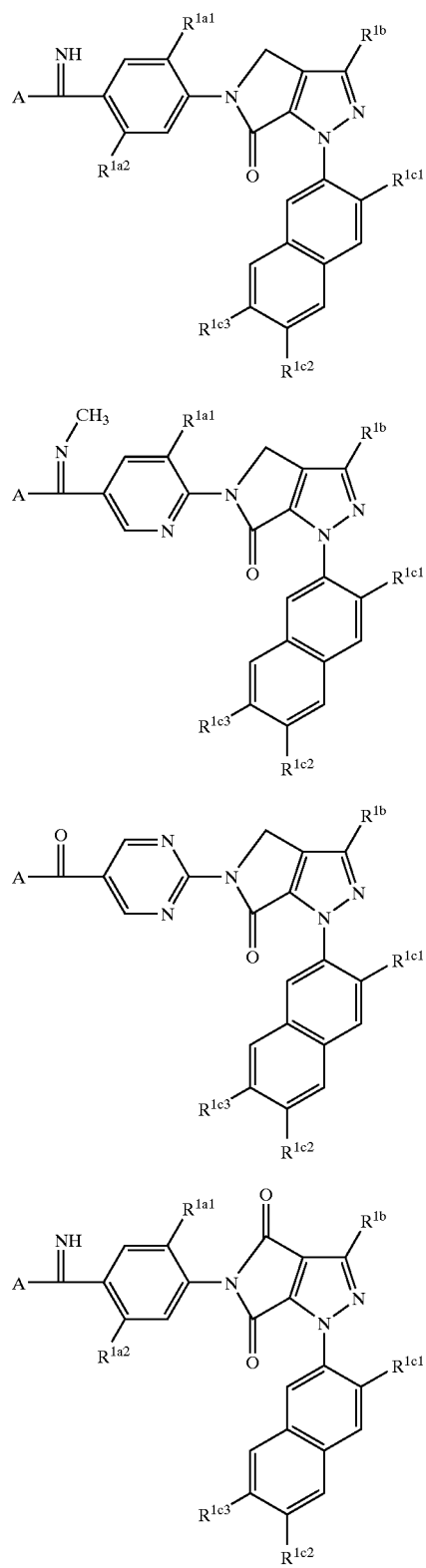

TABLE 18-continued
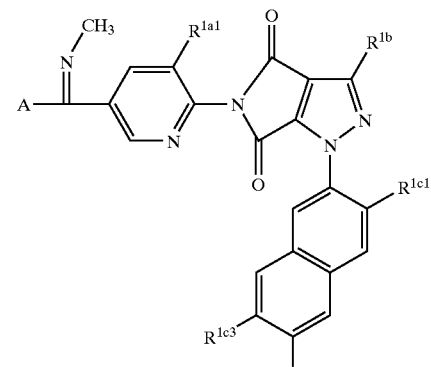
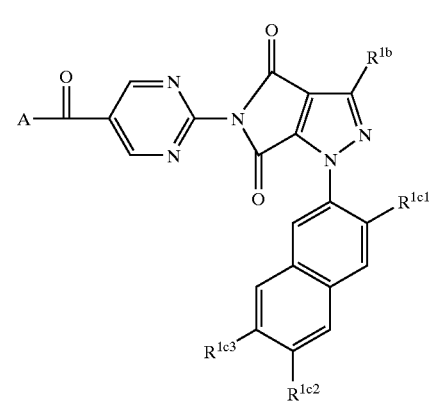
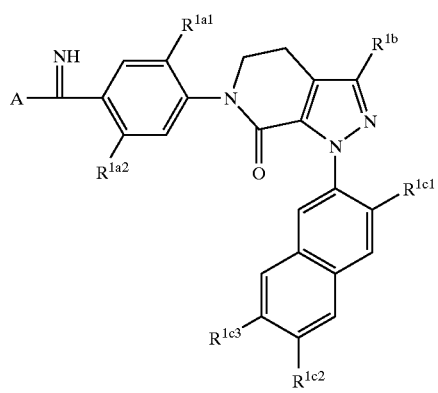
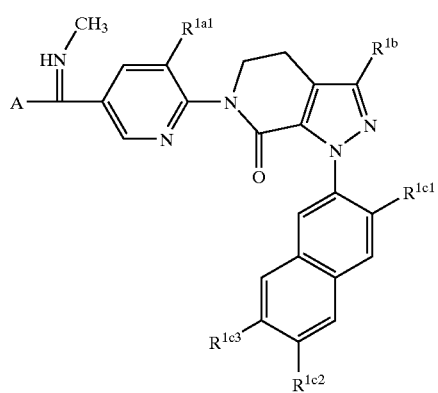
TABLE 18-continued
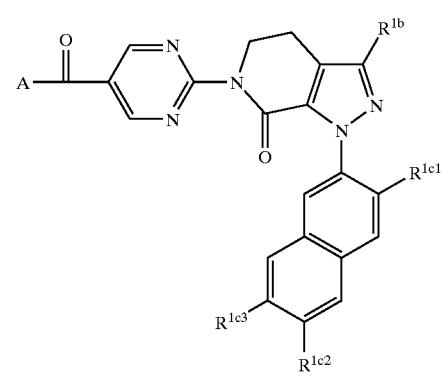
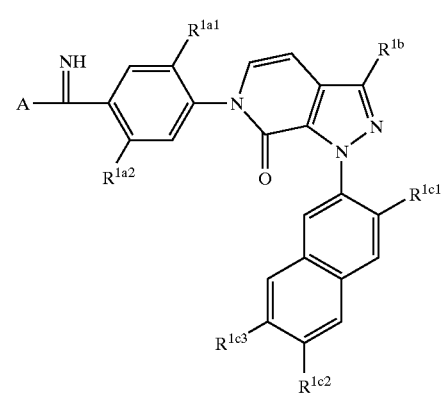
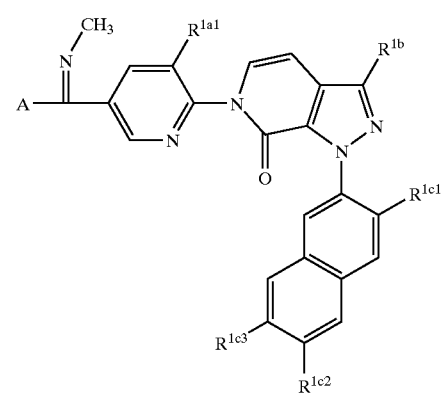
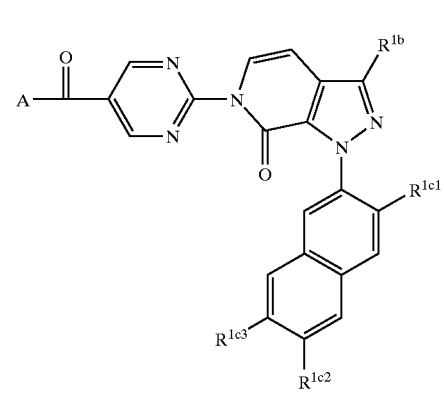

TABLE 18-continued
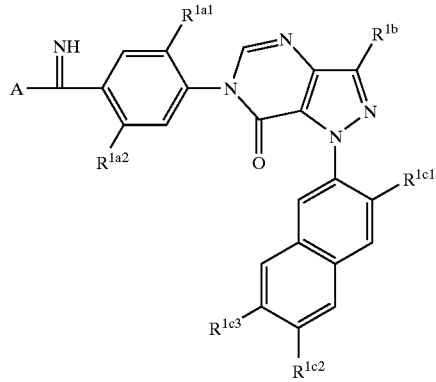
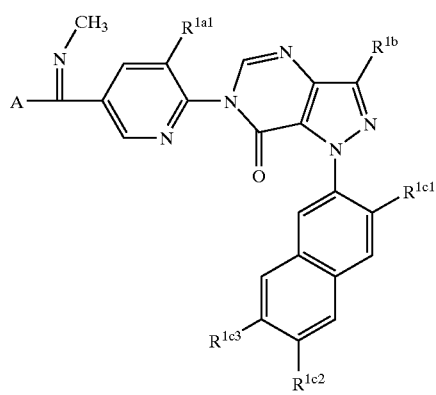
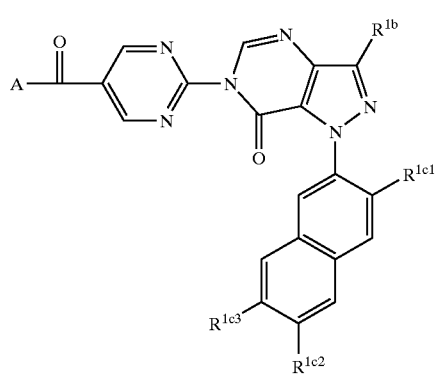
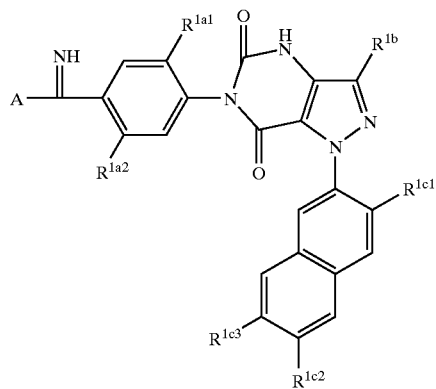
TABLE 18-continued
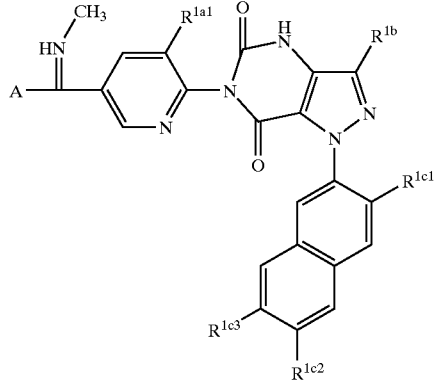
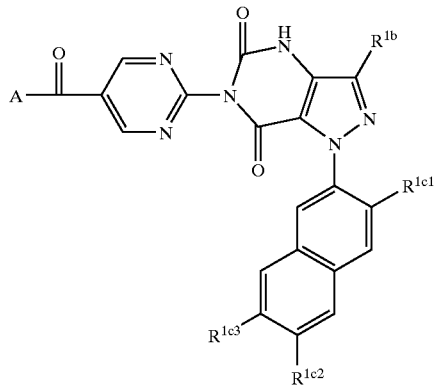
wherein:
A is selected from the group consisting of:
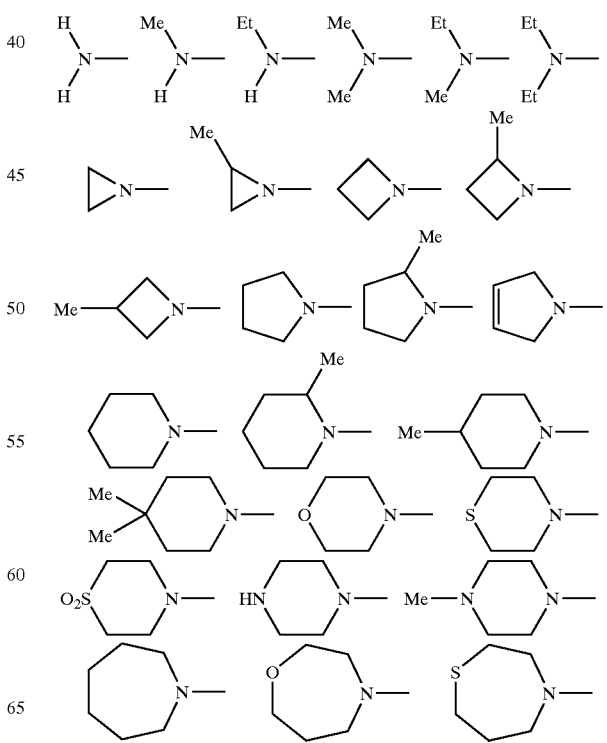

-continued

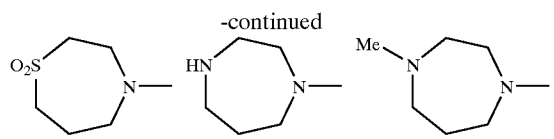

$R^{1a1}$ and $R^{1a2}$ are independently selected from the group consisting of —H, —F, —Cl and Br;

$R^{1b}$ is selected from the group consisting of —H, —CH$_3$ and —CF$_3$;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, —OH, —OCH$_3$, and —NH$_2$; and $R^{1c3}$ is selected from the group consisting of —H, —F, —Cl, —Br, —OH, —OCH$_3$, and —NH$_2$.

TABLE 19

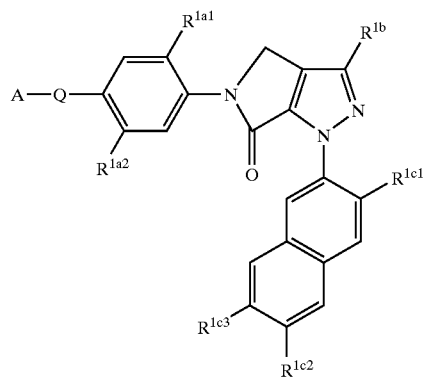

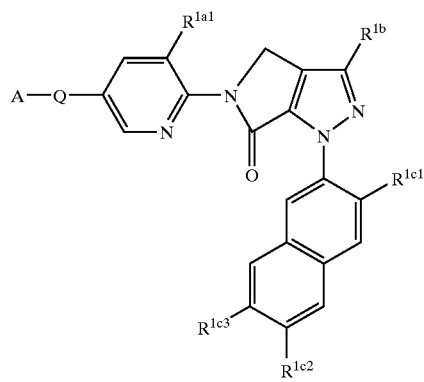

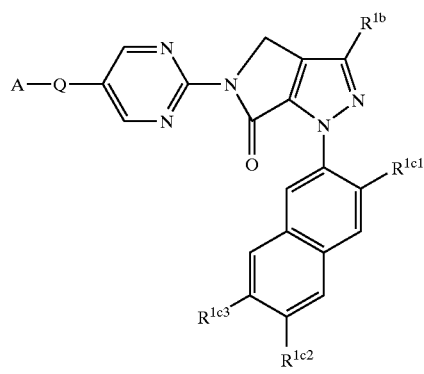

TABLE 19-continued

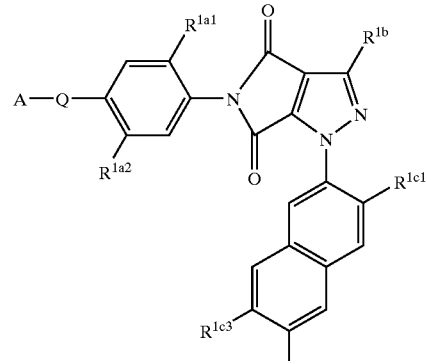

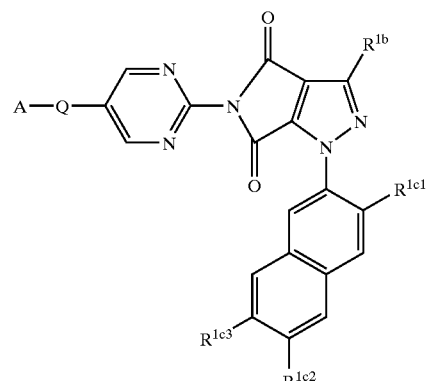

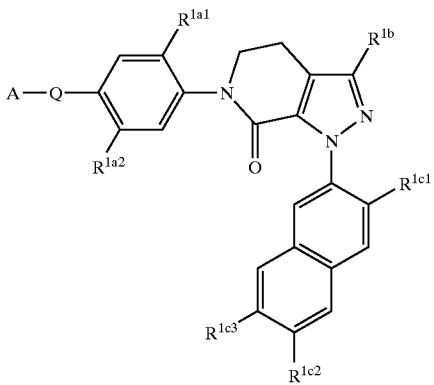

TABLE 19-continued
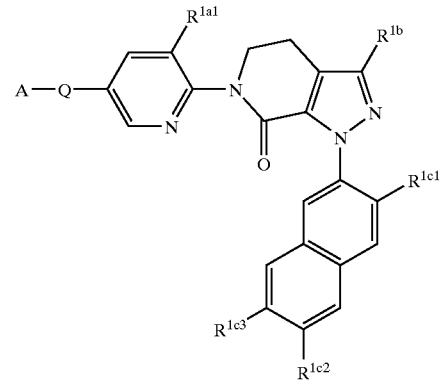
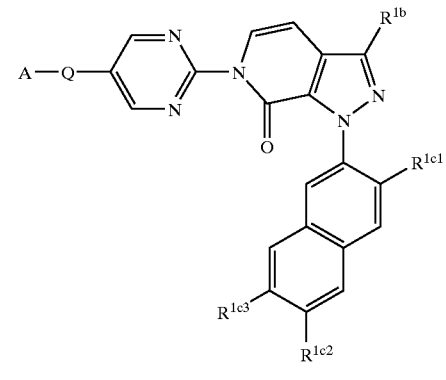
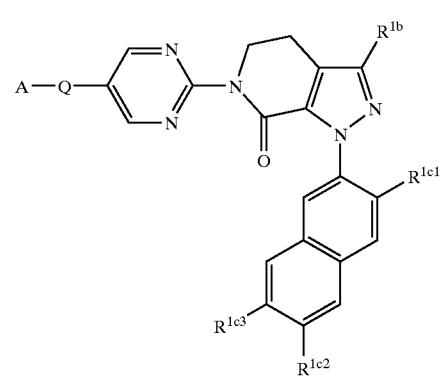
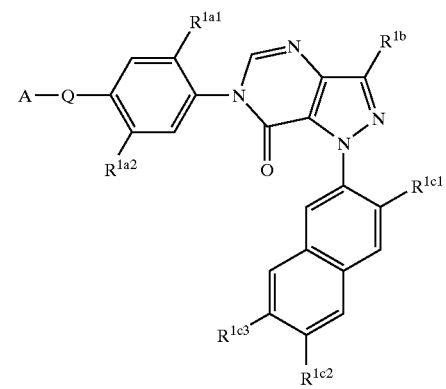
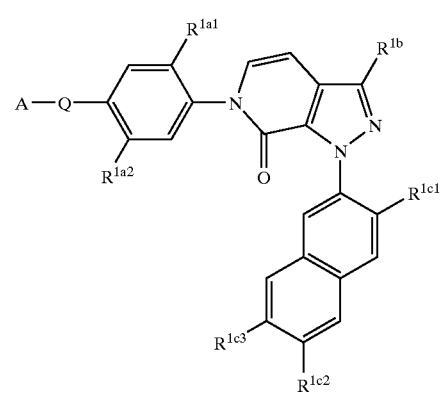
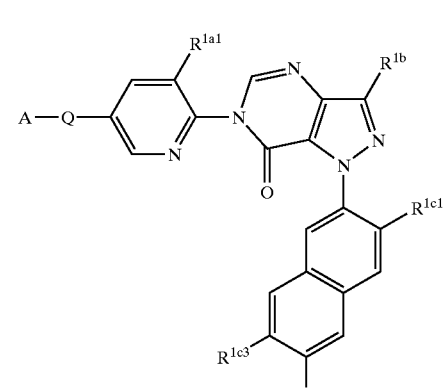
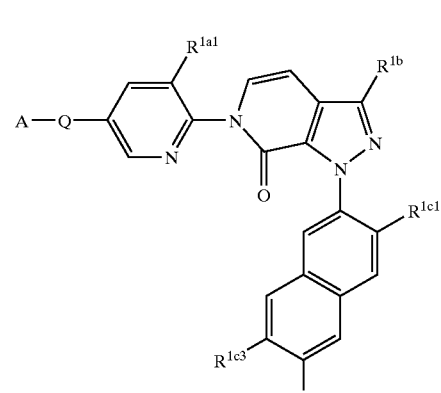
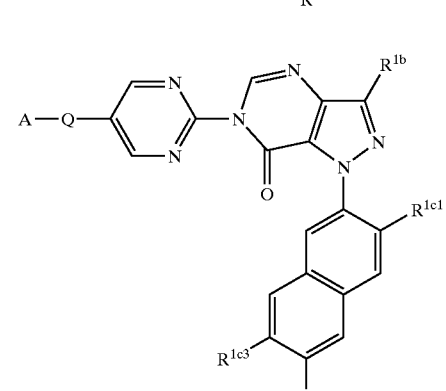

TABLE 19-continued wherein:

A—Q is selected from the group consisting of: [structures shown]

R$^{1a1}$ and R$^{1a2}$ are independently selected from the group consisting of —H, —F, —Cl and Br;

R$^{1b}$ is selected from the group consisting of —H, —CH$_3$ and —CF$_3$;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, —OH, —OCH$_3$, and —NH$_2$; and R$^{1c3}$ is selected from the group consisting of —H, —F, —Cl, —Br, —OH, —OCH$_3$, and —NH$_2$.

TABLE 20

TABLE 20-continued wherein:

R$^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R$^{1a1}$ and R$^{1a2}$ are independently selected from the group consisting of —H, —F, —Cl and —Br;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, and —OCH$_3$;

R$^{1c3}$ is selected from the group consisting of —H, —F, —Cl, —Br, —OH, —OCH$_3$, —NH$_2$, —CONH$_2$, —CH$_2$NH$_2$, —CH$_2$NHCH$_3$, —CH$_2$N(CH$_3$)$_2$, —C(=NH)NH$_2$; and G is selected from the group consisting of:

wherein:

R$^{1b1}$ is selected from the group consisting of —H, —CH$_3$ and —F$_3$;

R$^{1b2}$ is selected from the group consisting of —H, —CH$_3$ and —CF$_3$;

R$^{1b3}$ is selected from the group consisting of —Cl, —NH$_2$, —CH$_3$ and —CF$_3$.

TABLE 21

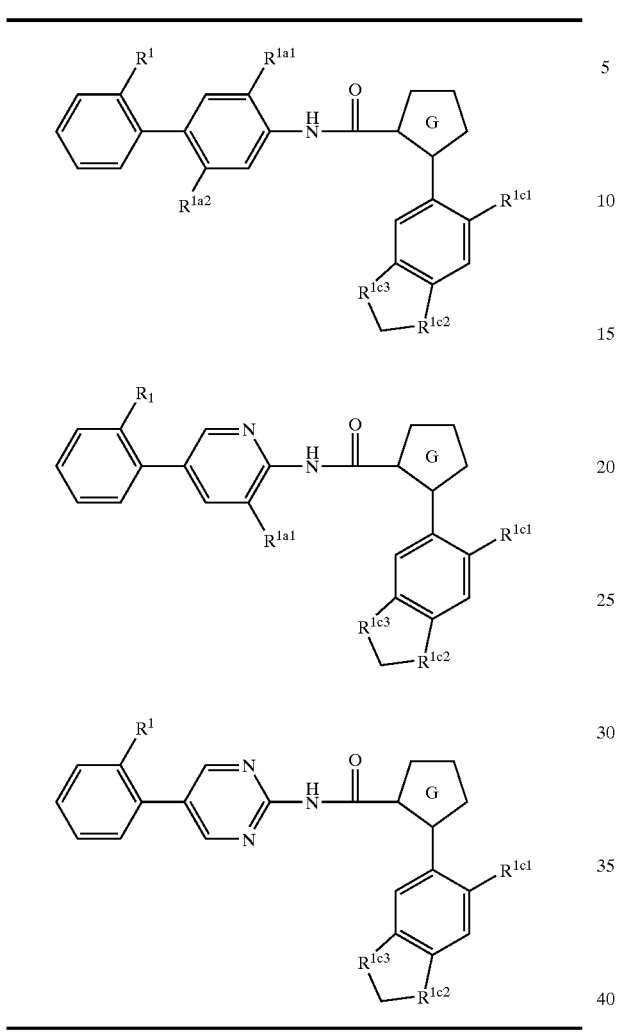

wherein:

R[1] is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R$^{1a1}$ and R$^{1a2}$ are independently selected from the group consisting of —H, —F, —Cl and —Br;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —CH$_2$—, —O—, —NH—, —N(CH$_3$)—, —CH$_2$CH$_2$—, —O—CH$_2$—, —NH—CH$_2$—, and —N(CH$_3$)—CH$_2$—;

R$^{1c3}$ is selected from the group consisting of —CH$_2$—, —O—, —NH—, —N(CH$_3$)—, and —CH(NH$_2$)—; and G is selected from the group consisting of:

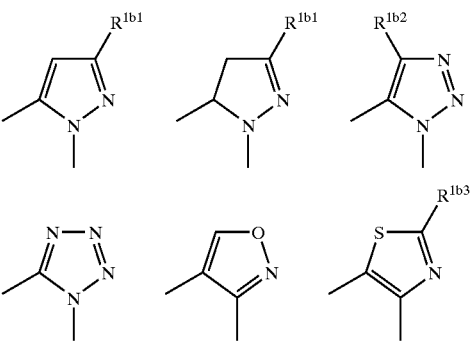

wherein:

R$^{1b1}$ is selected from the group consisting of —H, —CH$_3$ and —CF$_3$;

R$^{1b2}$ is selected from the group consisting of —H, —CH$_3$ and —CF$_3$; and

R$^{1b3}$ is selected from the group consisting of —Cl, —NH$_2$, —CH$_3$ and —CF$_3$.

TABLE 22

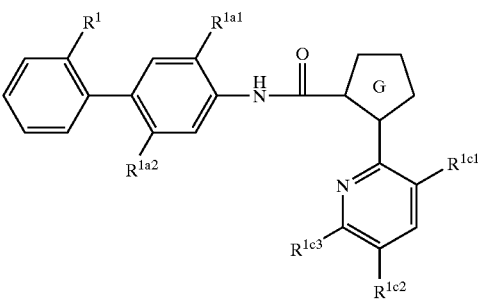

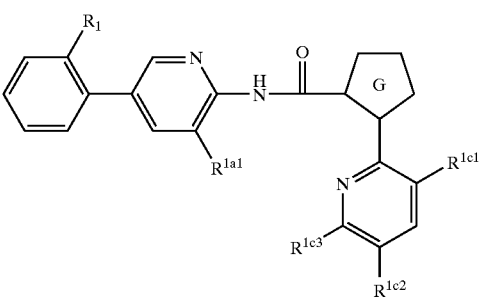

TABLE 22-continued

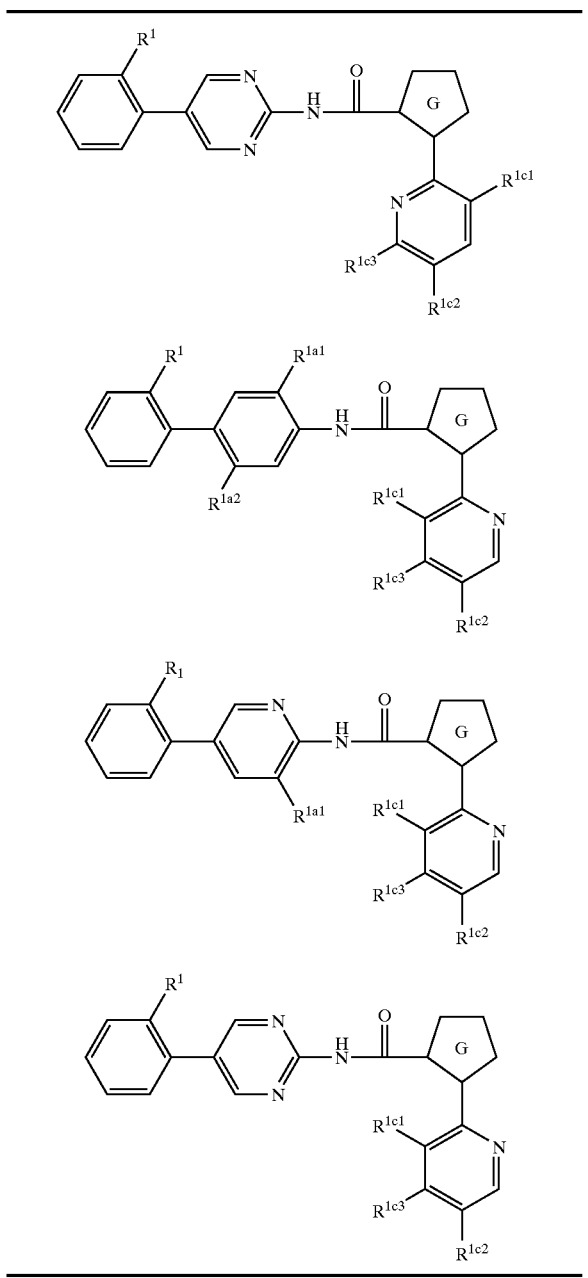

wherein:
R[1] is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R[1a1] and R[1a2] are independently selected from the group consisting of —H, —, —Cl and —Br;

R[1c1] is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R[1c2] is selected from the group consisting of —H, —F, —Cl, —Br, and —OCH$_3$;

R[1c3] is selected from the group consisting of —H, —F, —Cl, —Br, —OH, —OCH$_3$, —NH$_2$, —CONH$_2$, —CH$_2$NH$_2$, —CH$_2$NHCH$_3$, —CH$_2$N(CH$_3$)$_2$, —C(=NH)NH$_2$; and G is selected from the group consisting of:

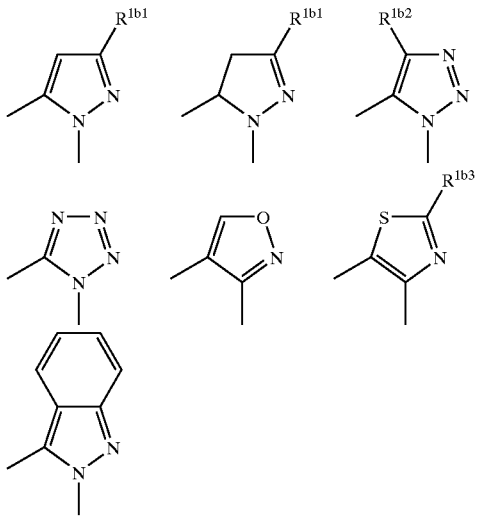

wherein:

R[1b1] selected from the group consisting of —H, —CH$_3$ and —CF$_3$;

R[1b2] is selected from the group consisting of —H, —CH$_3$ and —CF$_3$; and

R[1b3] is selected from the group consisting of —Cl, —NH$_2$, —CH$_3$ and —CF$_3$.

TABLE 23

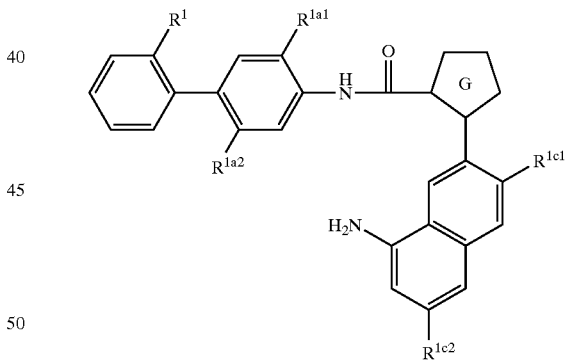

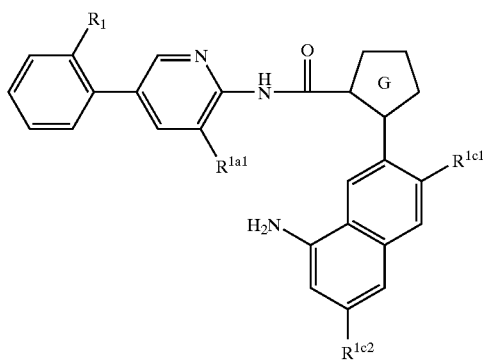

TABLE 23-continued

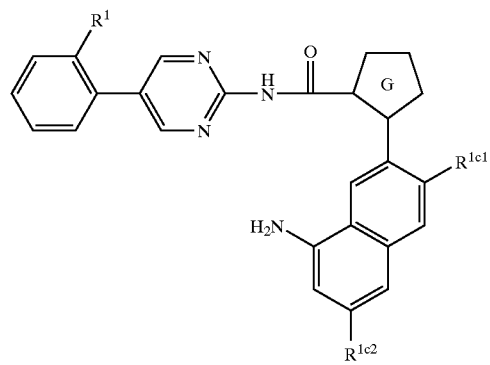

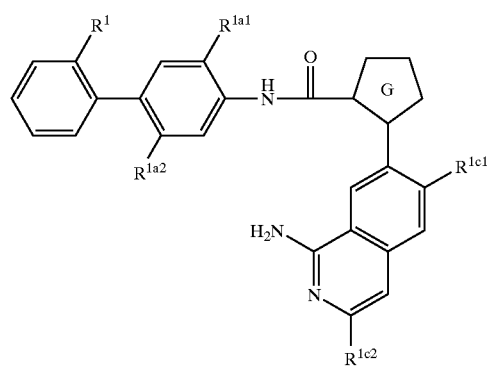

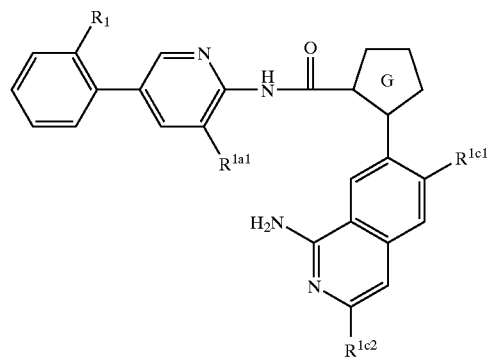

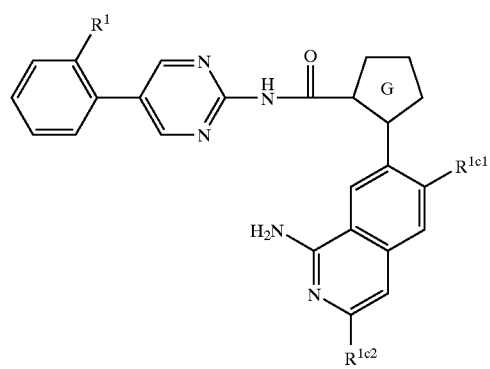

TABLE 23-continued

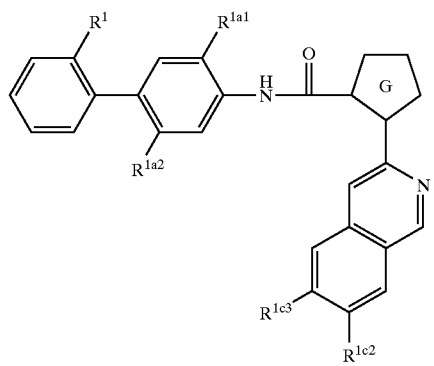

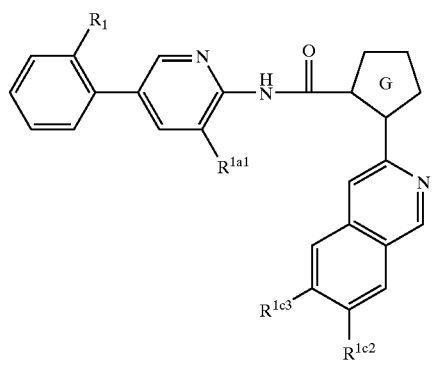

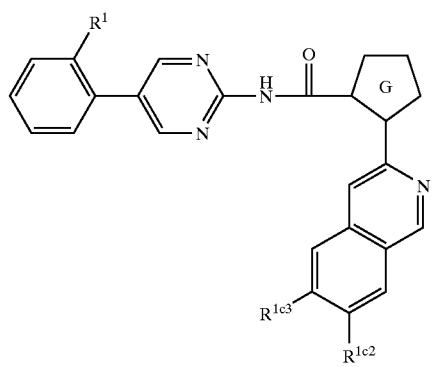

wherein:

$R^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1a1}$ and $R^{1a2}$ are independently selected from the group consisting of —H, —F, —Cl and —Br;

$R^{1c1}$ is selected from the group consisting of —H, —F, —I, —Br, —CN, —CH$_2$NH$_2$, —CH$_2$OH, —CONH$_2$, C(=NH)NH$_2$, —CO$_2$H, —CO$_2$Me, —SO$_2$Me, —SO$_2$NH$_2$, —OH, —NH$_2$, and —NO$_2$;

$R^{1c2}$ and $R^{1c3}$ are independently selected from the group consisting of —H, —F, —Cl, —Br, and —OCH$_3$; and G is selected from the group consisting of:

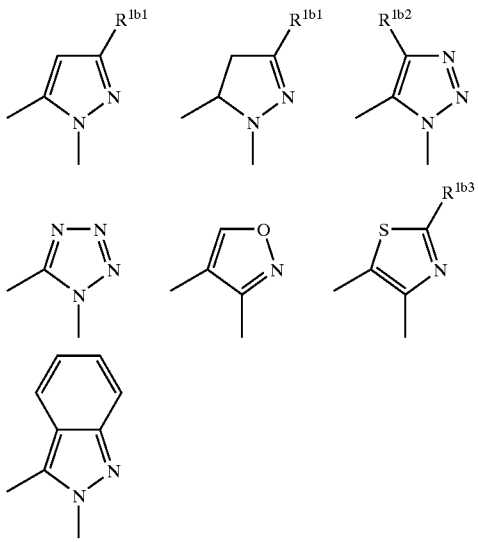

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 24

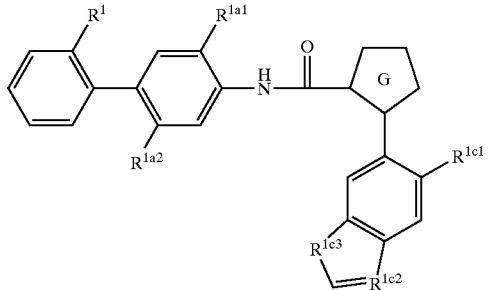

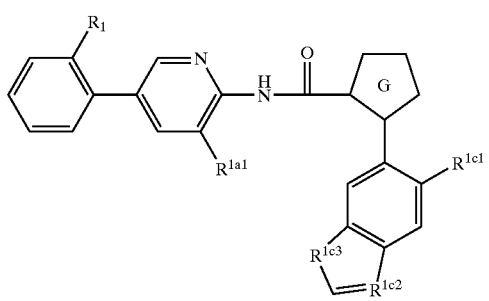

TABLE 24-continued

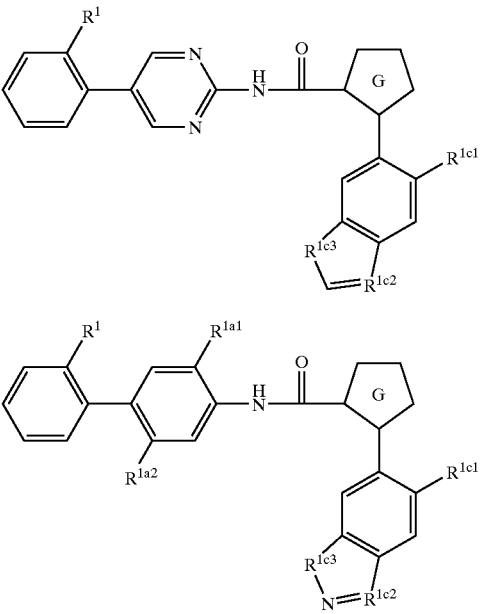

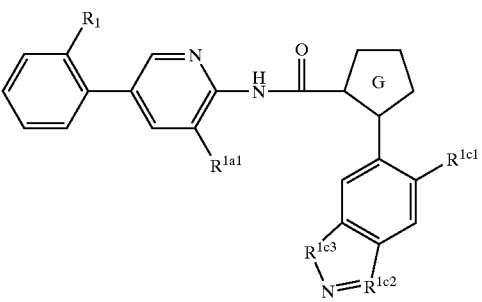

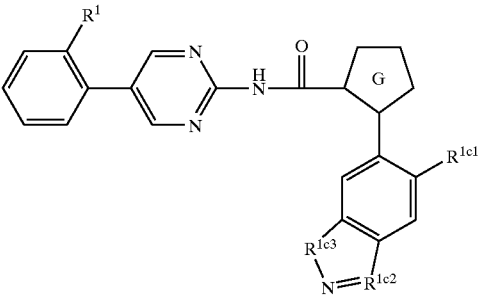

wherein:

$R^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H—, and —N—;

$R^{1c3}$ is selected from the group consisting of —NH—, and —O—; and

G is selected from the group consisting of:

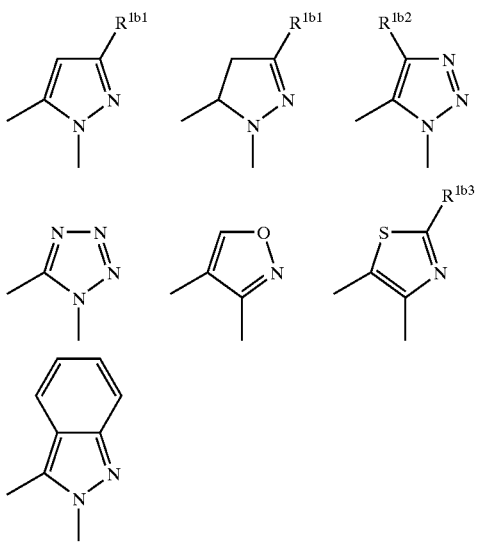

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 25

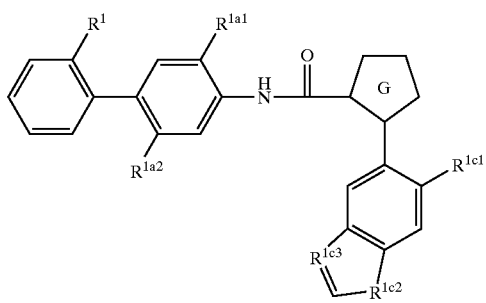

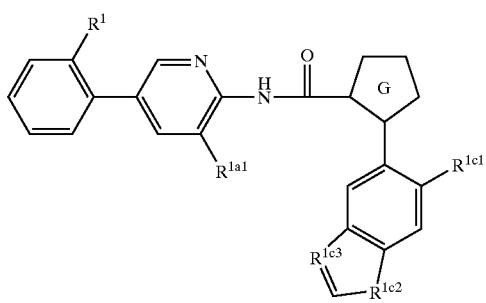

TABLE 25-continued

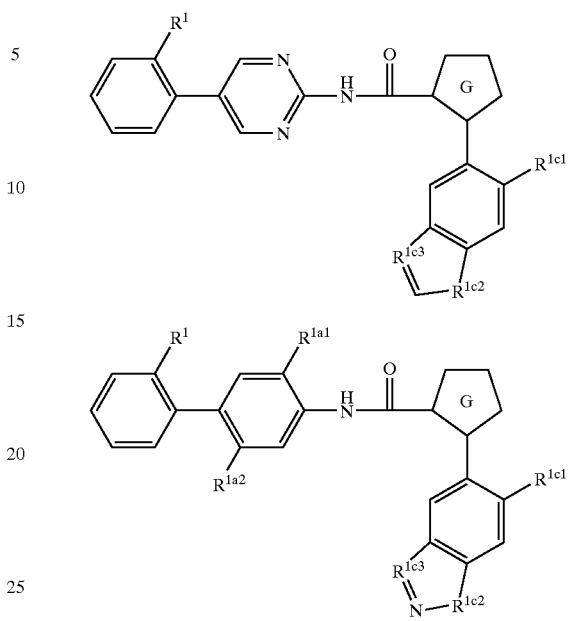

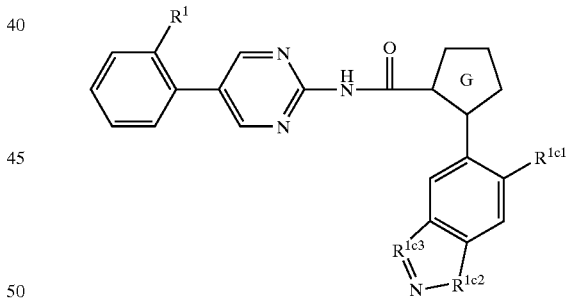

wherein:

$R^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —CH$_2$—, —O— and —NH—;

$R^{1c3}$ is selected from the group consisting of —CH—, —C(NH$_2$)— and —N—; and G is selected from the group consisting of:
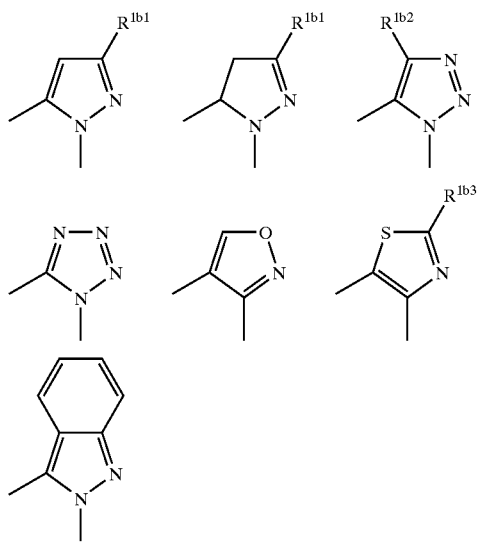
wherein:
R$^{1b1}$ is selected from the group consisting of —H, —CH$_3$ and —CF$_3$;
R$^{1b2}$ is selected from the group consisting of —H, —CH$_3$ and CF$_3$; and
R$^{1b3}$ is selected from the group consisting of —Cl, —NH$_2$, —CH$_3$ and —CF$_3$.
TABLE 26
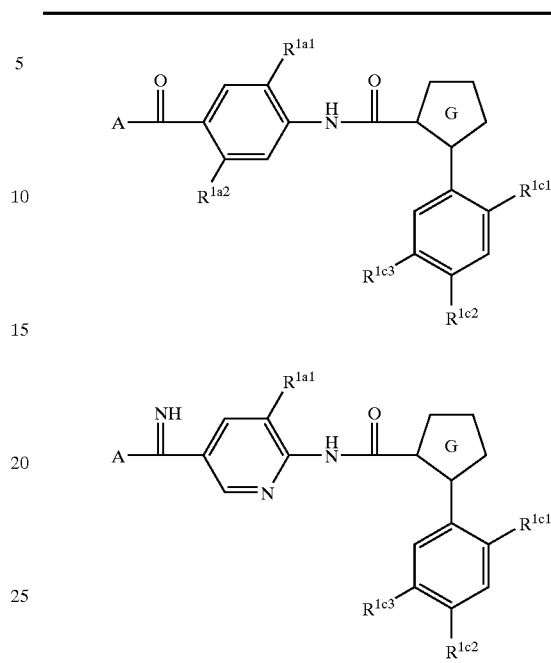
TABLE 26-continued
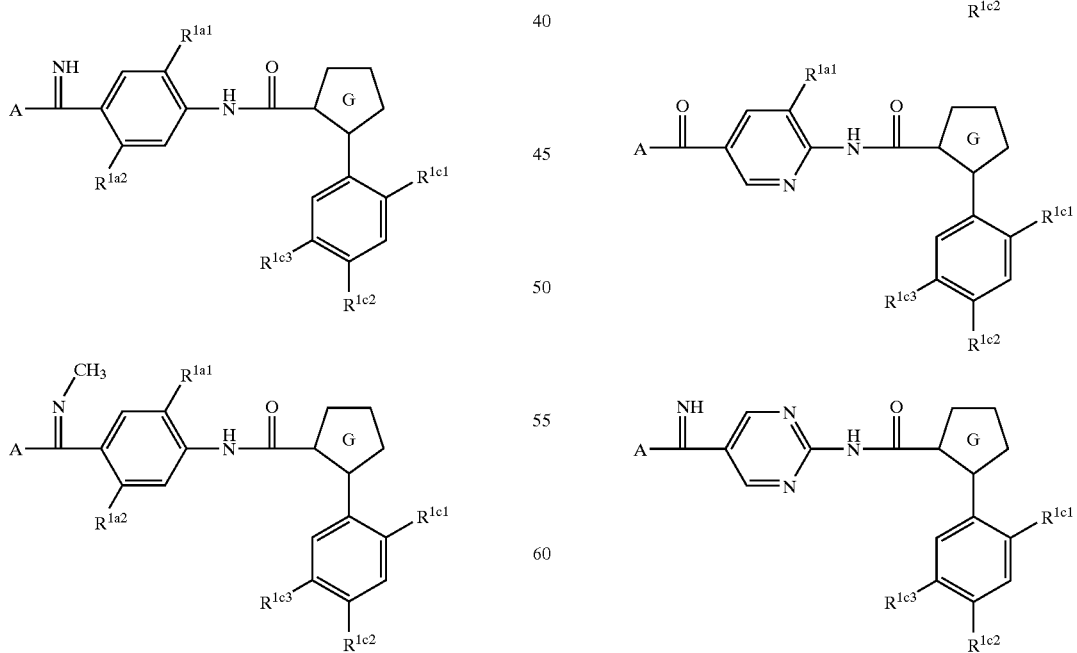

TABLE 26-continued

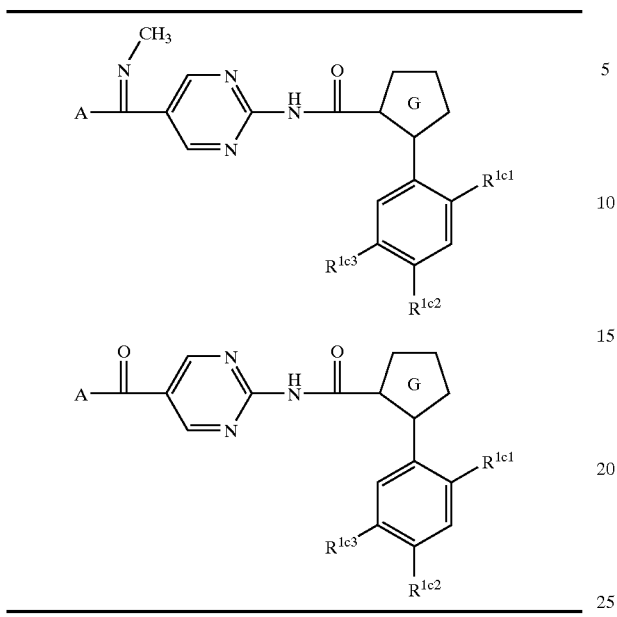

wherein:

A is selected from the group consisting of:

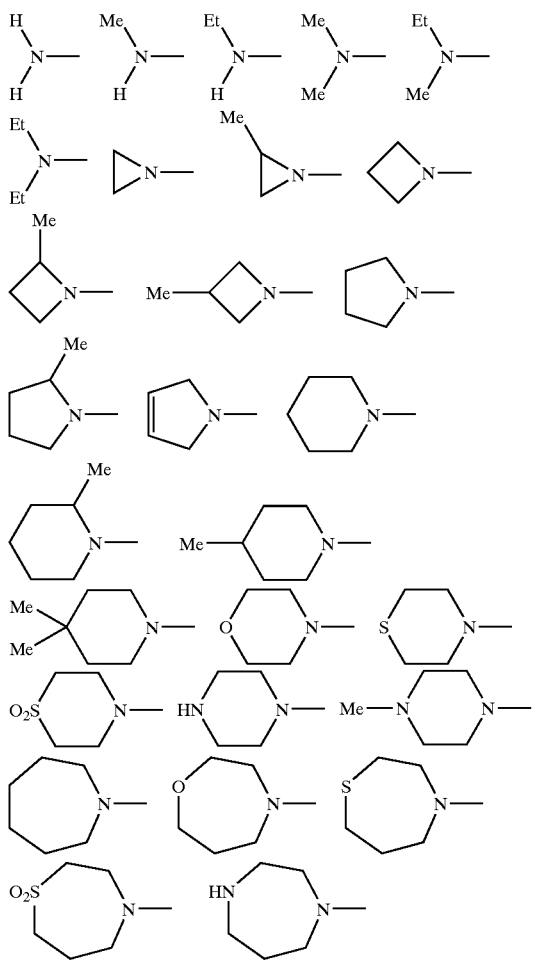

-continued

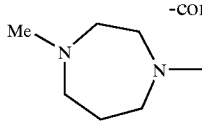

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, and —OCH$_3$;

$R^{1c3}$ is selected from the group consisting of —H, —F, —Cl, —Br, —OH, —OCH$_3$, —NH$_2$, —CONH$_2$, —CH$_2$NH$_2$, —CH$_2$NHCH$_3$, —CH$_2$N(CH$_3$)$_2$, —C(=NH)NH$_2$; and G is selected from the group consisting of:

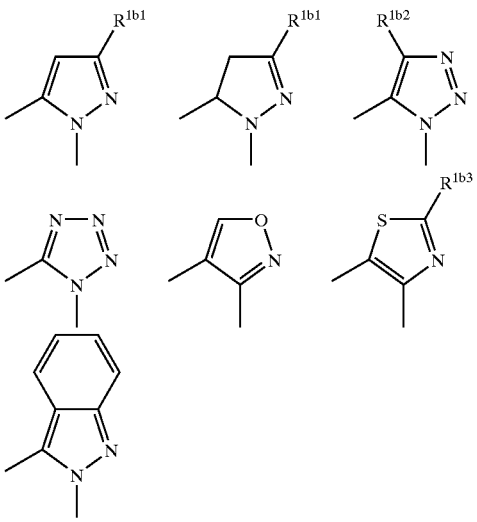

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 27

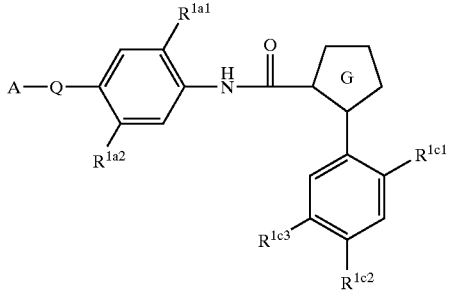

TABLE 27-continued
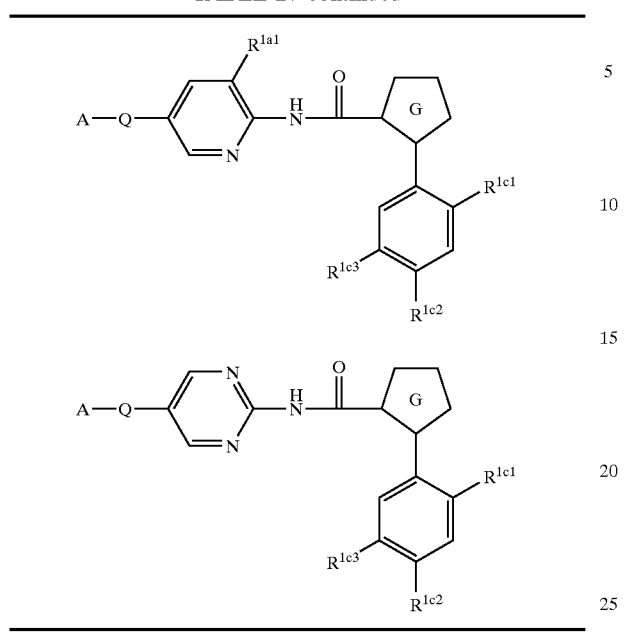
wherein:
A—Q is selected from the group consisting of:
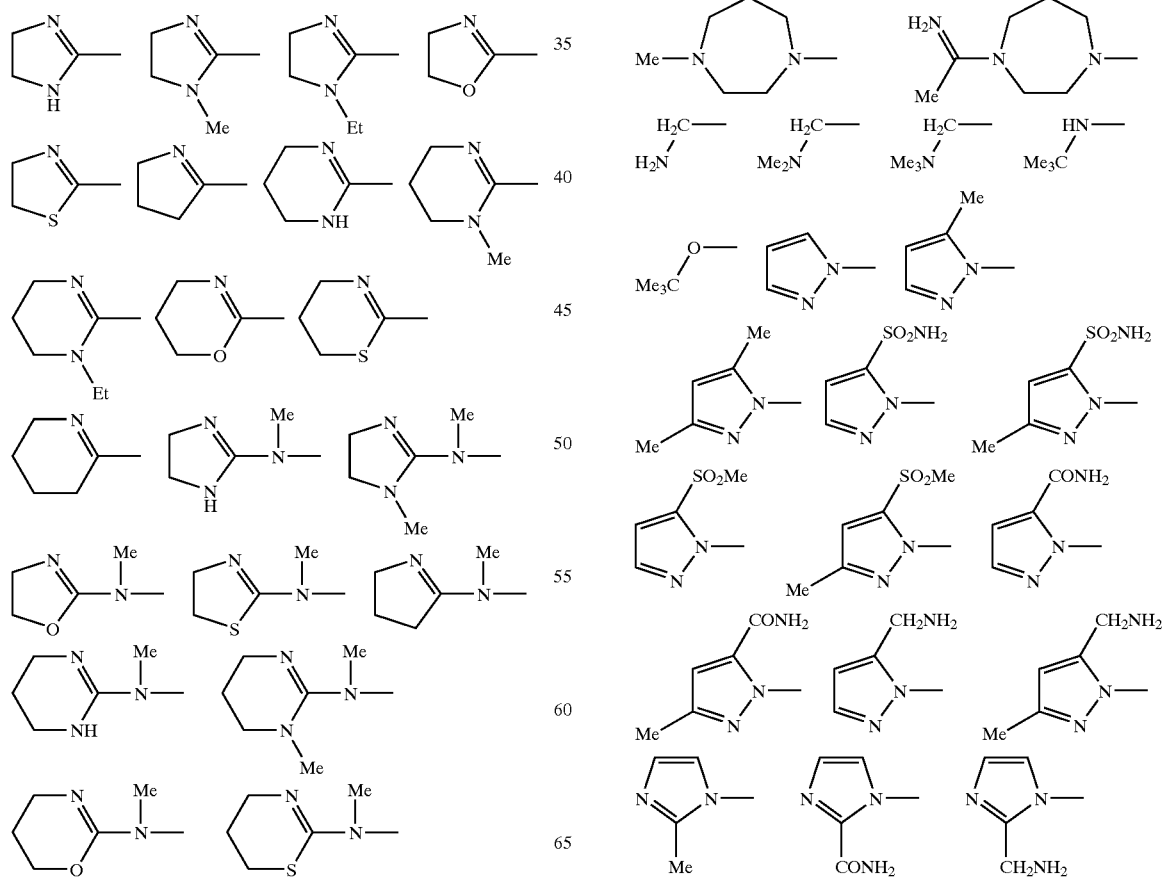
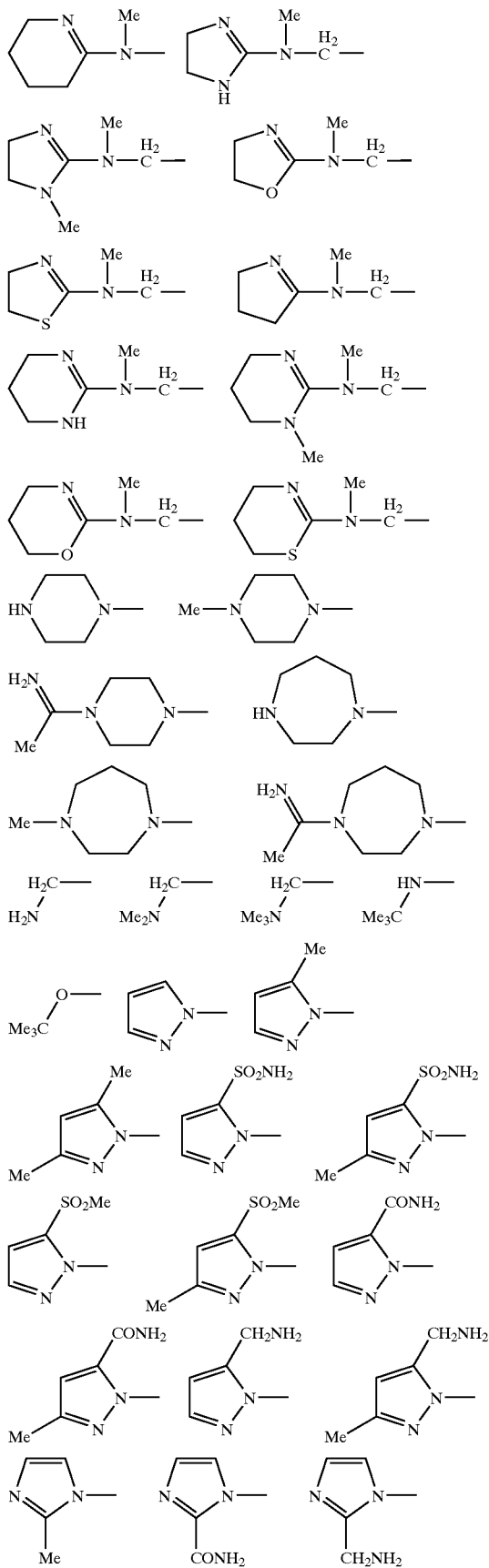

-continued

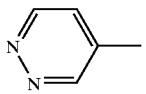

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, and —OCH$_3$;

$R^{1c3}$ is selected from the group consisting of —H, —F, —Cl, —Br, —OH, —OCH$_3$, —NH$_2$, —CONH$_2$, —CH$_2$NH$_2$, —CH$_2$NHCH$_3$, —CH$_2$N(CH$_3$)$_2$, —C(=NH)NH$_2$; and G is selected from the group consisting of:

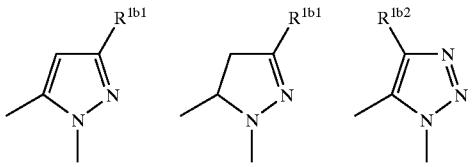

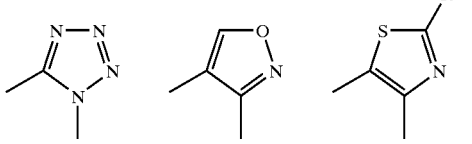

wherein:
$R^{1b1}$ is selected from the group consisting of —H, —CH$_3$ and —CF$_3$;
$R^{1b2}$ is selected from the group consisting of —H, —CH$_3$ and —CF$_3$; and
$R^{1b3}$ is selected from the group consisting of —Cl, —NH$_2$, —CH$_3$ and —CF$_3$.

TABLE 28

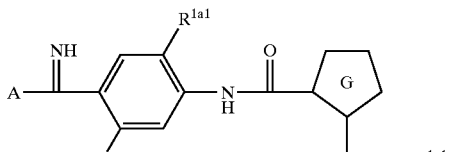

TABLE 28-continued

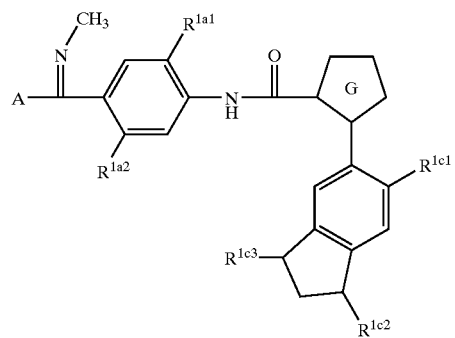

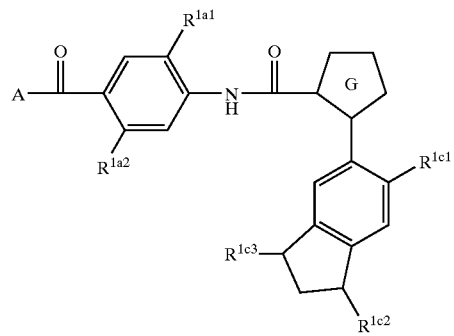

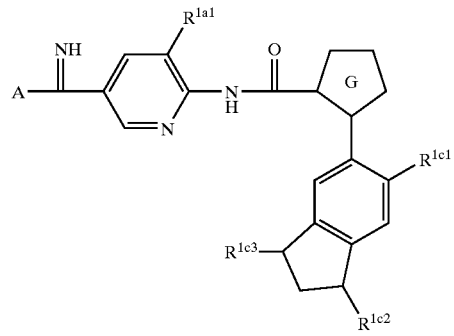

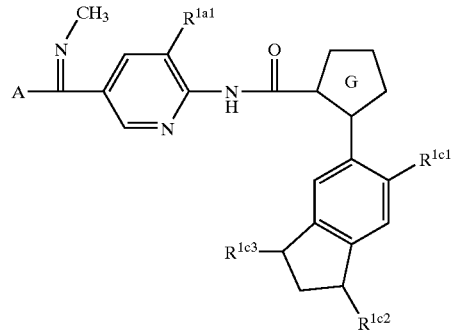

TABLE 28-continued

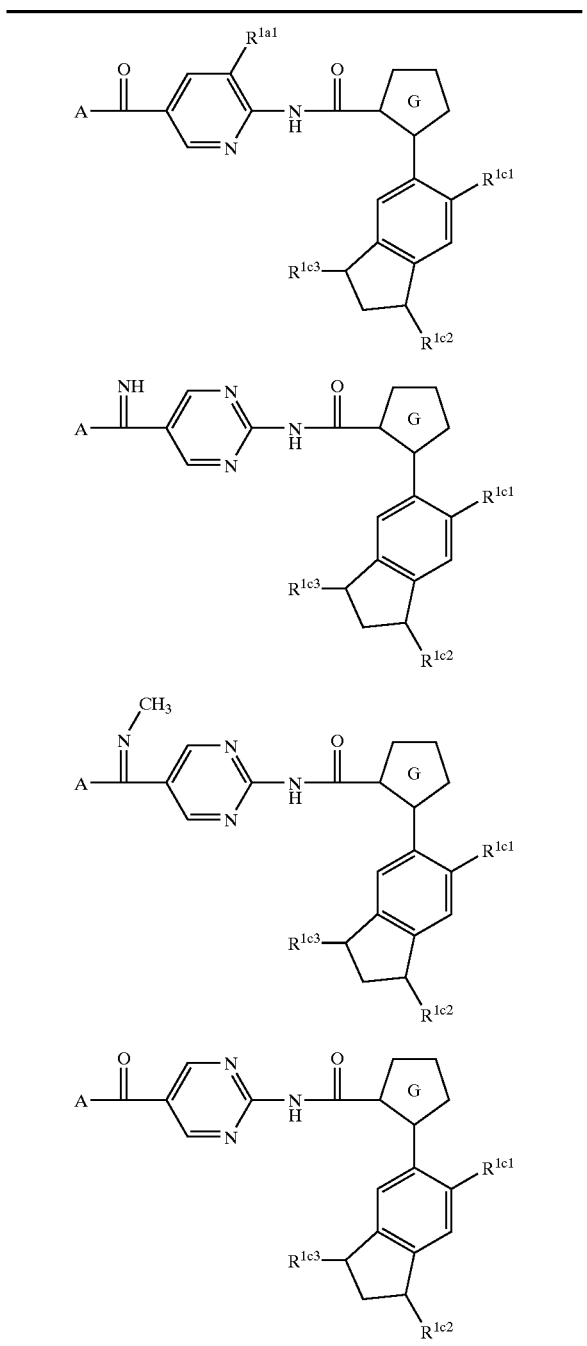

wherein:

A is selected from the group consisting of:

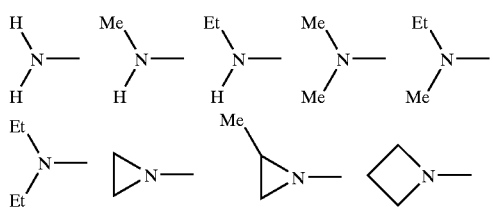

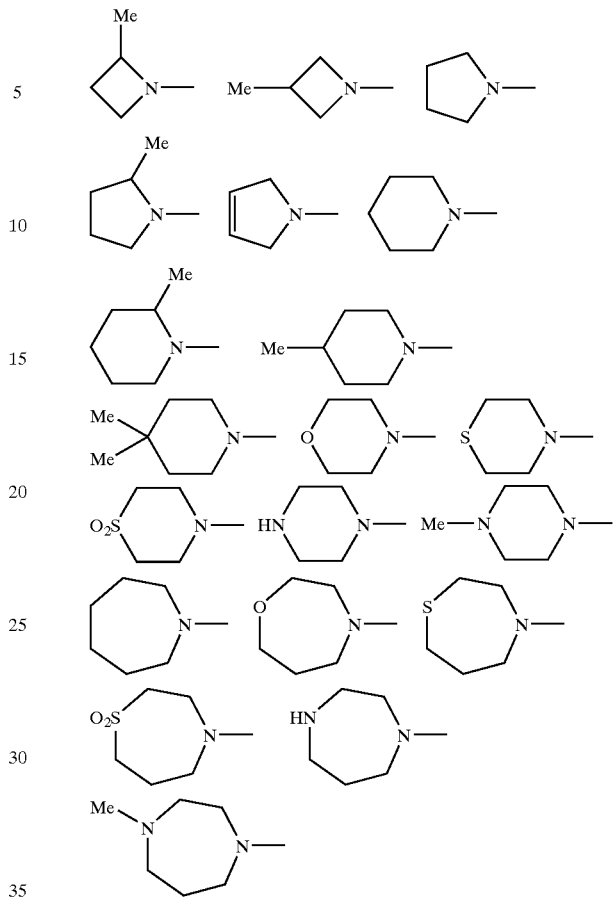

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —$CH_2NH_2$, —$CH_2OH$, —$CONH_2$, —C(=NH)$NH_2$, —$CO_2H$, —$CO_2Me$, —$SO_2Me$, —$SO_2NH_2$, —OH, —$NH_2$, and —$NO_2$;

$R^{1c2}$ is selected from the group consisting of —H, —F, —Cl, —Br, and —$OCH_3$;

$R^{1c3}$ is selected from the group consisting of —H, —F, —Cl, —Br, —OH, —$OCH_3$, —$NH_2$, —$CONH_2$, —$CH_2NH_2$, —$CH_2NHCH_3$, —$CH_2N(CH_3)_2$, —C(=NH)$NH_2$;

G is selected from the group consisting of:

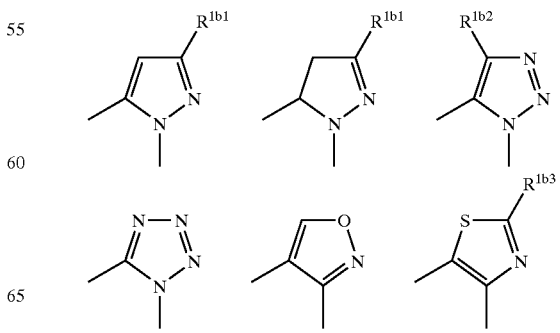

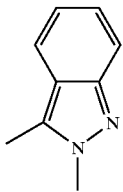
wherein:
R[1b1] is selected from the group consisting of —H, —CH₃ and —CF₃;
R[1b2] is selected from the group consisting of —H, —CH₃ and —CF₃; and
R[1b3] is selected from the group consisting of —Cl, —NH₂, —CH₃ and —CF₃.
TABLE 29
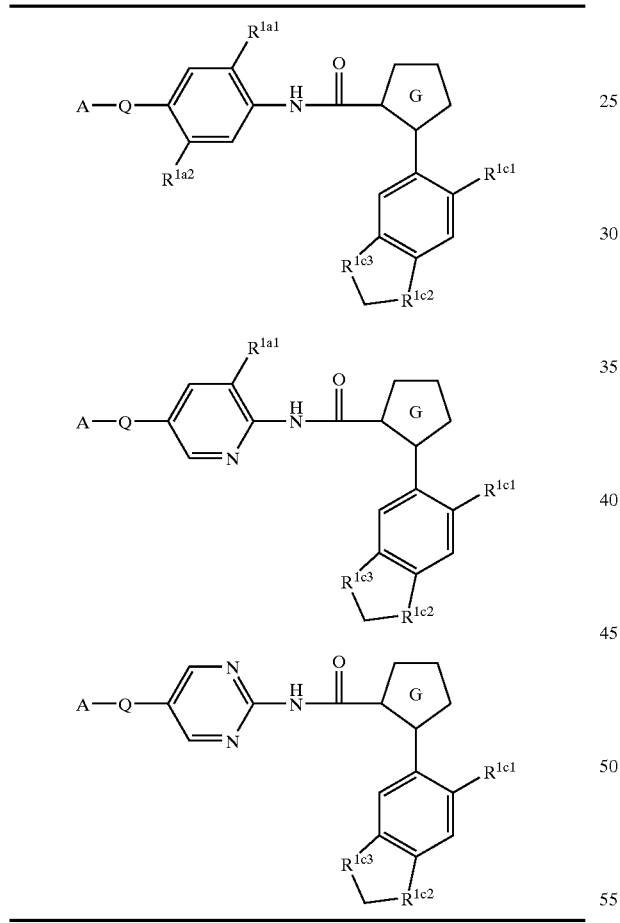
wherein:
A—Q is selected from the group consisting of:
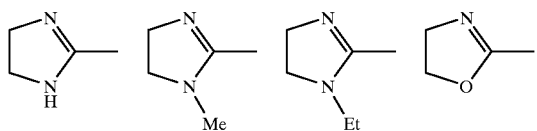
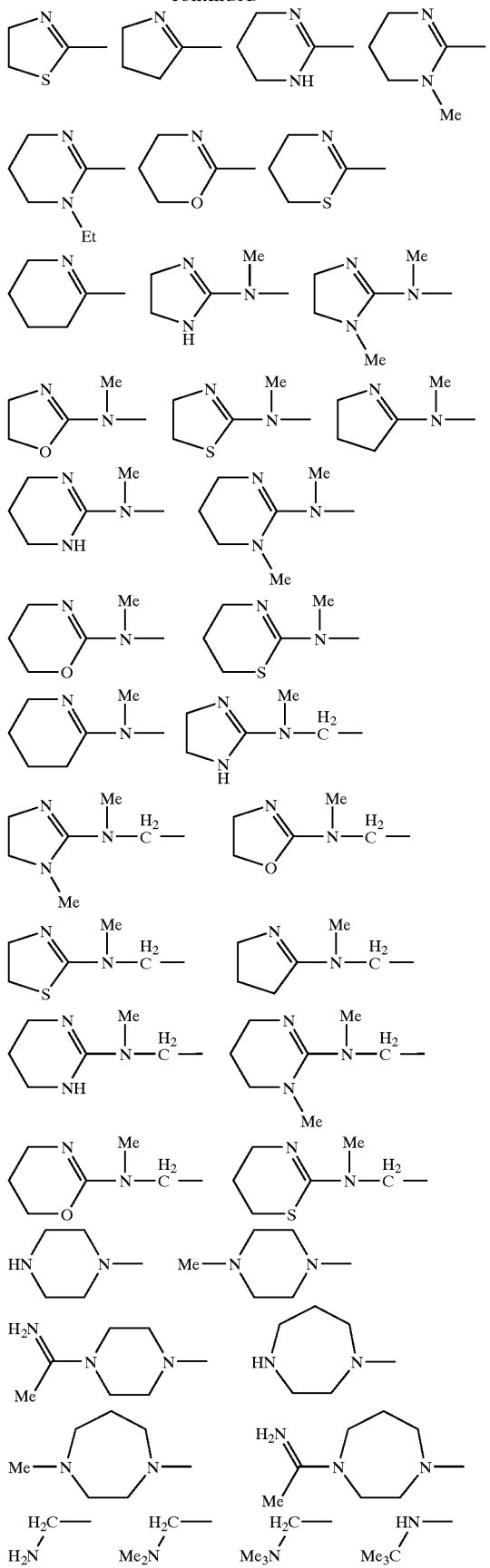

-continued

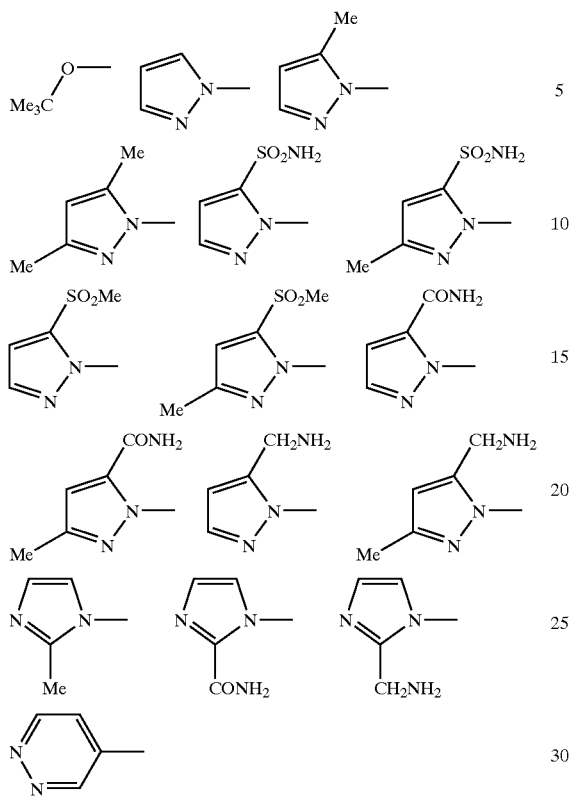

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —CH$_2$—, —O—, —NH—, —N(CH$_3$)—, —CH$_2$CH$_2$—, —O—CH$_2$—, —NH—CH$_2$—, and —N(CH$_3$)—CH$_2$—;

$R^{1c3}$ is selected from the group consisting of —CH$_2$—, —O—, —NH—, —N(CH$_3$)—, and —CH(NH$_2$)—; and G is selected from the group consisting of:

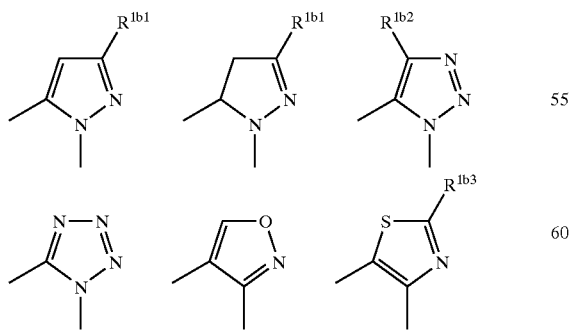

-continued

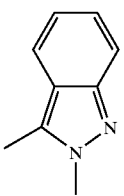

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 30

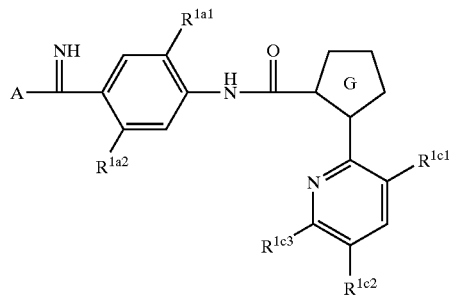

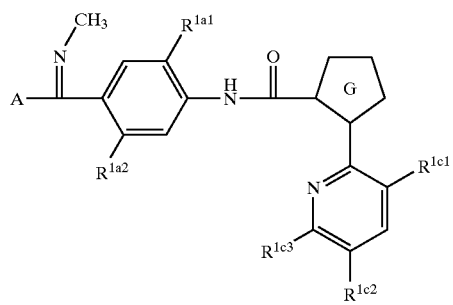

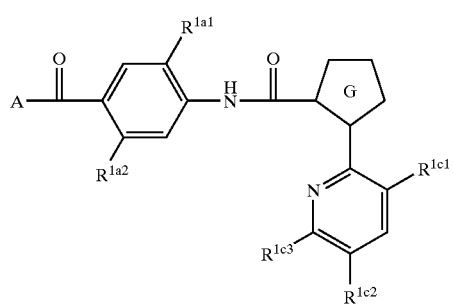

TABLE 30-continued
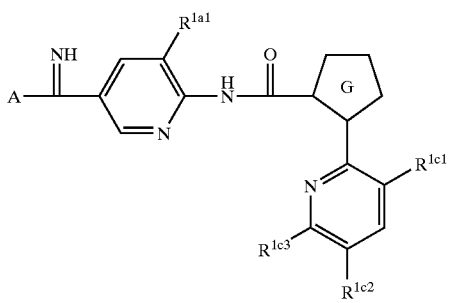
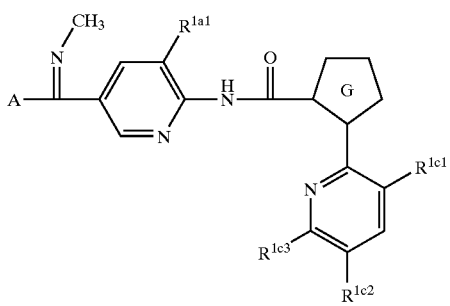
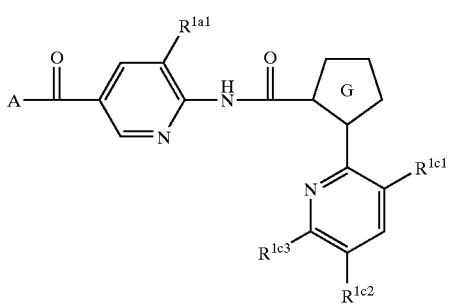
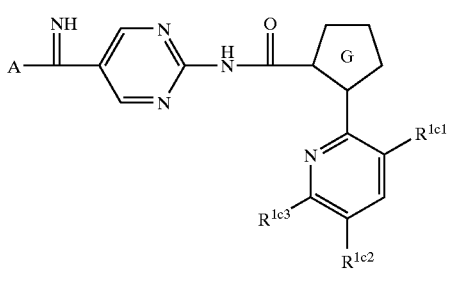
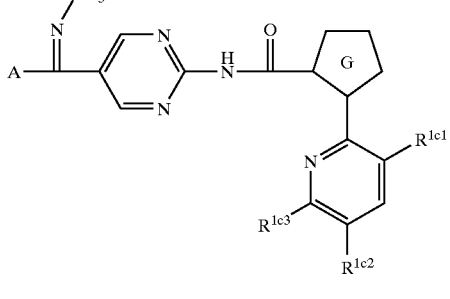
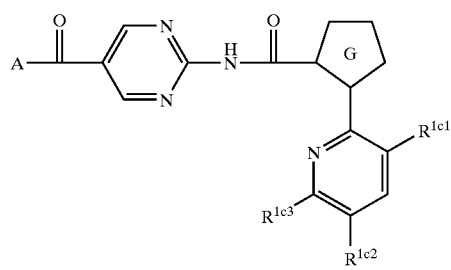
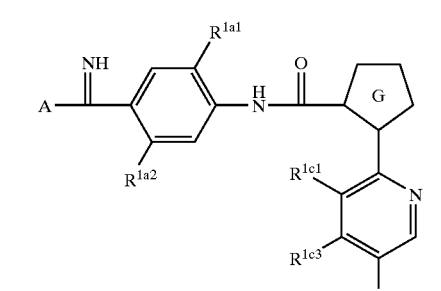
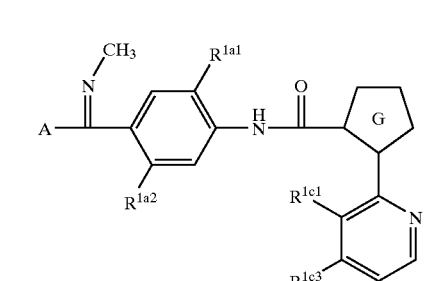
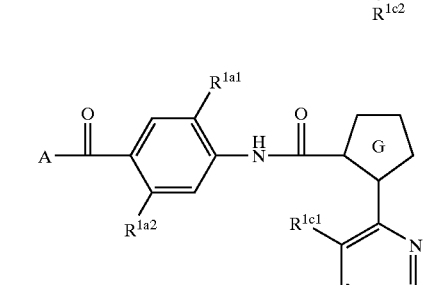
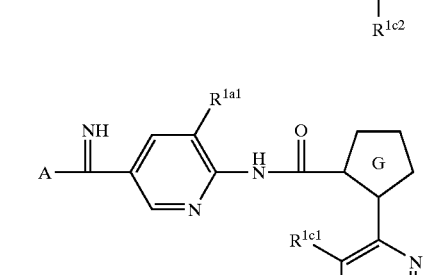

TABLE 30-continued

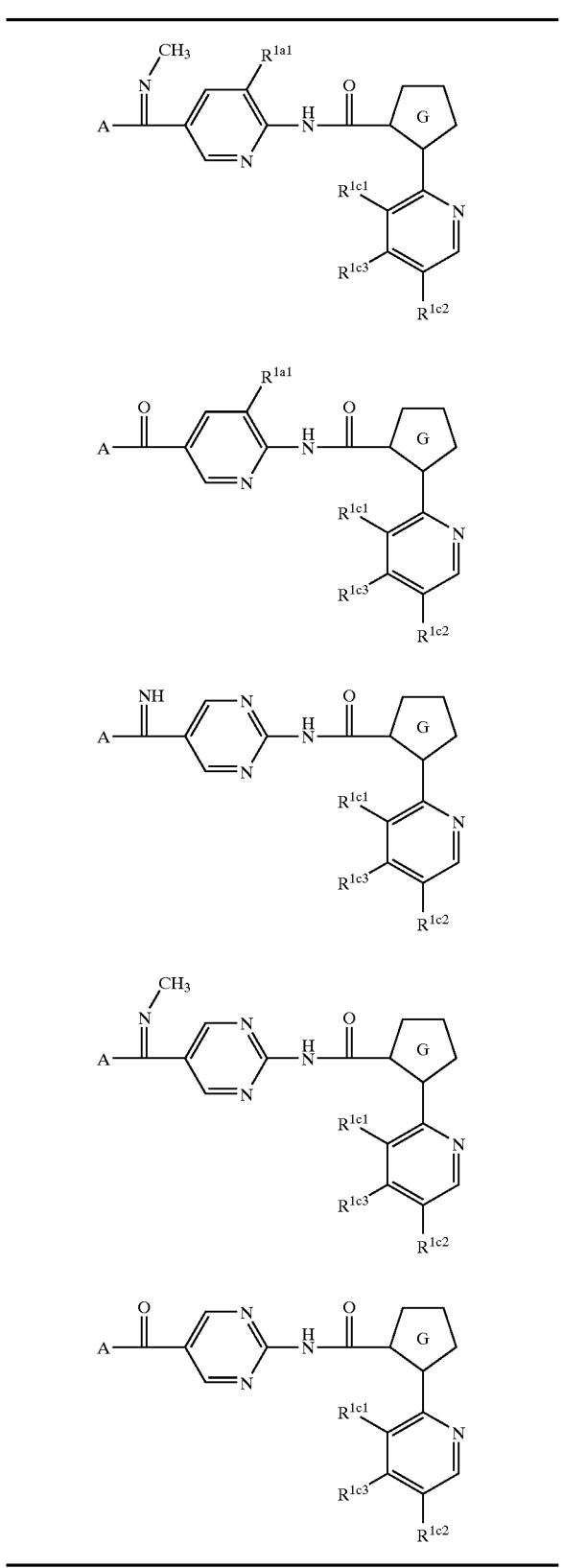

A is selected from the group consisting of:

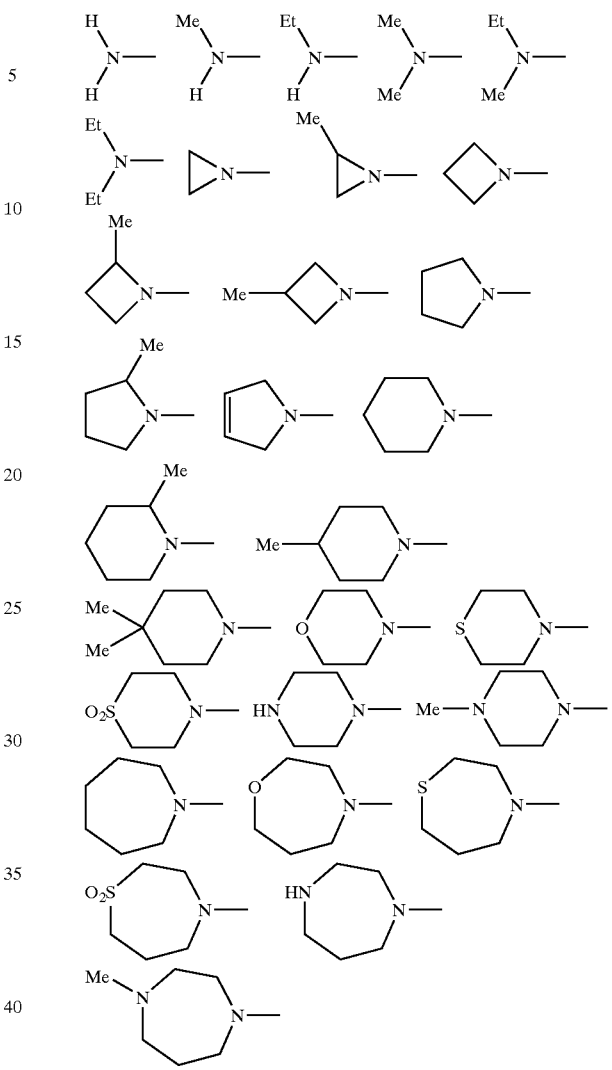

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, and —OCH$_3$;

$R^{1c3}$ is selected from the group consisting of —H, —F, —Cl, —Br, —OH, —OCH$_3$, —NH$_2$, —CONH$_2$, —CH$_2$NH$_2$, —CH$_2$NHCH$_3$, —CH$_2$N(CH$_3$)$_2$, —C(=NH)NH$_2$, —C(=NH)NH(CH$_3$) —C(=NH)NH(CH$_3$)$_2$; and G is selected from the group consisting of:

wherein:

-continued
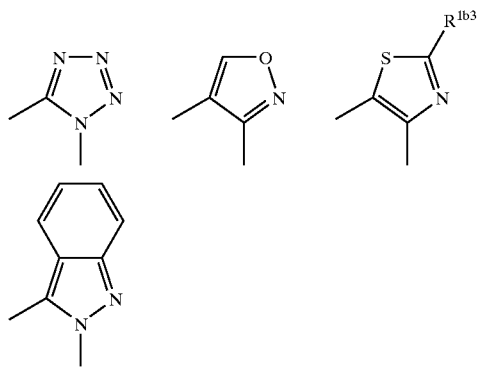
wherein:
$R^{1b1}$ is selected from the group consisting of —H, —CH$_3$ and —CF$_3$;
$R^{1b2}$ is selected from the group consisting of —H, —CH$_3$ and —CF$_3$; and
$R^{1b3}$ is selected from the group consisting of —Cl, —NH$_2$, —CH$_3$ and —CF$_3$.
TABLE 31
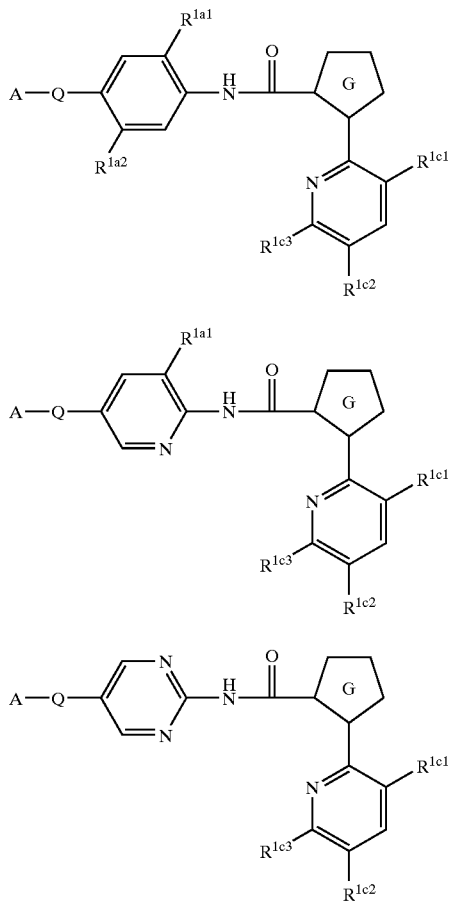
TABLE 31-continued
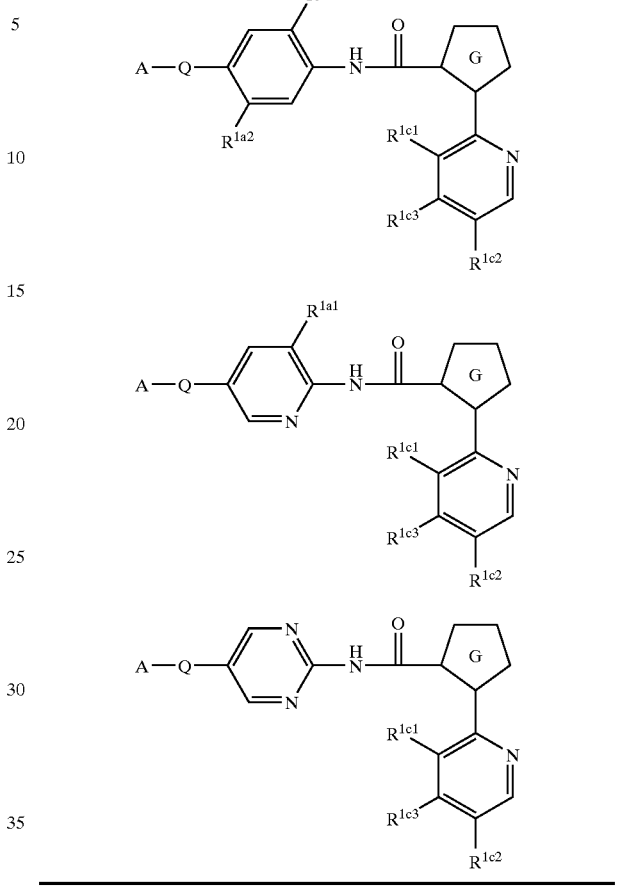
wherein:
A—Q is selected from the group consisting of:
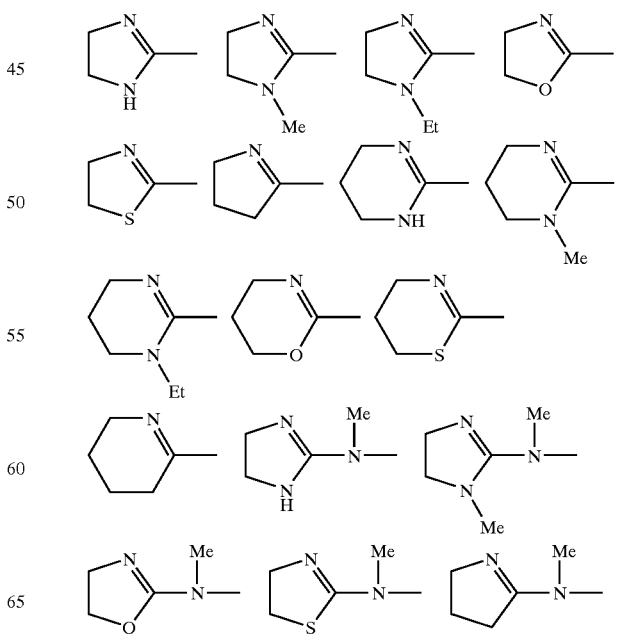

-continued

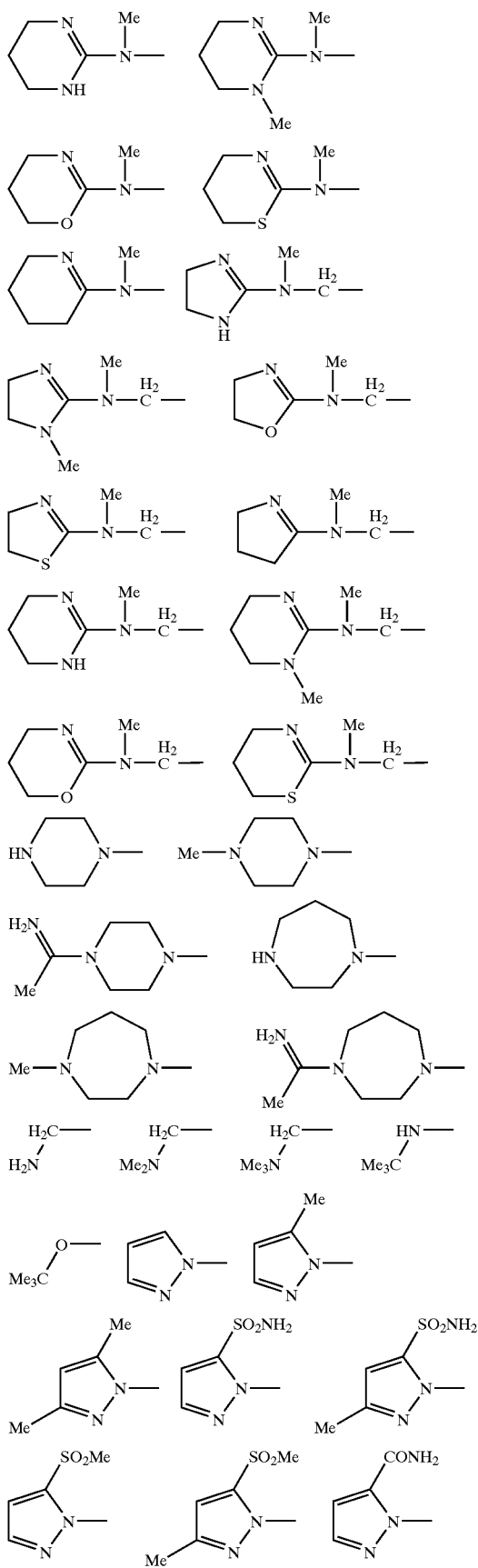

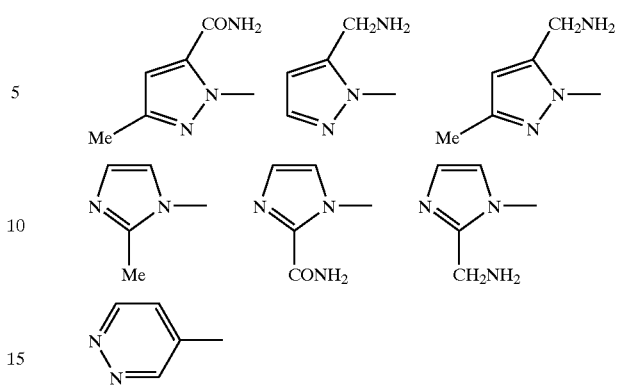

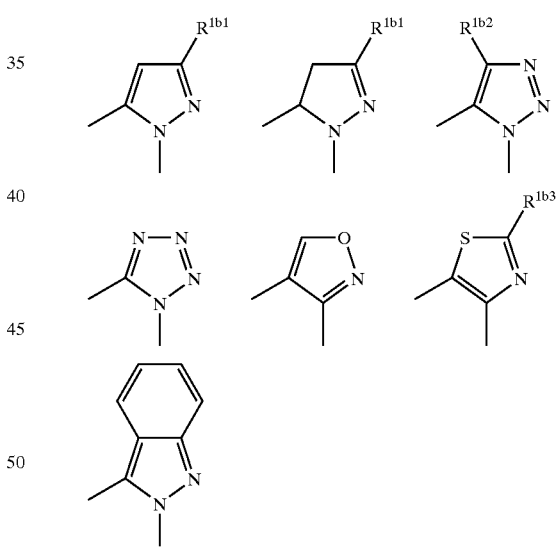

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, —OH, —OCH$_3$, and —NH$_2$;

$R^{1c3}$ is selected from the group consisting of —H, —F, —Cl, —Br, —OH, —OCH$_3$, and —NH$_2$; and G is selected from the group consisting of:

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

wherein:
TABLE 32
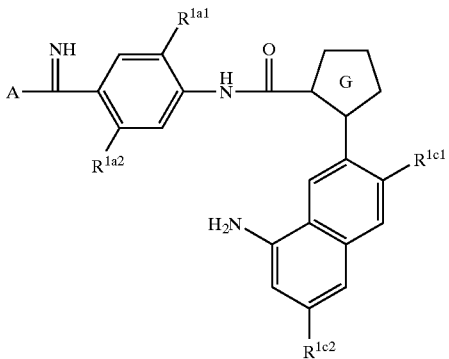
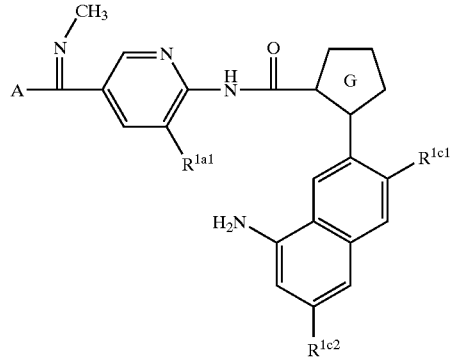
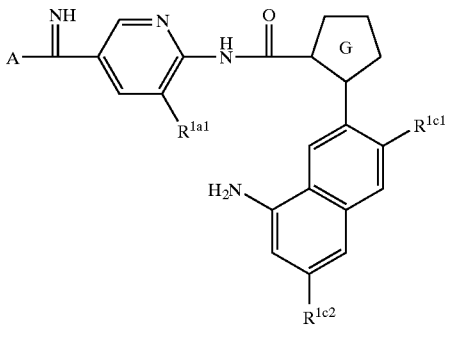
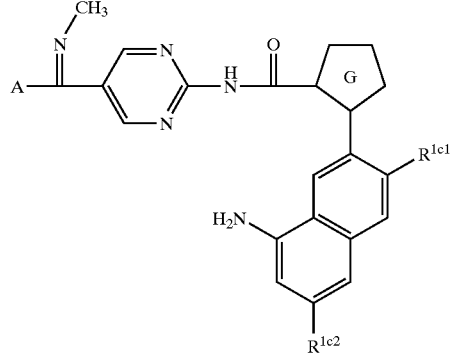
TABLE 32-continued
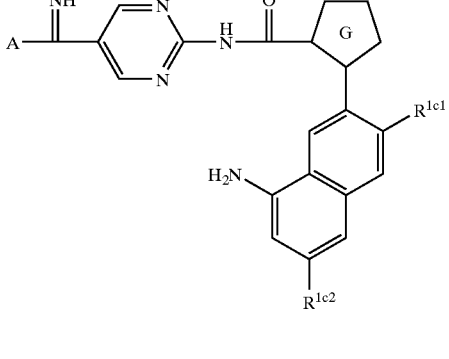
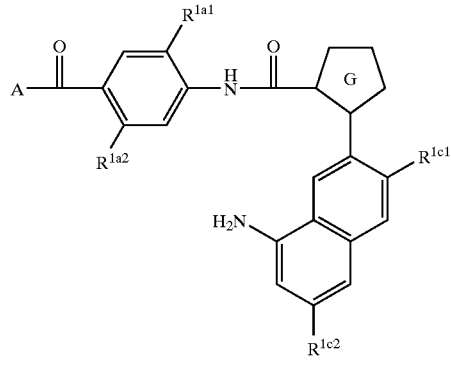

TABLE 32-continued

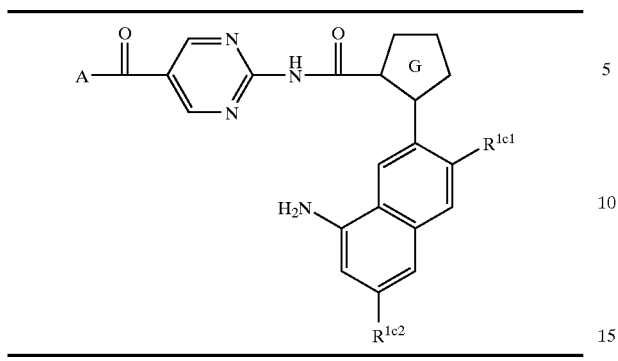

A is selected from the group consisting of:

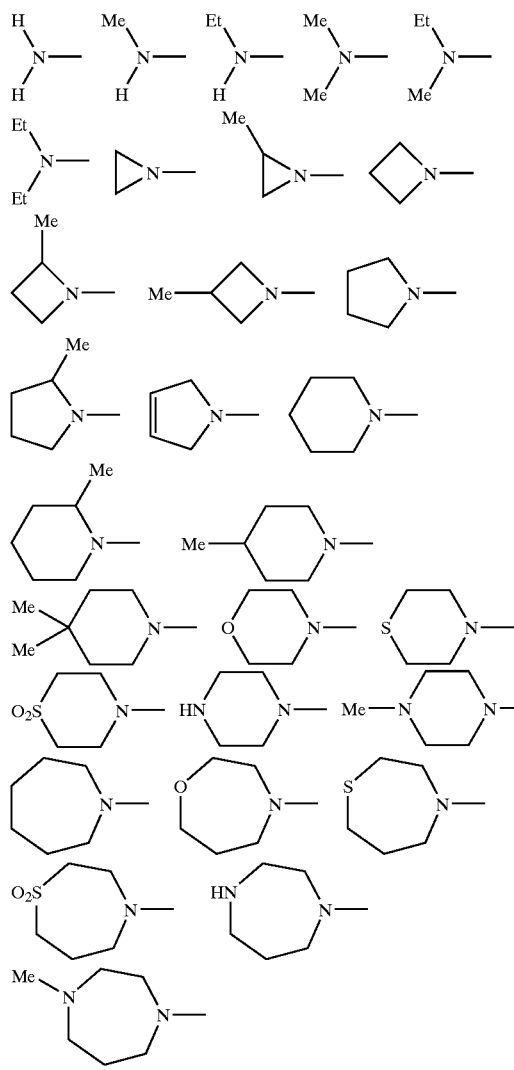

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, and —OCH$_3$; and G is selected from the group consisting of:

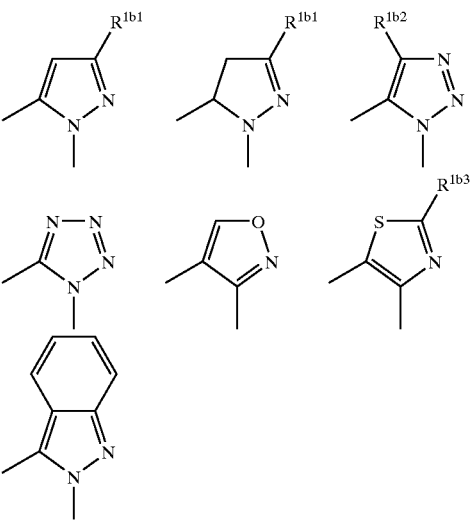

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

wherein:

TABLE 33

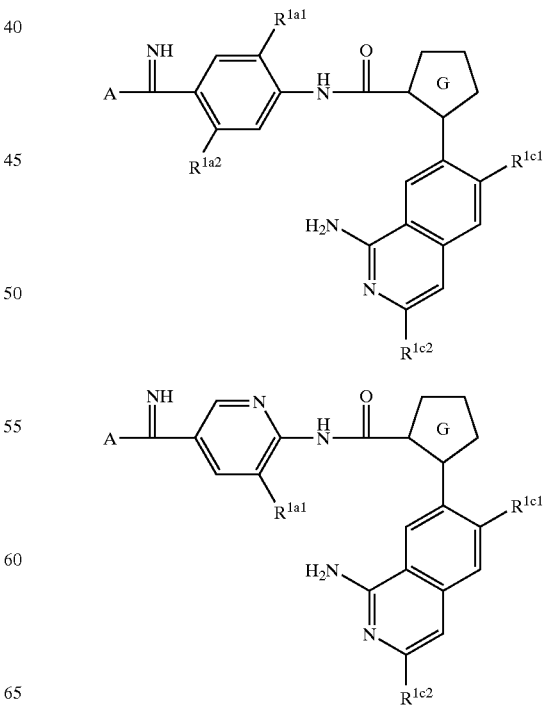

TABLE 33-continued
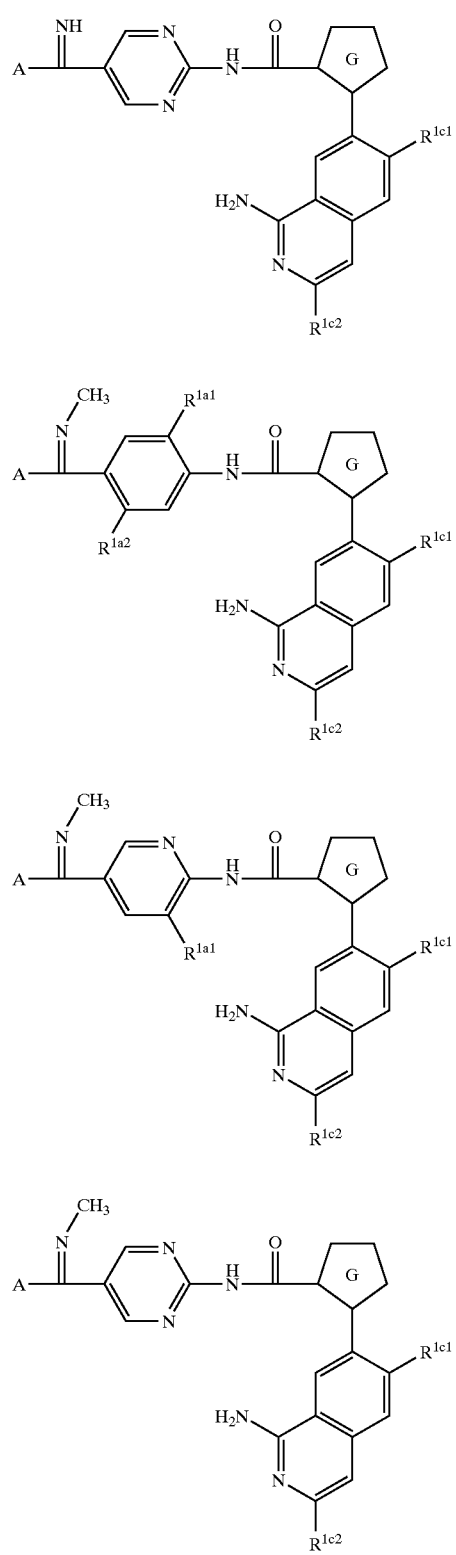
TABLE 33-continued
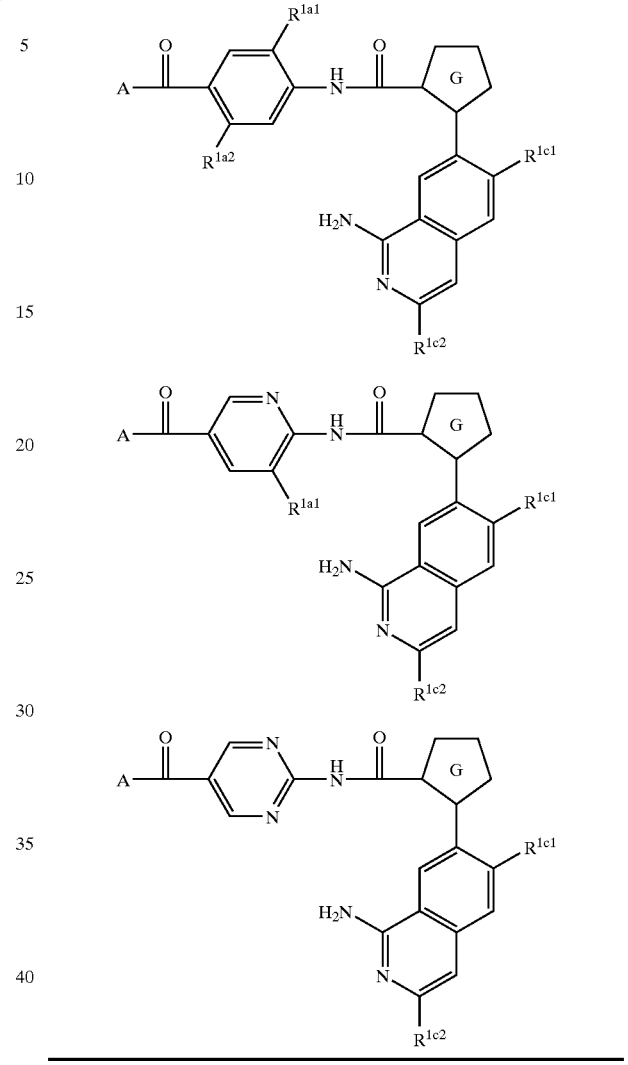
A is selected from the group consisting of:
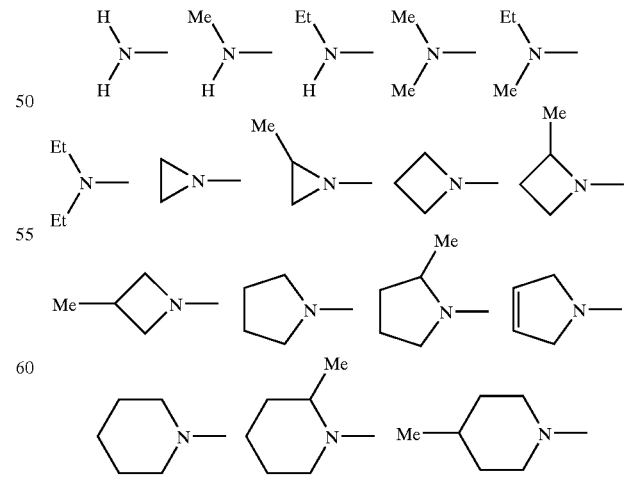

-continued

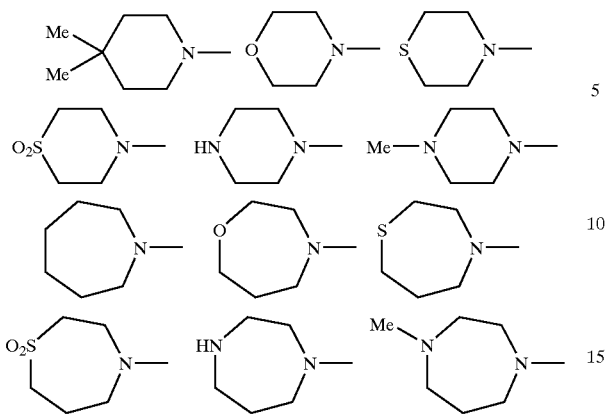

R$^{1a1}$ and R$^{1a2}$ are independently selected from the group consisting of —H, —F, —Cl and —Br;

R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R$^{1c2}$ is selected from the group consisting of —H, —F, —Cl, —Br, and —OCH$_3$; and G is selected from the group consisting of:

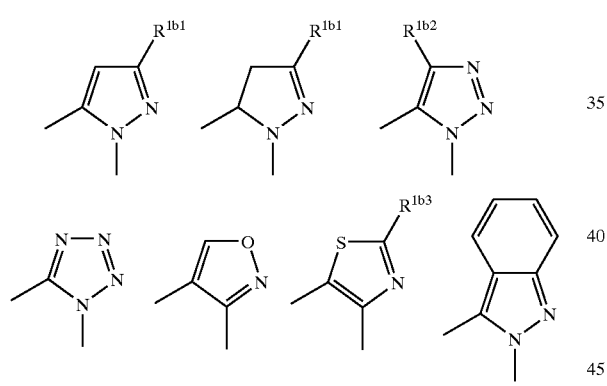

wherein:

R$^{1b1}$ is selected from the group consisting of —H, —CH$_3$ and —CF$_3$;

R$^{1b2}$ is selected from the group consisting of —H, —CH$_3$ and —CF$_3$; and

R$^{1b3}$ is selected from the group consisting of —Cl, —NH$_2$, —CH$_3$ and —CF$_3$.

TABLE 34

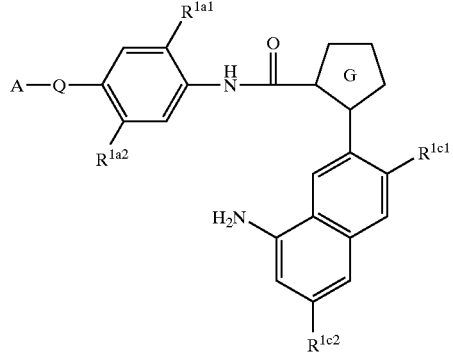

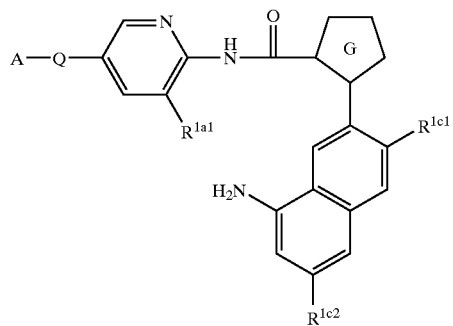

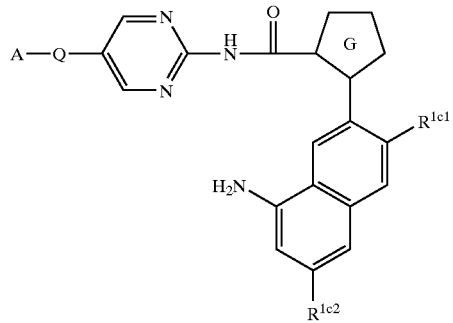

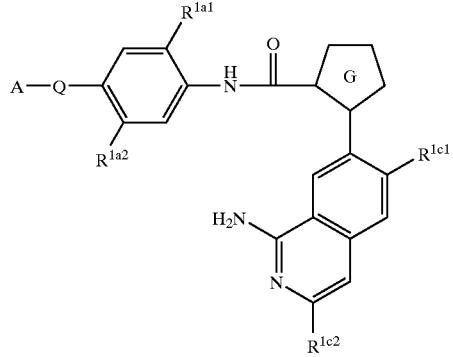

TABLE 34-continued
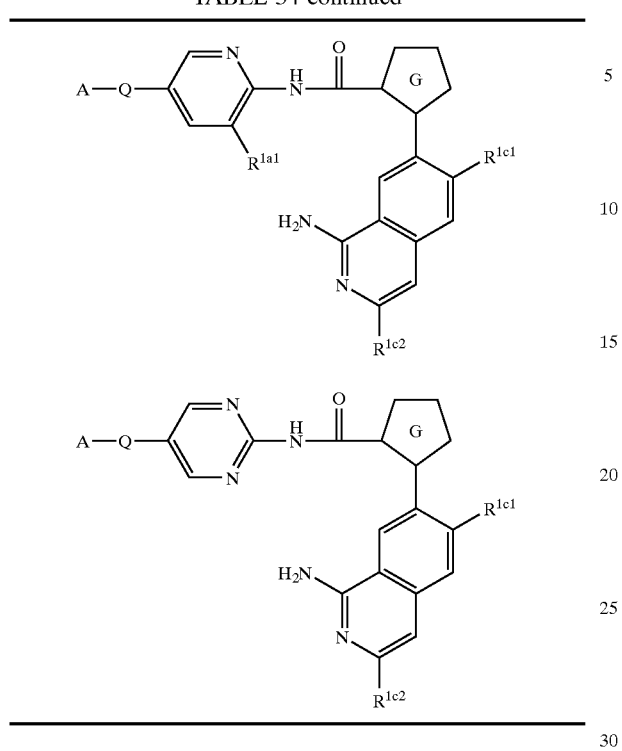
wherein:
A—Q is selected from the group consisting of:
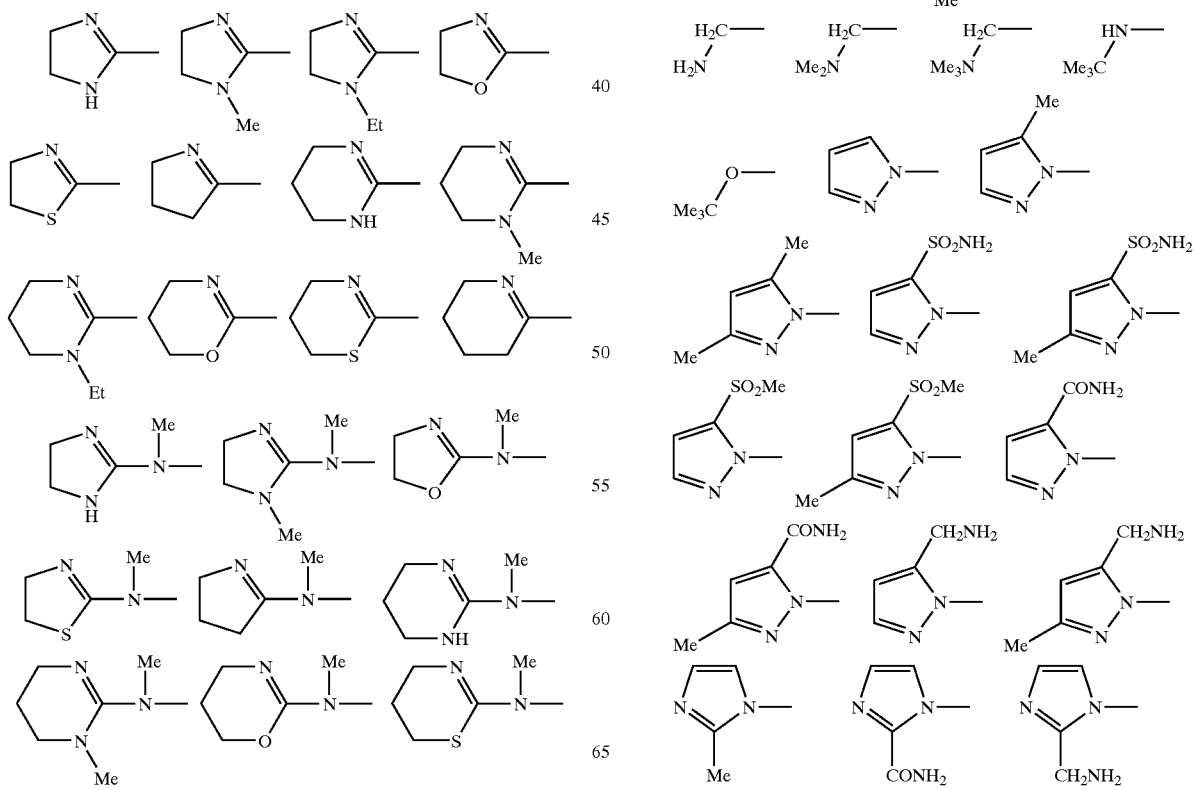

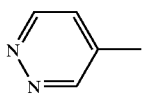

$R^{1a1}$ and $R^{1a2}$ are independently selected from the group consisting of —H, —F, —Cl and —Br;

$R^{1c1}$ is selected front the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl, —Br, and —OCH$_3$; and G is selected from the group consisting of:

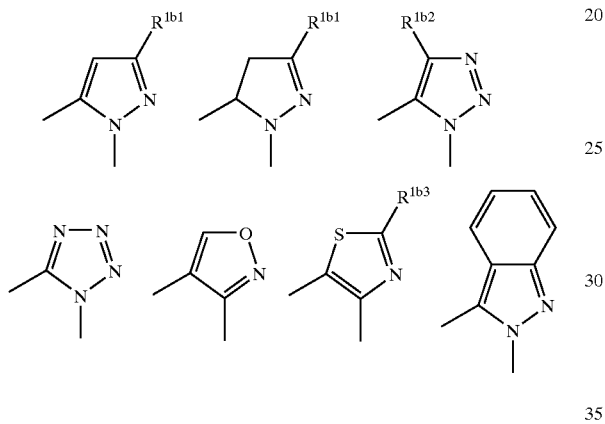

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 35

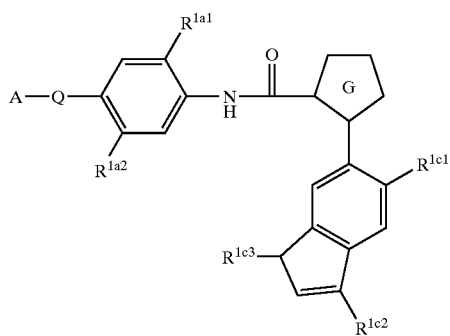

TABLE 35-continued

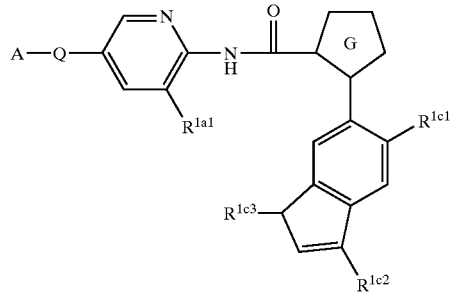

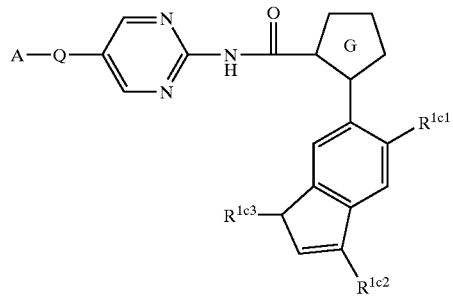

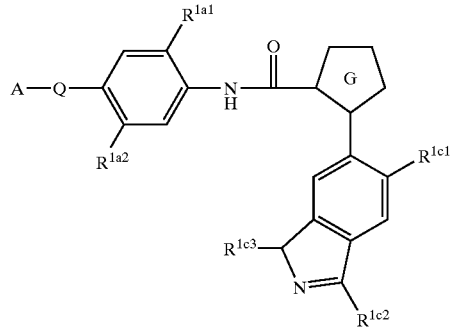

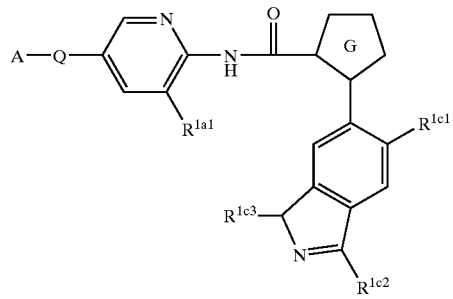

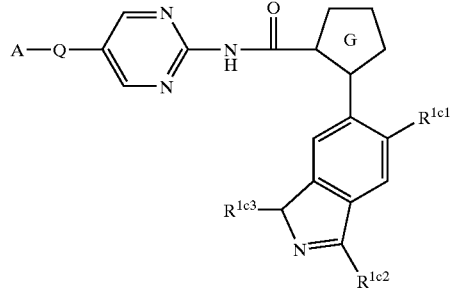

wherein:

A—Q is selected from the group consisting of:
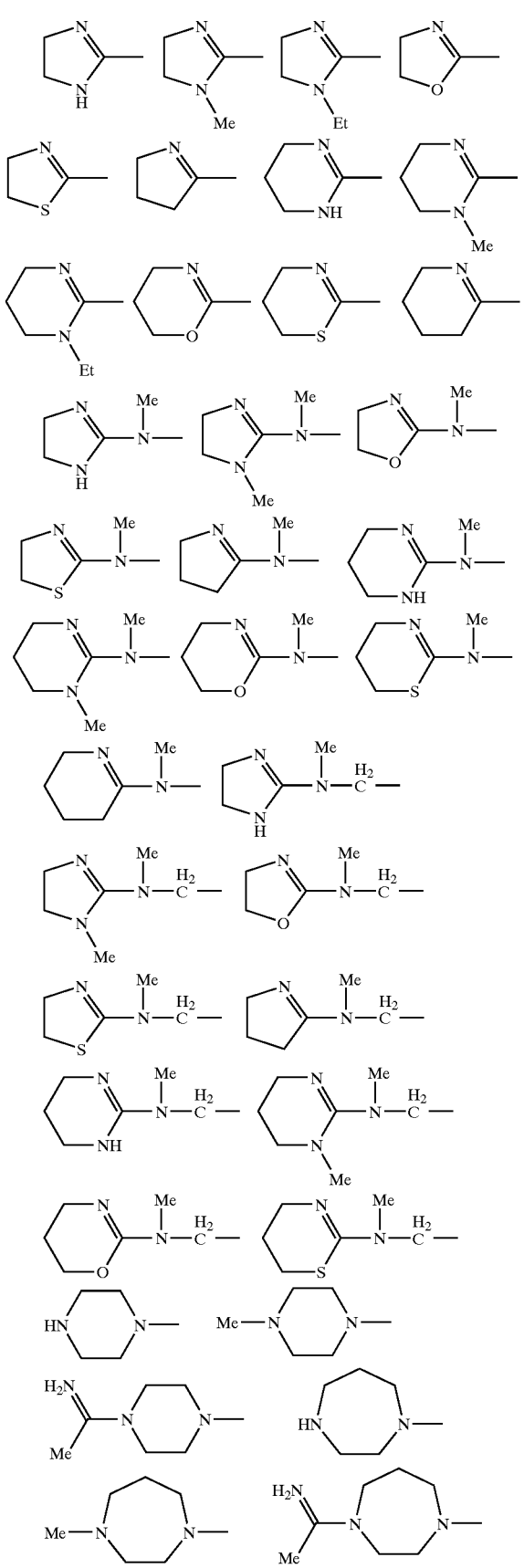
-continued
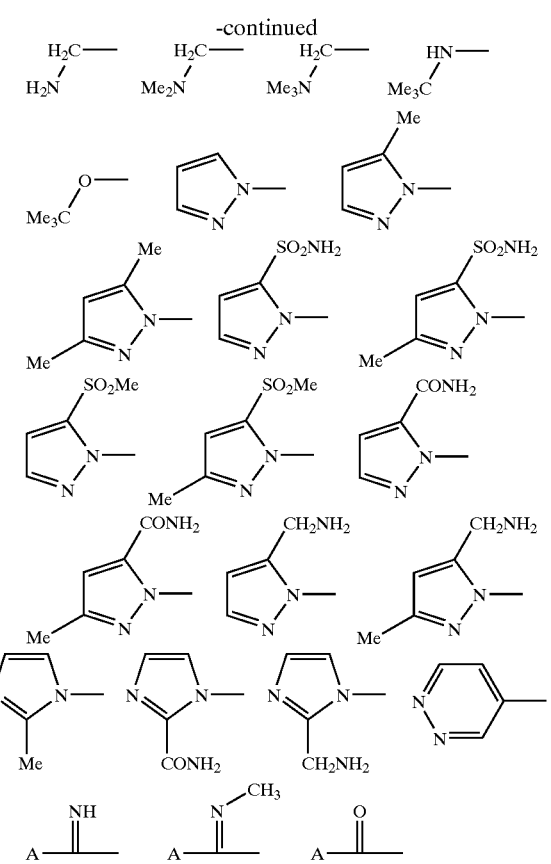
wherein:
A is selected from the group consisting of:
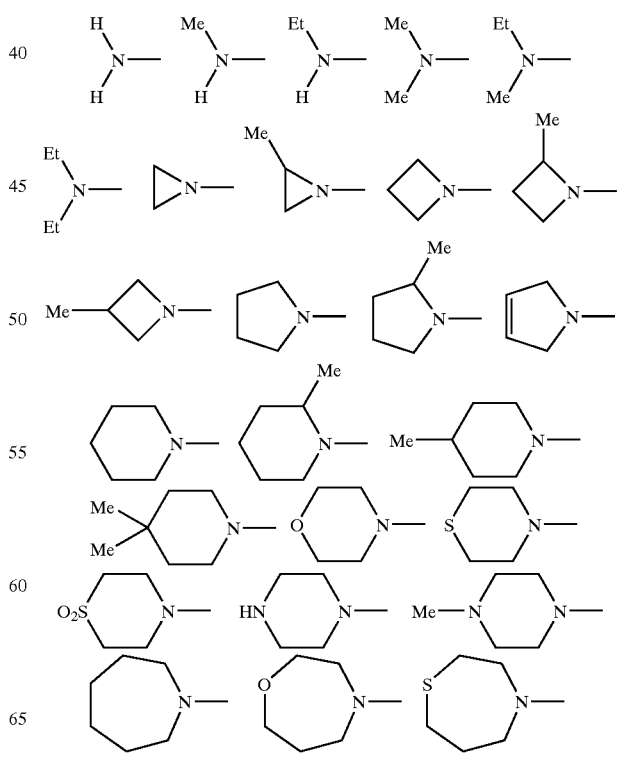

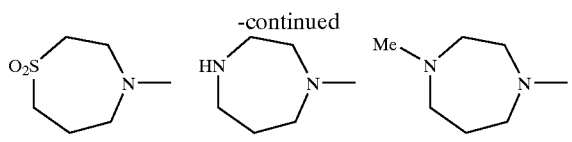

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1b2}$ and $R^{1b3}$ are independently selected from the group consisting of —H, —F, —Cl, —Br, and —OCH$_3$; and G is selected from the group consisting of:

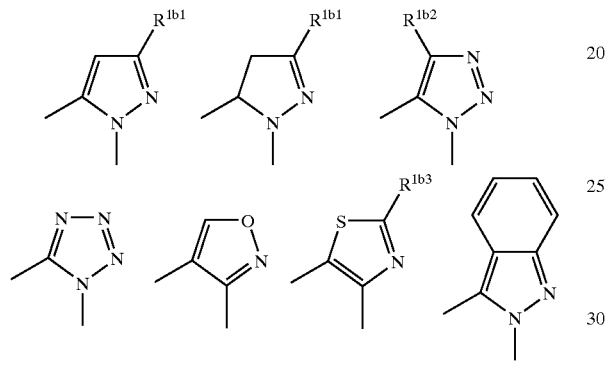

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 36

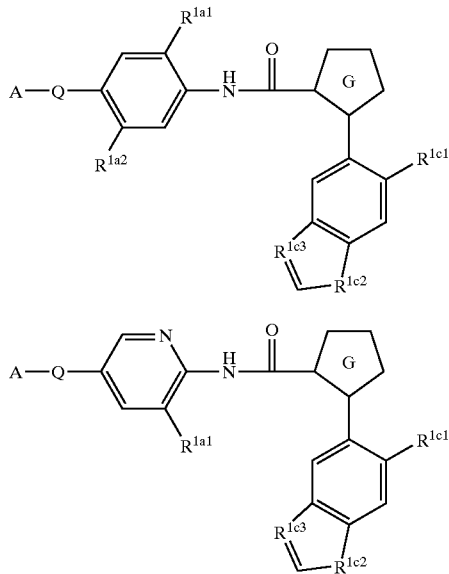

TABLE 36-continued

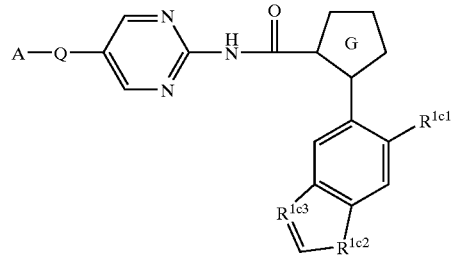

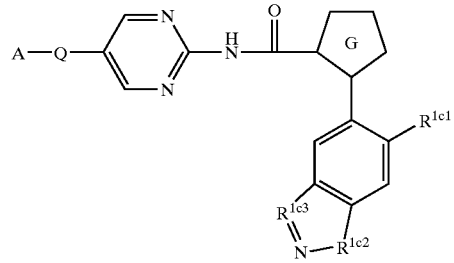

wherein:

A—Q is selected from the group consisting of:

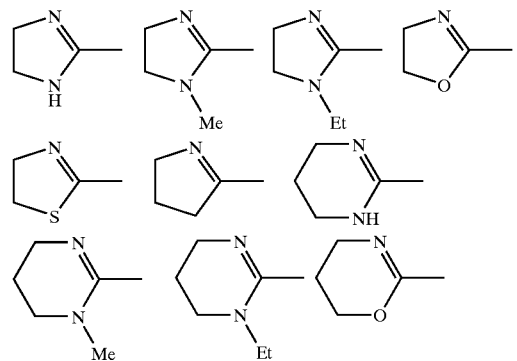

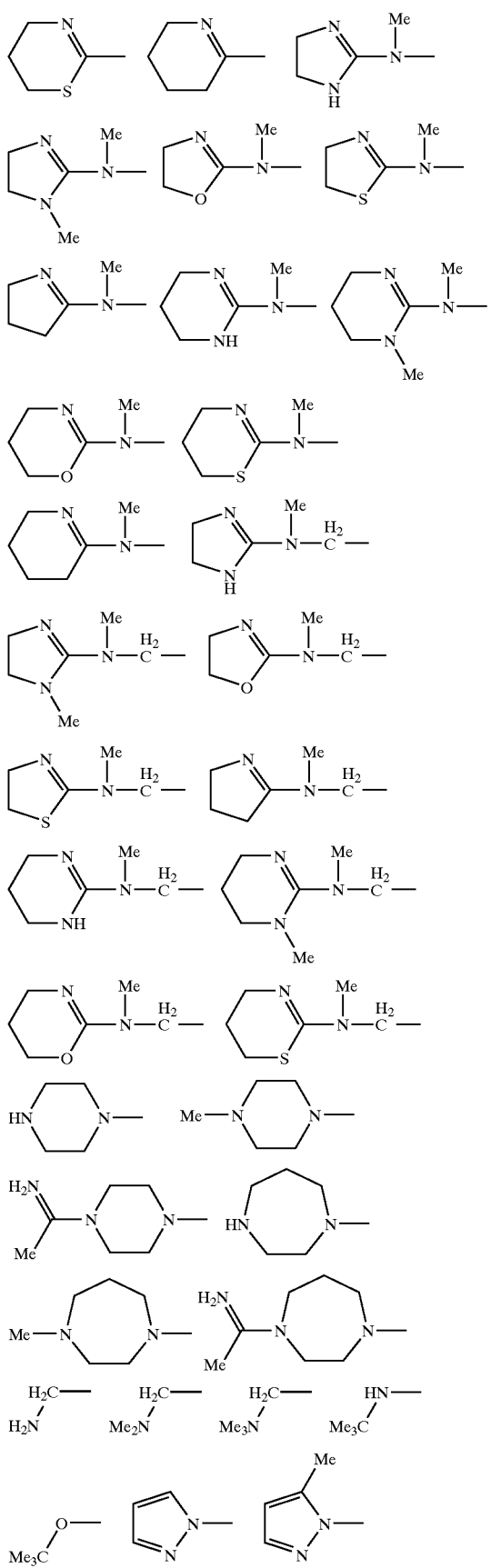
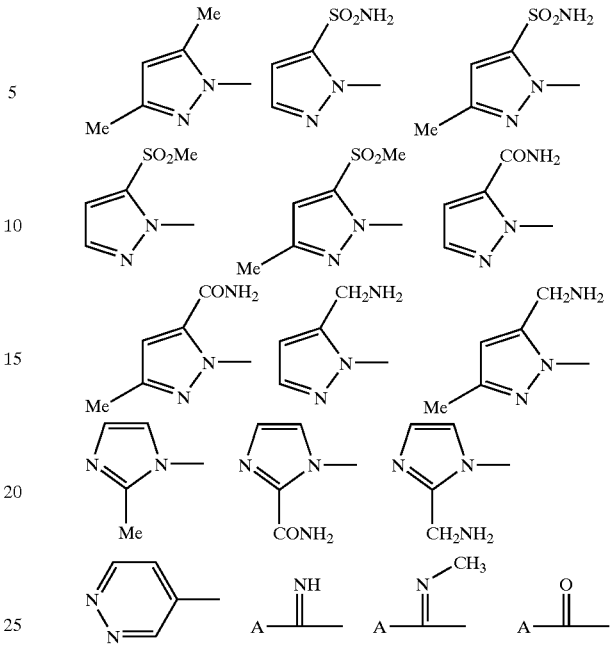
wherein:
A is selected from the group consisting of:
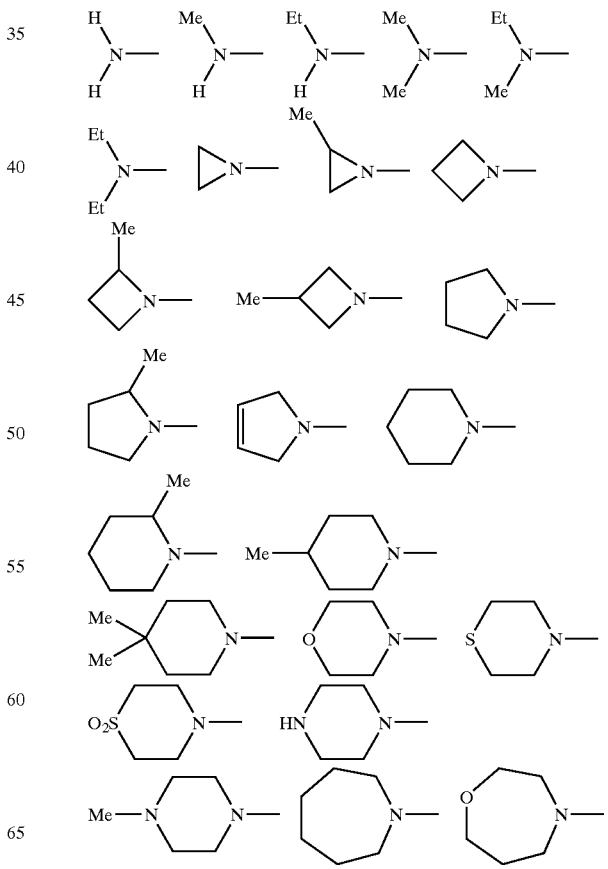

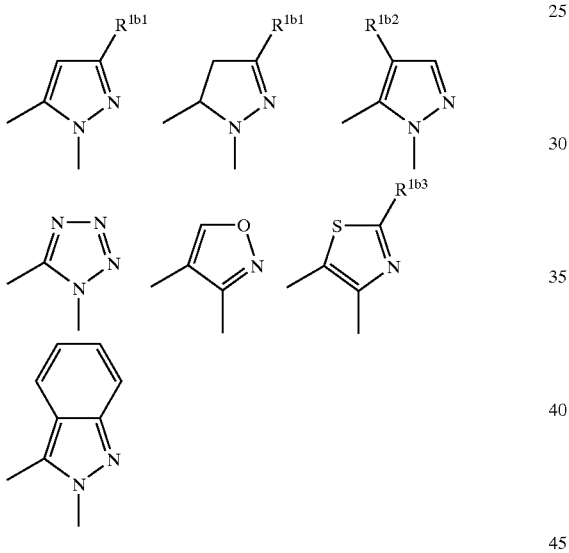

$R^{1a1}$ and $R^{1a2}$ are independently selected from the group consisting of —H, —F, —Cl and —Br;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —CH$_2$—, —O— and —NH—;

$R^{1c3}$ is selected from the group consisting of —CH—, —C(NH$_2$)— and —N—; and G is selected from the group consisting of:

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 37

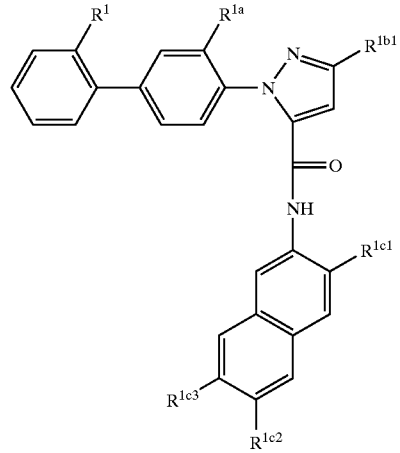

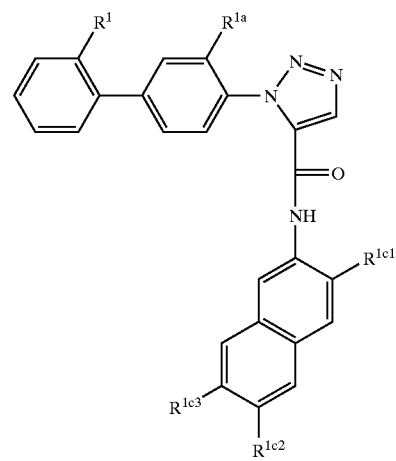

TABLE 37-continued

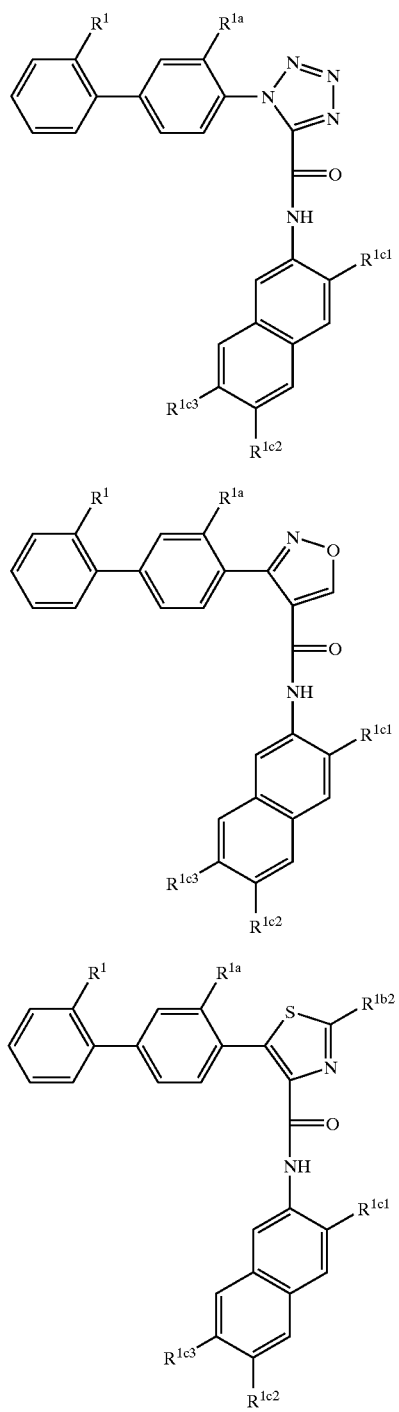

TABLE 38

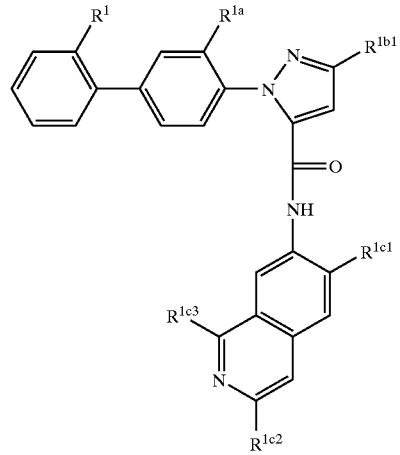

wherein:

$R^1$ is selected from the group consisting of —$SO_2NH_2$, —$SO_2CH_3$, —CN, —$CONH_2$, —$CONH(CH_3)$, —$CON(CH_3)_2$, —$CH_2NH_2$, —$CH_2NH(CH_3)$, —$CH_2N(CH_3)_2$;

$R^{1a}$ is selected from the group consisting of —H, —F, —Cl and —Br;

$R^{1b1}$ is selected from the group consisting of —H, —$CH_3$ and —$CF_3$;

$R^{1b2}$ is selected from the group consisting of —Cl, —$NH_2$, —$CH_3$ and —$CF_3$;

$R^{1c1}$ is selected from the group consisting of —H, —F, —Cl, —Br, —CN, —$CH_2NH_2$, —$CH_2OH$, —$CONH_2$, —C(=NH)$NH_2$, —$CO_2H$, —$CO_2Me$, —$SO_2Me$, —$SO_2NH_2$, —OH, —$NH_2$, and —$NO_2$;

$R^{1c2}$ is selected from the group consisting of —H, —F, —Cl and —Br; and $R^{1c3}$ is selected from the group consisting of —H, —F, —Cl and —Br.

TABLE 38-continued

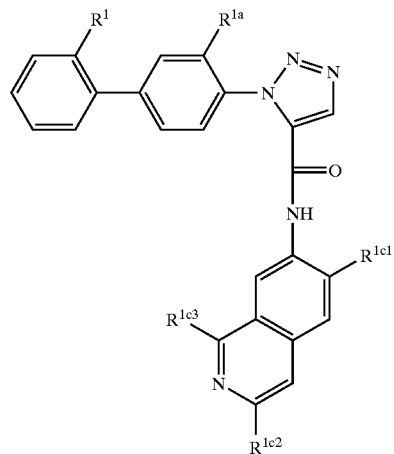

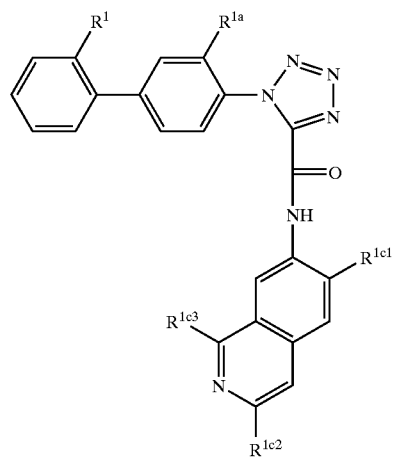

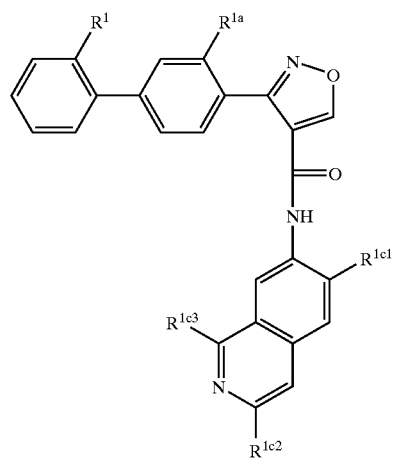

TABLE 38-continued

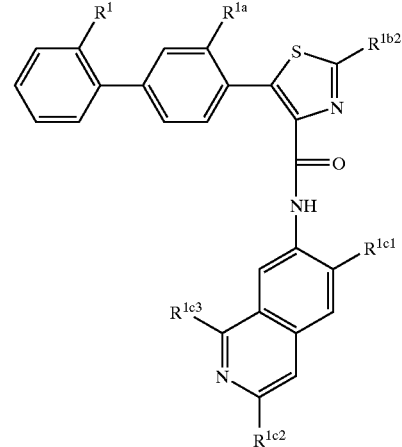

wherein:
R$^1$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;
R$^{1a}$ is selected from the group consisting of —H, —F, —Cl and —Br;
R$^{1b1}$ is selected from the group consisting of —H, —CH$_3$ and —CF$_3$;
R$^{1b2}$ is selected from the group consisting of —Cl, —NH$_2$, —CH$_3$ and —CF$_3$;
R$^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;
R$^{1c2}$ is selected from the group consisting of —H, —F, —Cl and —Br; and
R$^{1c3}$ is selected from the group consisting of —H and —NH$_2$.

TABLE 39

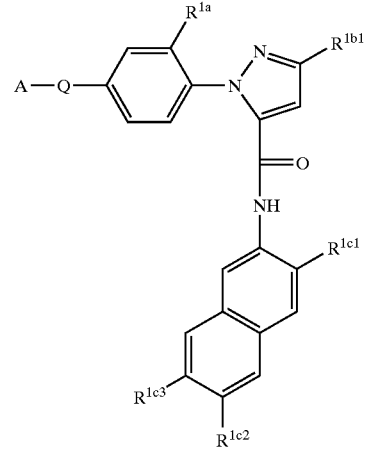

TABLE 39-continued
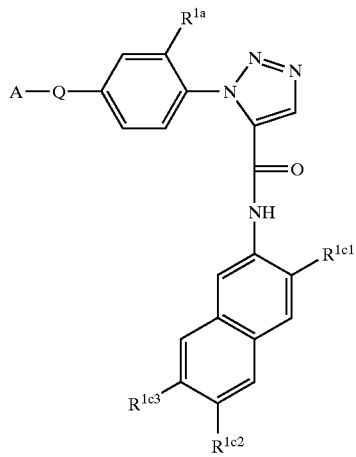
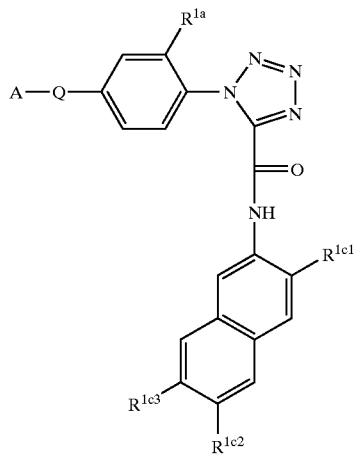
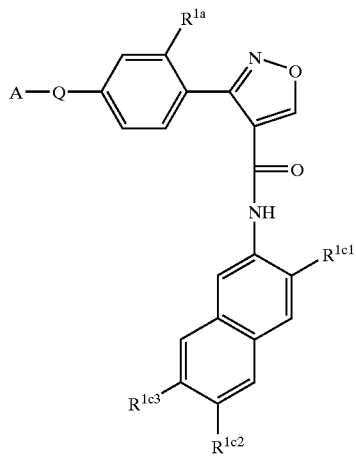
TABLE 39-continued
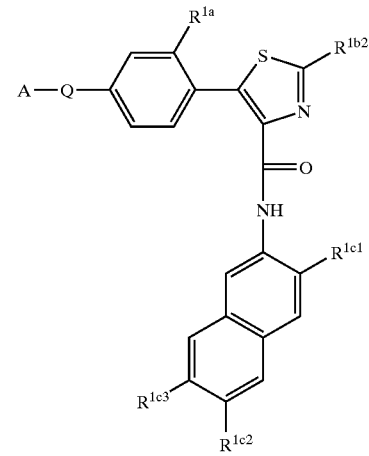
wherein:
A—Q is selected from the group consisting of:
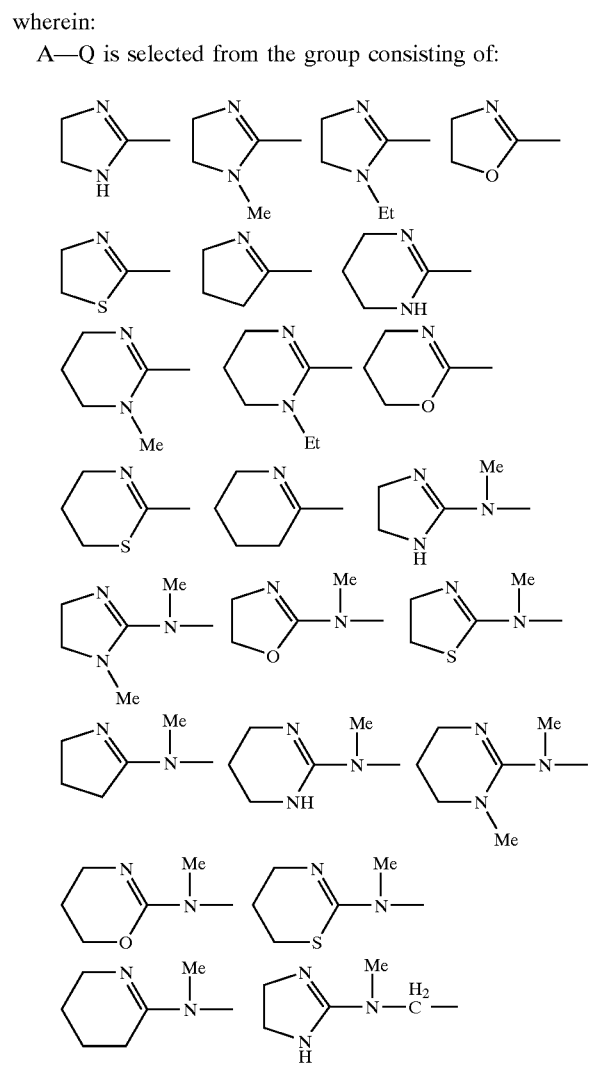

-continued

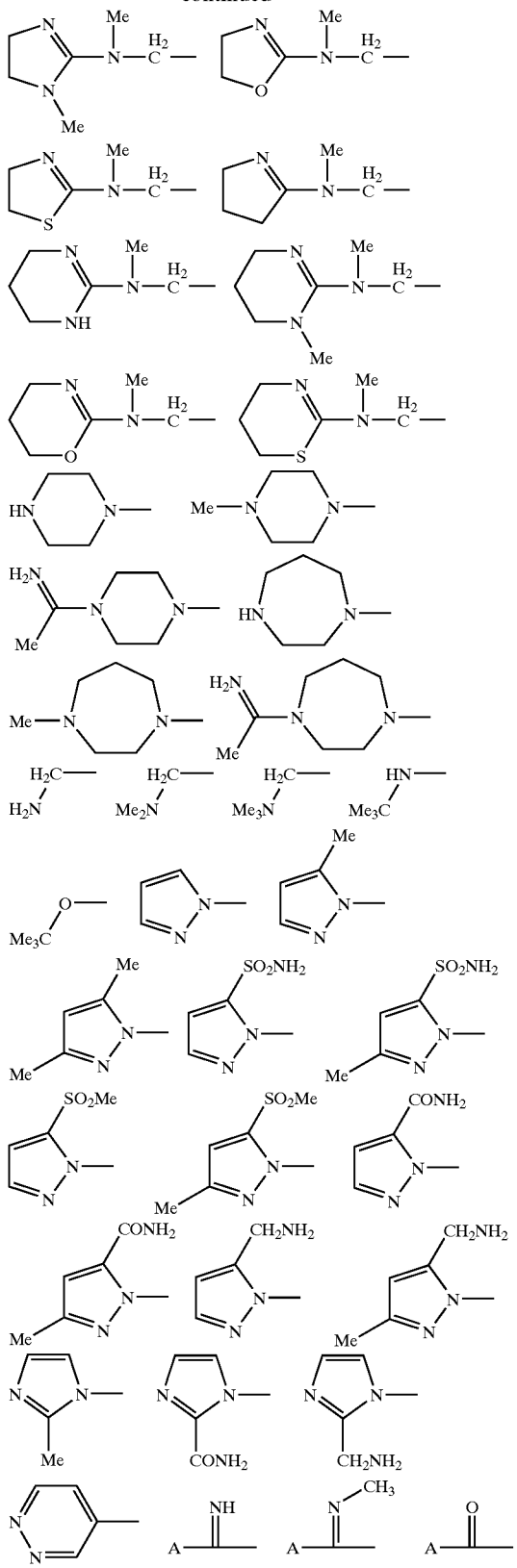

wherein:

A is selected from the group consisting of:

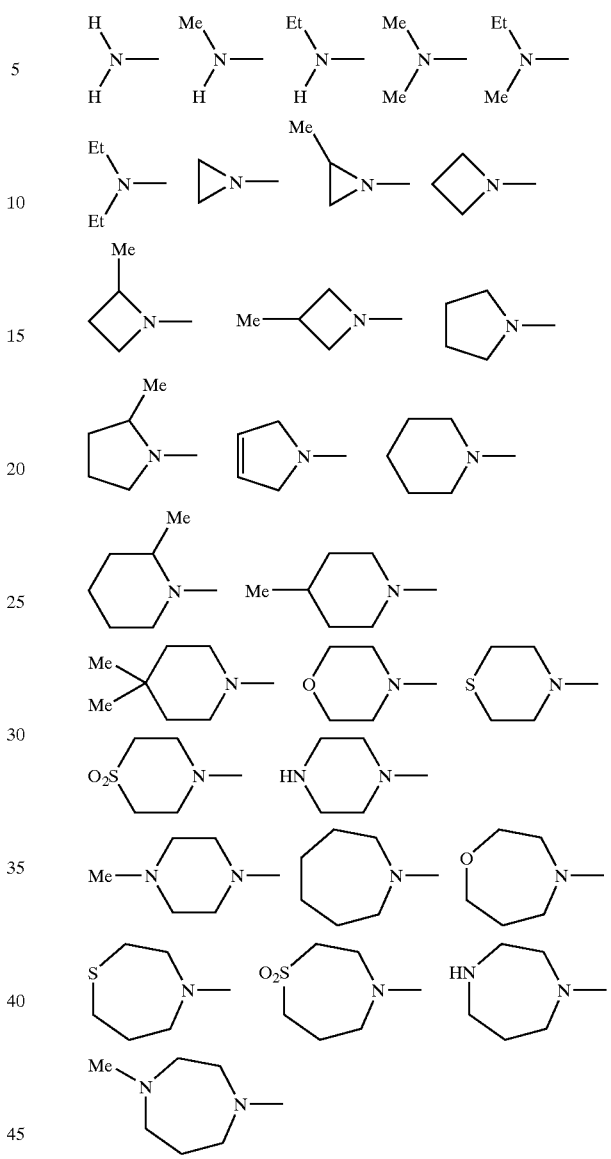

$R^{1a}$ is selected from the group consisting of —H, —F, —Cl and —Br;

$R^{1b1}$ is selected from the group consisting of —H, —CH$_3$ and —CF$_3$;

$R^{1b2}$ is selected from the group consisting of —Cl, —NH$_2$, —CH$_3$ and —CF$_3$;

$R^{1c1}$ is selected from the group consisting of —H, —F, —Cl, —Br, —CN, —H$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl and —Br; and $R^{1c3}$ is selected from the group consisting of —H, —F, —Cl and —Br.

TABLE 40
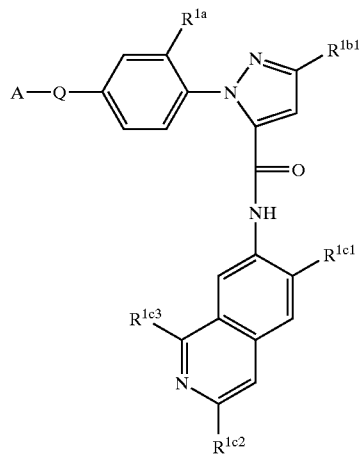
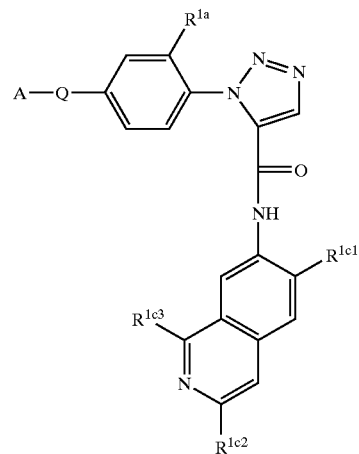
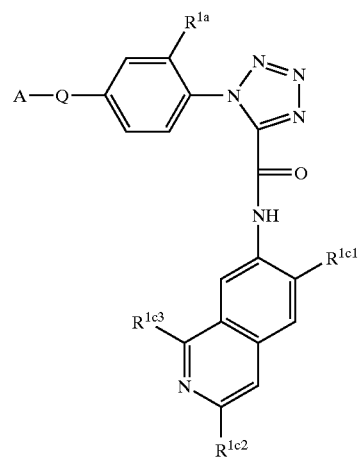
TABLE 40-continued
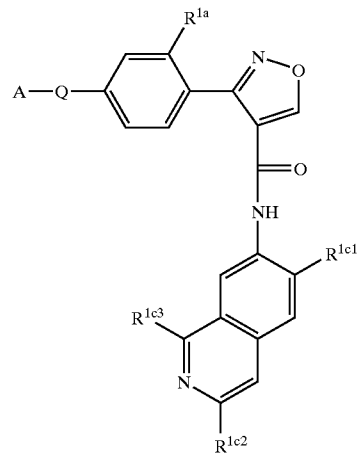
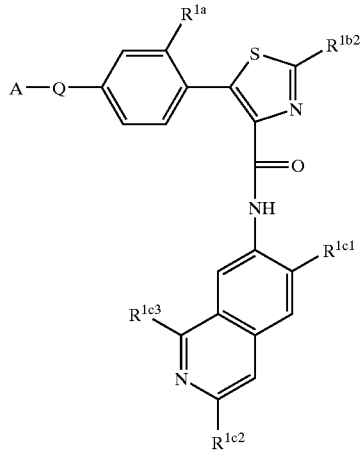
wherein:
A—Q is selected from the group consisting of:
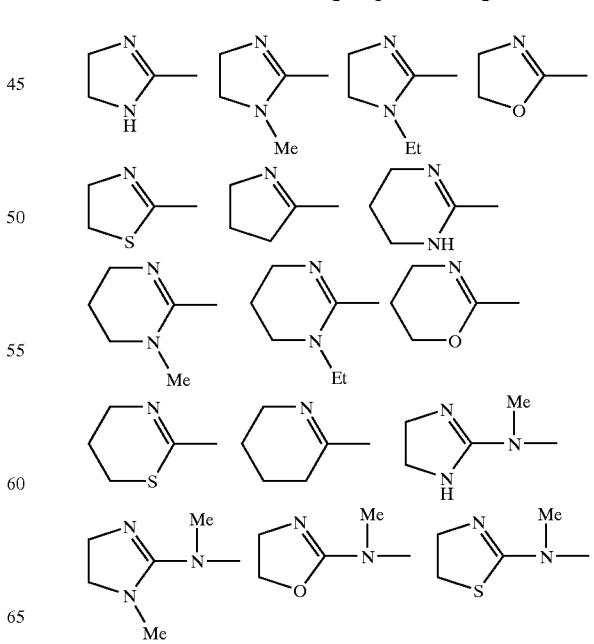

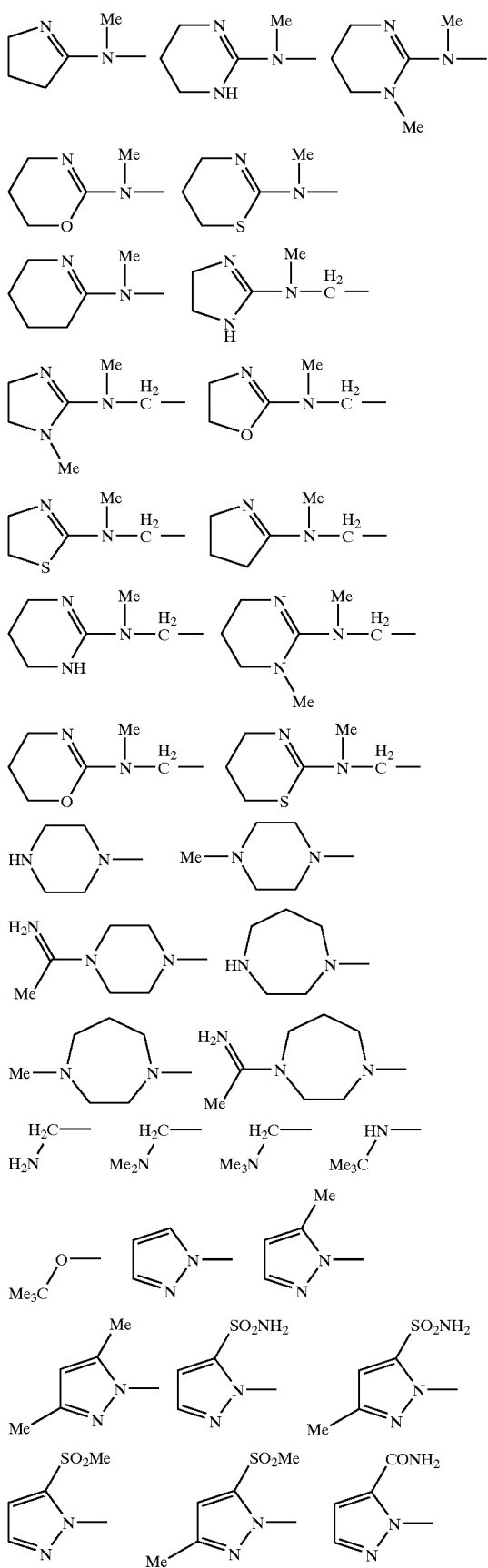
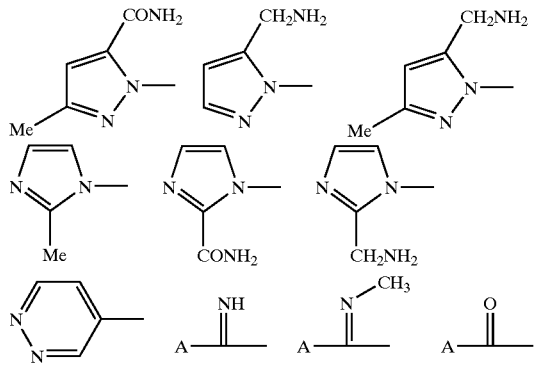
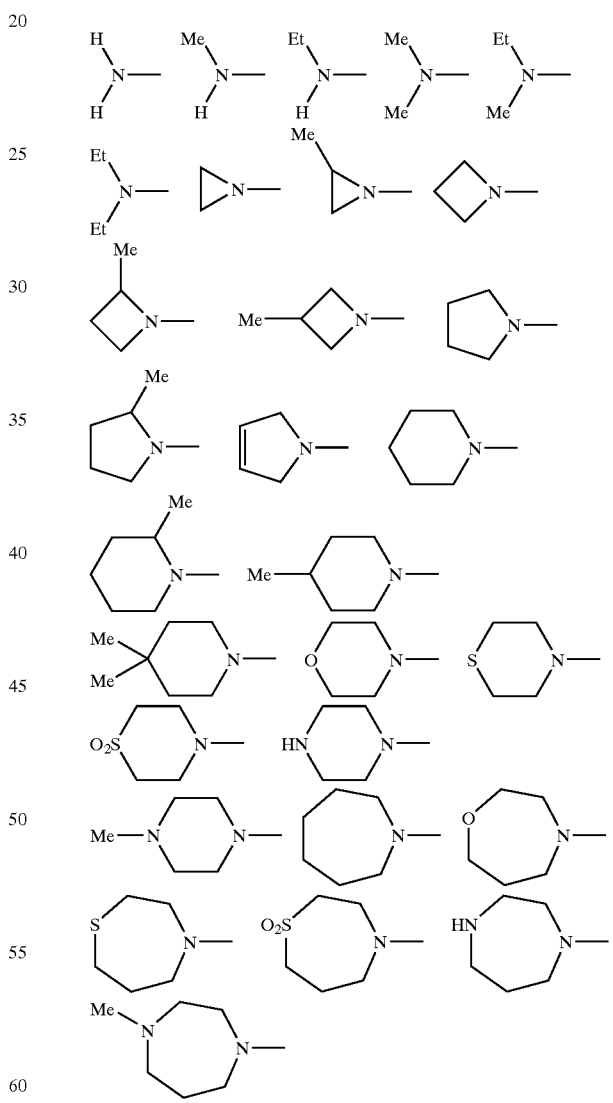
wherein:
A is selected from the group consisting of:
$R^{1a}$ is selected from the group consisting of —H, —F, —Cl and —Br;
$R^{1b1}$ is selected from the group consisting of —H, —CH$_3$ and —CF$_3$; $R^{1b2}$ is selected from the group consisting of —Cl, —NH$_2$, —CH$_3$ and —CF$_3$;

$R^{1c1}$ is selected from the group consisting of —H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

$R^{1c2}$ is selected from the group consisting of —H, —F, —Cl and —Br; and $R^{1c3}$ is selected from the group consisting of —H and —NH$_2$.

TABLE 41

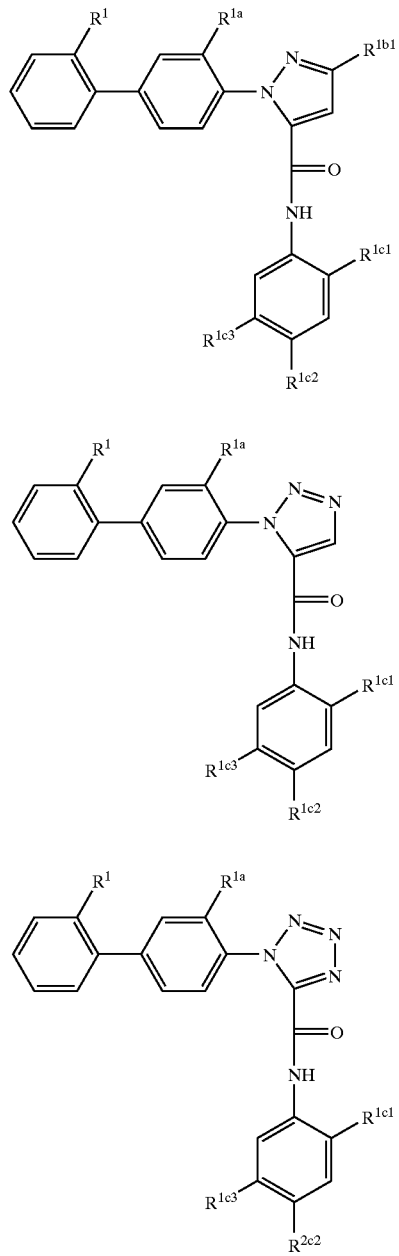

TABLE 41-continued

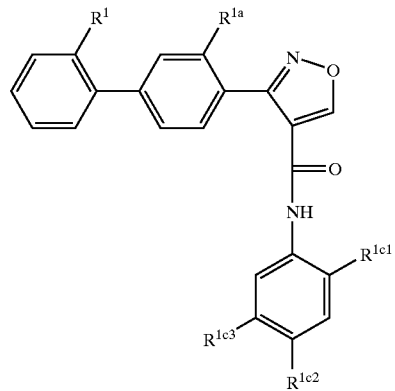

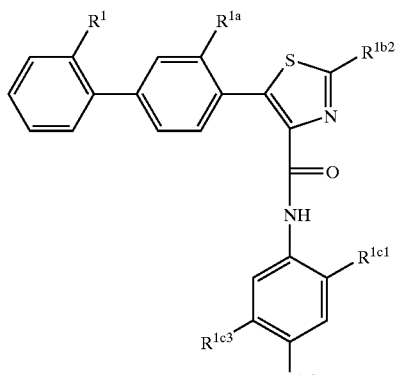

wherein:

$R^1$ is selected from the group consisting of —SO$_2$NH$_2$, —SO$_2$CH$_3$, N, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

$R^{1a}$ is selected from the group consisting of —H, —F, —Cl and —Br;

$R^{1b1}$ is selected from the group consisting of —H, —CH$_3$ and CF$_3$;

$R^{1b2}$ is selected from the group consisting of —Cl, —NH$_2$, —CH$_3$ and CF$_3$;

$R^{1c1}$ is selected from the group consisting of —H, —F, —CN, —CH$_2$NH$_2$, —CONH$_2$, —SO$_2$Me, —SO$_2$NH$_2$ and —NO$_2$;

$R^{1c2}$ is selected from the group consisting of —H, —F, —Cl, —Br and OCH$_3$; and $R^{1c3}$ is selected from the group consisting of —H, —F, —Cl, Br, —OCH$_3$, —CH$_2$NH$_2$, —CONH$_2$ and —C(N=H)NH$_2$.

TABLE 42
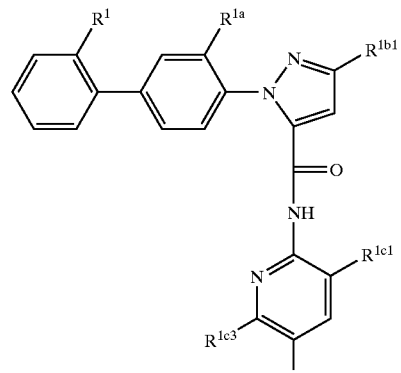
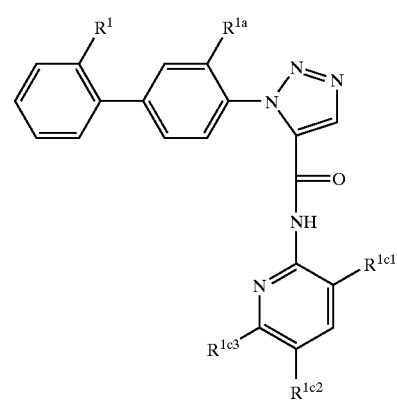
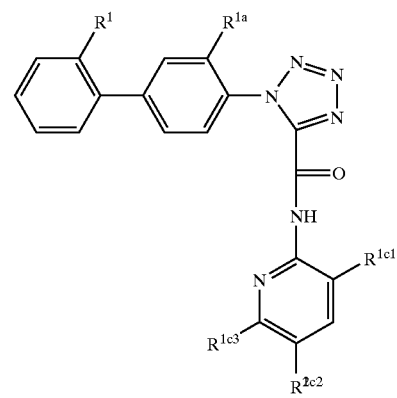
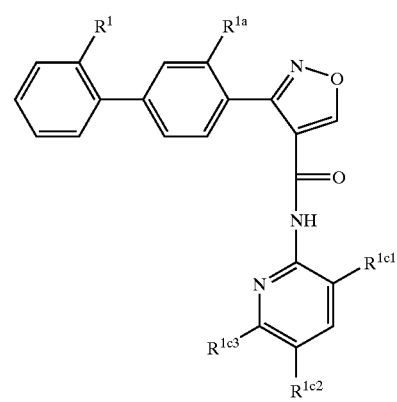
TABLE 42-continued
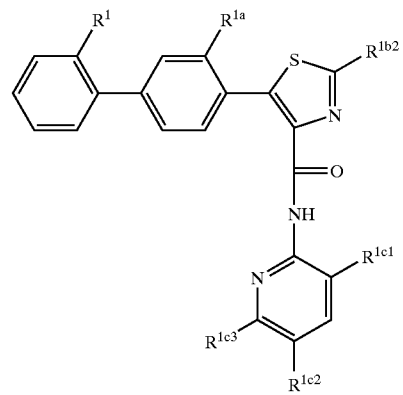
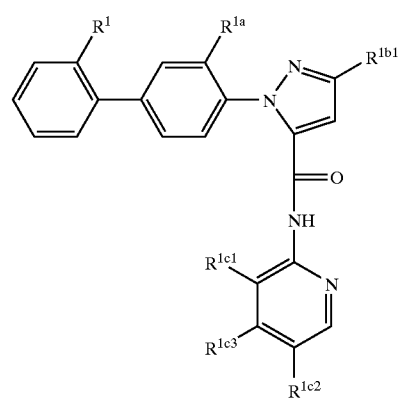
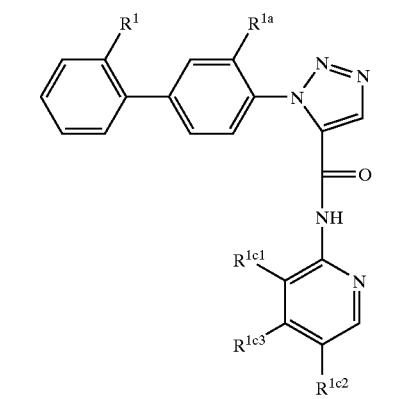
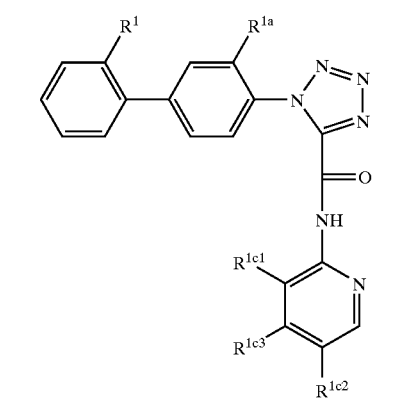

TABLE 42-continued

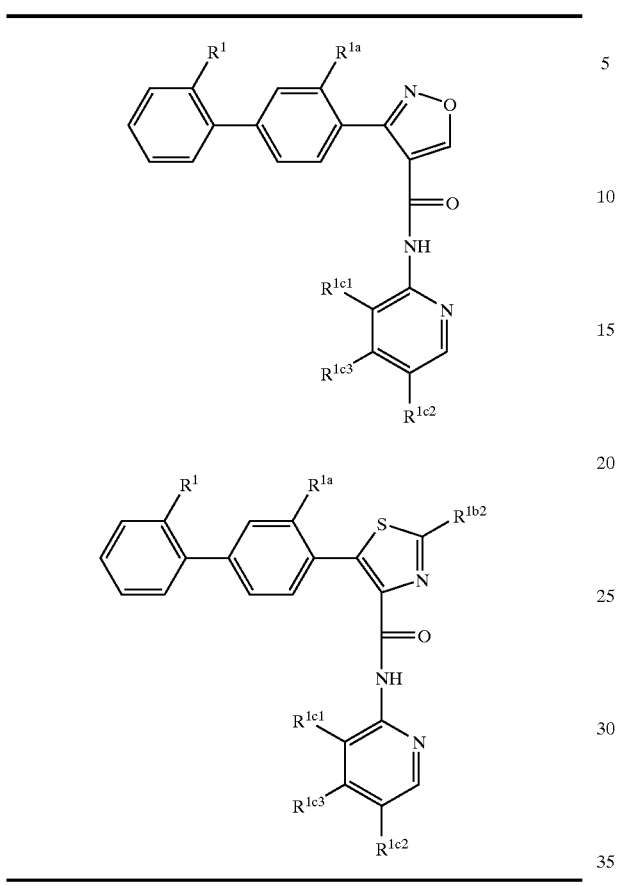

TABLE 43

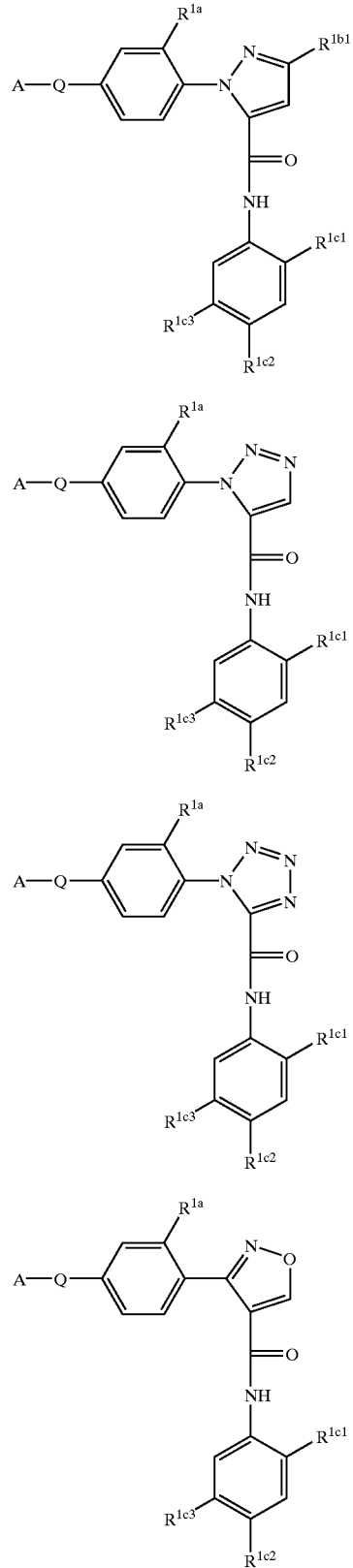

wherein:

R¹ is selected from the group consisting of —SO₂NH₂, —SO₂CH₃, —CN, —CONH₂, —CONH(CH₃), —CON(CH₃)₂, —CH₂NH₂, —CH₂NH(CH₃), —CH₂N(CH₃)₂;

R¹ᵃ is selected from the group consisting of —H, —F, —Cl and —Br;

R¹ᵇ¹ is selected from the group consisting of —H, —CH₃ and —CF₃;

R¹ᵇ² is selected from the group consisting of —Cl, —NH₂, —CH₃ and —CF₃;

R¹ᶜ¹ is selected from the group consisting of —H, —F, —CN, —CH₂NH₂, —CONH₂, —SO₂Me, —SO₂NH₂ and —NO₂;

R¹ᶜ² is selected from the group consisting of —H, —F, —Cl, —Br and —OCH₃; and

R¹ᶜ³ is selected from the group consisting of —H, —F, —Cl, Br, —OCH₃, —CH₂NH₂, —CONH₂ and —C(N=H)NH₂.

TABLE 43-continued
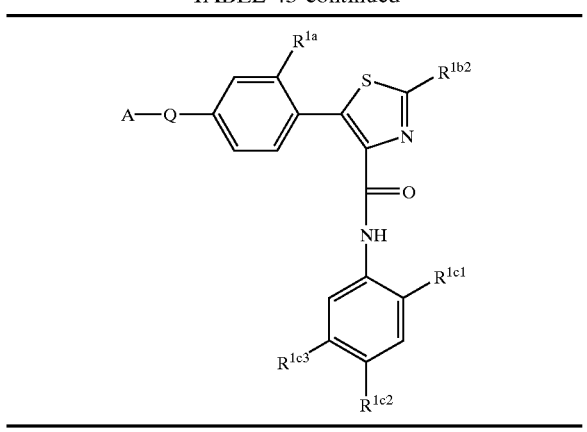
wherein:
A—Q is selected from the group consisting of:
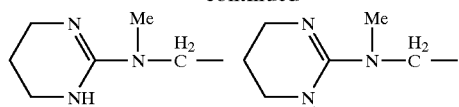
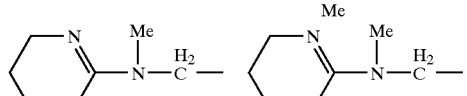
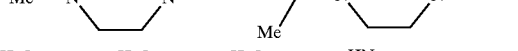
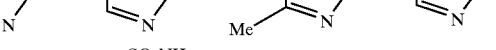
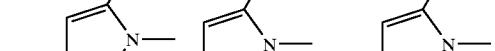
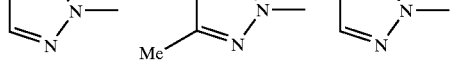
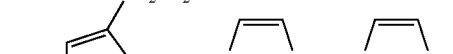
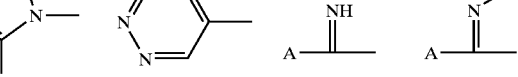
wherein:
A is selected from the group consisting of:
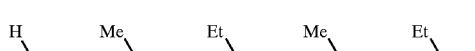
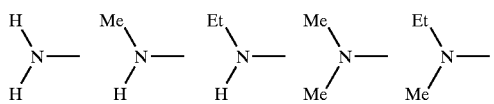

-continued

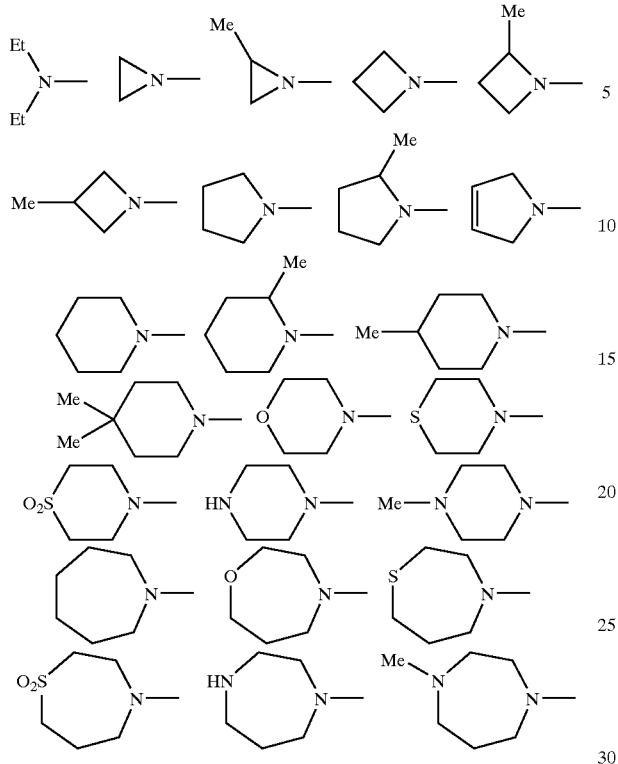

R$^{1a}$ is selected from the group consisting of —H, —F, —Cl and —Br;

R$^{1b1}$ is selected from the group consisting of —H, —CH$_3$ and —CF$_3$;

R$^{1b2}$ is selected from the group consisting of —Cl, —NH$_2$, —CH$_3$ and —CF$_3$;

R$^{1c1}$ is selected from the group consisting of —H, —F, —CN, —CH$_2$NH$_2$, —CONH$_2$, —SO$_2$Me, —SO$_2$NH$_2$ and —NO$_2$;

R$^{1c2}$ is selected from the group consisting of —H, —F, —Cl, —Br and —OCH$_3$; and R$^{1c3}$ is selected from the group consisting of —H, —F, —Cl, Br, —OCH$_3$, —CH$_2$NH$_2$, —CONH$_2$ and —C(N═H)NH$_2$.

TABLE 44

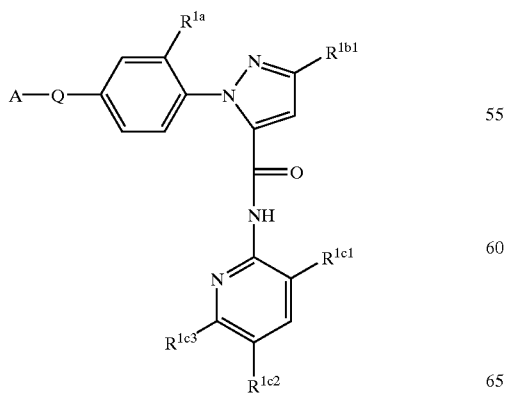

TABLE 44-continued

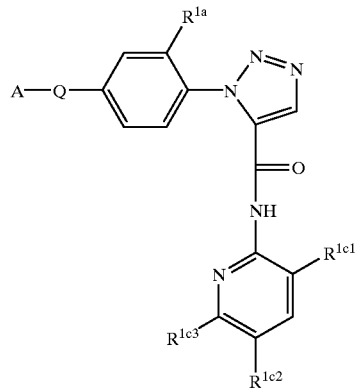

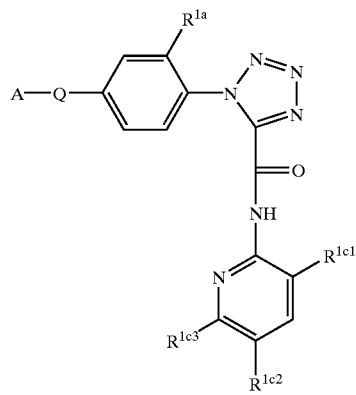

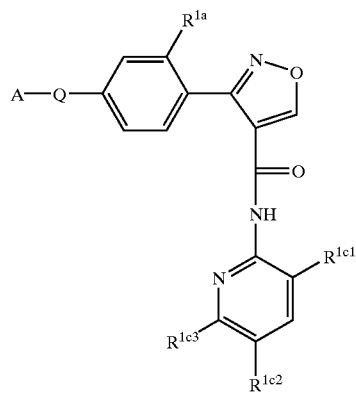

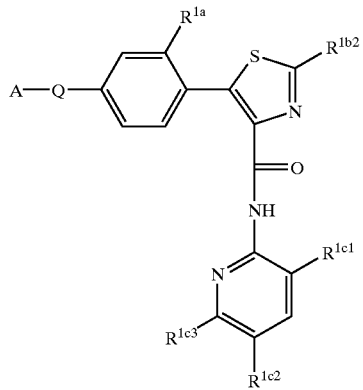

TABLE 44-continued
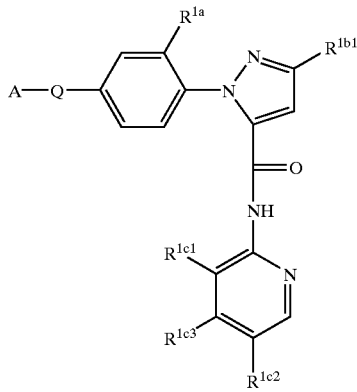
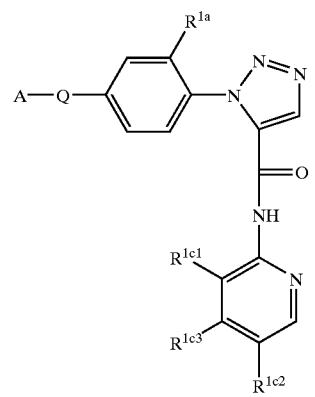
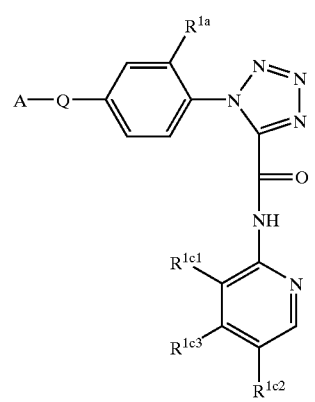
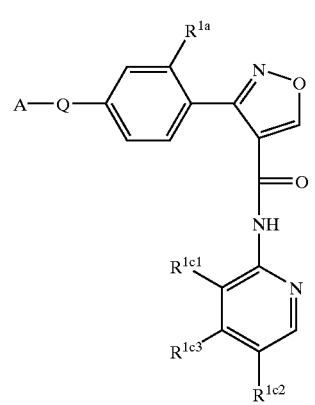
TABLE 44-continued
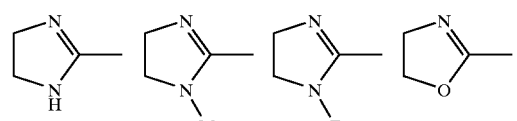
wherein:
A—Q is selected from the group consisting of:
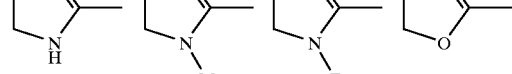
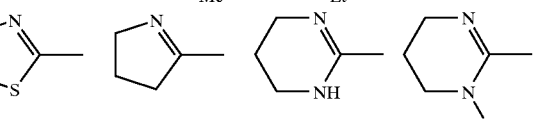
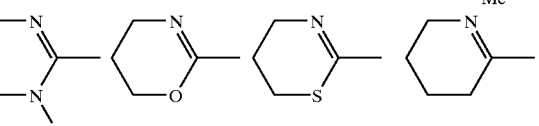
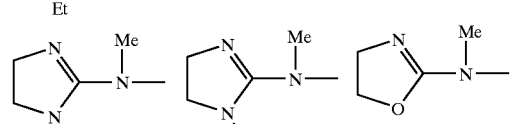
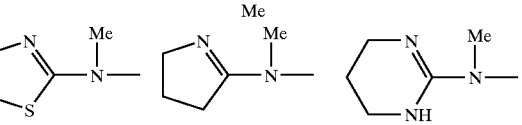
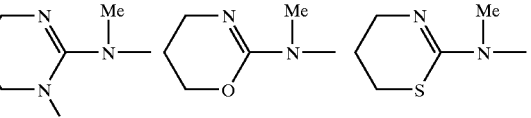
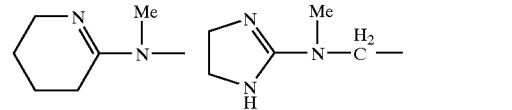
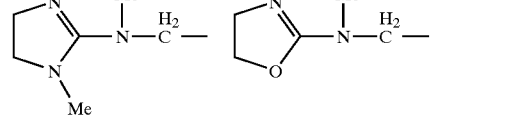
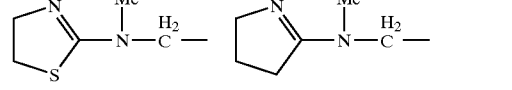

-continued

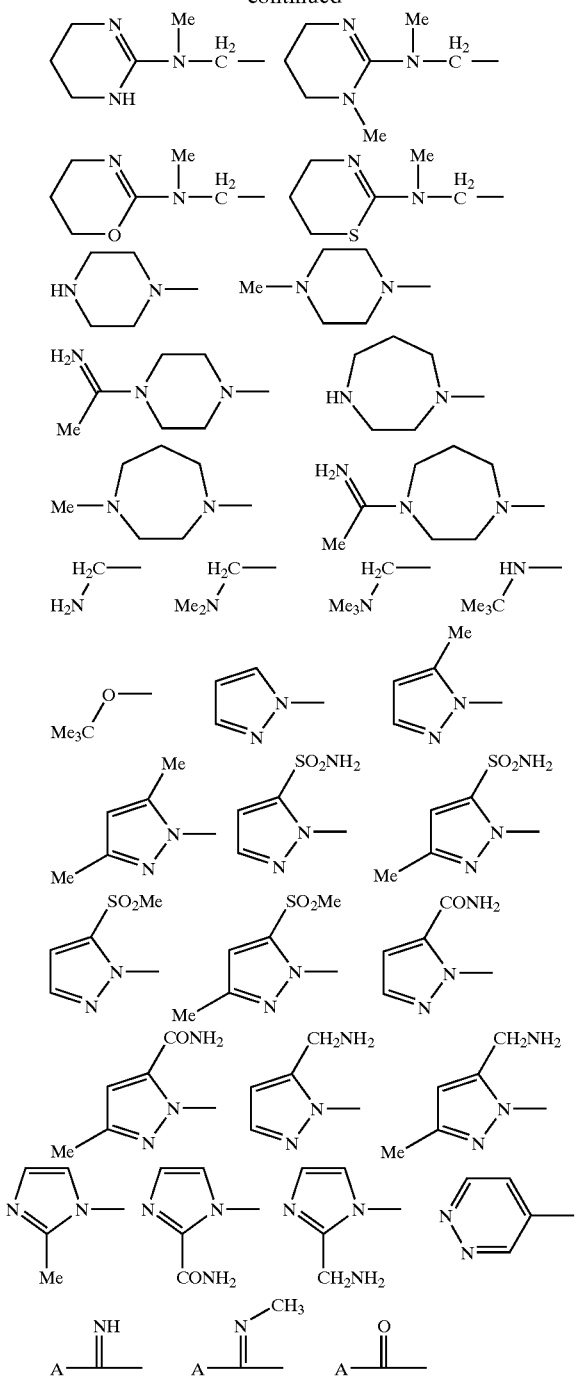

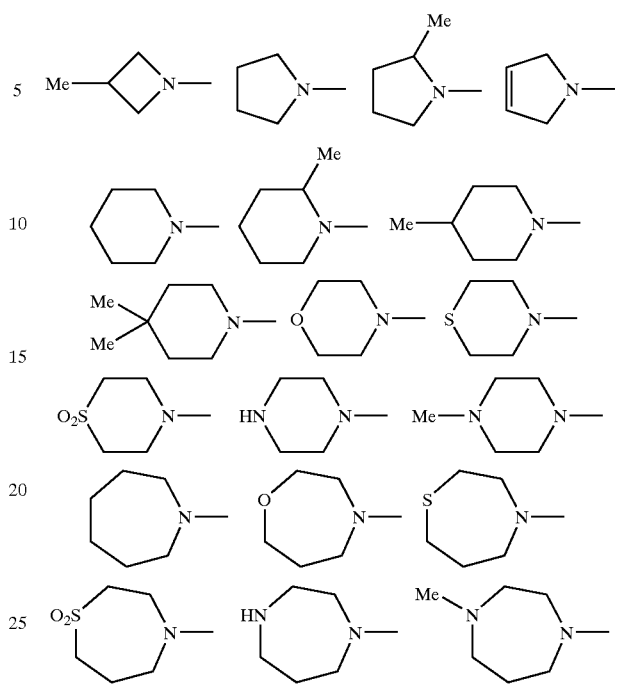

wherein:

A is selected from the group consisting of:

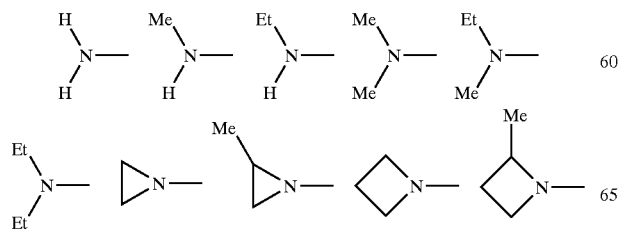

$R^{1a}$ is selected from the group consisting of —H, —F, —Cl and —Br;

$R^{1b1}$ is selected from the group consisting of —H, —CH$_3$ and —CF$_3$;

$R^{1b2}$ is selected from the group consisting of —Cl, —NH$_2$, —CH$_3$ and —CF$_3$;

$R^{1c1}$ is selected from the group consisting of —H, —F, —CN, —CH$_2$NH$_2$, —CONH$_2$, —SO$_2$Me, —SO$_2$NH$_2$ and —NO$_2$;

$R^{1c2}$ is selected from the group consisting of —H, —F, —Cl, —Br and —OCH$_3$; and $R^{1c3}$ is selected from the group consisting of —H, —F, —Cl, Br, —OCH$_3$, —CH$_2$NH$_2$, —CONH$_2$ and —C(N=H)NH$_2$.

TABLE 45

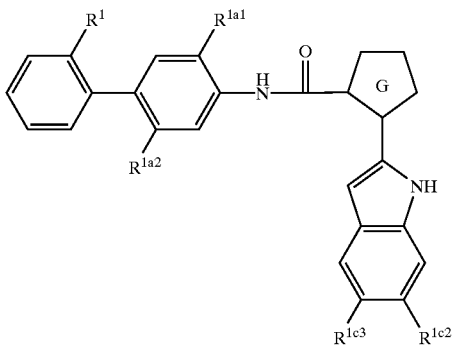

TABLE 45-continued
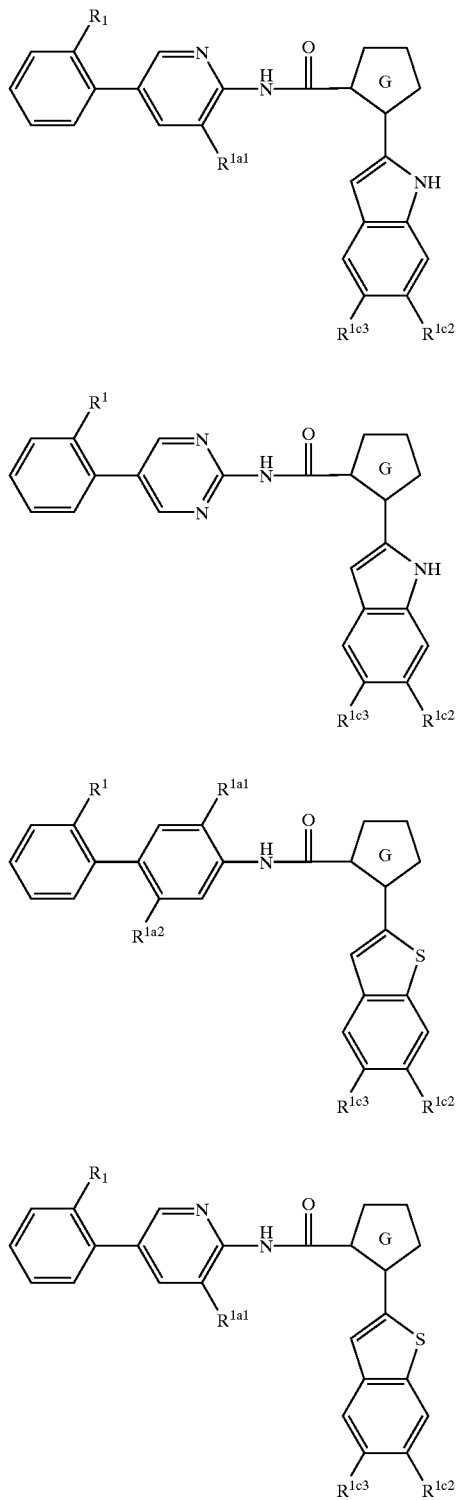
TABLE 45-continued
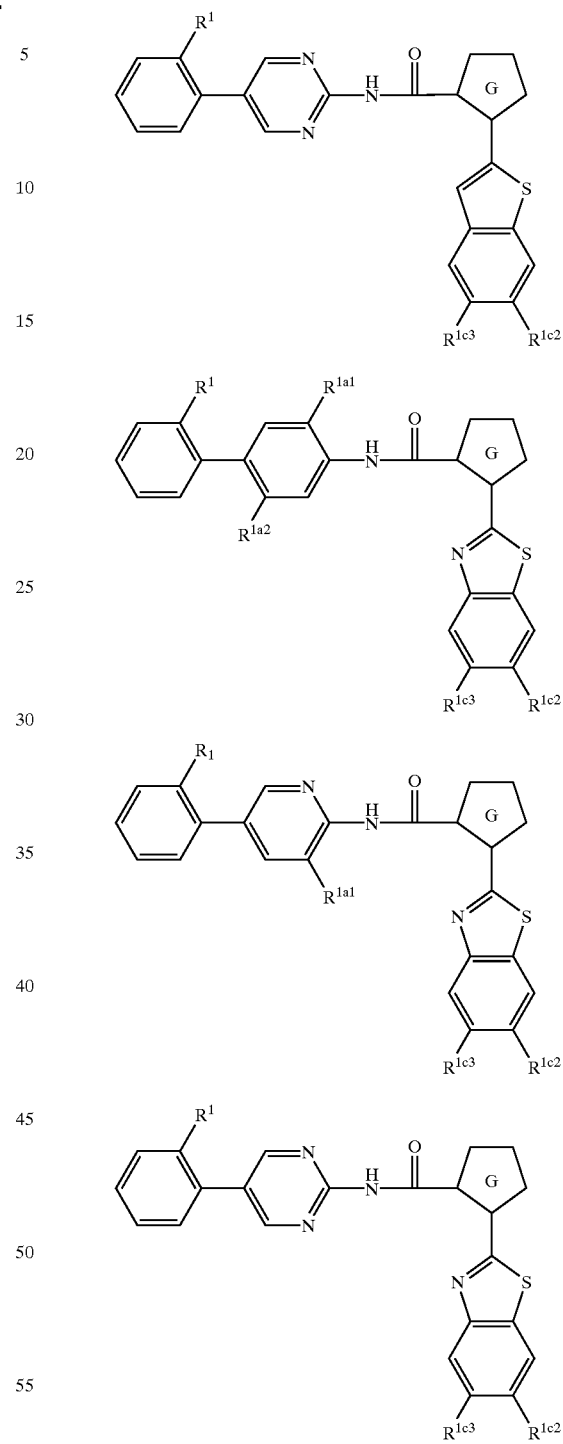
wherein:
R[1] is selected from the group consisting of —SO$_2$NH$_2$, —SO$_2$CH$_3$, —CN, —CONH$_2$, —CONH(CH$_3$),

—CON(CH$_3$)$_2$, —CH$_2$NH$_2$, —CH$_2$NH(CH$_3$), —CH$_2$N(CH$_3$)$_2$;

R$^{1a1}$ and R$^{1a2}$ are independently selected from the group consisting of —H, —F, —Cl and —Br;

R$^{1c2}$ and R$^{1c3}$ are independently selected from the group consisting of —H, —F, —Cl, —Br, and —OCH$_3$; and G is selected from the group consisting of:

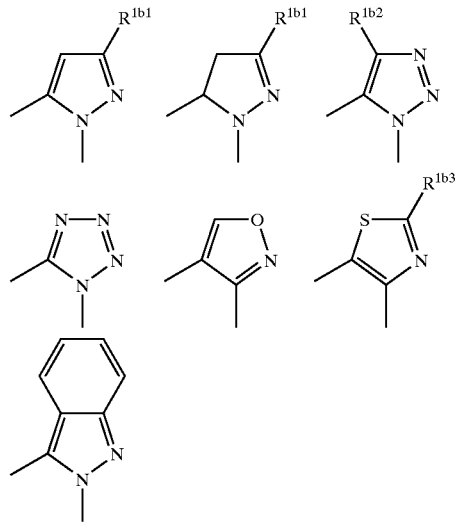

wherein:

R$^{1b1}$ is selected from the group consisting of —H, —CH$_3$ and —CF$_3$;

R$^{1b2}$ is selected from the group consisting of —H, —CH$_3$ and —CF$_3$; and

R$^{1b3}$ is selected from the group consisting of —Cl, —NH$_2$, —CH$_3$ and —CF$_3$.

TABLE 46

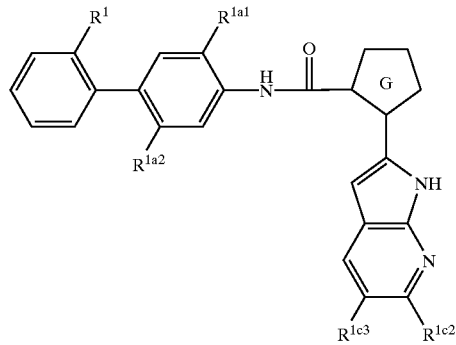

TABLE 46-continued

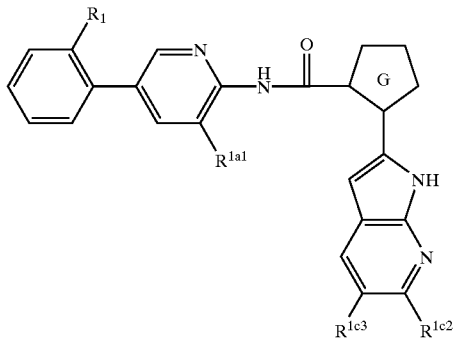

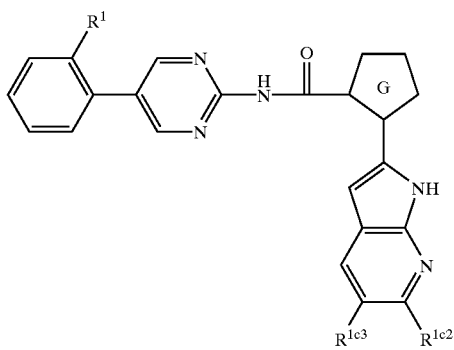

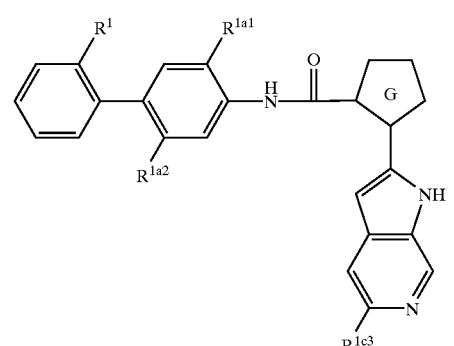

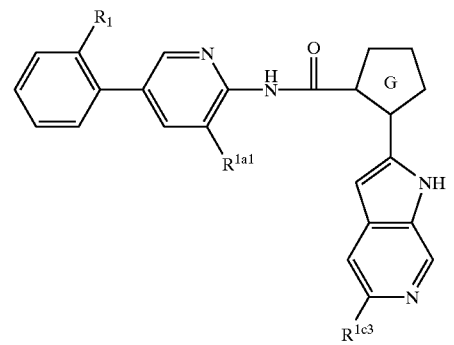

TABLE 46-continued

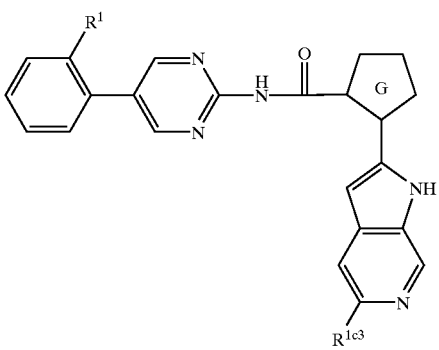

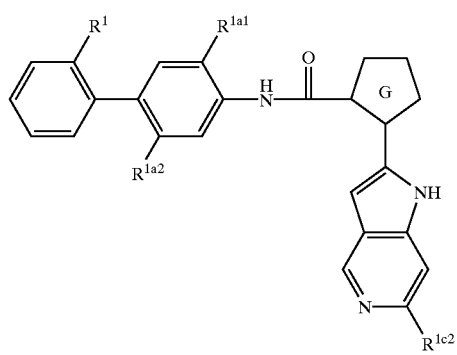

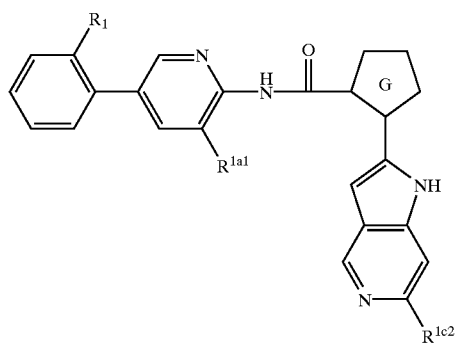

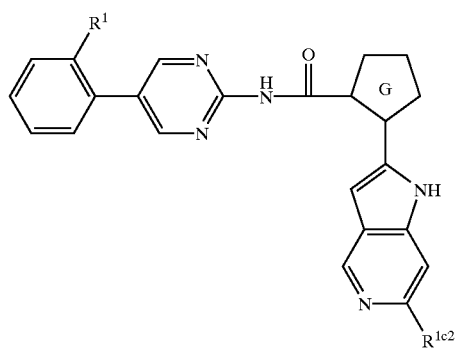

wherein:

R¹ is selected from the group consisting of —SO₂NH₂, —SO₂CH₃, —CN, —CONH₂, —CONH(CH₃), —CON(CH₃)₂, —CH₂NH₂, —CH₂NH(CH₃), —CH₂N(CH₃)₂;

$R^{1a1}$ and $R_{1a2}$ are independently selected from the group consisting of —H, —F, —Cl and —Br;

$R^{1c2}$ and $R^{1c3}$ are independently selected from the group consisting of —H, —F, —Cl, —Br, and —OCH₃; and G is selected from the group consisting of:

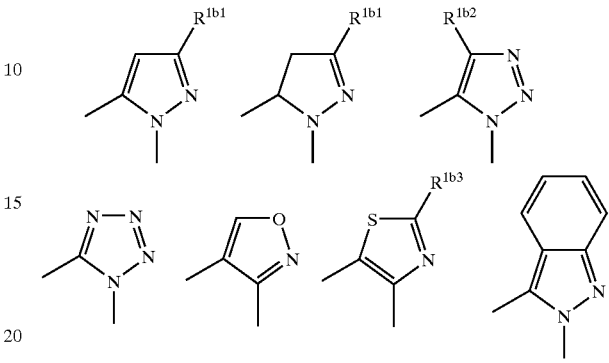

wherein:

$R^{1b1}$ is selected from the group consisting of —H, —CH₃ and —CF₃;

$R^{1b2}$ is selected from the group consisting of —H, —CH₃ and —CF₃; and $R^{1b3}$ is selected from the group consisting of —Cl, —NH₂, —CH₃ and —CF₃.

TABLE 47

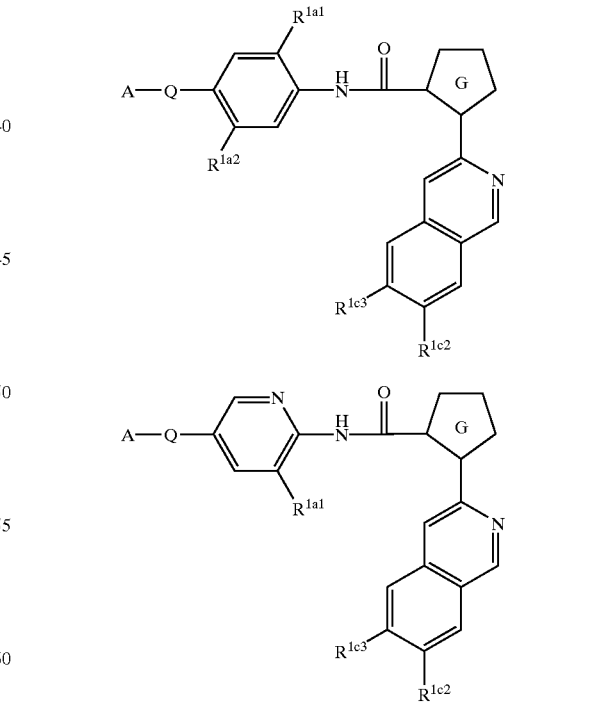

TABLE 47-continued
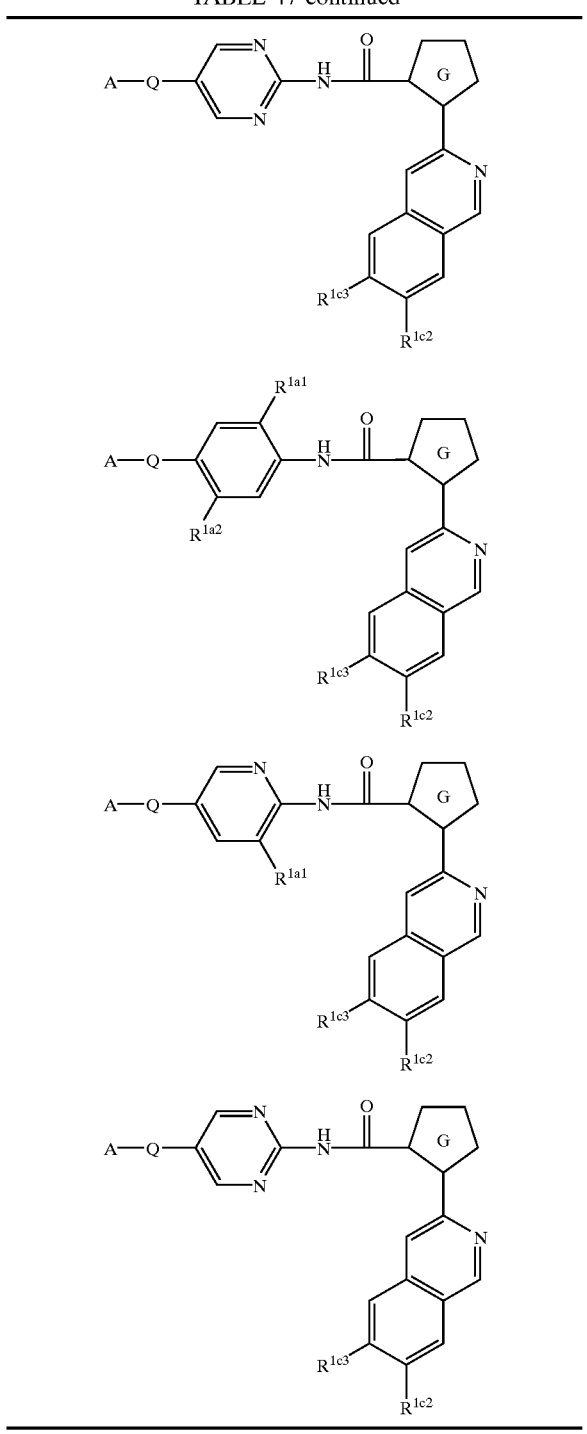
wherein:
A—Q is selected from the group consisting of:
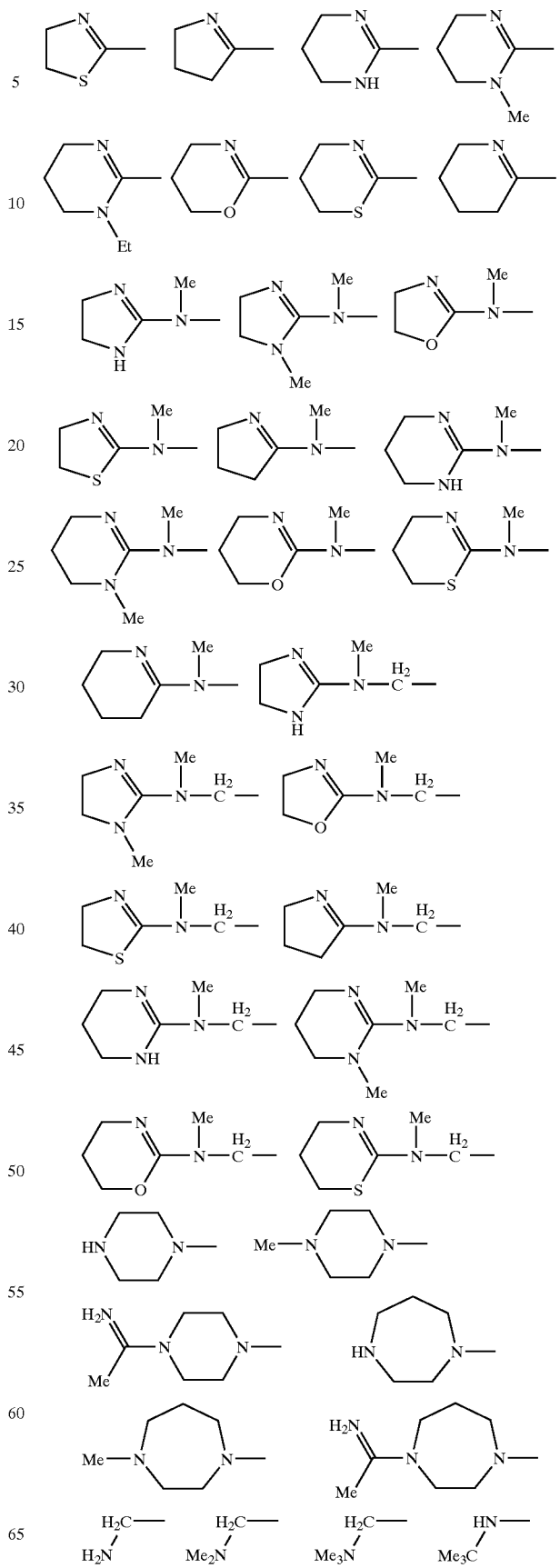

-continued

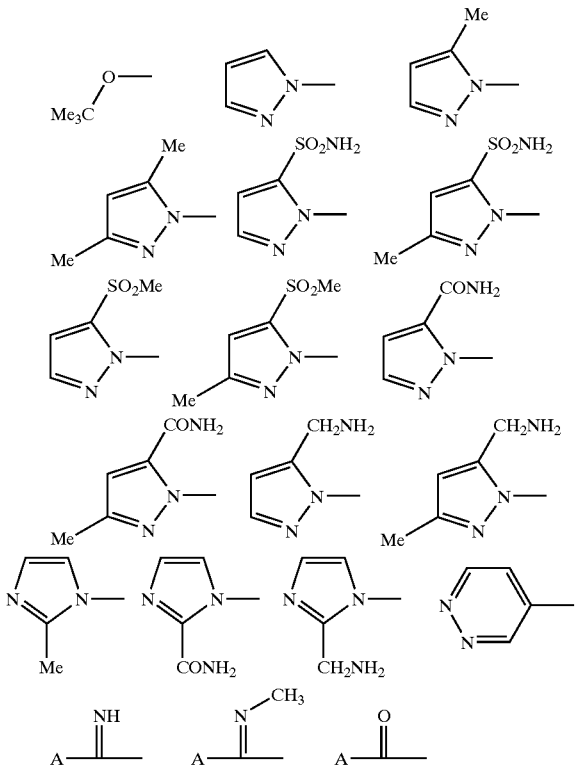

wherein:

A is selected from the group consisting of:

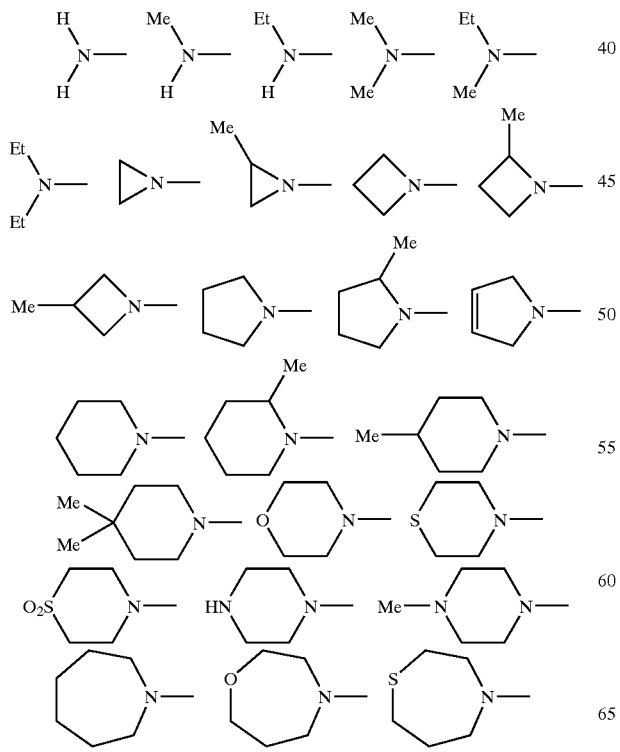

-continued

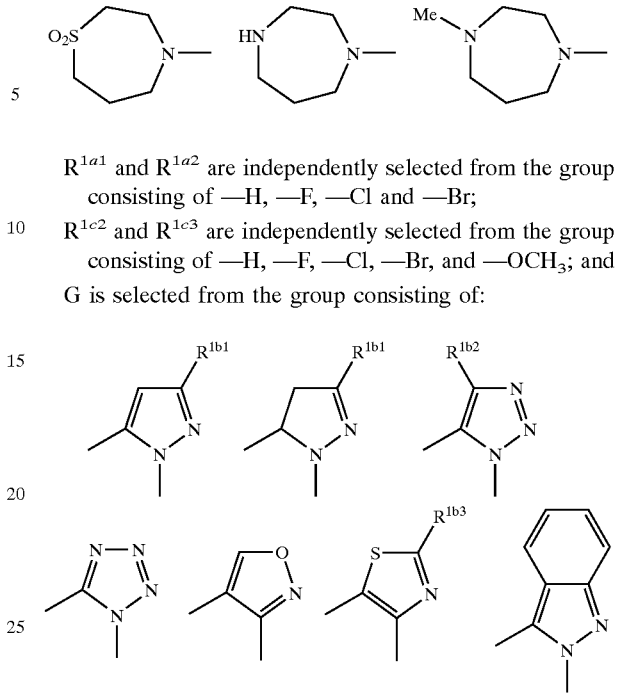

$R^{1a1}$ and $R^{1a2}$ are independently selected from the group consisting of —H, —F, —Cl and —Br;

$R^{1c2}$ and $R^{1c3}$ are independently selected from the group consisting of —H, —F, —Cl, —Br, and —OCH$_3$; and G is selected from the group consisting of:

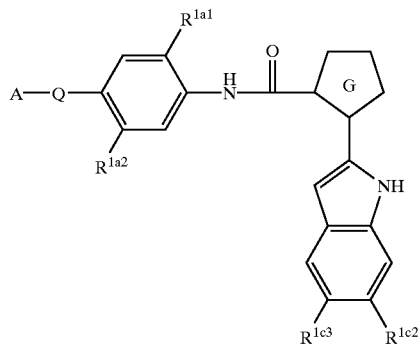

wherein:

$R^{1b1}$ is selected from the group consisting of —H, —CH$_3$ and —CF$_3$;

$R^{1b2}$ is selected from the group consisting of —H, —CH$_3$ and —CF$_3$; and $R^{1b3}$ is selected from the group consisting of —Cl, —NH$_2$, —CH$_3$ and CF$_3$.

TABLE 48

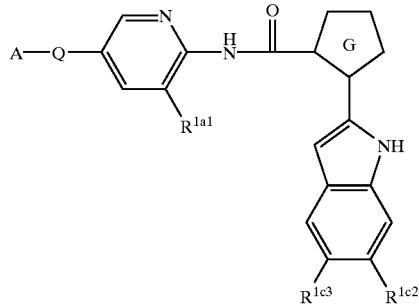

TABLE 48-continued
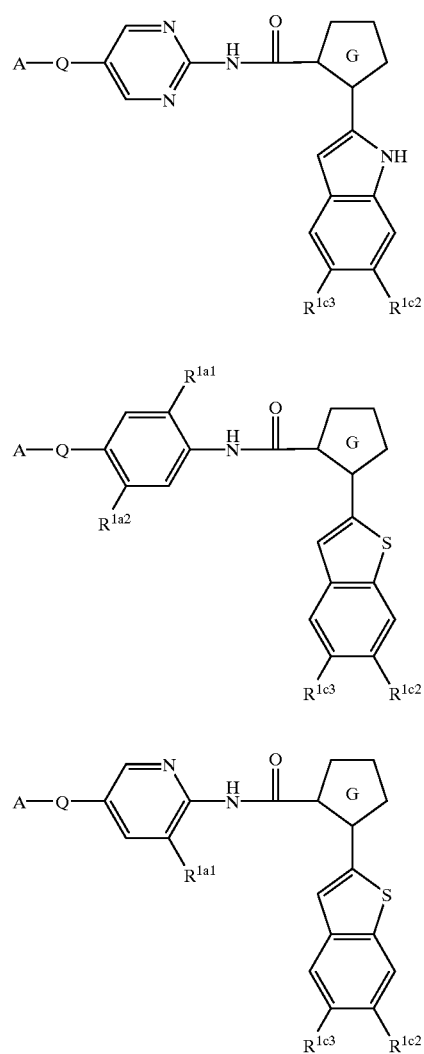
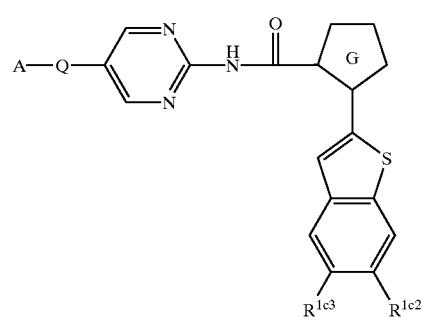
TABLE 48-continued
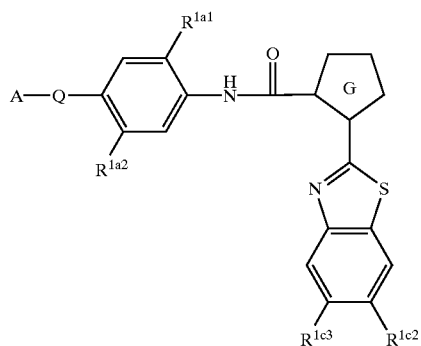
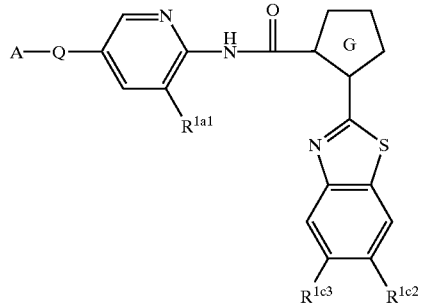
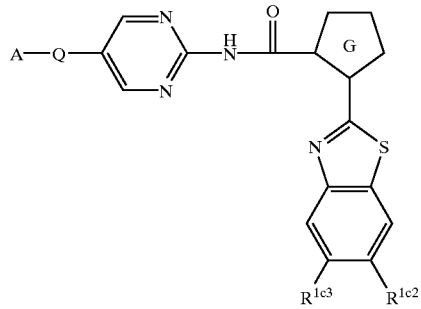
wherein:
A—Q is selected from the group consisting of:
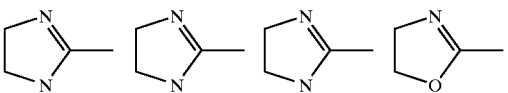
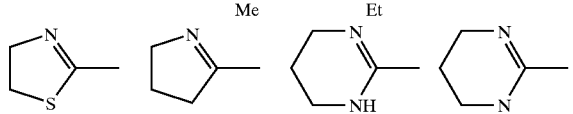
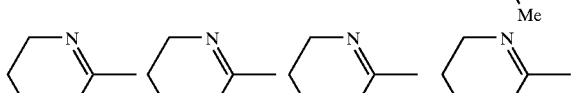
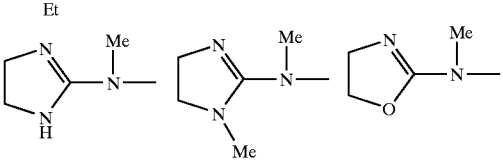

-continued
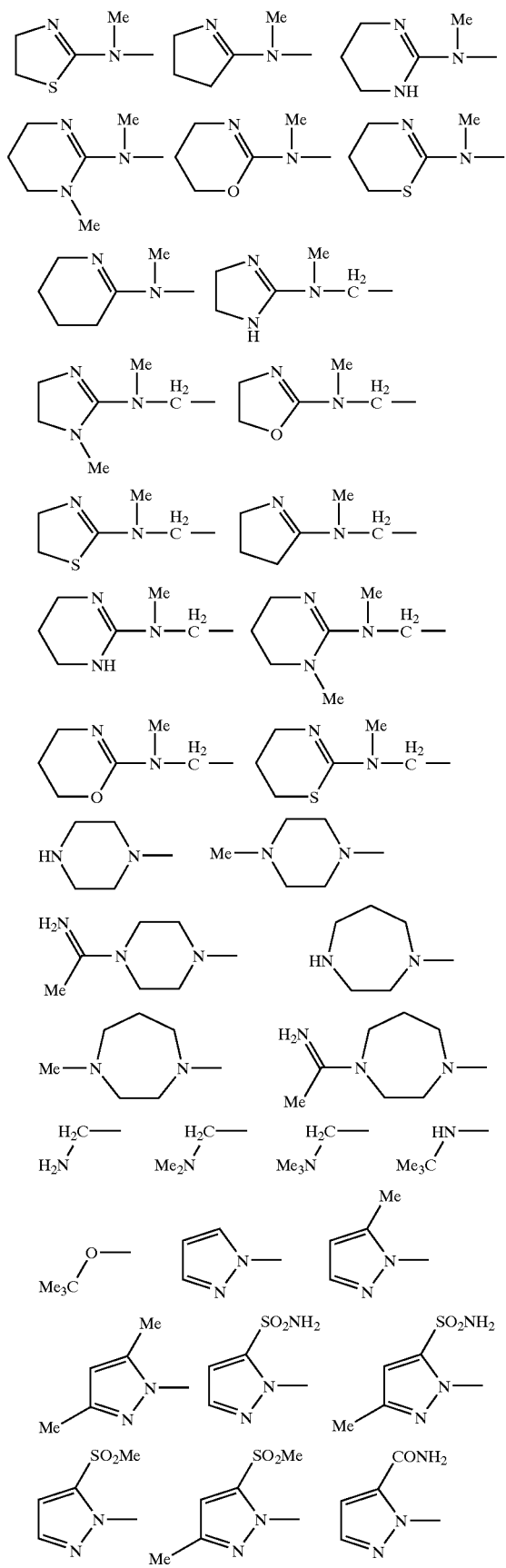
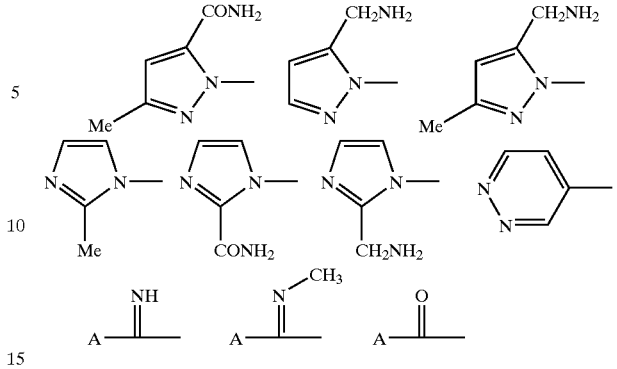
wherein
A is selected from the group consisting of:
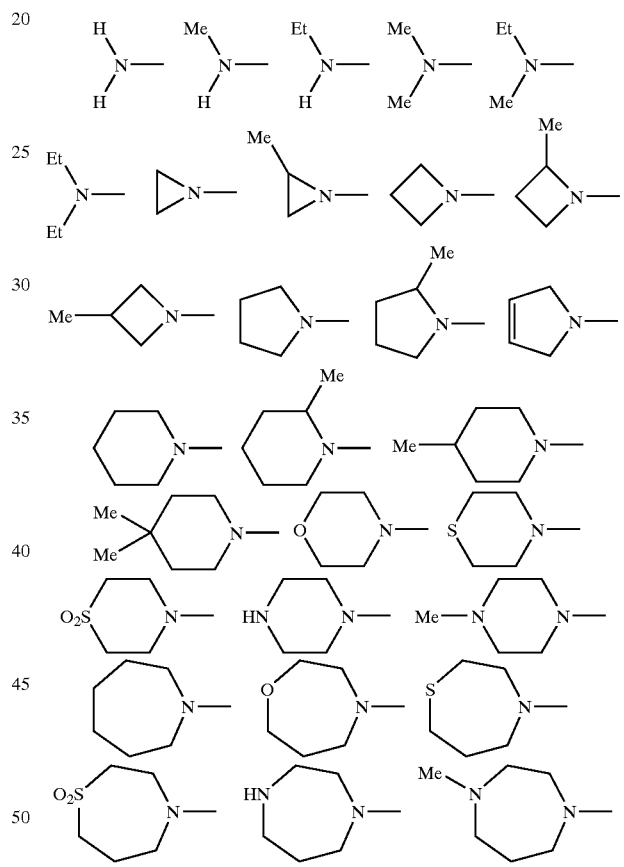
$R^{1a1}$ and $R^{1a2}$ are independently selected from the group consisting of —H, —F, —Cl and —Br;
$R^{1c2}$ and $R^{1c3}$ are independently selected from the group consisting of —H, —F, —Cl, —Br, and —OCH$_3$; and
G is selected from the group consisting of:
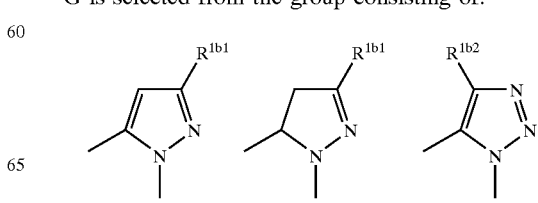

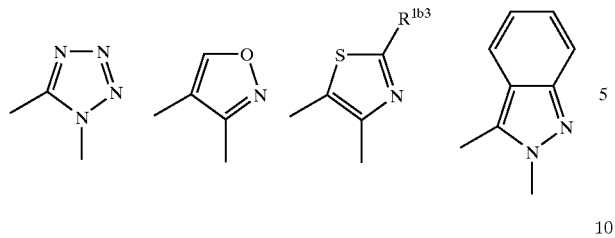
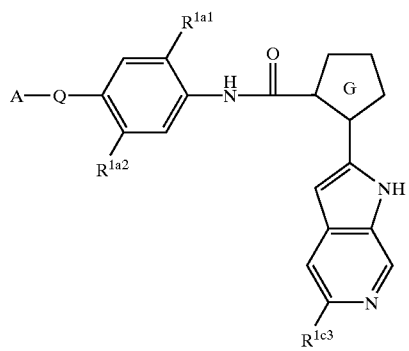
wherein:
$R^{1b1}$ is selected from the group consisting of —H, —CH$_3$ and —CF$_3$;
$R^{1b2}$ is selected from the group consisting of —H, —CH$_3$ and —CF$_3$; and
$R^{1b3}$ is selected from the group consisting of —Cl, —NH$_2$, —CH$_3$ and —CF$_3$.
TABLE 49
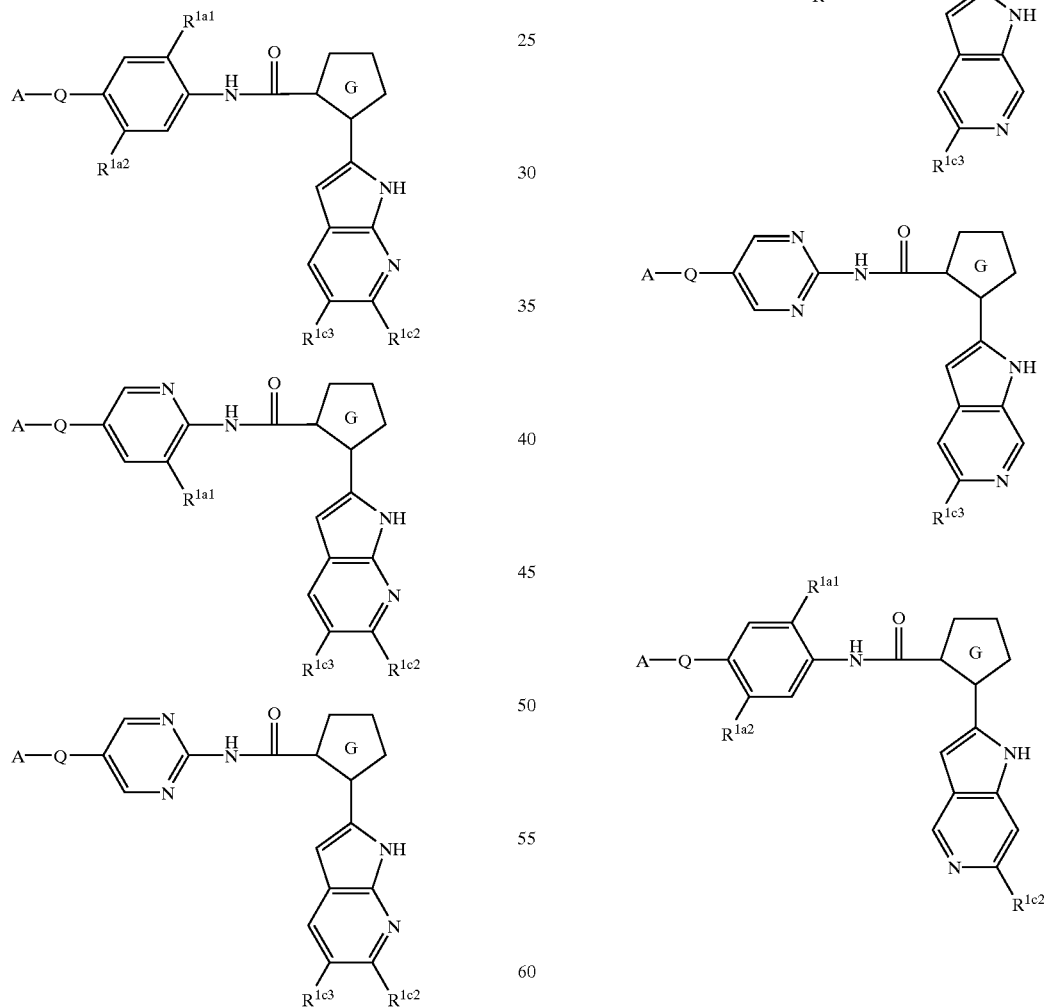
TABLE 49-continued TABLE 49-continued
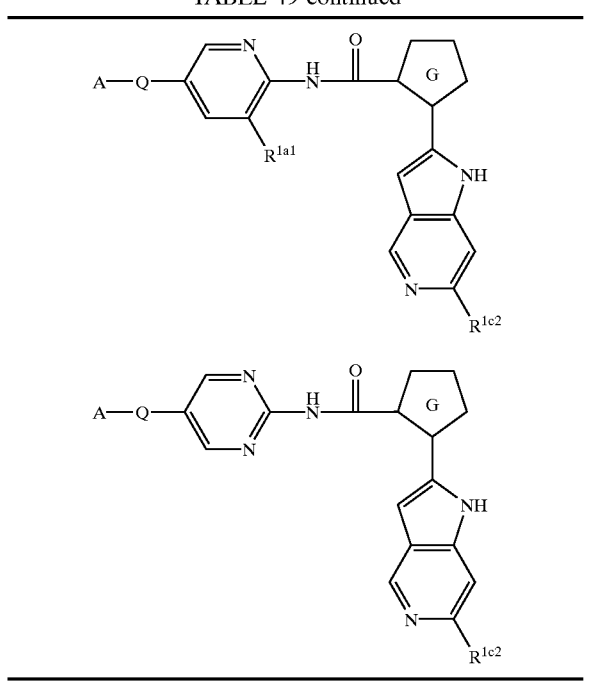
wherein:
A—Q is selected from the group consisting of:
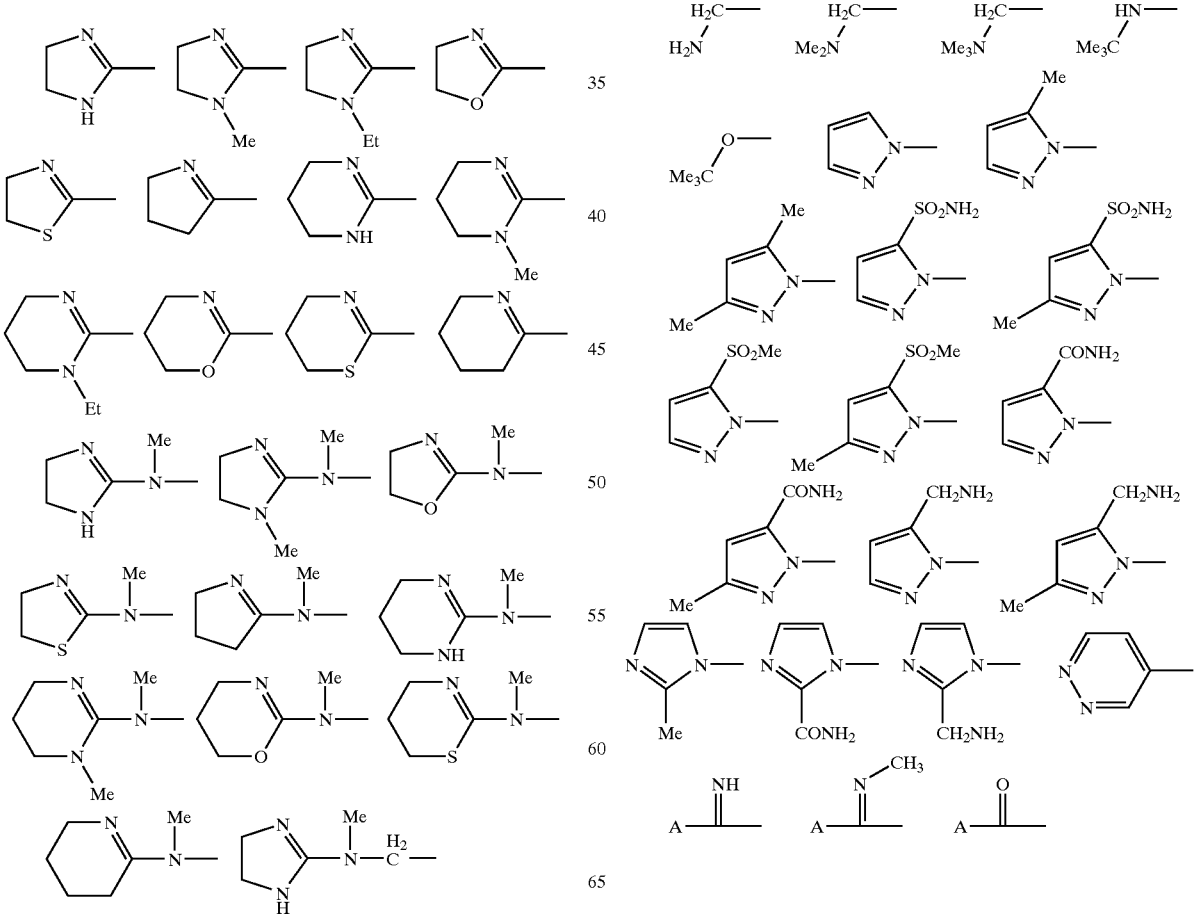
wherein:

A is selected from the group consisting of:

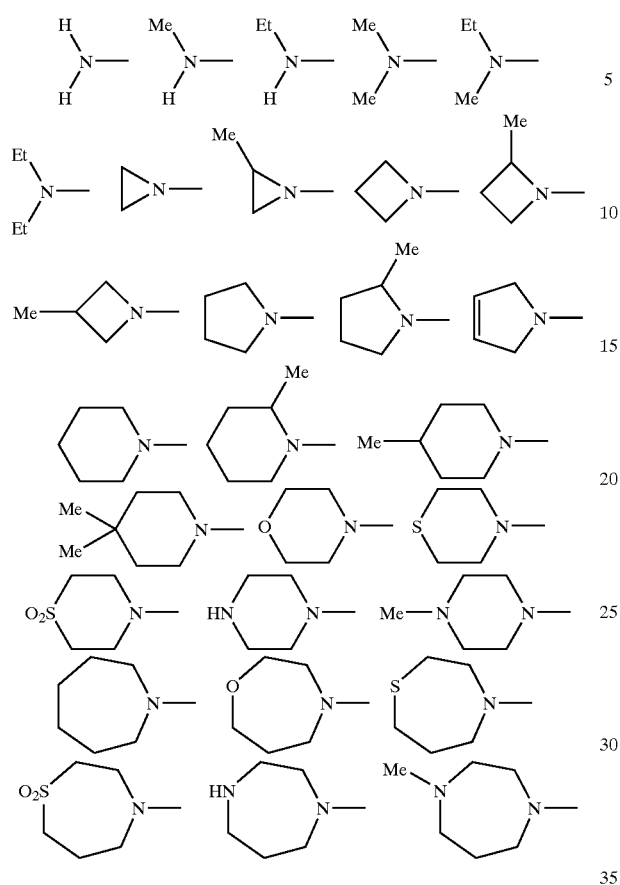

$R^{1a1}$ and $R^{1a2}$ are independently selected from the group consisting of —H, —F, —Cl and —Br;
$R^{1c2}$ and $R^{1c3}$ are independently selected from the group consisting of —H, —F, —Cl, —Br, and —OCH$_3$; and
G is selected from the group consisting of:

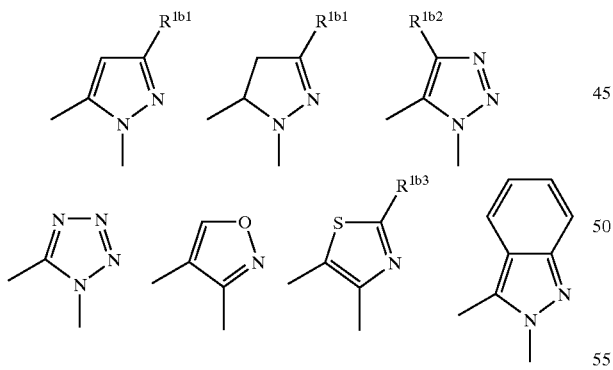

wherein:
$R^{1b1}$ is selected from the group consisting of —H, —CH$_3$ and —CF$_3$;
$R^{1b2}$ is selected from the group consisting of —H, —CH$_3$ and —CF$_3$; and $R^{1b3}$ is selected from the group consisting of —Cl, —NH$_2$, —CH$_3$ and —CF$_3$.

TABLE 50

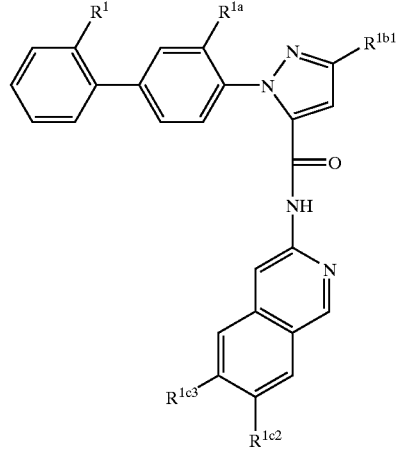

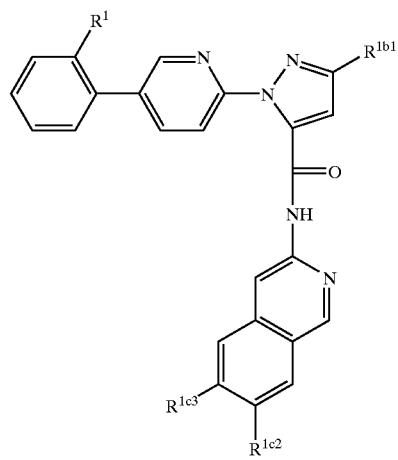

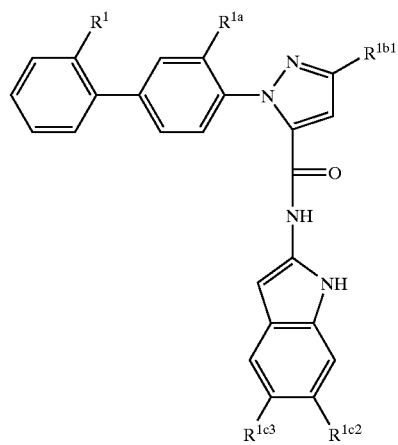

TABLE 50-continued

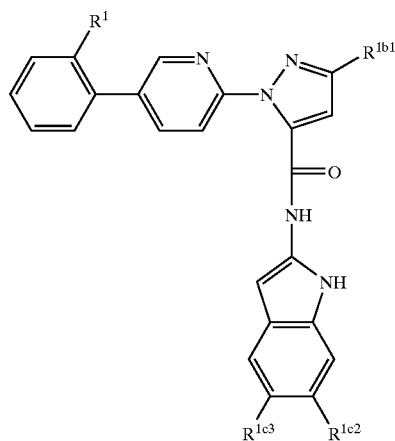

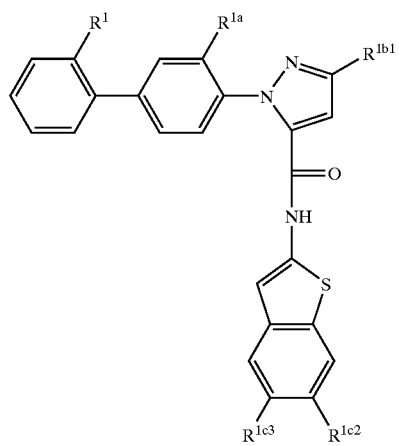

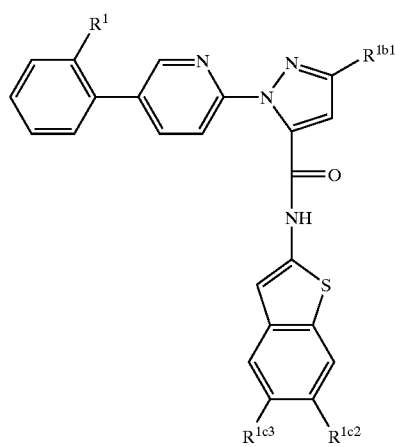

TABLE 50-continued

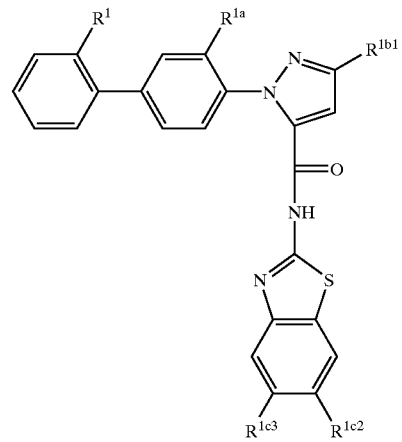

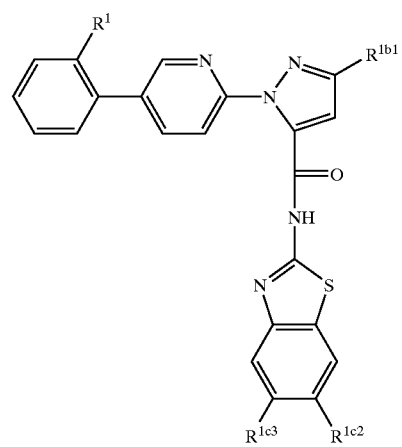

wherein:

R$^{1}$ is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R$^{1a}$ is selected from the group consisting of —H, —F, —Cl and —Br;

R$^{1b1}$ is selected from the group consisting of —H, —CH$_3$ and —CF$_3$; and

R$^{1c2}$ and R$^{1c3}$ are independently selected from the group consisting of —H, —F, —Cl, —Br, and —OCH$_3$.

TABLE 51
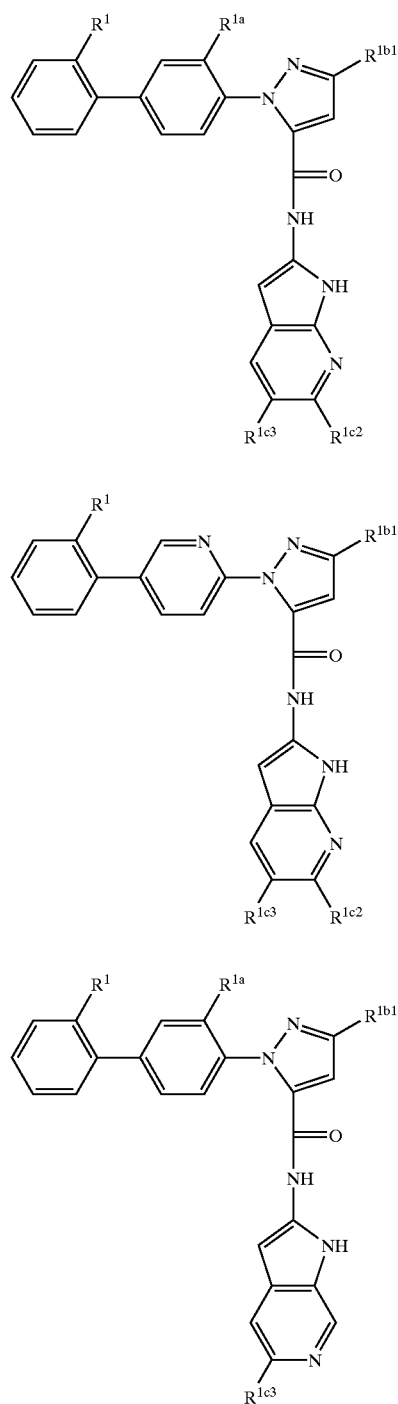
TABLE 51-continued
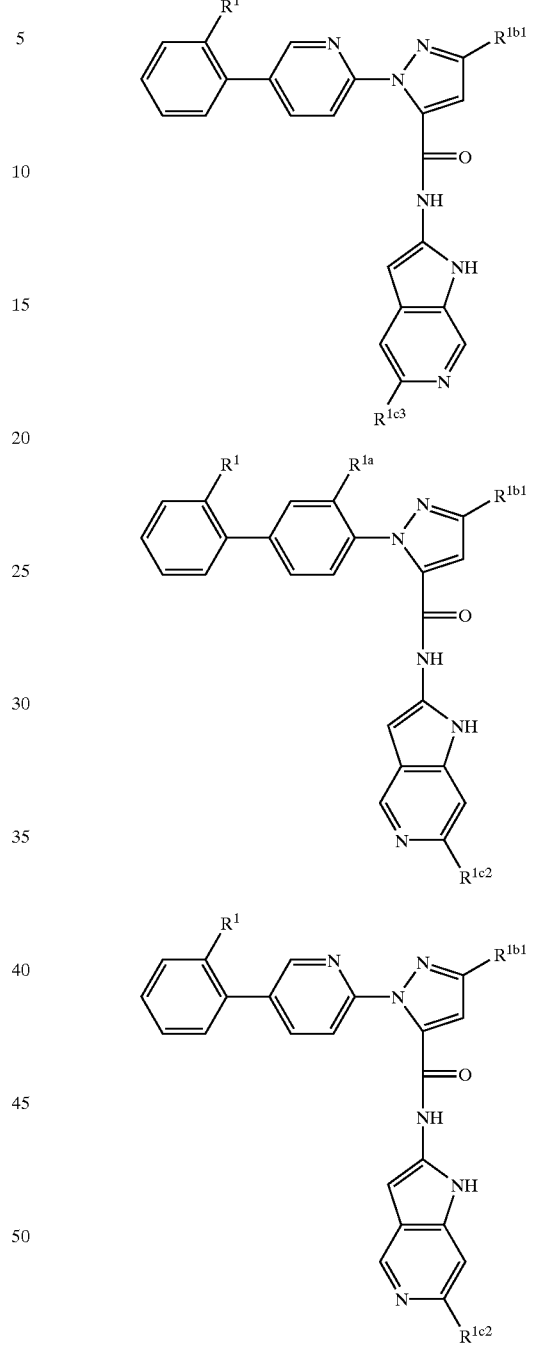
wherein:
R[1] is selected from the group consisting of —SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;
R$^{1a}$ is selected from the group consisting of —H, —F, —Cl and —Br;
R$^{1b1}$ is selected from the group consisting of —H, —CH$_3$ and —CF$_3$; and
R$^{1c2}$ and R$^{1c3}$ are independently selected from the group consisting of —H, —F, —Cl, —Br, and —OCH$_3$.
TABLE 52
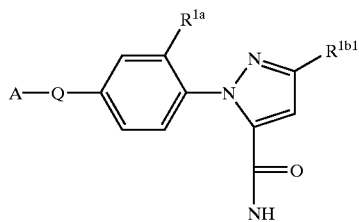
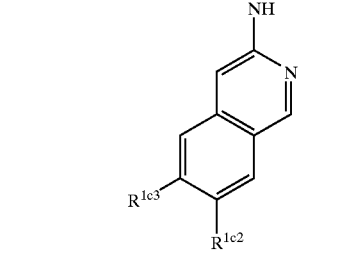
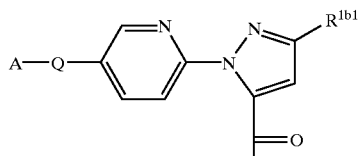
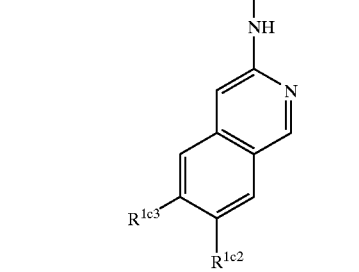
TABLE 52-continued
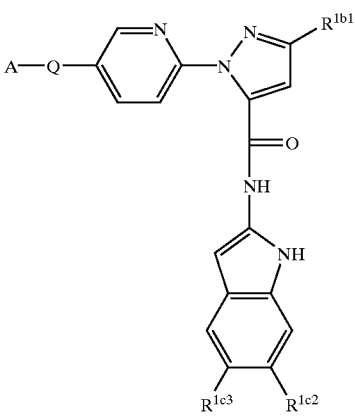
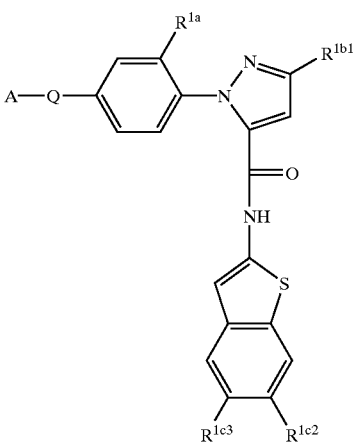
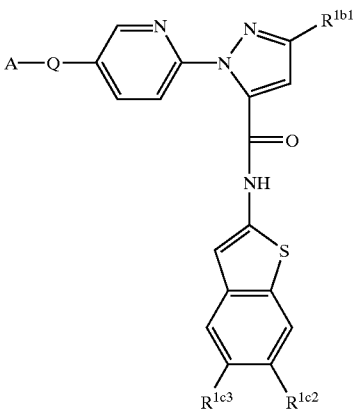

TABLE 52-continued
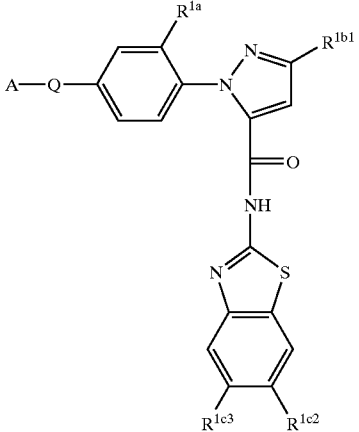
wherein:
A—Q is selected from the group consisting of:
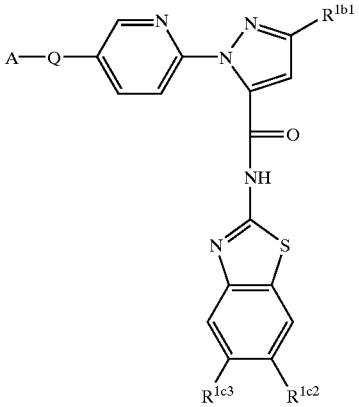

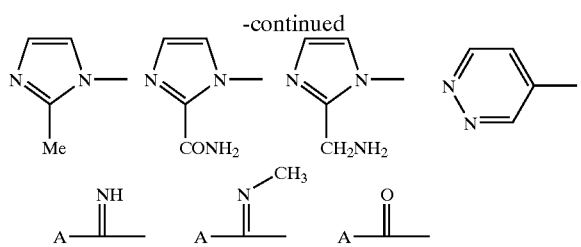
wherein:
A is selected from the group consisting of:
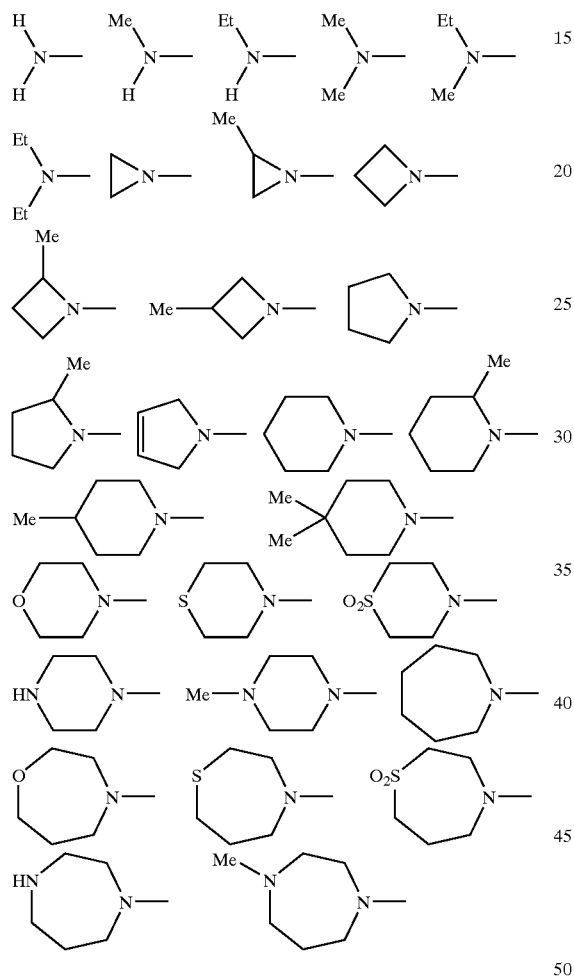
$R^{1a}$ is selected from the group consisting of —H, —F, —Cl and —Br;
$R^{1b1}$ is selected from the group consisting of —H, —CH$_3$ and —CF$_3$; and
$R^{1c2}$ and $R^{1c3}$ are independently selected from the group consisting of —H, —F, —Cl, —Br and —OCH$_3$.
TABLE 53
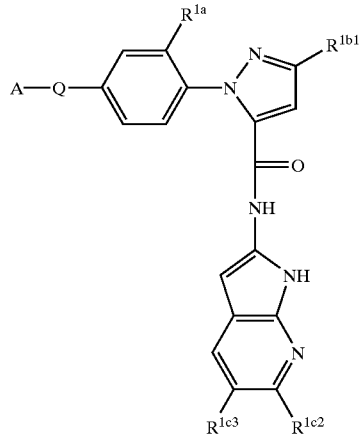
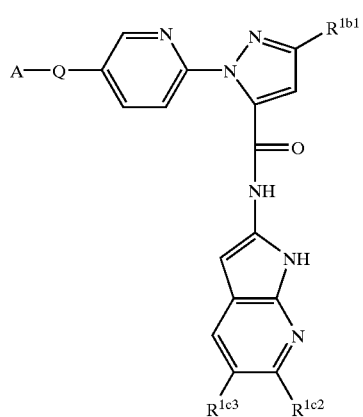
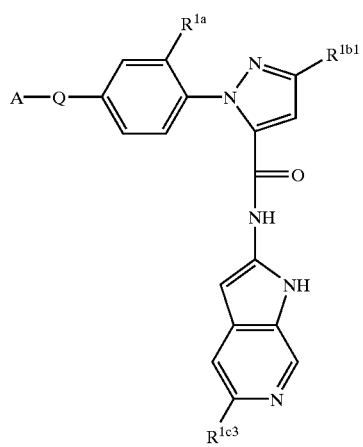

TABLE 53-continued
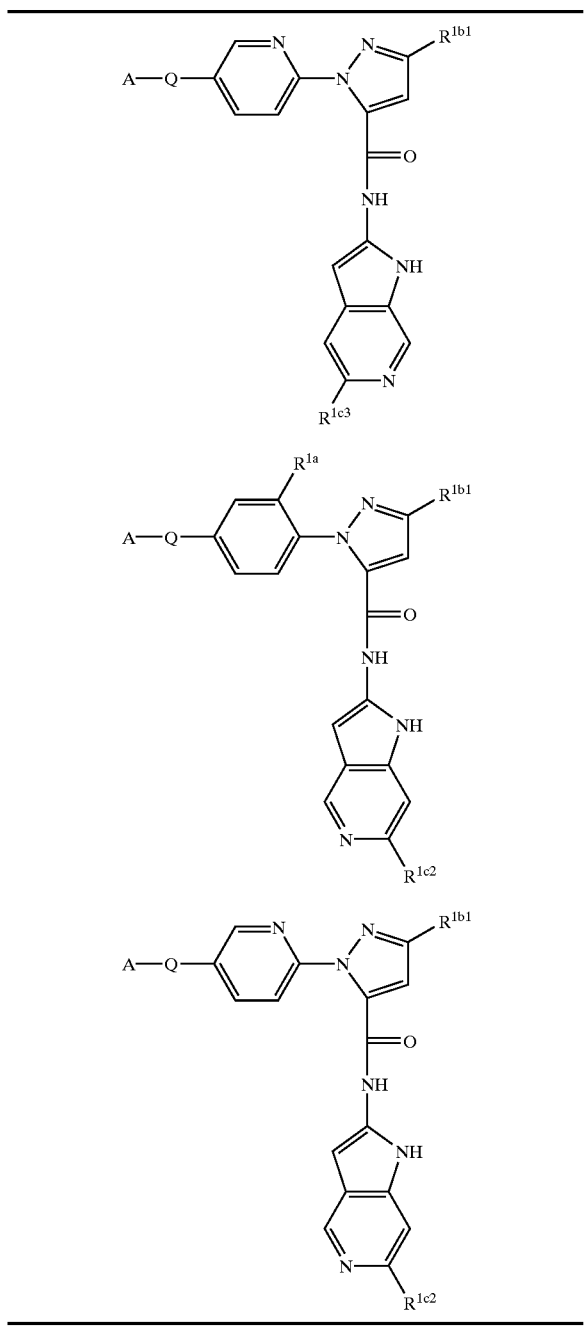
wherein:
A—Q is selected from the group consisting of:
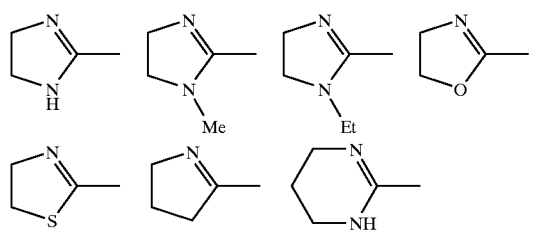
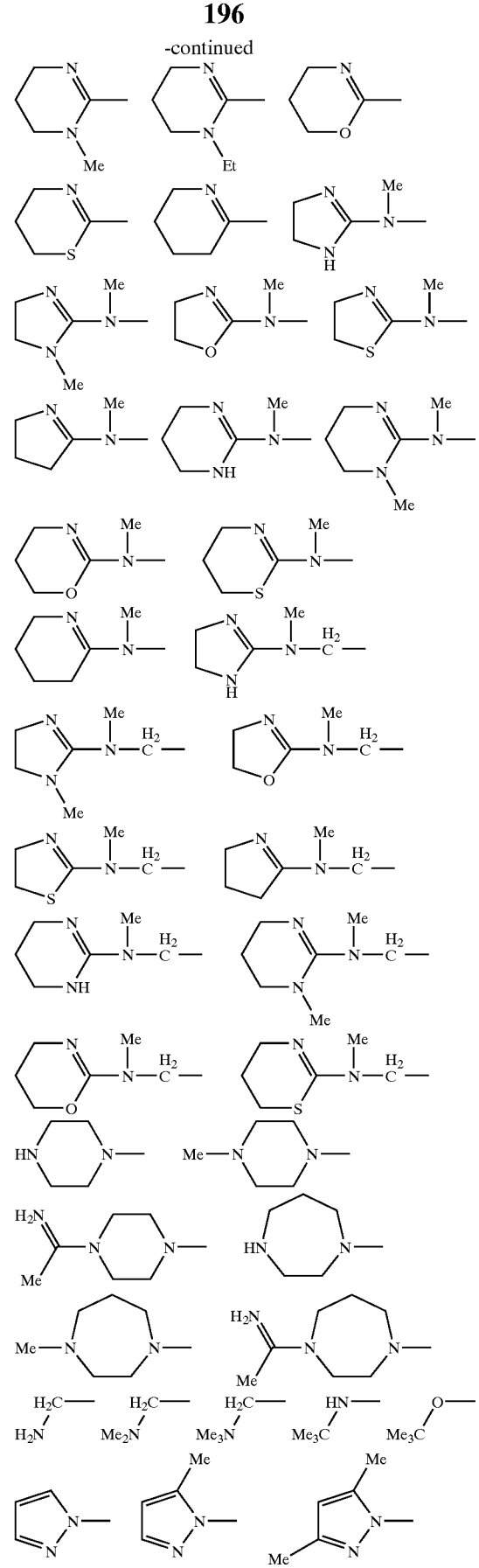

-continued

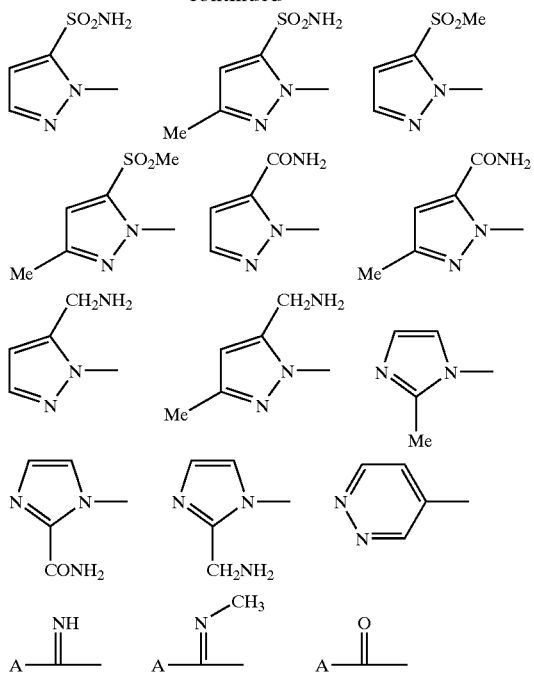

wherein:

A is selected from the group consisting of:

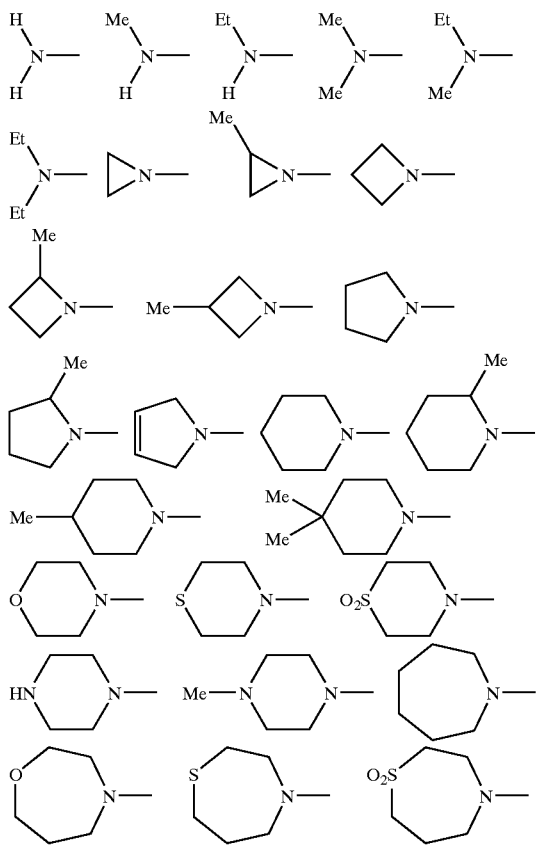

-continued

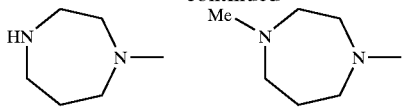

$R^{1a}$ is selected from the group consisting of —H, —F, —Cl and —Br;

$R^{1b1}$ is selected from the group consisting of —H, —CH$_3$ and —CF$_3$; and $R^{1c2}$ and $R^{1c3}$ are independently selected from the group consisting of —H, —F, —Cl, —Br and —OCH$_3$.

The following compounds are an embodiment of the present invention:

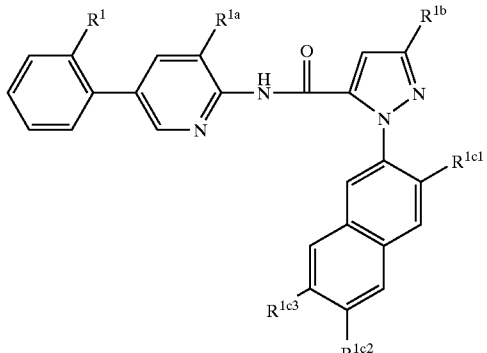

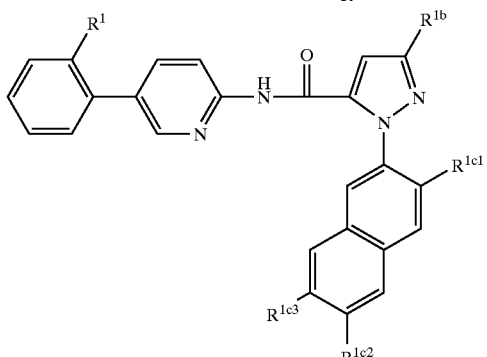

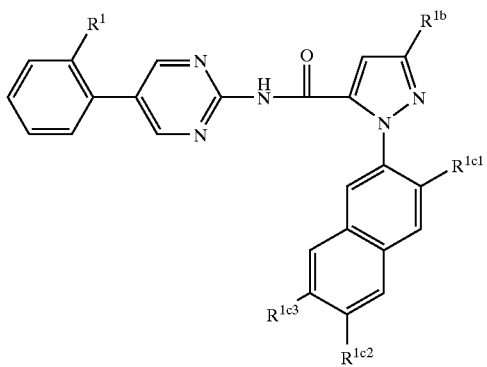

wherein:
$R^1$ is selected from the group consisting of:
—SO$_2$NH$_2$, —SO$_2$Me, —CH$_2$NH$_2$ and —CH$_2$NMe$_2$;
$R^{1a}$ is selected from the group consisting of:
—H, —F, —Cl and —Br;
$R^{1b}$ is selected from the group consisting of:
—CH$_3$, —CF$_3$, —CH$_2$CH$_3$, —SO$_2$Me, —CONH$_2$ and —NHSO$_2$Me;

$R^{1c1}$ is selected from the group consisting of:
—H, —F, —Cl, —Br, —NH₂, —OH, —SO₂Me, —SO₂Et, —SO₂NH₂, —NO₂, —CH₂NH₂, —CN, —CONH₂, —CH₂OH;
$R^{1c2}$ is selected from the group consisting of:
—H, —F, —Cl and —Br; and
$R^{1c3}$ is selected from the group consisting of:
—H, —F, —Cl and —Br.

The following compounds are an embodiment of the present invention:

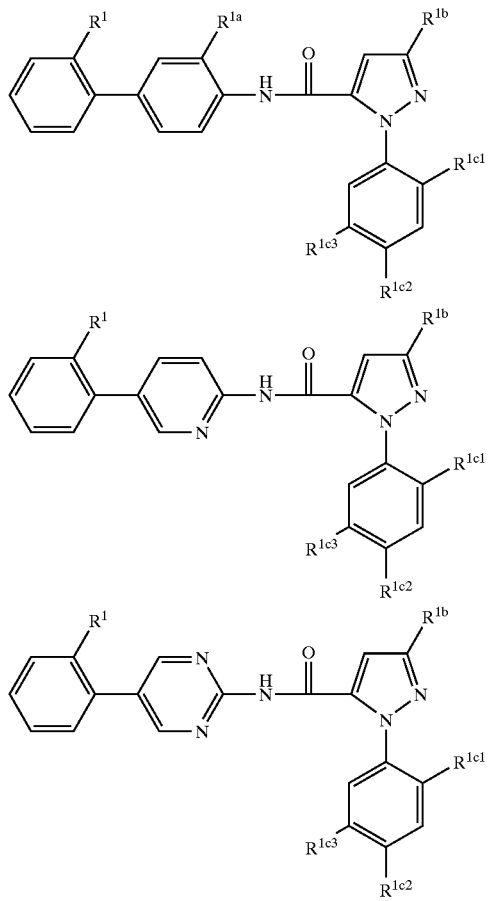

wherein:
$R^1$ is selected from the group consisting of:
—SO₂NH₂, —SO₂Me, —CH₂NH₂ and —CH₂NMe₂;
$R^{1a}$ is selected from the group consisting of:
—H, —F, —Cl and —Br;
$R^{1b}$ is selected from the group consisting of:
—CH₃, —CF₃, —CH₂CH₃, —SO₂Me, —CONH₂ and —NHSO₂Me;
$R^{1c1}$ is selected from the group consisting of:
—H, —F, —Cl, —Br, —NH₂, —OH, —SO₂Me, —SO₂Et, —SO₂NH₂, —NO₂, —CH₂NH₂, —CN, —CONH₂, —CH₂OH;
$R^{1c2}$ is selected from the group consisting of:
—H, —F, —Cl, —Br and —OMe; and
$R^{1c3}$ is selected from the group consisting of:
—H, —F, —Cl, —Br, —OCH₃, —NH₂, —CH₂NH₂, —CONH₂, —CONHMe, —CONMe₂.

The following compounds are an embodiment of the present invention:

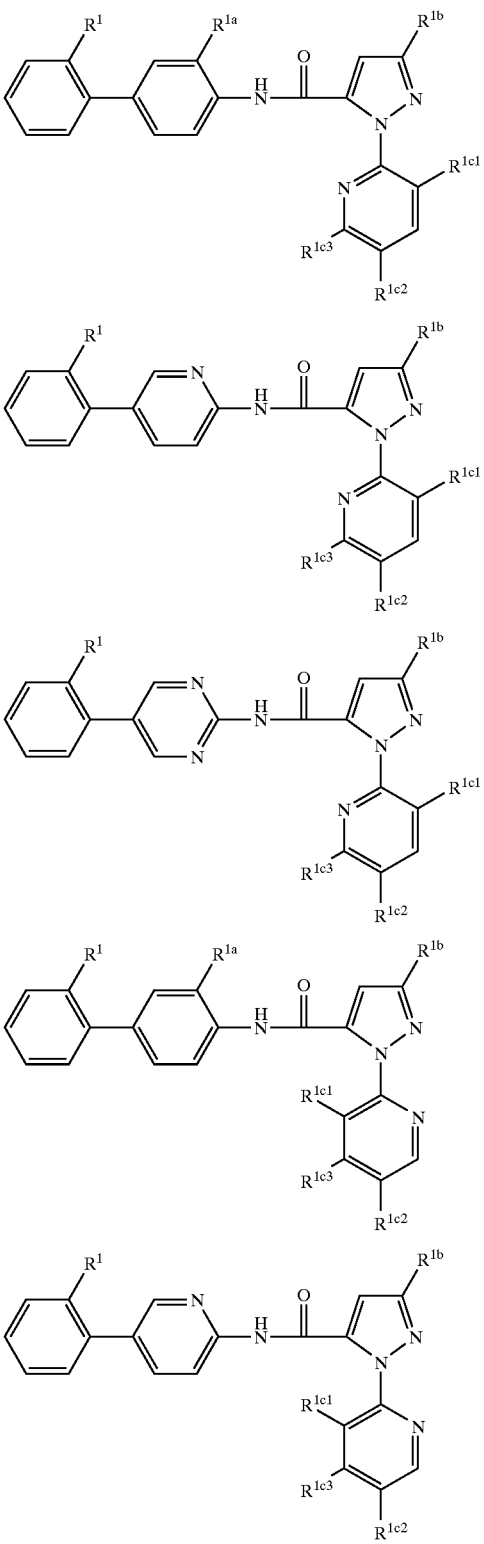

201

-continued

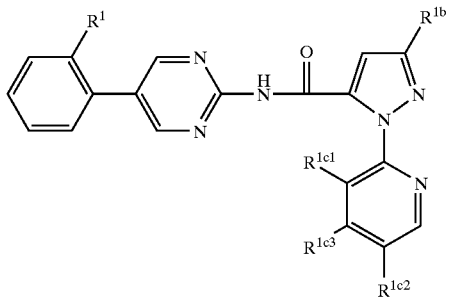

wherein:

R¹ is selected from the group consisting of:
—SO₂NH₂, —SO₂CH₃, —CN, —CONH₂, —CONH(CH₃), —CON(CH₃)₂, —CH₂NH₂, —CH₂NH(CH₃), —CH₂N(CH₃)₂;

R$^{1a}$ is selected from the group consisting of:
—H, —F, —Cl and —Br;

R$^{1b}$ is selected from the group consisting of:
—CH₃ and —CF₃;

R$^{1c1}$ is selected from the group consisting of:
—H, —F, —Cl, —Br, —CN, —CH₂NH₂, —CH₂OH, —CONH₂, —C(=NH)NH₂, —CO₂H, —CO₂Me, —SO₂Me, —SO₂NH₂, —OH, —NH₂, and —NO₂;

R$^{1c2}$ is selected from the group consisting of:
—H, —F, —Cl, —Br, and —OCH₃; and R$^{1c3}$ is selected from the group consisting of:
—H, —F, —Cl, —Br, —OCH₃, —NH₂, —CH₂NH₂, —CONH₂, —CONHMe, —CONMe₂.

The following compounds are an embodiment of the present invention:

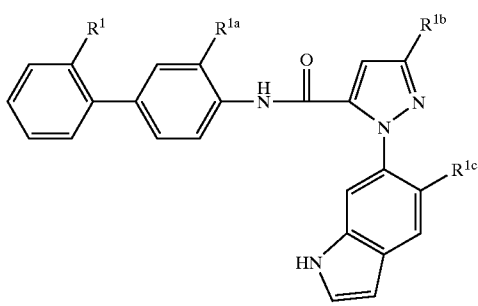

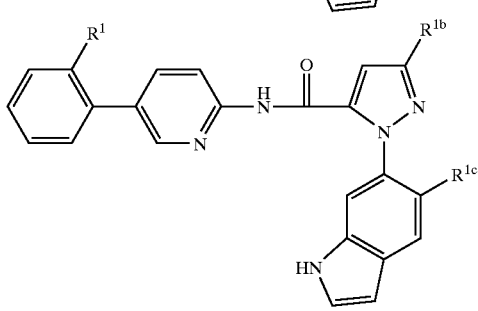

202

-continued

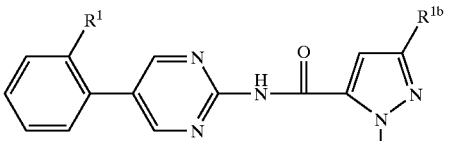

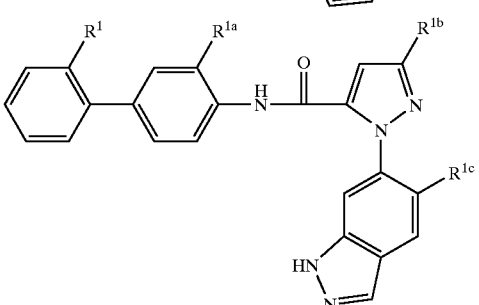

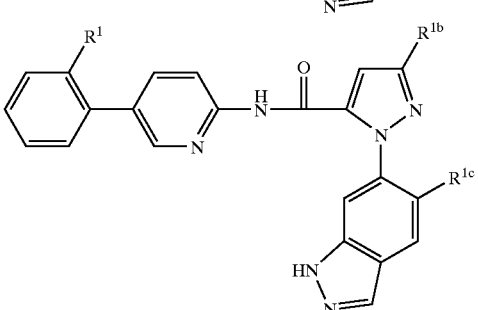

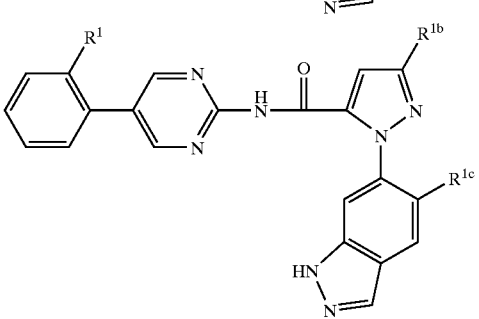

wherein:

R¹ is selected from the group consisting of:
—SO₂NH₂, —SO₂Me, —CH₂NH₂ and —CH₂NMe₂;

R$^{1a}$ is selected from the group consisting of:
—H, —F, —Cl and —Br;

R$^{1b}$ is selected from the group consisting of:
—CH₃, —CF₃, —CH₂CH₃, —SO₂Me, —CONH₂ and —NHSO₂Me; and R$^{1c}$ is selected from the group consisting of:
—H, —F, —Cl, —Br, —NH₂, —OH, —SO₂Me, —SO₂Et, —SO₂NH₂, —NO₂, —CH₂NH₂, —CN, —CONH₂, —CH₂OH;

The following compounds are an embodiment of the present invention:

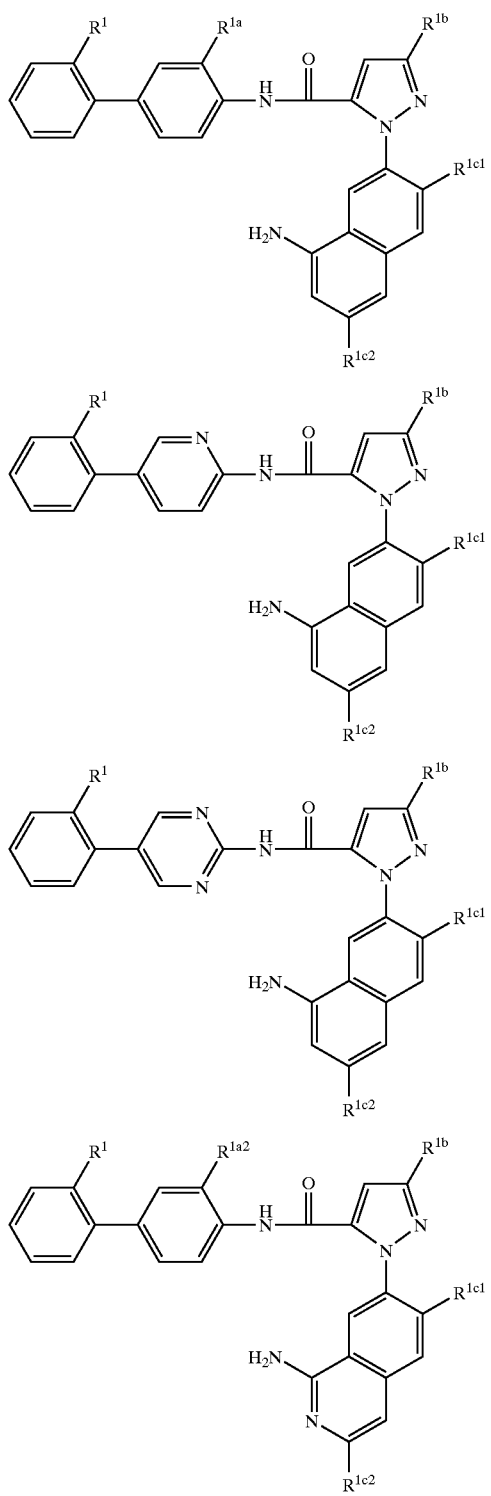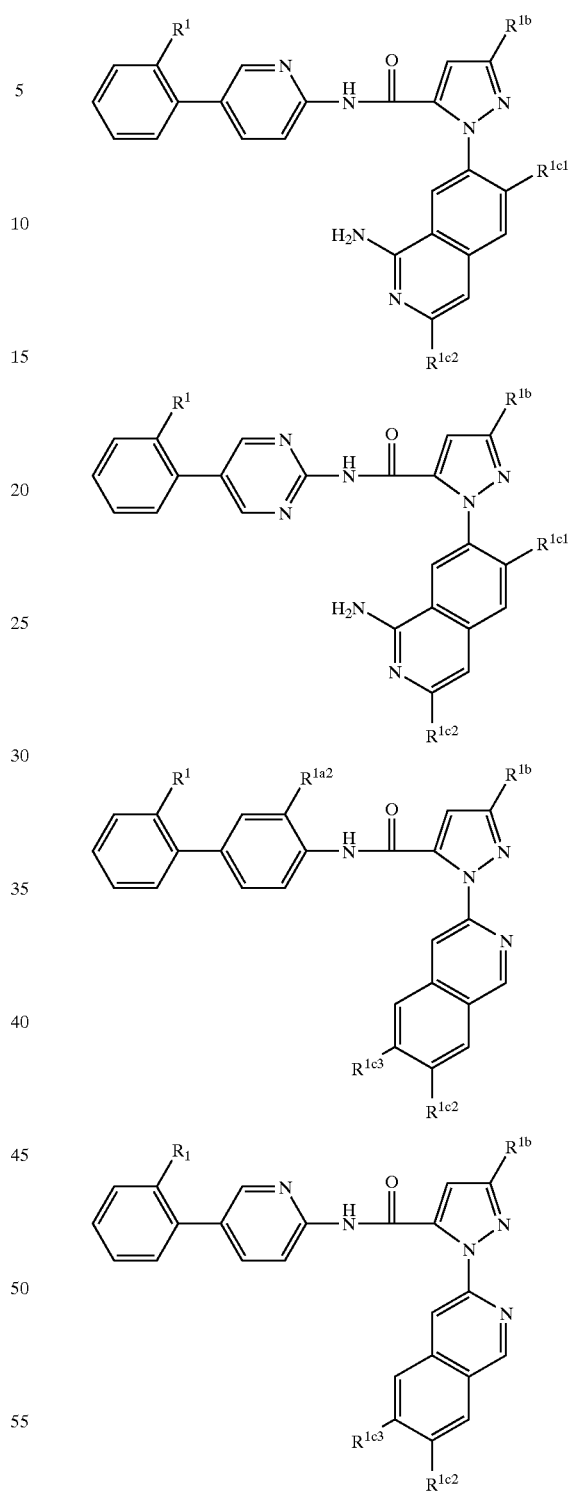

205
-continued

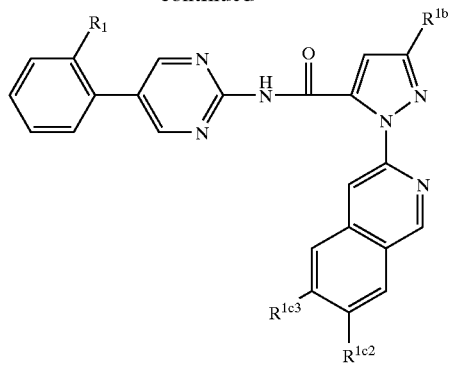

wherein:

$R^1$ is selected from the group consisting of:
—SO$_2$NH$_2$, —SO$_2$Me, —CH$_2$NH$_2$ and —CH$_2$NMe$_2$;

$R^{1a}$ is selected from the group consisting of:
—H, —F, —Cl and —Br;

$R^{1b}$ is selected from the group consisting of:
—CH$_3$, —CF$_3$, —CH$_2$CH$_3$, —SO$_2$Me, —CONH$_2$ and —NHSO$_2$Me;

$R^{1c1}$ is selected from the group consisting of:
—H, —F, —Cl, —Br, —NH$_2$, —OH, —SO$_2$Me, —SO$_2$Et, —SO$_2$NH$_2$, —NO$_2$, —CH$_2$NH$_2$, —CN, —CONH$_2$, —CH$_2$OH; and $R^{1c2}$ and $R^{1c3}$ are independently selected from the group consisting of:
—H, —F, —Cl and —Br.

The following compounds are an embodiment of the present invention:

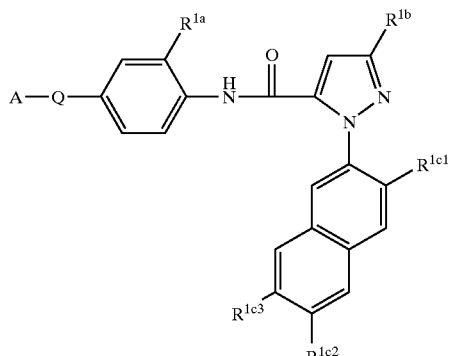

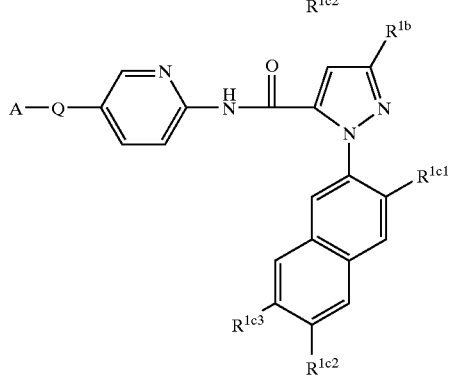

206
-continued

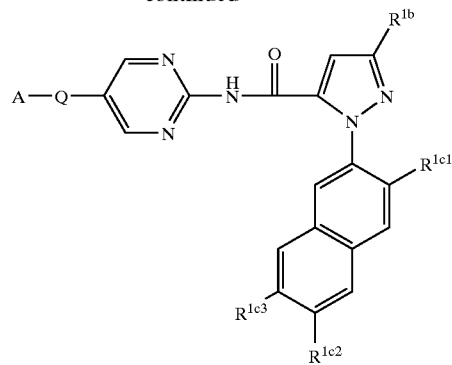

wherein:

A—Q is selected from the group consisting of:

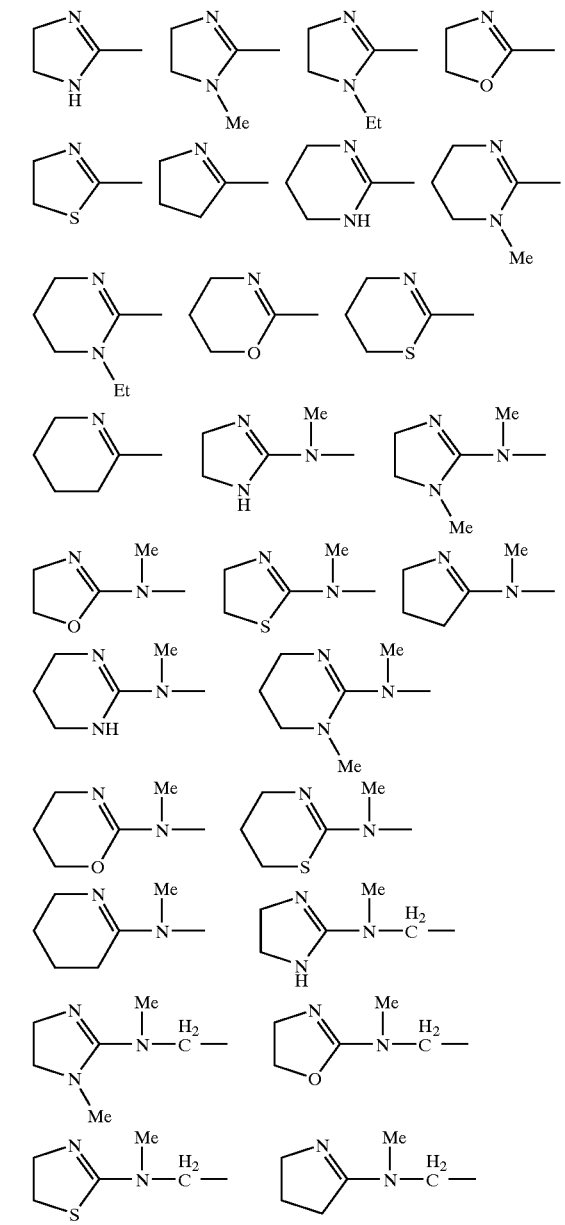

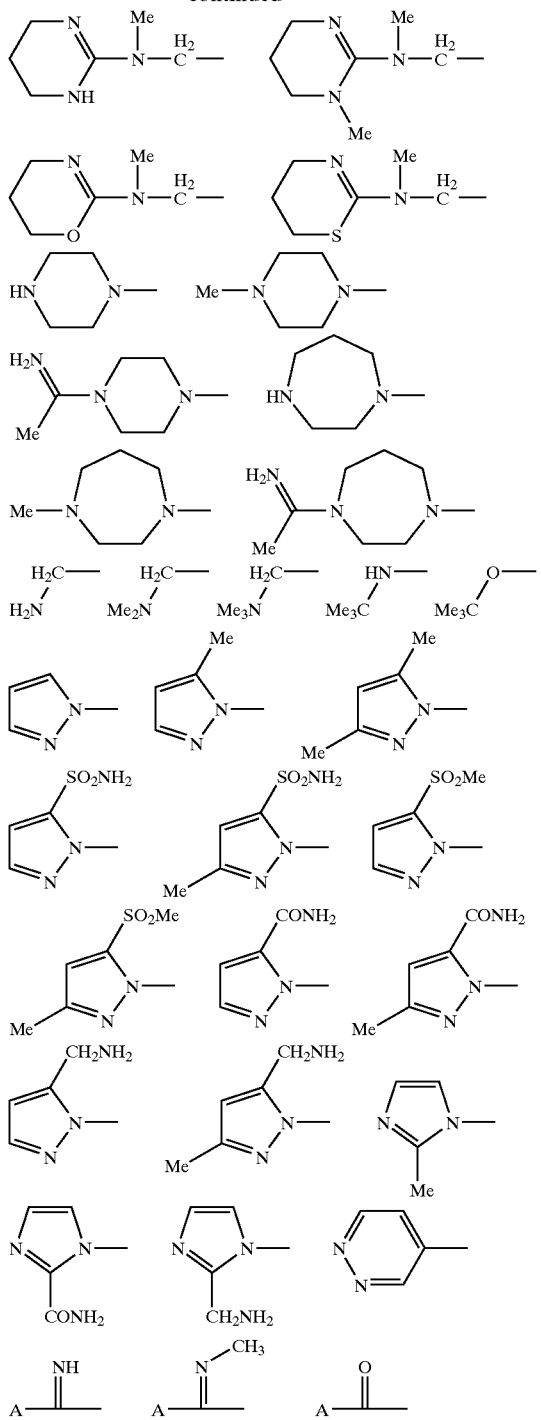

wherein:

A is selected from the group consisting of:

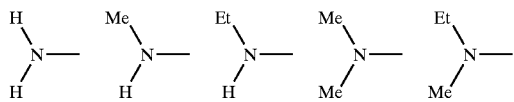

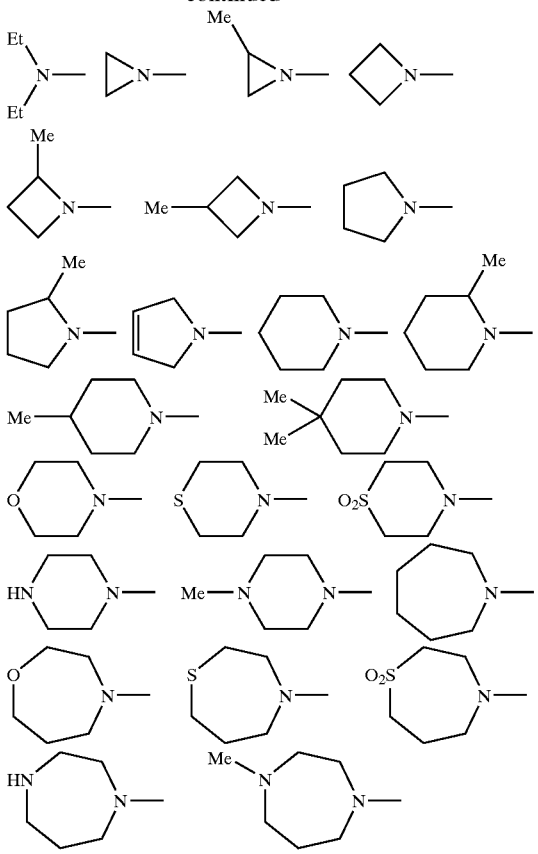

$R^{1a}$ is selected from the group consisting of —H, —F, —Cl and —Br;

$R^{1b}$ is selected from the group consisting of:
 -Me, —CF$_3$, —Et, —SO$_2$Me, —CONH$_2$ and —NHSO$_2$Me;

$R^{1c1}$ is selected from the group consisting of:
 —H, —F, —Cl, —Br, —NH$_2$, —OH, —SO$_2$Me, —SO$_2$Et, —SO$_2$NH$_2$, —NO$_2$, —CH$_2$NH$_2$, —CN, —CONH$_2$, —CH$_2$OH;

$R^{1c2}$ is selected from the group consisting of:
 —H, —F, —Cl and —Br; and $R^{1c3}$ is selected from the group consisting of:
 —H, —F, —Cl and —Br.

The following compounds are an embodiment of the present invention:

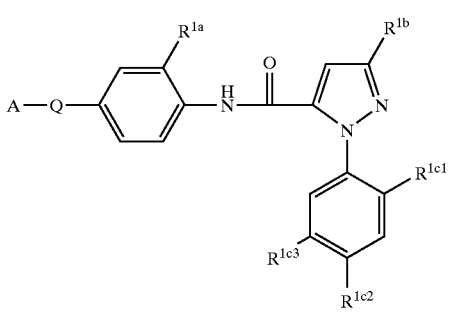

209
-continued
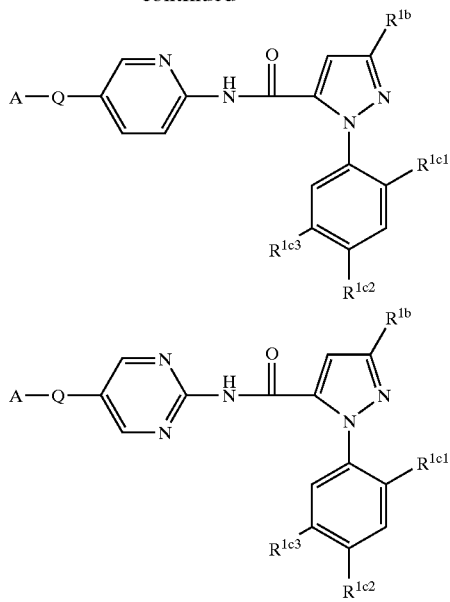
wherein:
A—Q is selected from the group consisting of:
210
-continued
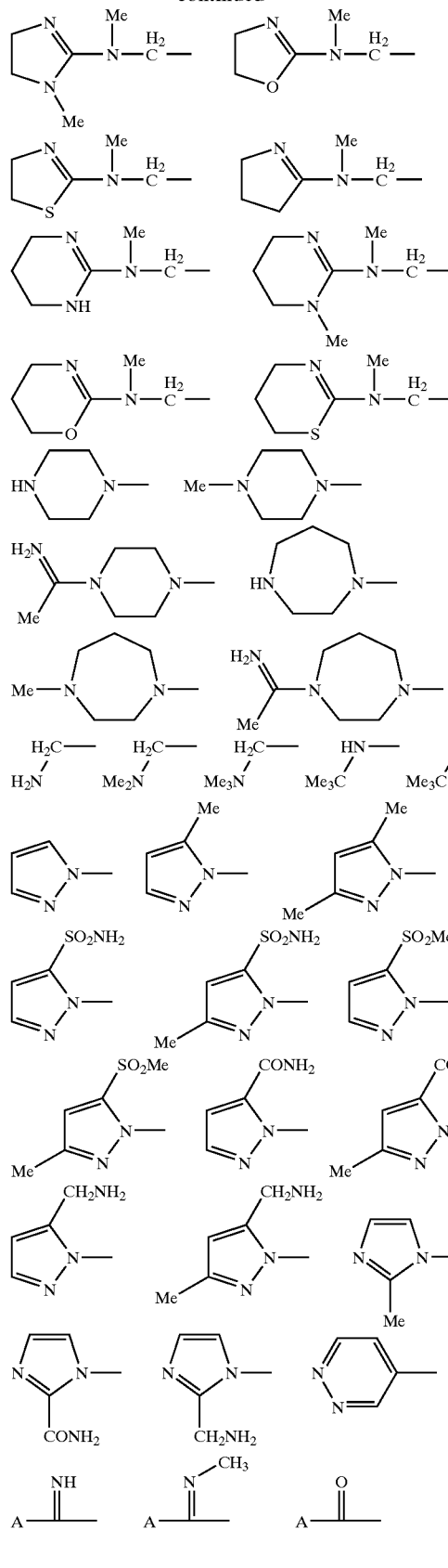
wherein:

A is selected from the group consisting of:

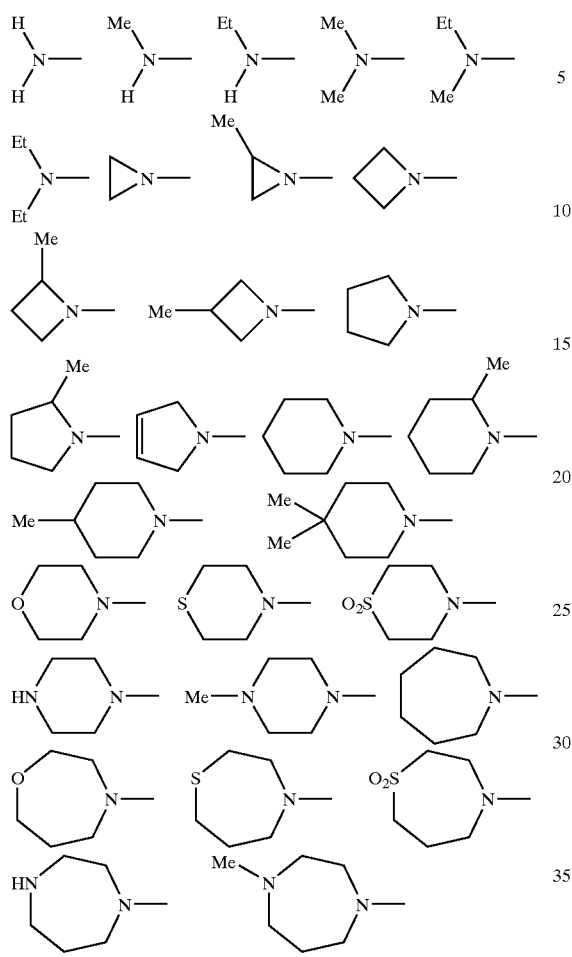

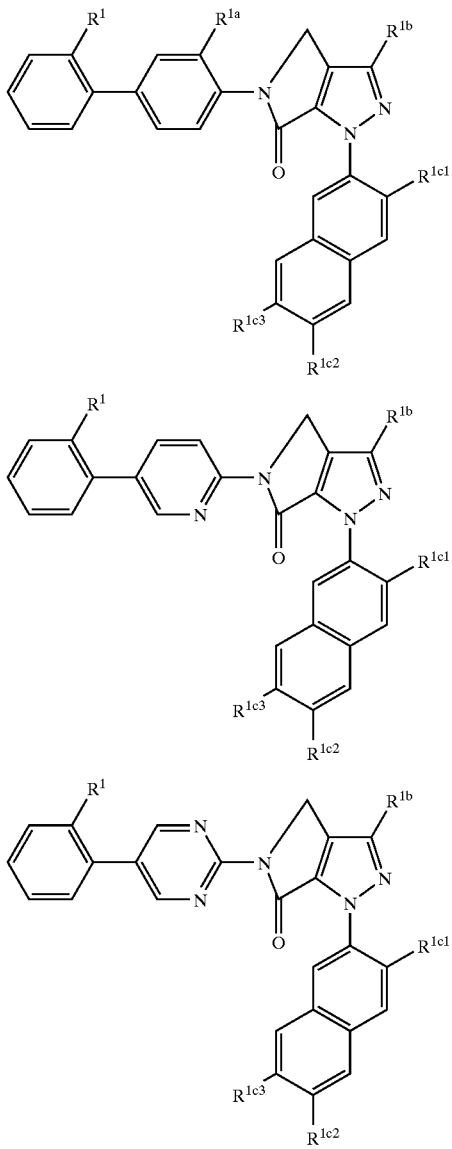

$R^{1a}$ is selected from the group consisting of:
—H, —F, —Cl and —Br;

$R^{1b}$ is selected from the group consisting of:
—$CH_3$, —$CF_3$, —$CH_2CH_3$, —$SO_2Me$, —$CONH_2$ and —$NHSO_2Me$;

$R^{1c1}$ is selected from the group consisting of:
—H, —F, —Cl, —Br, —$NH_2$, —OH, —$SO_2Me$, —$SO_2Et$, —$SO_2NH_2$, —$NO_2$, —$CH_2NH_2$, —CN, —$CONH_2$, —$CH_2OH$;

$R^{1c2}$ is selected from the group consisting of:
—H, —F, —Cl, —Br and —OMe; and $R^{1c3}$ is selected from the group consisting of:
—H, —F, —Cl, —Br, —OH, —$OCH_3$, —$NH_2$, —$CONH_2$, —$CH_2NH_2$.

The following compounds are an embodiment of the present invention:

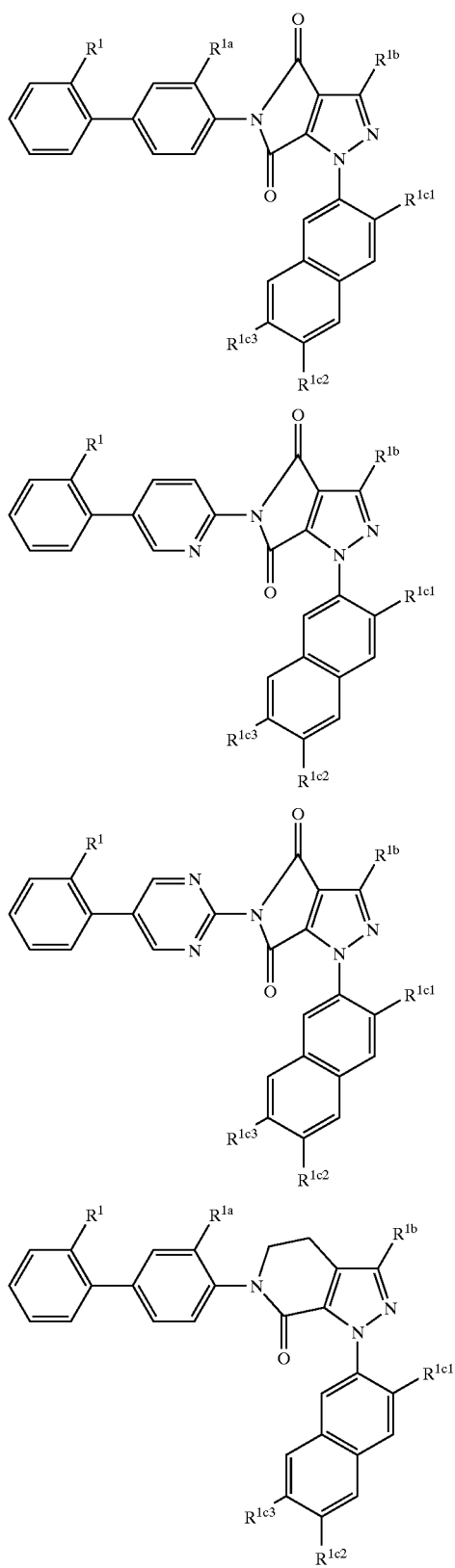
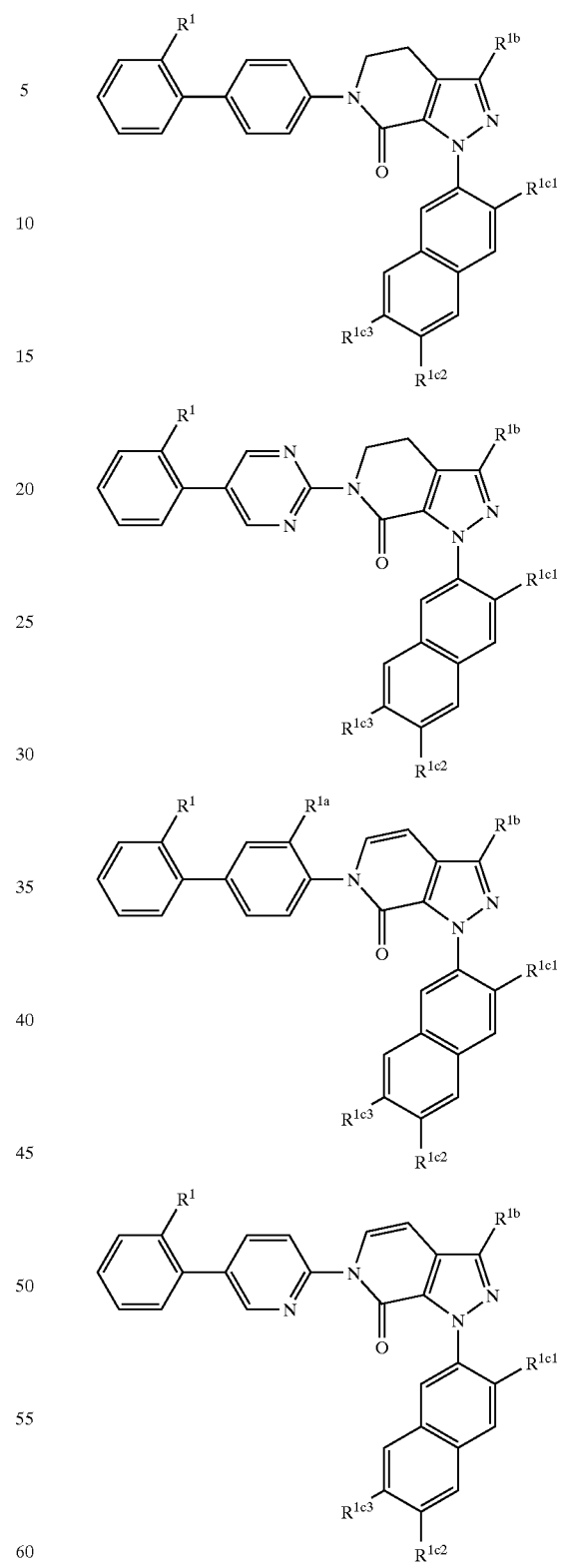

-continued

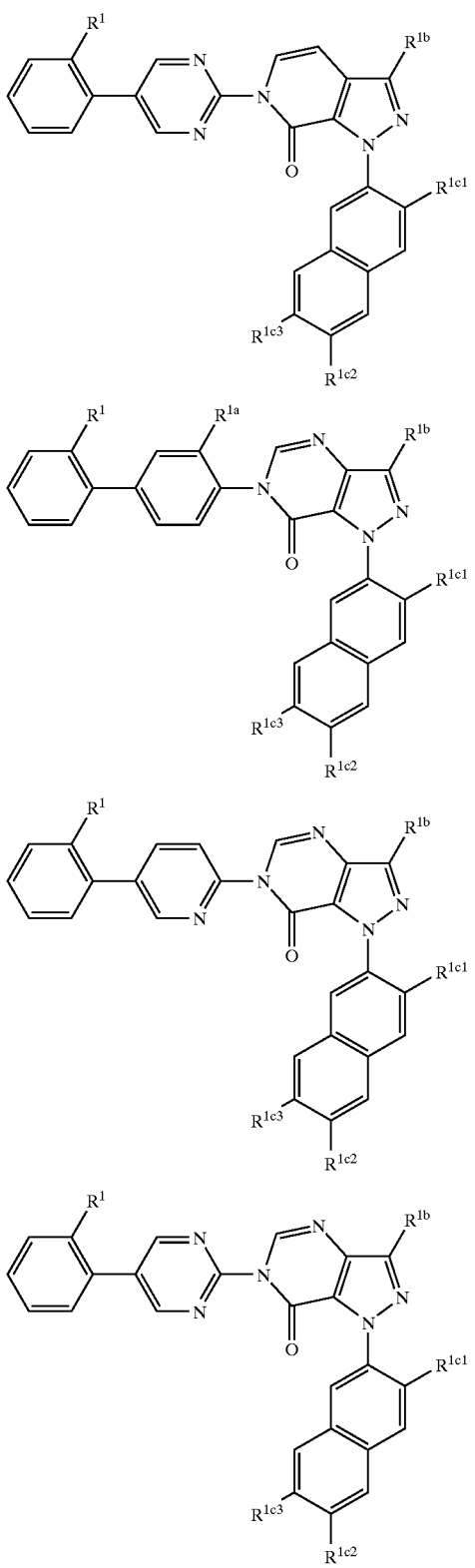

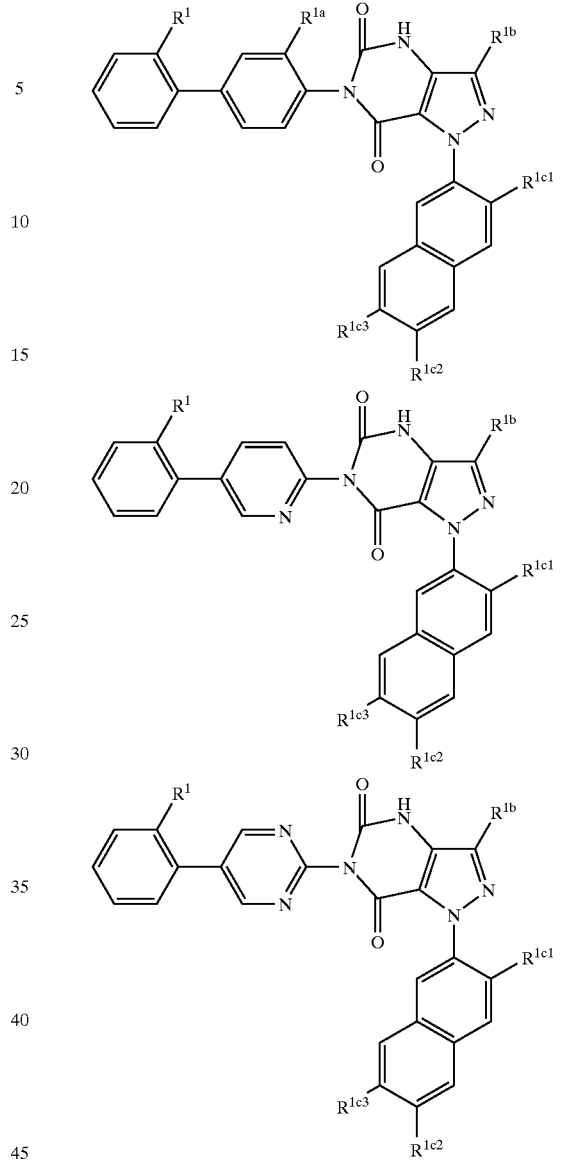

wherein:
R[1] is selected from the group consisting of:
—SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;

R[1a] is selected from the group consisting of:
—H, —F, —Cl and Br;

R[1b] is selected from the group consisting of:
—CH$_3$ and —CF$_3$;

R[1c1] is selected from the group consisting of:
—H, —F, —Cl, —Br, —CN, —CH$_2$NH$_2$, —CH$_2$OH, —CONH$_2$, —C(=NH)NH$_2$, —CO$_2$H, CO$_2$Me, —SO$_2$Me, —SO$_2$NH$_2$, —OH, —NH$_2$, and —NO$_2$;

R[1c2] is selected from the group consisting of:

—H, —F, —Cl and —Br; and
$R^{1c3}$ is selected from the group consisting of:
—H, —F, —Cl and —Br.
The following compounds are an embodiment of the present invention:
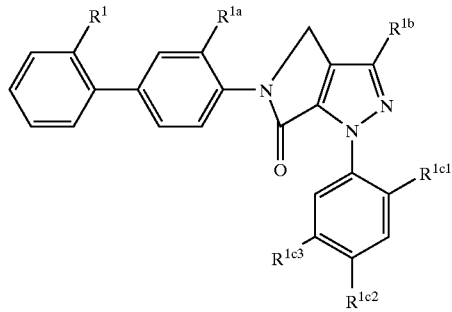
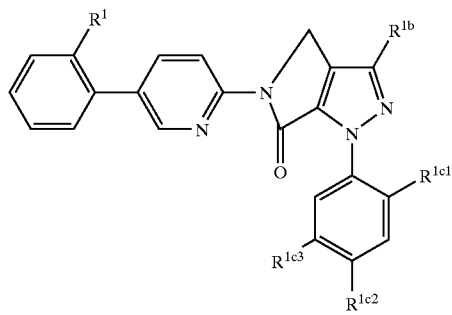
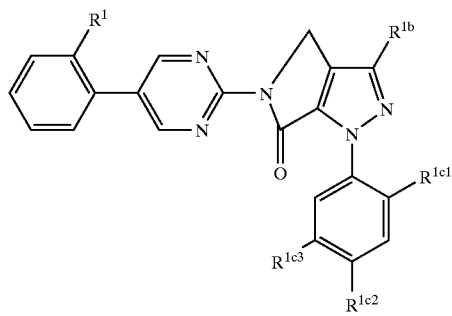
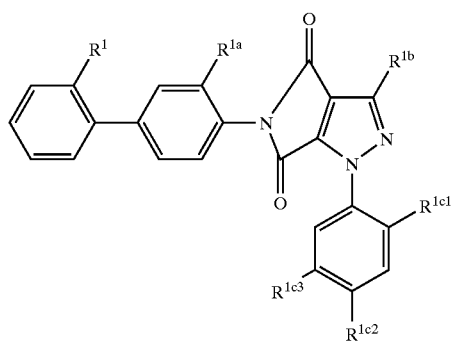
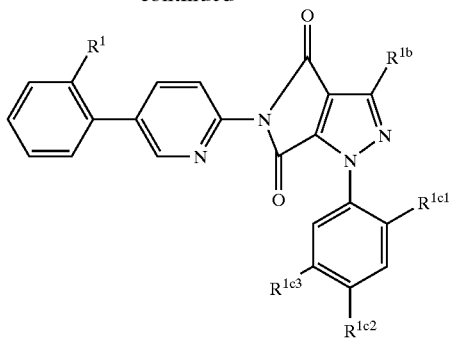
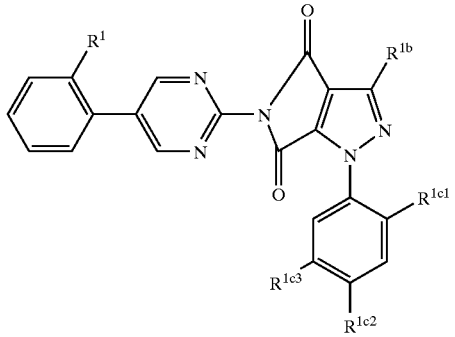
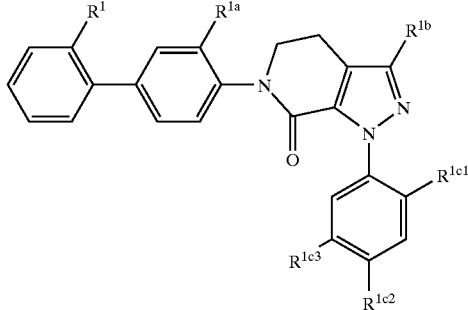
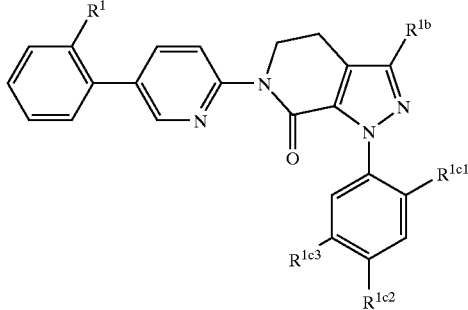
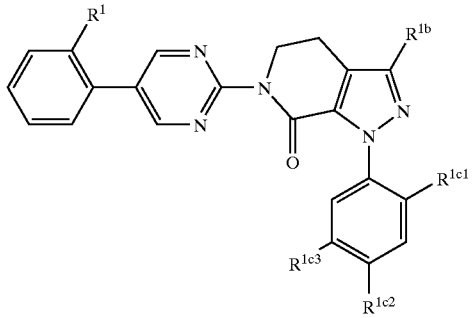

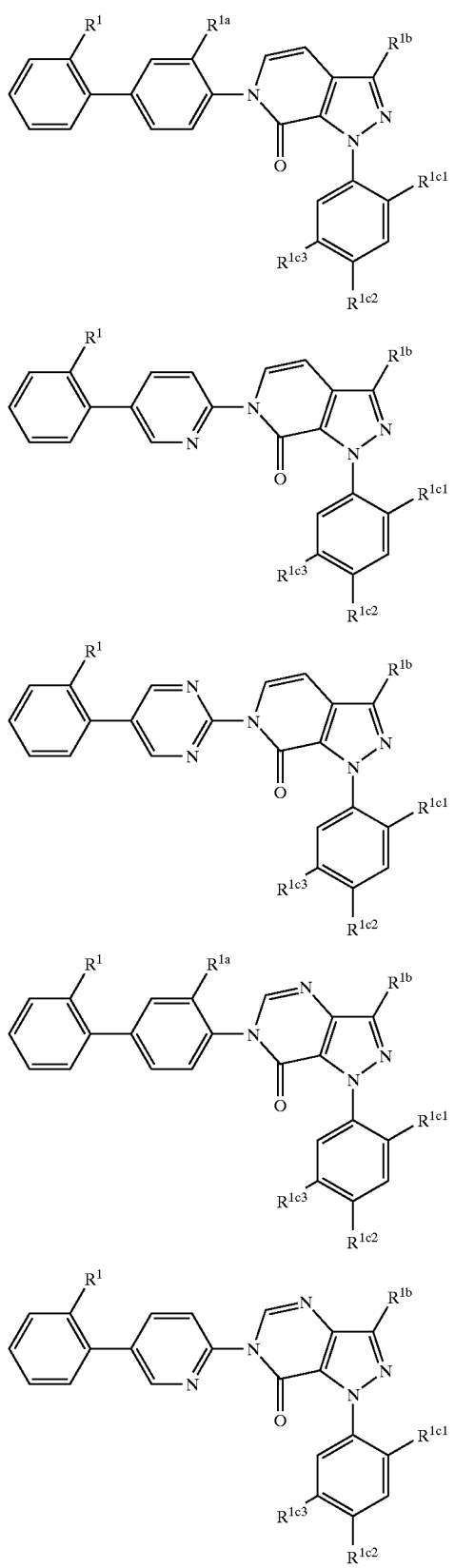
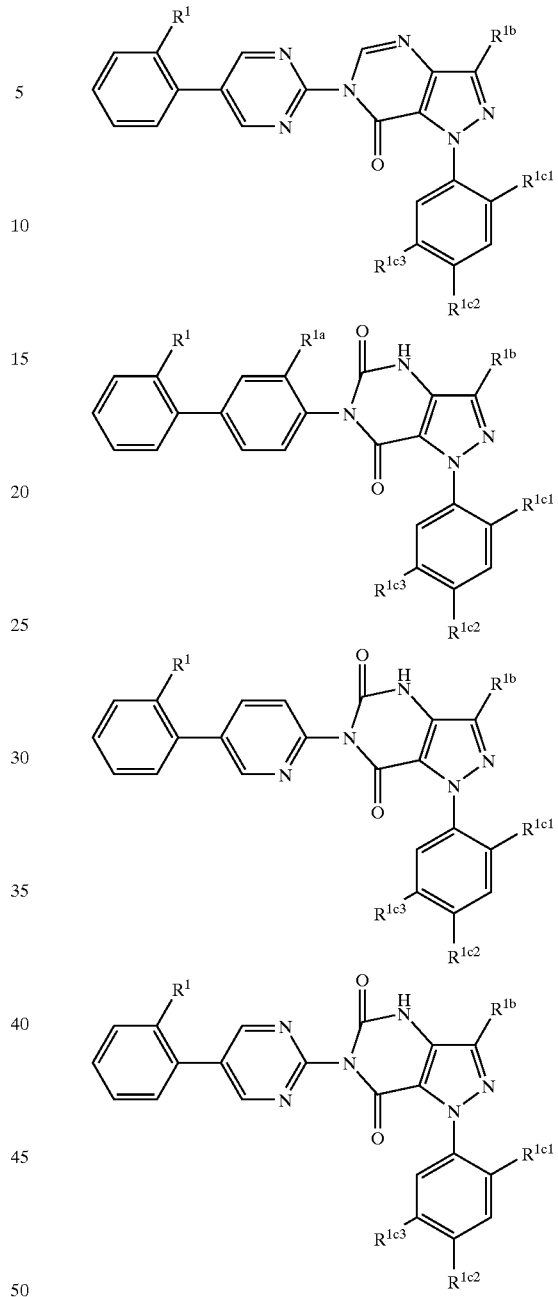
wherein:
R[1] is selected from the group consisting of: —CN, —CH₂NH₂, —CONH₂, —C(=NH)NH₂, —SO₂Me, —SO₂NH₂, and —NH₂;
R[1a] is selected from the group consisting of: —H, —F, —Cl and —Br;
R[1b] is selected from the group consisting of: —CH₃, —CF₃, —CH₂CH₃, —SO₂Me, —CONH₂ and —NHSO₂Me;
R[1c1] is selected from the group consisting of: —H, —F, —Cl, —Br, —NH₂, —OH, —SO₂Me, —SO₂Et, —SO₂NH₂, —NO₂, —CH₂NH₂, —CN, —CONH₂, —CH₂OH;

$R^{1c2}$ is selected from the group consisting of:
—H, —F, —Cl, —Br and —OCH$_3$;
$R^{1c3}$ is selected from the group consisting of:
—H, —F, —Cl, —Br, —OCH$_3$, —NH$_2$, —CH$_2$NH$_2$, —CONH$_2$, —CONHMe, —CONMe$_2$.
The following compounds are an embodiment of the present invention:
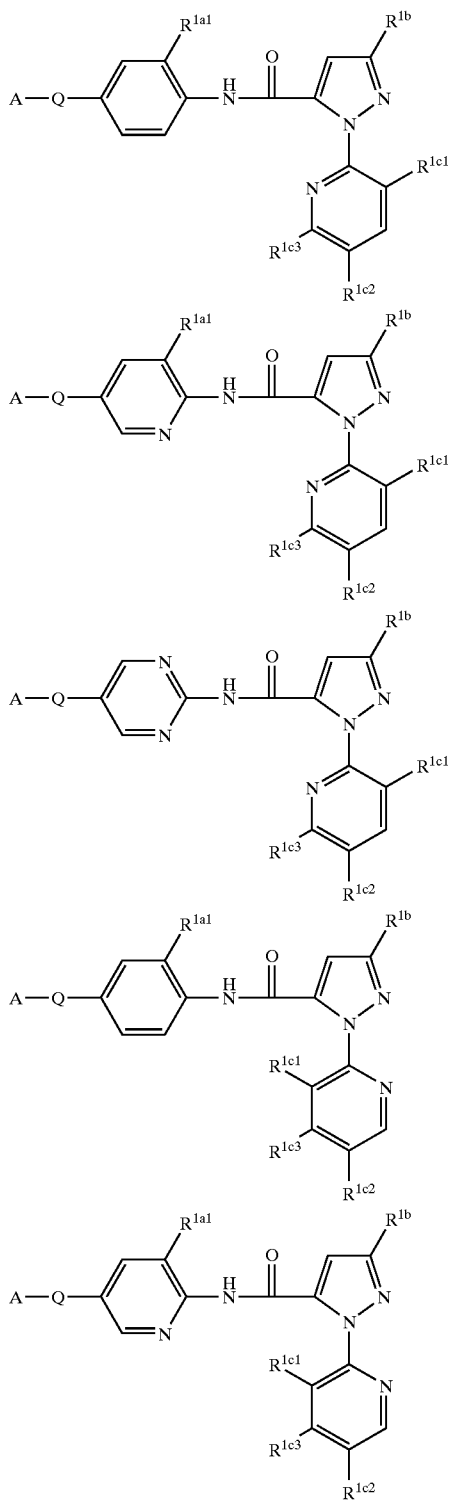
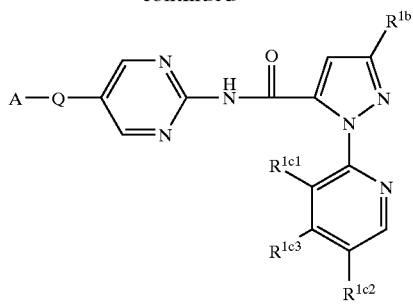
wherein:
A—Q is selected from the group consisting of:
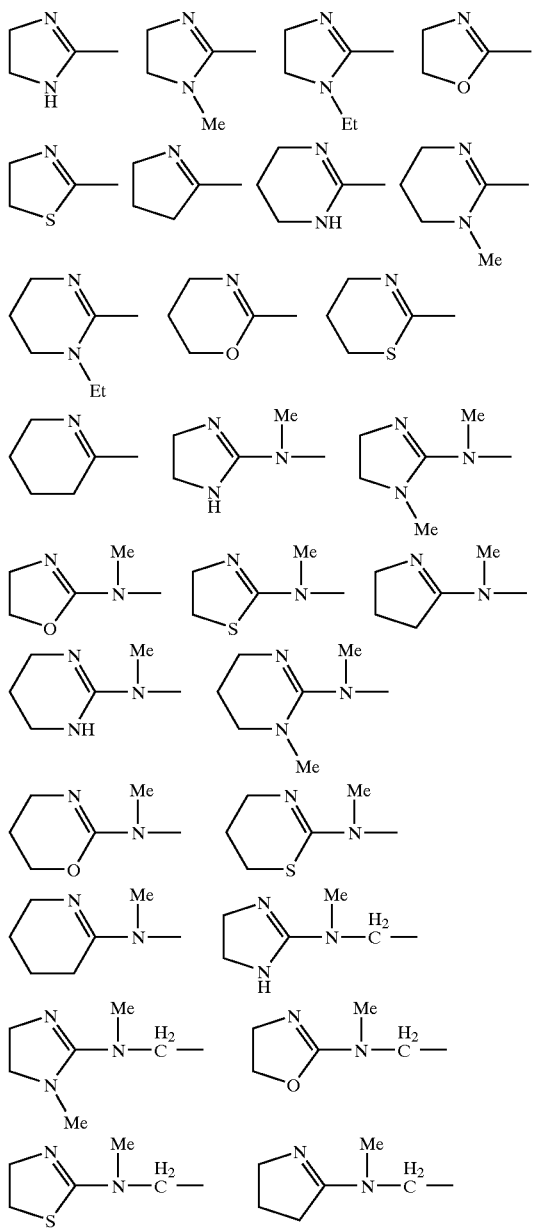

-continued

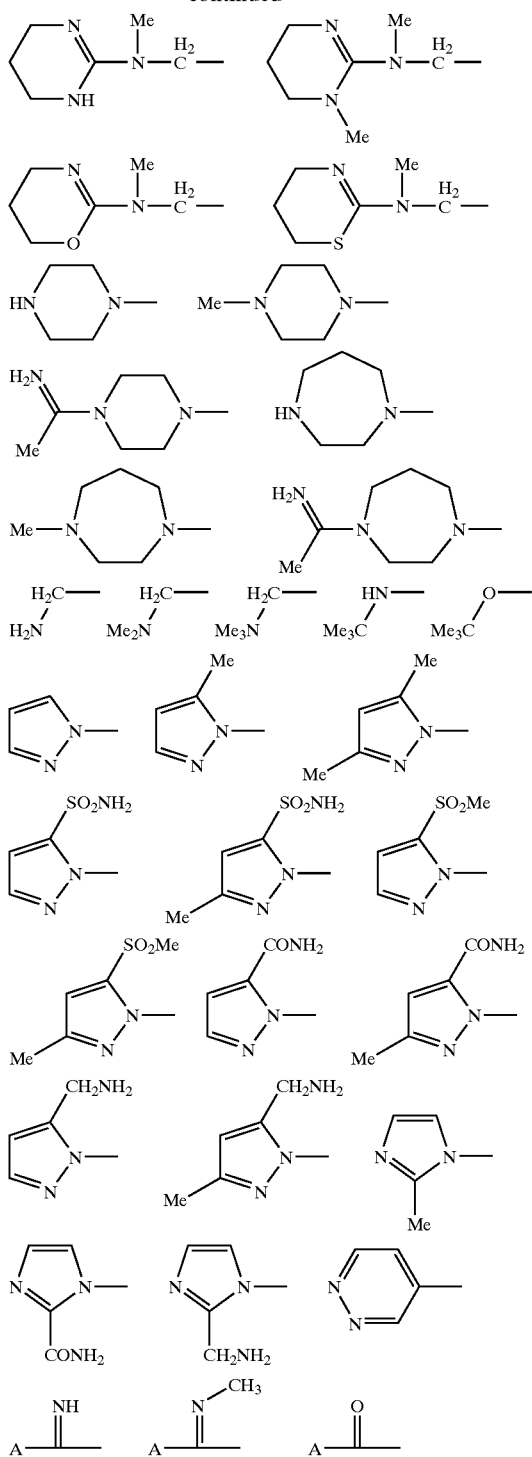

wherein:

A is selected from the group consisting of:

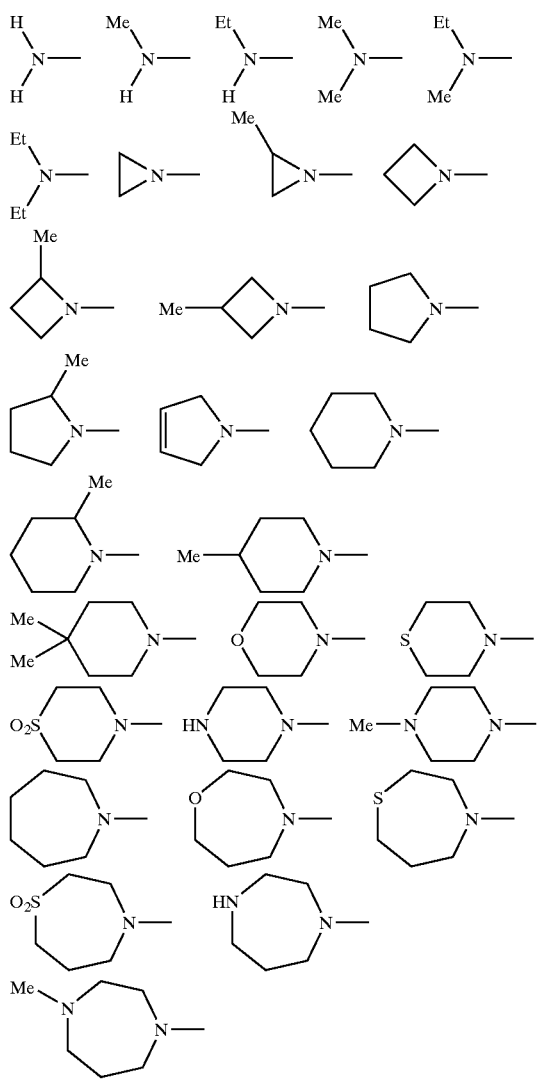

$R^{1a1}$ is selected from the group consisting of:
—H, —F, —Cl and —Br;

$R^{1b}$ is selected from the group consisting of:
—$CH_3$ and —$CF_3$;

$R^{1c1}$ is selected from the group consisting of:
—H, —F, —Cl, —Br, —CN, —$CH_2NH_2$, —$CH_2OH$, —$CONH_2$, —C(=NH)$NH_2$, —$CO_2H$, —$CO_2Me$, —$SO_2Me$, —$SO_2NH_2$, —OH, —$NH_2$, and —$NO_2$;

$R^{1c2}$ is selected from the group consisting of:
—H, —F, —Cl, —Br, and —$OCH_3$; and $R^{1c3}$ is selected from the group consisting of:
—H, —F, —Cl, —Br, —$OCH_3$, —$NH_2$, —$CH_2NH_2$, —$CONH_2$, —CONHMe, —$CONMe_2$.

The following compounds are an embodiment of the present invention:

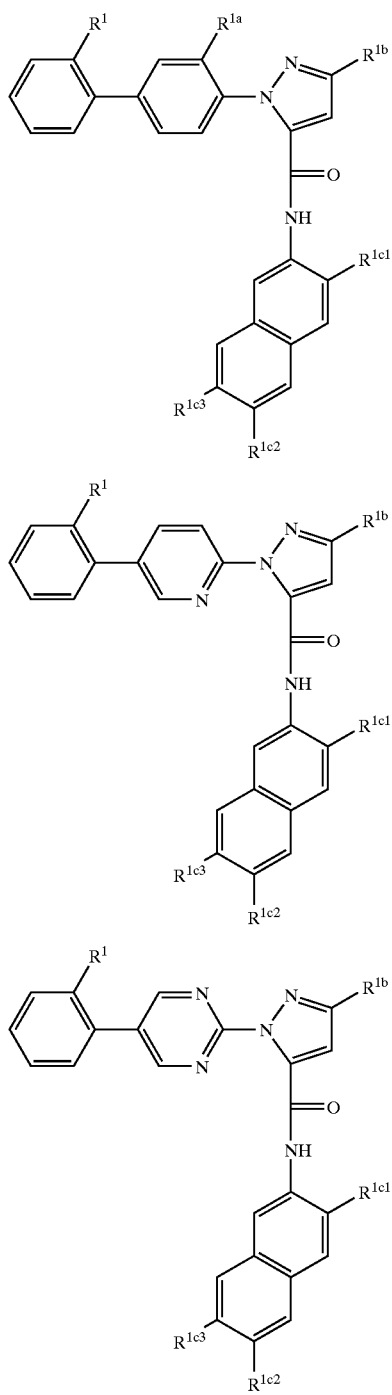
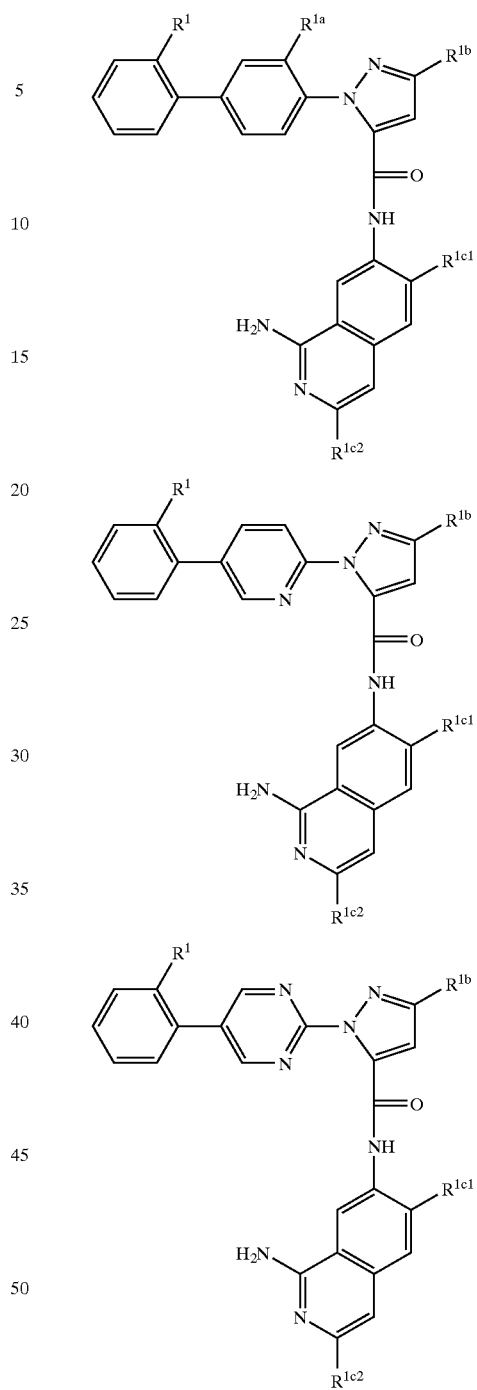

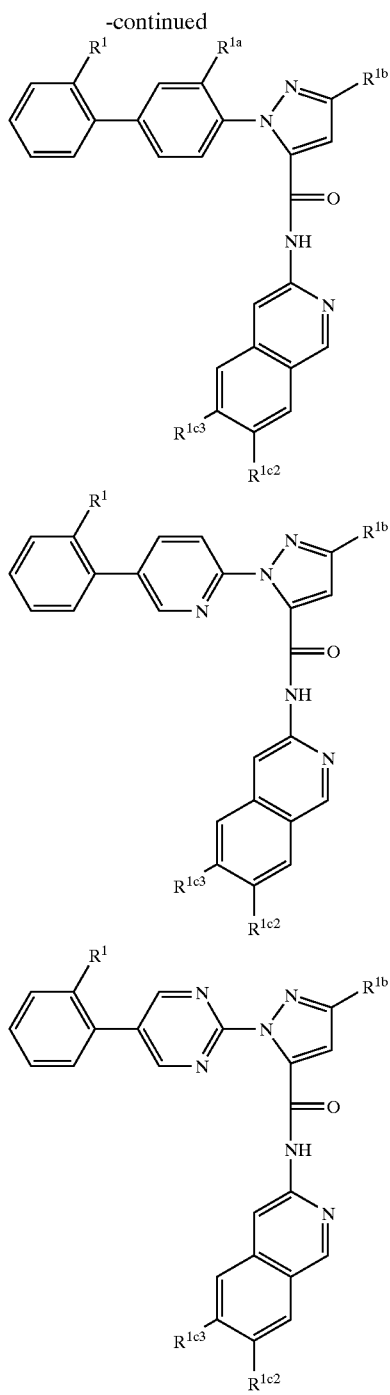

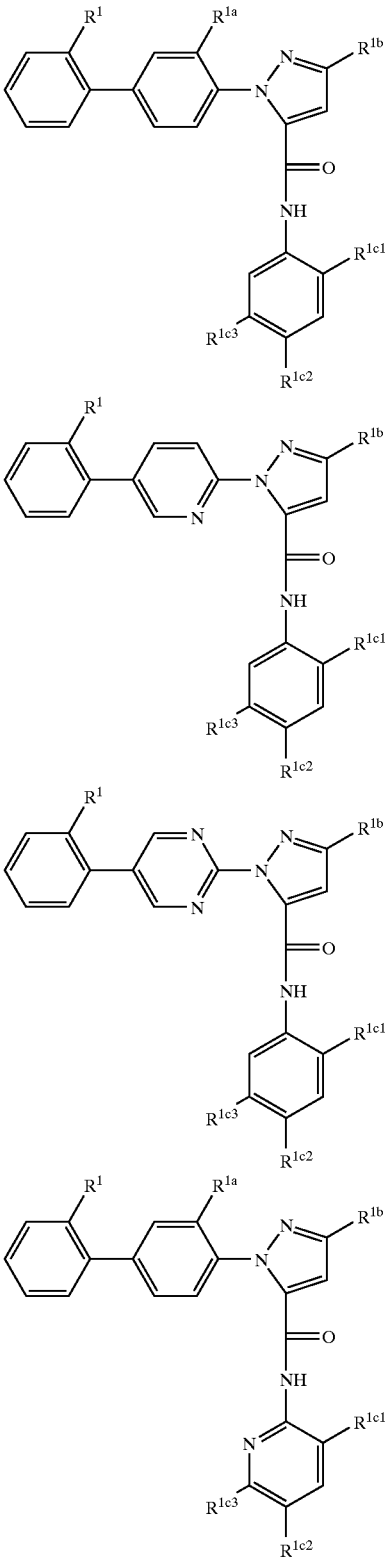

wherein:
R[1] is selected from the group consisting of:
—SO$_2$NH$_2$, —SO$_2$CH$_3$, —CN, —CONH$_2$, —CONH(CH$_3$), —CON(CH$_3$)$_2$, —CH$_2$NH$_2$, —CH$_2$NH(CH$_3$), —CH$_2$N(CH$_3$)$_2$;
R[1a] is selected from the group consisting of:
—H, —F, —Cl and —Br;
R[1b] is selected from the group consisting of:
—H, —CH$_3$ and —CF$_3$;
R[1c1] is selected from the group consisting of:
—H, —F, —Cl, —Br, —CN, —CH$_2$NE$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;

R[1c2] is selected from the group consisting of:
—H, —F, —Cl and —Br; and
R[1c3] is selected from the group consisting of:
—H, —F, —Cl and —Br.

The following compounds are an embodiment of the present invention:

-continued

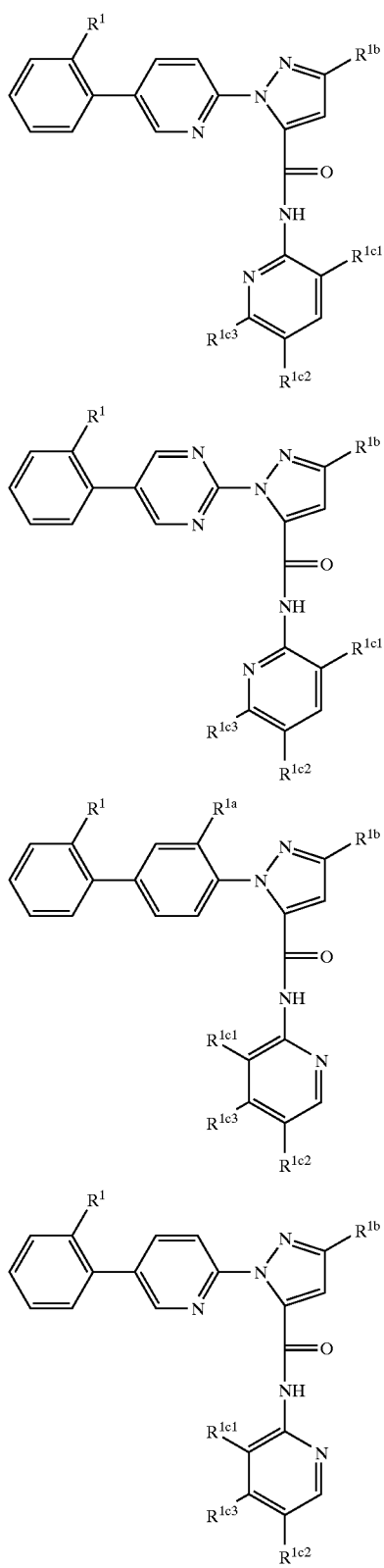

-continued

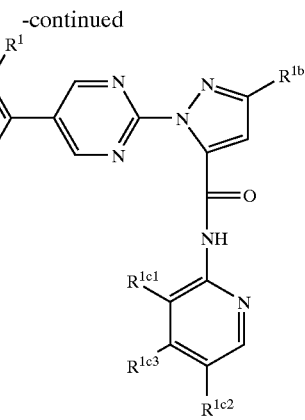

wherein:

R¹ is selected from the group consisting of:
—SO₂NH₂, —SO₂CH₃, —CN, —CONH₂, —CONH(CH₃), —CON(CH₃)₂, —CH₂NH₂, —CH₂NH(CH₃), —CH₂N(CH₃)₂;

$R^{1a}$ is selected from the group consisting of:
—H, —F, —Cl and —Br;

$R^{1b}$ is selected from the group consisting of:
—H, —CH₃ and —CF₃;

$R^{1c1}$ is selected from the group consisting of:
—H, —F, —CN, —CH₂NH₂, —CONH₂, —SO₂Me, —SO₂NH₂ and —NO₂;

$R^{1c2}$ is selected from the group consisting of:
—H, —F, —Cl, —Br and —OCH₃; and $R^{1c3}$ is selected from the group consisting of:
—H, —F, —Cl, —Br, —OCH₃, —NH₂, —CH₂NH₂, —CONH₂, —CONHMe, —CONMe₂.

The following compounds are an embodiment of the present invention:

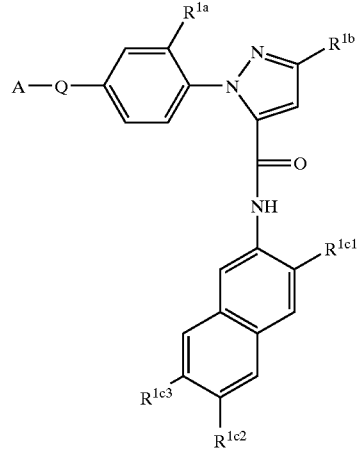

-continued
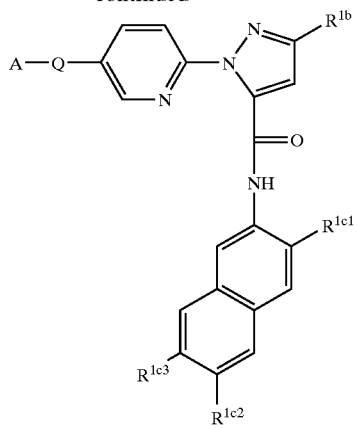
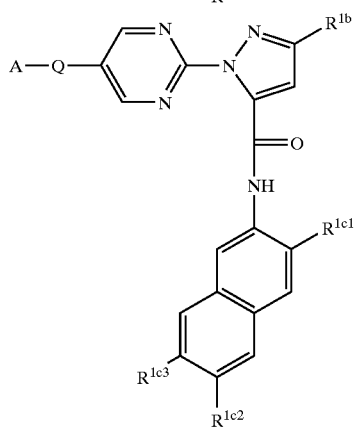
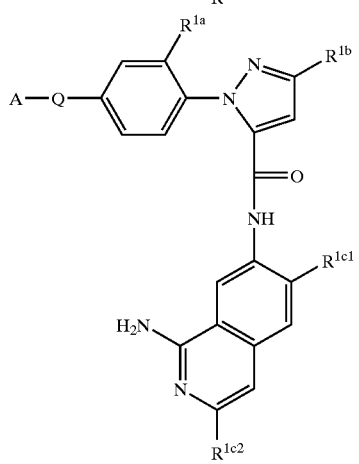
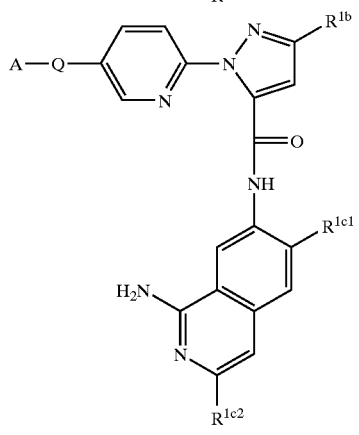
-continued
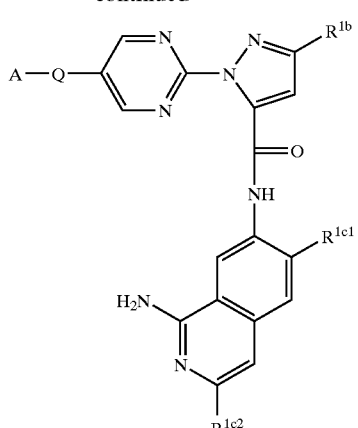
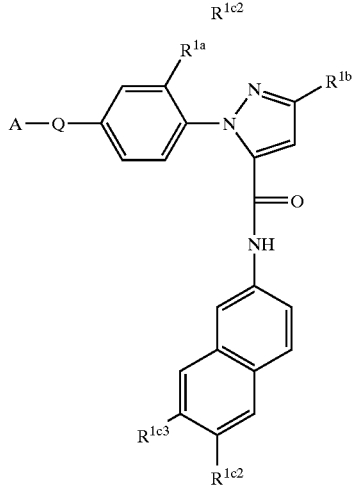
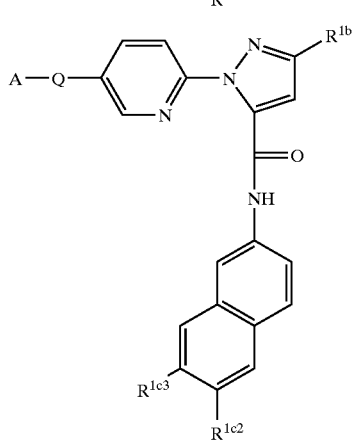

-continued
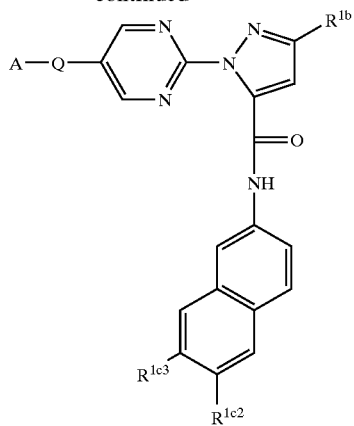
wherein:
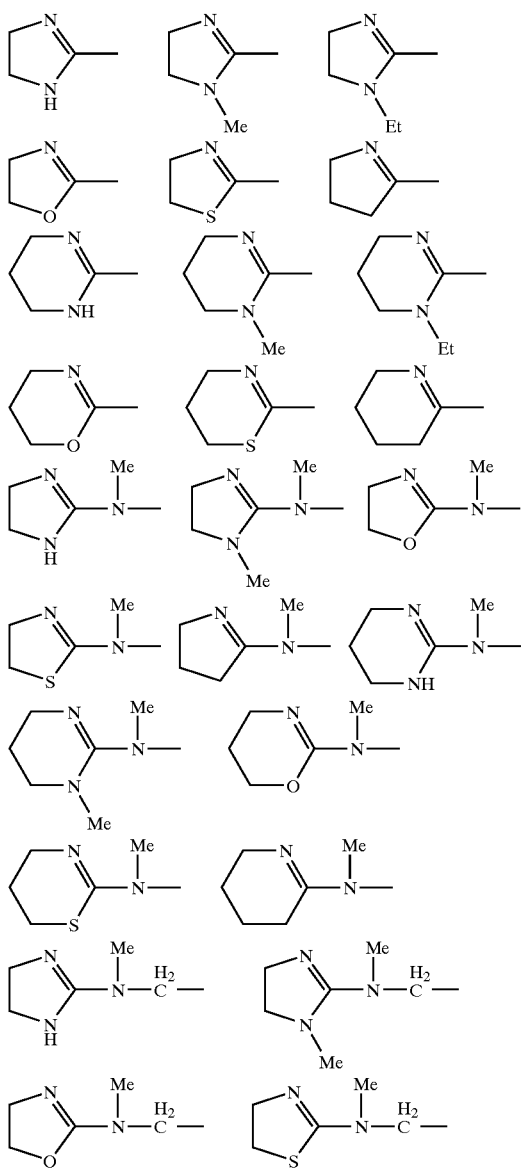
-continued
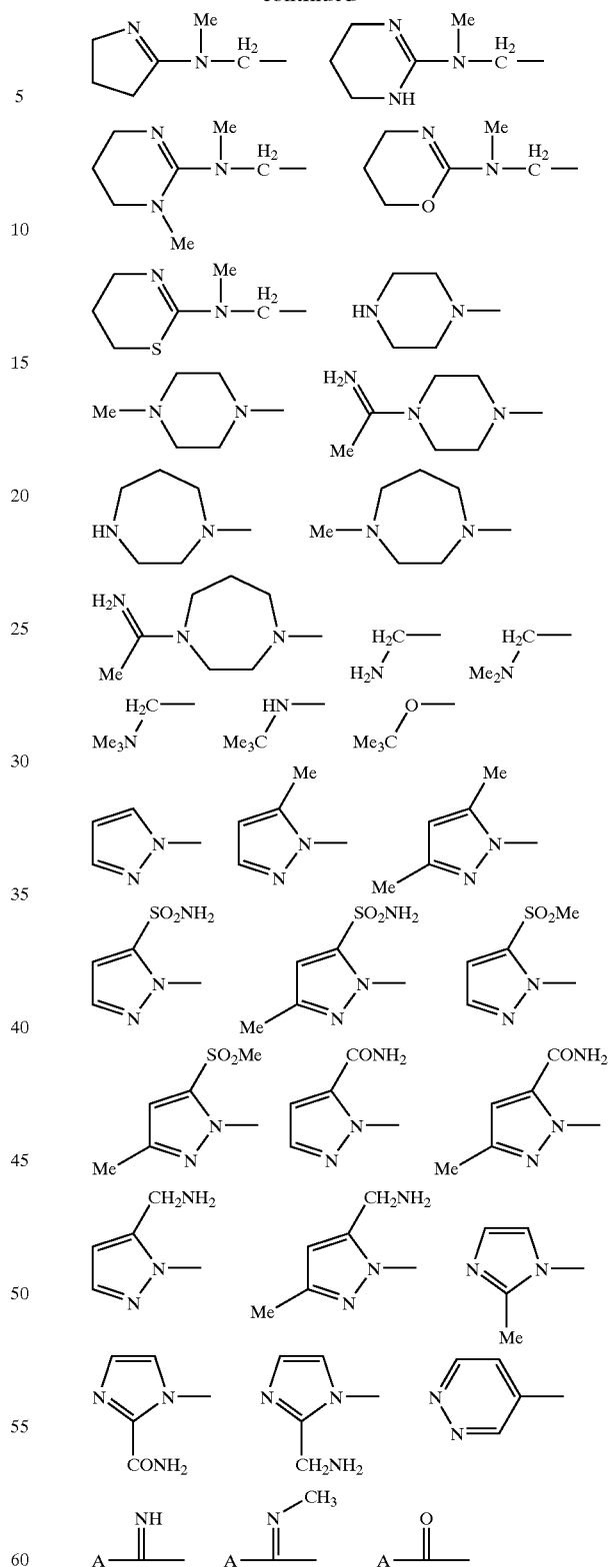
A—Q is selected from the group consisting of:
wherein:

A is selected from the group consisting of:

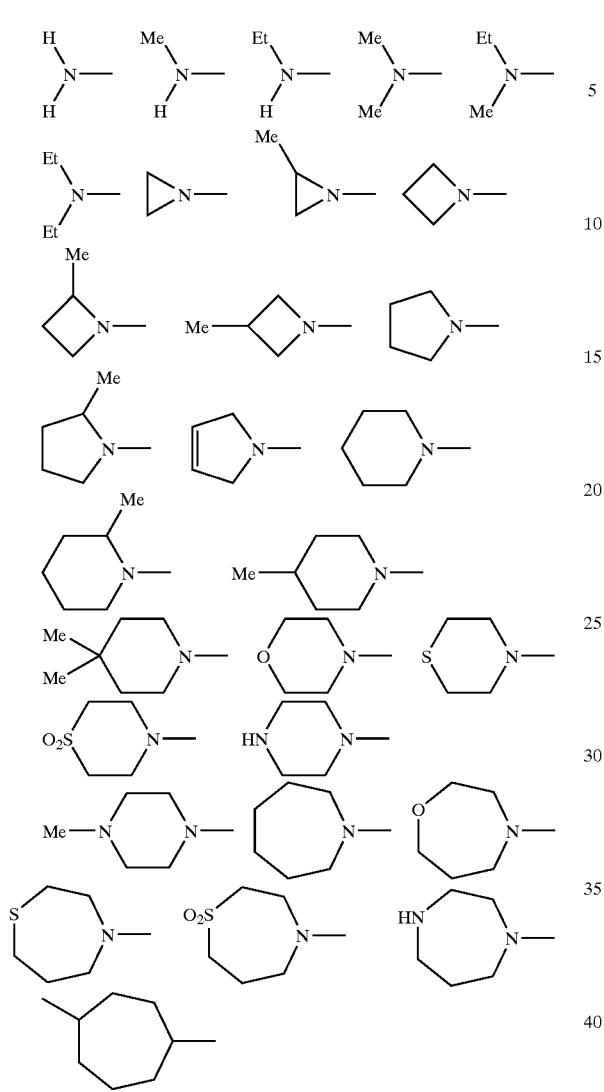

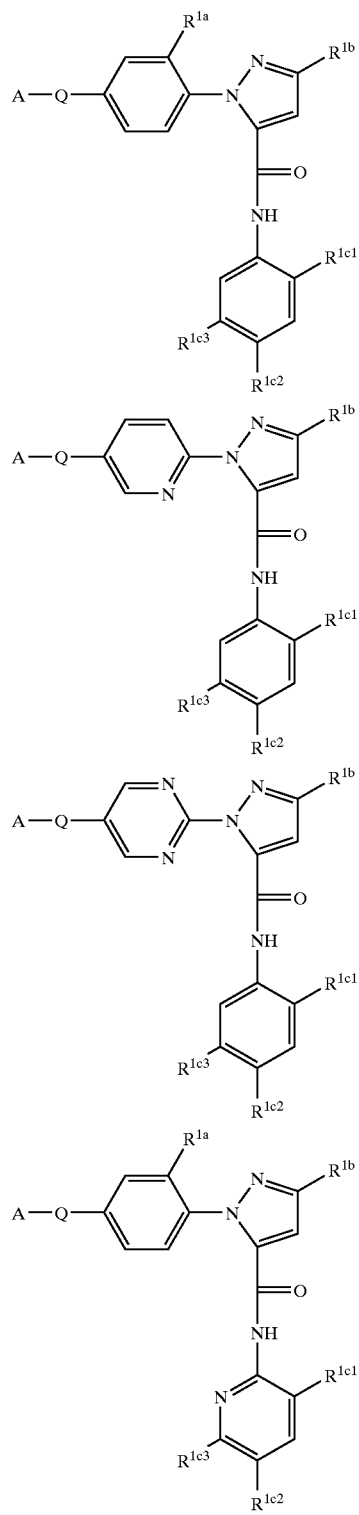

$R^{1a}$ is selected from the group consisting of:
—H, —F, —Cl and —Br;
$R^{1b}$ is selected from the group consisting of:
—H, —CH$_3$ and —CF$_3$;
$R^{1c1}$ is selected from the group consisting of:
—H, —F, —Cl, —Br, —CN, —CH$_2$NH$_2$, —CH$_2$OH, —CONH$_2$, —C(=NH)NH$_2$, —CO$_2$H, —CO$_2$Me, —SO$_2$Me, —SO$_2$NH$_2$, —OH, —NH$_2$, and —NO$_2$;
$R^{1c2}$ is selected from the group consisting of:
—H, —F, —Cl and —Br; and
$R^{1c3}$ is selected from the group consisting of:
—H, —F, —Cl and —Br.

The following compounds are an embodiment of the present invention:

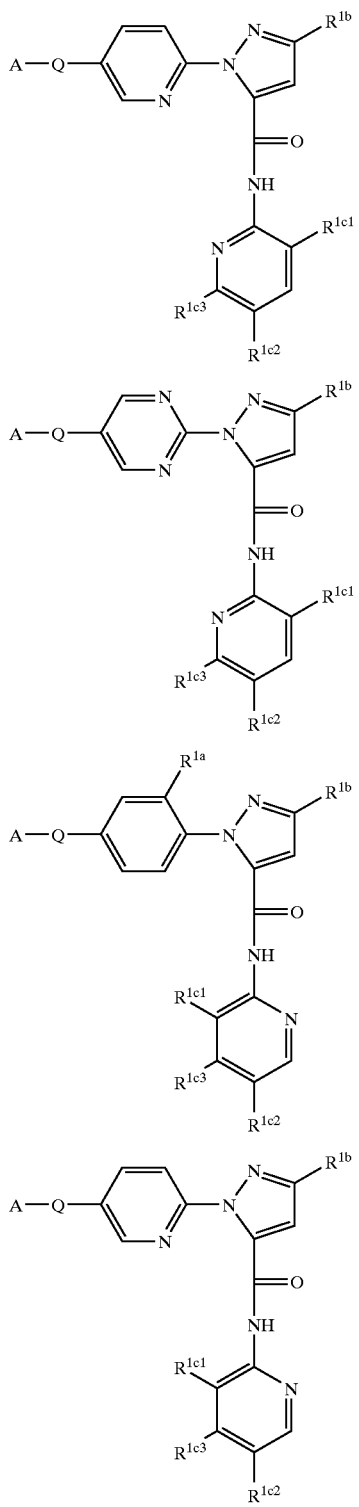
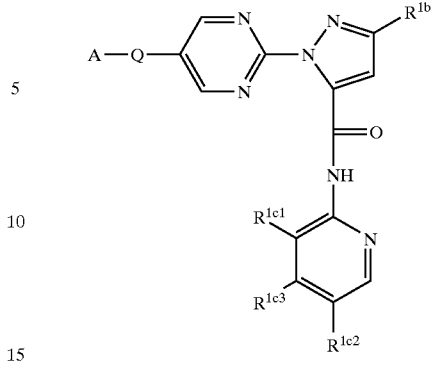
wherein:
A—Q is selected from the group consisting of:
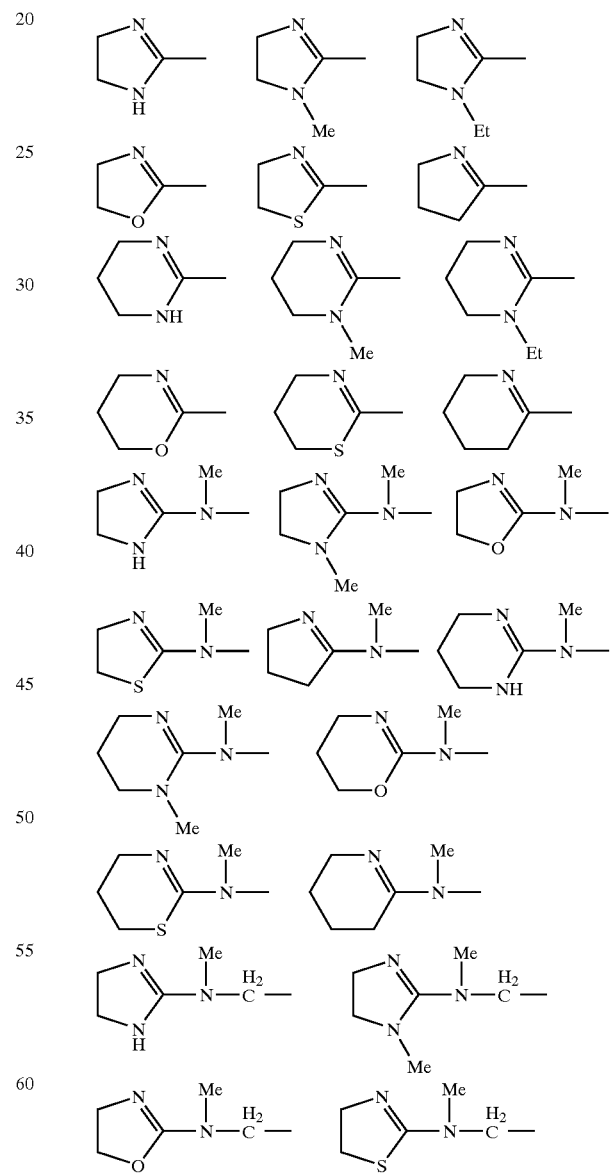

-continued

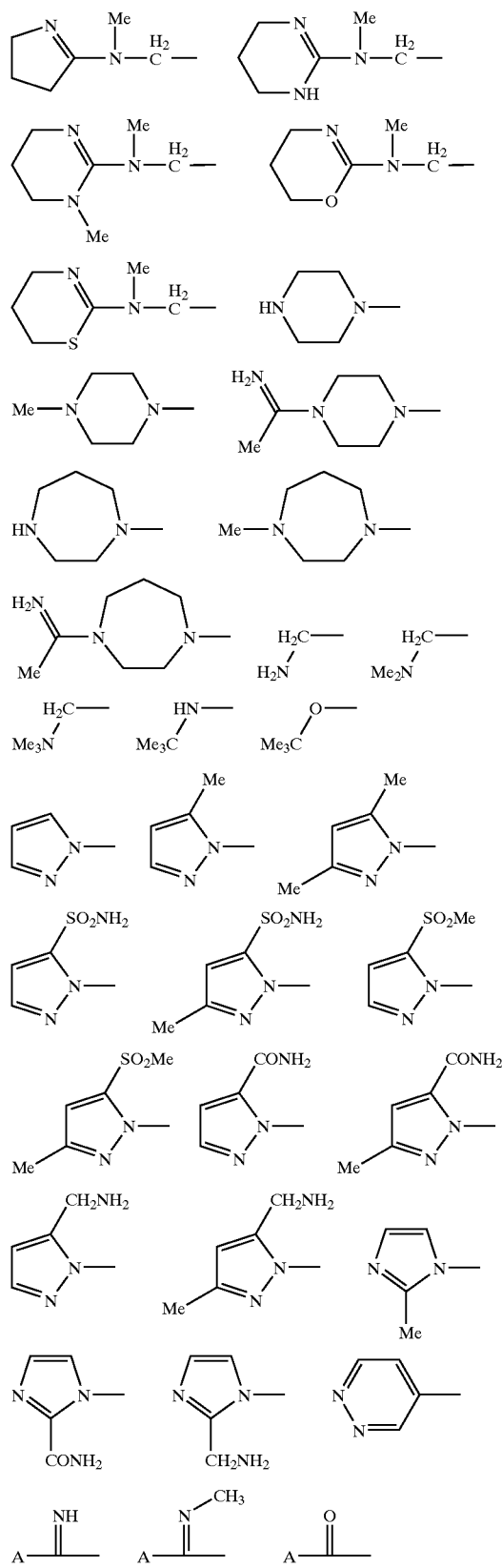

wherein:

A is selected from the group consisting of:

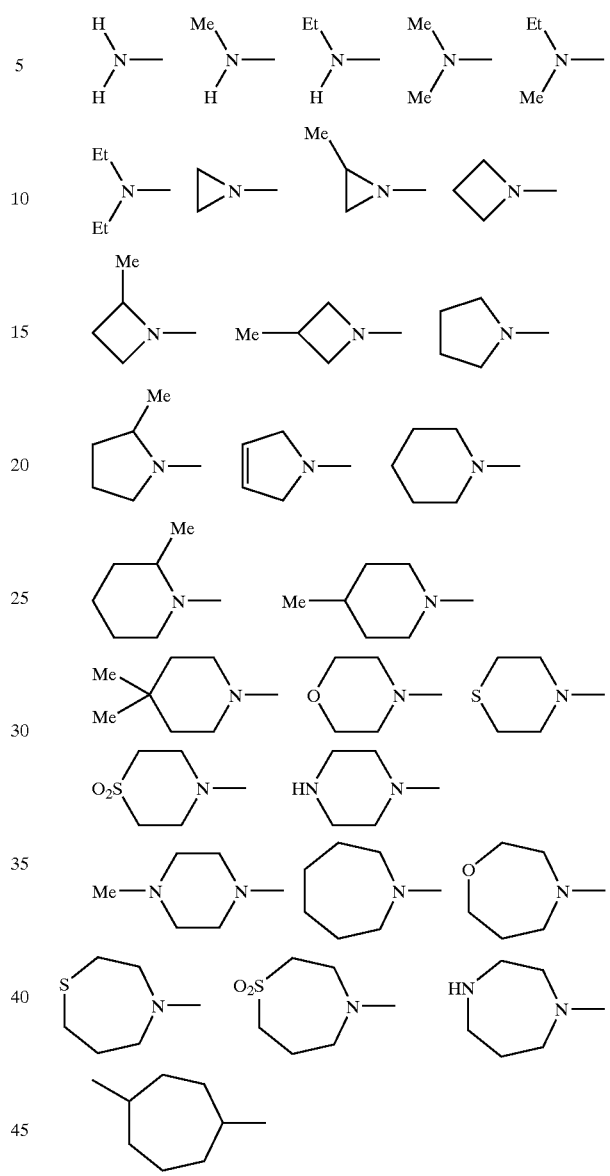

$R^{1a}$ is selected from the group consisting of:
—H, —F, —Cl and —Br;

$R^{1b}$ is selected from the group consisting of:
—H, —CH$_3$ and —CF$_3$;

$R^{1c1}$ is selected from the group consisting of:
—H, —F, —CN, —CH$_2$NH$_2$, —CONH$_2$, —SO$_2$Me, —SO$_2$NH$_2$ and —NO$_2$;

$R^{1c2}$ is selected from the group consisting of:
—H, —F, —Cl, —Br and —OCH$_3$; and $R^{1c3}$ is selected from the group consisting of:
—H, —F, —Cl, —Br, —OCH$_3$, —NH$_2$, —CH$_2$NH$_2$, —CONH$_2$, —CONHMe, —CONMe$_2$.

The following compounds are an embodiment of the present invention:

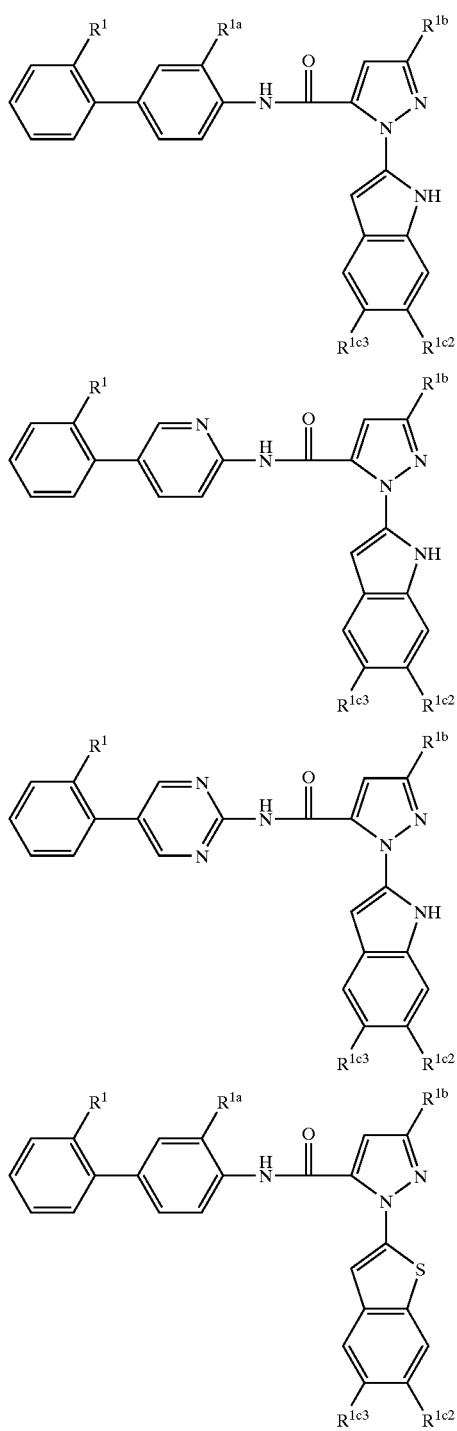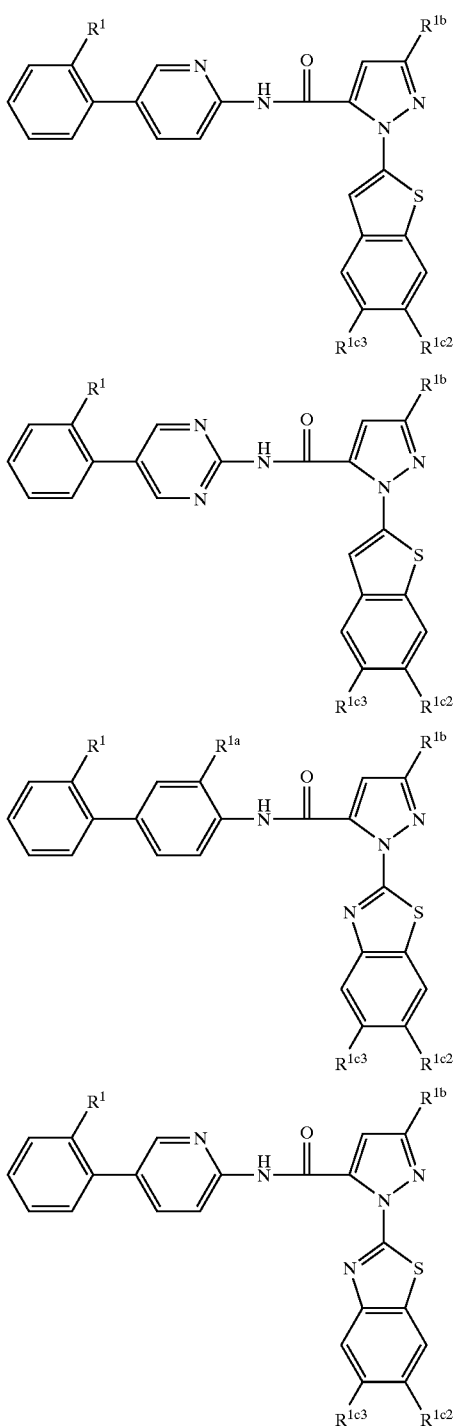

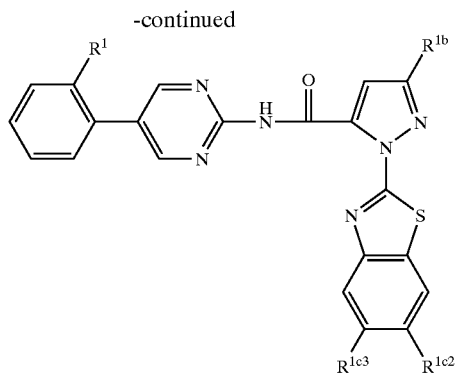

wherein:

R[1] is selected from the group consisting of:
  —SO$_2$NH$_2$, —SO$_2$Me, —CH$_2$NH$_2$ and —CH$_2$NMe$_2$;

R[1a] is selected from the group consisting of:
  —H, —F, —Cl and Br,

R[1b] is selected from the group consisting of:
  —CH$_3$, —CF$_3$, —CH$_2$CH$_3$, —SO$_2$Me, —CONH$_2$ and —NHSO$_2$Me;

R[1c2] and R[1c3] are independently selected from the group consisting of:
  —H, —F, —Cl and —Br.

The following compounds are an embodiment of the present invention:

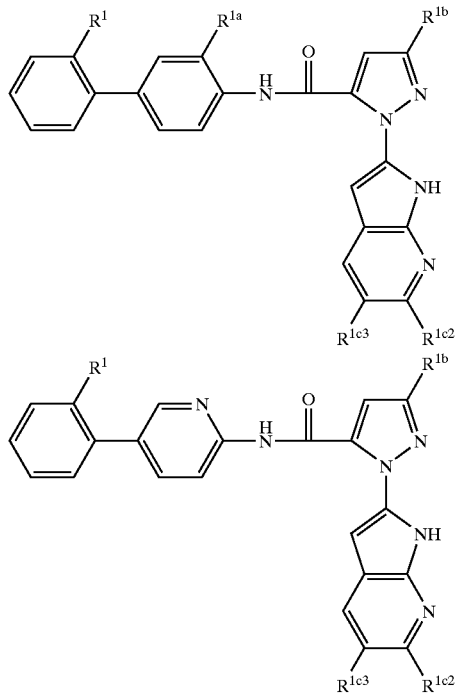

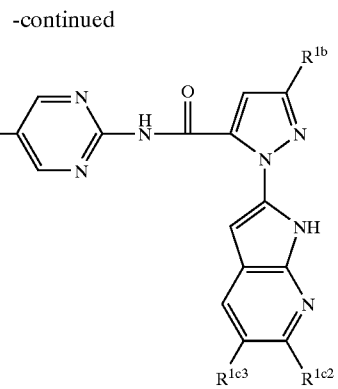

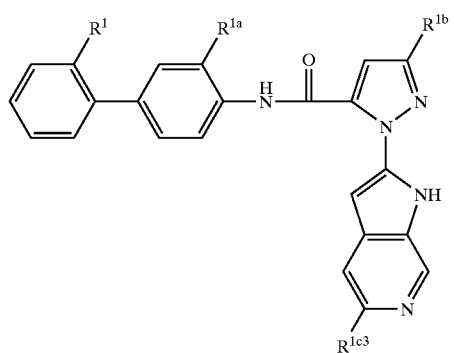

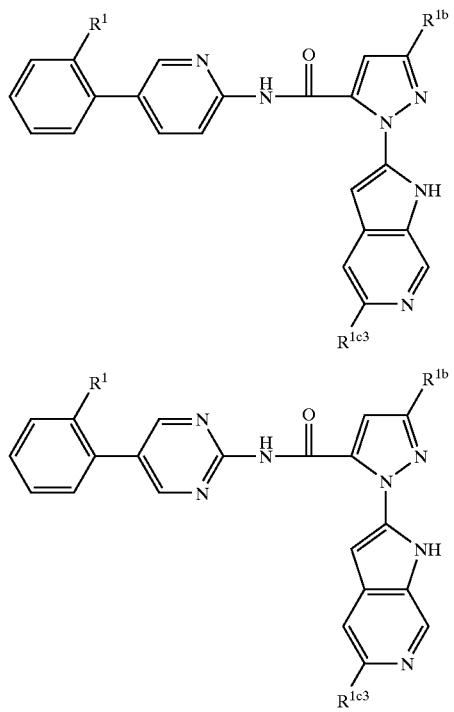

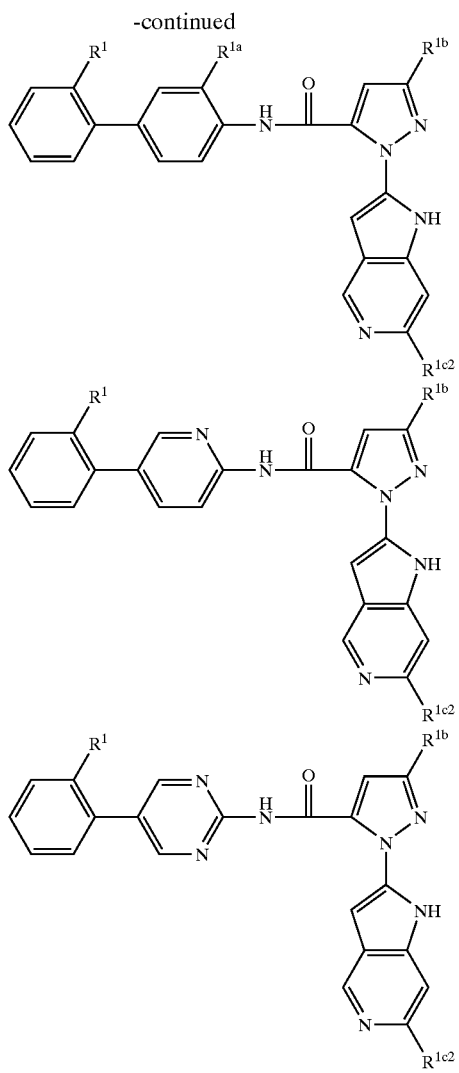

wherein:
R¹ is selected from the group consisting of:
—SO₂NH₂, —SO₂Me, —CH₂NH₂ and —CH₂NMe₂;
R¹ᵃ is selected from the group consisting of:
—H, —F, —Cl and —Br;
R¹ᵇ is selected from the group consisting of:
—CH₃, —CF₃, —CH₂CH₃, —SO₂Me, —CONH₂ and —NHSO₂Me;
R¹ᶜ² and R¹ᶜ³ are independently selected from the group consisting of:
—H, —F, —Cl and —Br.

This invention also encompasses all pharmaceutically acceptable isomers, salts, hydrates, solvates and prodrug derivatives of the compounds of the formula (I). In addition, the compounds of formula (I) can exist in various isomeric and tautomeric forms, and all such forms are meant to be included in the invention, along with pharmaceutically acceptable salts, hydrates, solvates and prodrug derivatives of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Preparation of Compounds

The compounds of the present invention may be synthesized by standard organic chemical synthetic methods as described and referenced in standard textbooks. These methods are well known in the art. See, e.g., March, "Advanced Organic Chemistry", John Wiley & Sons, New York, 1992; Joule, Mills and Smith, "Heterocyclic Chemistry", Chapman & Hall, London, 1995, et seq.

Starting materials used in any of these methods are commercially available from chemical vendors such as Aldrich, Fluka, Lancaster, TCI, Maybridge, Frontier, Fluorochem, Alfa Aesar, and the like, or may be readily synthesized by known procedures.

Reactions are carried out in standard laboratory glassware and reaction vessels under reaction conditions of standard temperature and pressure, except where otherwise indicated.

During the syntheses of these compounds, the functional groups of the substitutents are optionally protected by blocking groups to prevent cross reaction. Examples of suitable protective groups and their use are described in Kocienski, "Protecting Groups", Thieme, Stuttgart, 1994; Greene and Wuts, "Protective Groups in Organic Synthesis", John Wiley & Sons, New York, 1999, and the disclosures of which are incorporated herein by reference.

Non-limiting exemplary synthesis schemes are outlined directly below, and specific steps are described in the Examples. The reaction products are isolated and purified by conventional methods, typically by solvent extraction into a compatible solvent. The products may be further purified by any means known in the art such as, for example, flash column chromatography, reverse-phase preparative high performance liquid chromatography (HPLC) with high purity water and acetonitrile, or other appropriate methods.

General Synthesis

General synthesis for compounds with a N-linked G ring is outlined in Scheme 1 below. In Scheme 1, A', Q', D', E', J' and X' are protected functional structures which can be converted to A, Q, D, E, J and X respectively by methods known in the art (e.g. deprotection methods). For formation of the N-linked G ring, the appropriate aromatic amine precursor is treated under conditions described in Joule, Mills and Smith, "Heterocyclic Chemistry", Chapman & Hall, London, 1995, or the references cited therein, or as described later in the preparation section to give the G ring.

Scheme 1
For nitrogen-linked heterocycle G
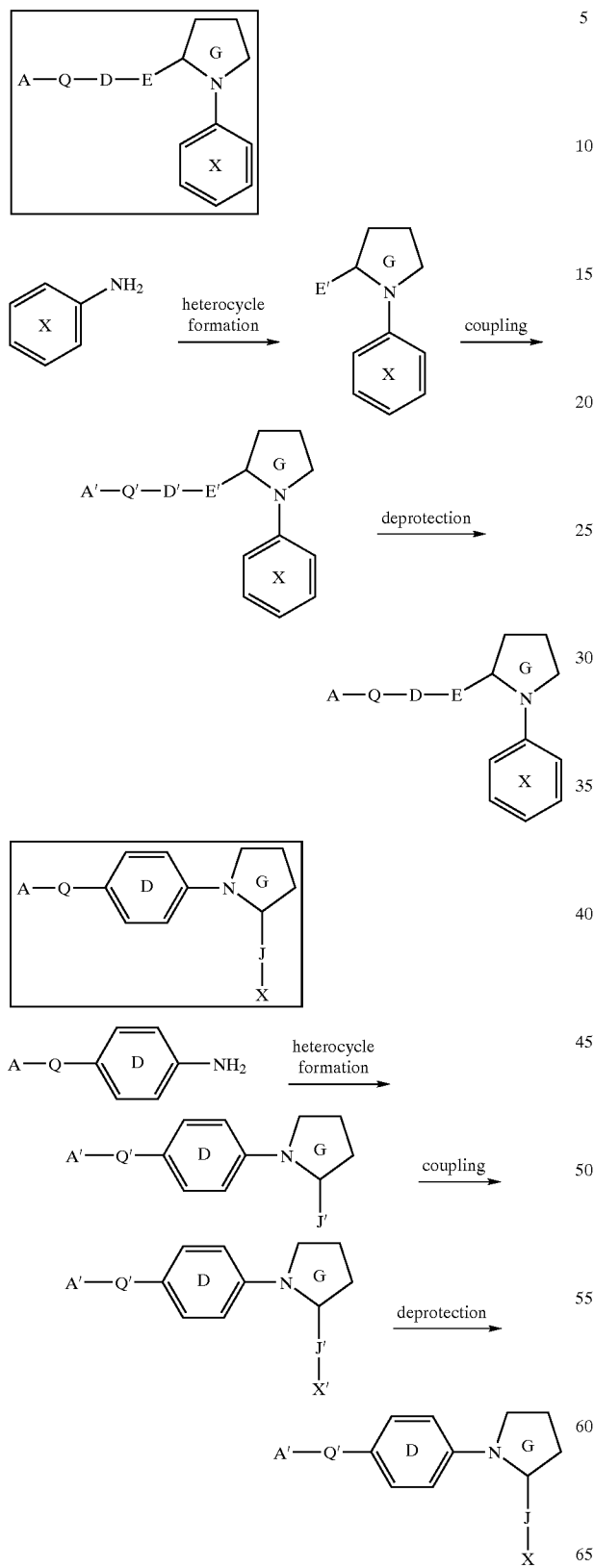
Scheme 2
For pyrazole-linked compounds
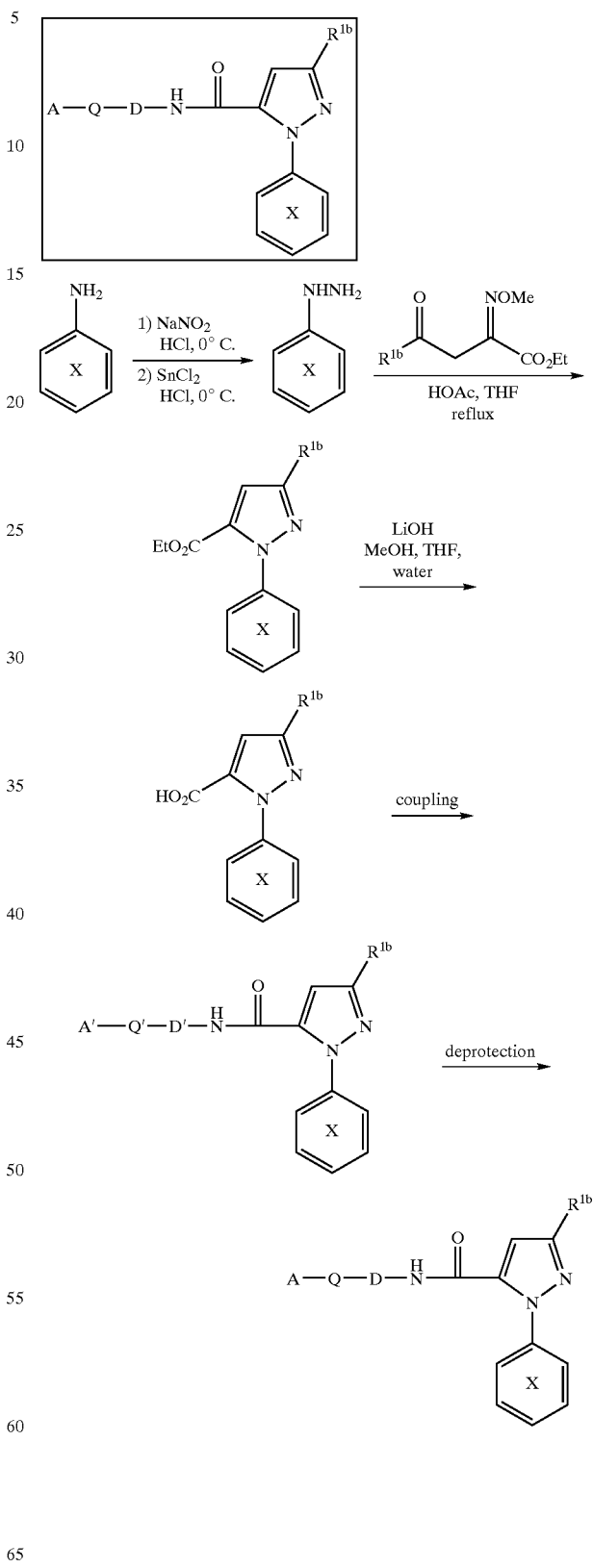

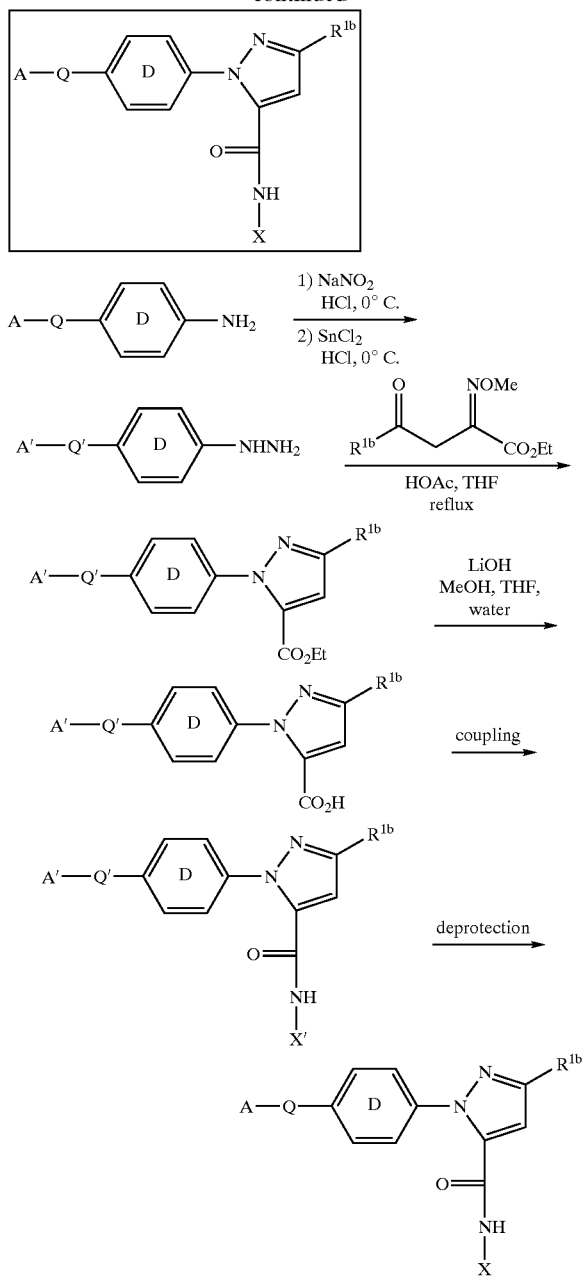

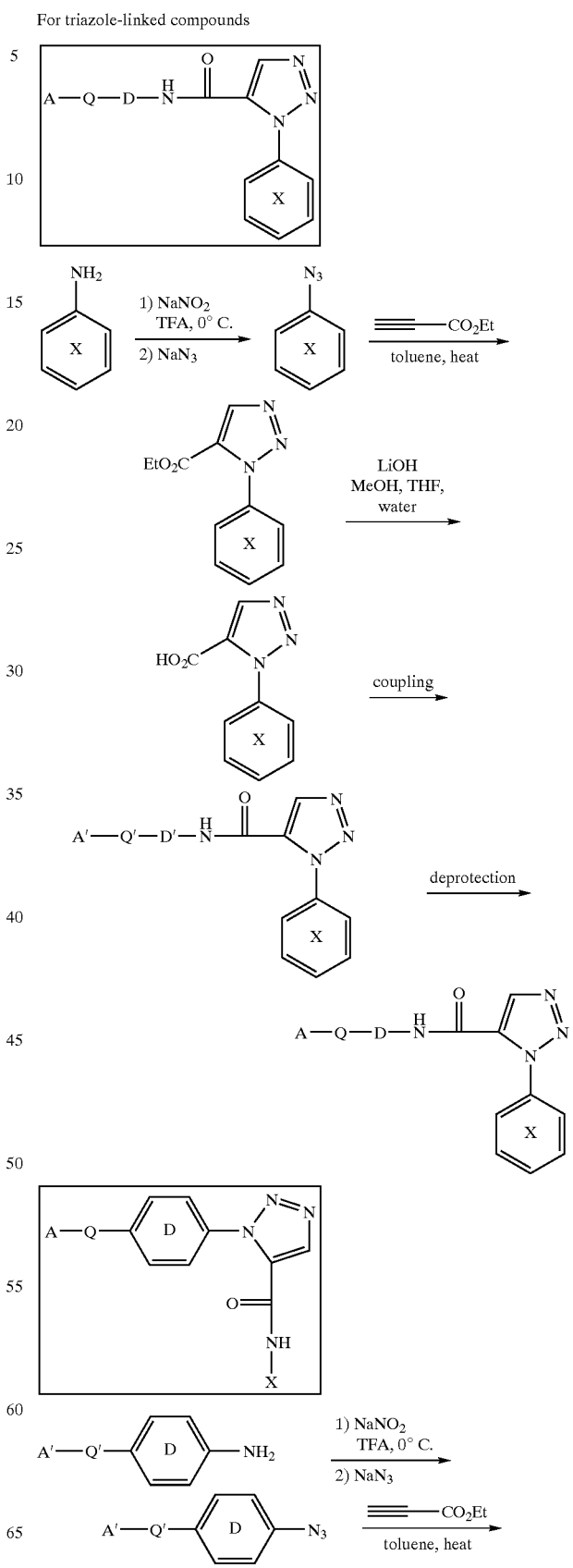

Scheme 2 above shows the general synthesis of compounds with a N-linked pyrazole G ring. Appropriately protected aromatic amines are converted to aromatic hydrazines by reduction of their diazonium salts. The hydrazines are condensed with 1,3-diketones to yield the pyrazole structures.

Scheme 3 shows the general synthesis of compounds with a N-linked triazole G ring. An appropriately protected aromatic amine is converted to aromatic azide from its diazonium salt. The azide is condensed with an alkyne to yield the triazole structure.

-continued

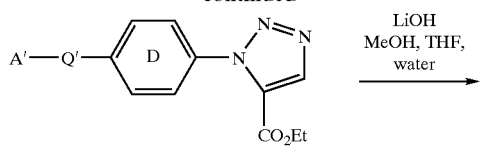

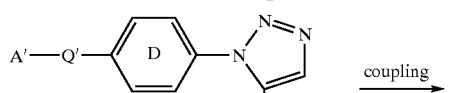

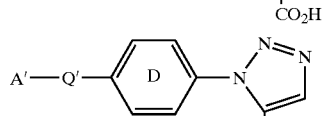

Scheme 4
For tetrazole-linked compounds

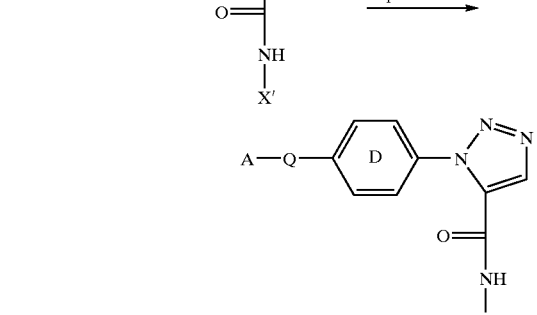

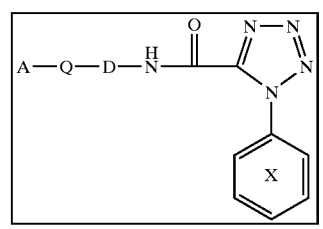

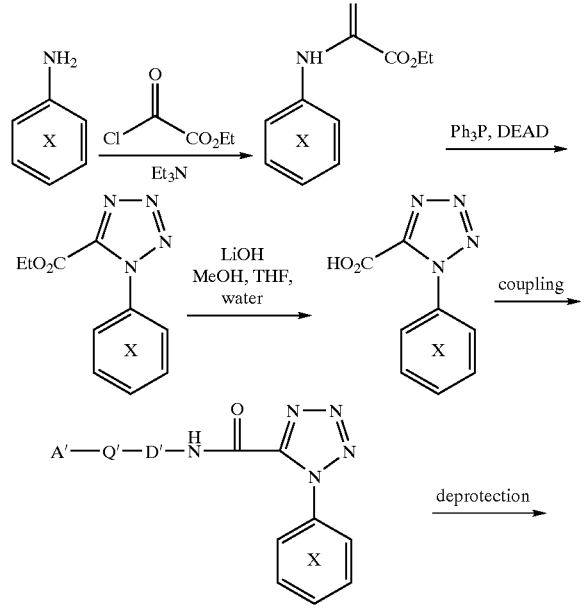

-continued

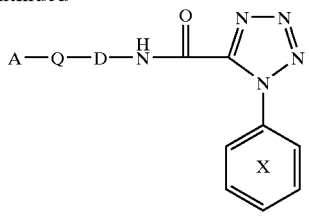

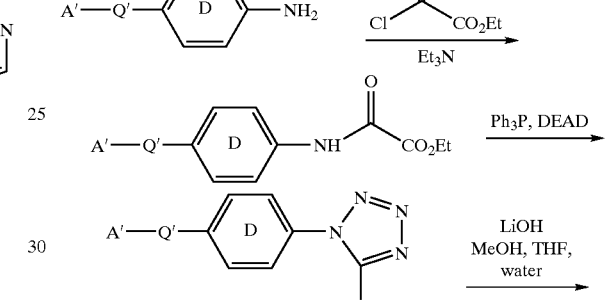

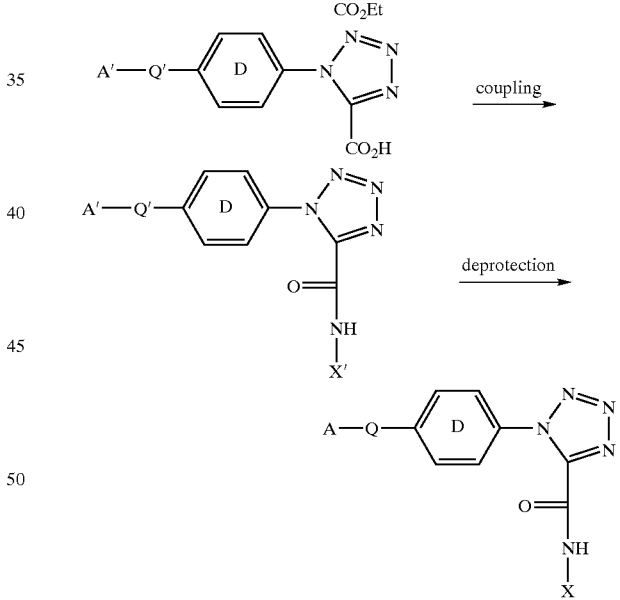

Scheme 4 shows the general synthesis of compounds with a N-linked tetrazole G ring. An appropriately protected aromatic amine is acylated with ethyl chlorooxoacetate. The resulting amide can be converted to the tetrazole by methods known in the art. See e.g. Journal of Organic Chemistry, 56, 2395 (1991); Synthesis, 767 (1993); Journal of Organic Chemistry, 58, 32 (1993); Bioorganic & Medicinal Chemistry Letters, 6, 1015 (1996)).

General synthesis for compounds with a C-linked G ring is outlined in Scheme 5. A', Q', D', E', J' and X' are protected functional structures which can be converted to A, Q, D, E, J and X respectively. For formation of the C-linked G ring, the appropriate aromatic aldehyde precursor is treated under conditions described in Joule, Mills and Smith, "Heterocyclic Chemistry", Chapman & Hall, London, 1995, or the references cited therein, or as described later in the preparation section to give the G ring. The C-linked G ring can also be connected to aromatic X or aromatic D using Suzuki cross-coupling method (Chemical Reviews, 95, 2457 (1995)).

Scheme 5
For carbon-linked heterocycle G

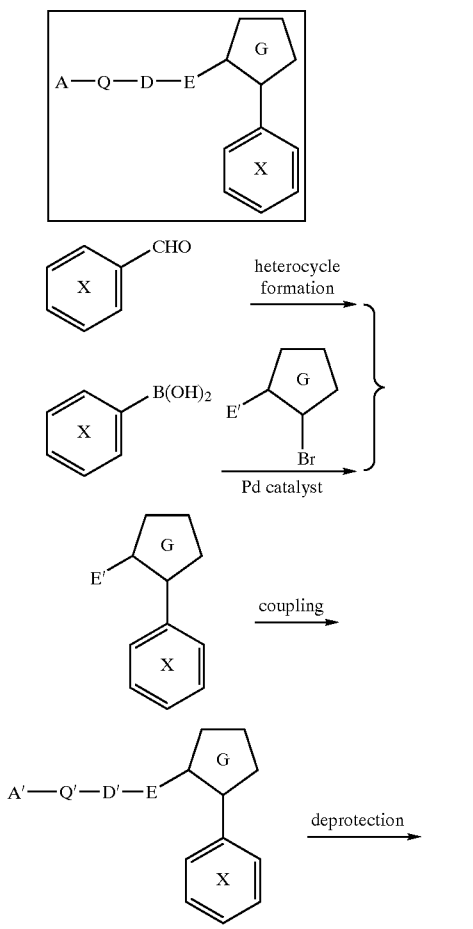

-continued

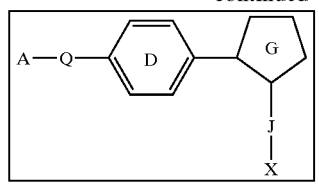

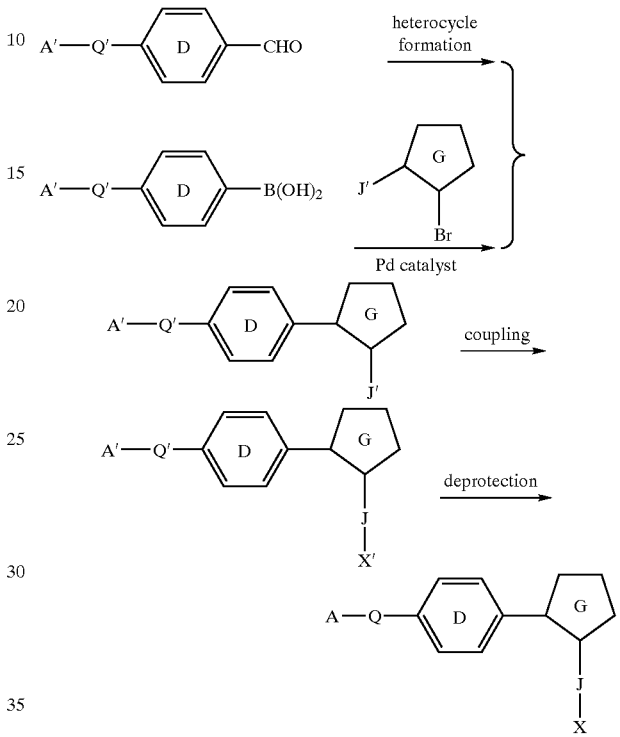

Scheme 6 shows the general synthesis of compounds with a C-linked isoxazole G ring. A substituted aromatic aldehyde is reacted with hydroxylamine and then chlorinated to yield the hydroximinoyl choride (Journal of Organic Chemistry, 45, 3916 (1980)). It is treated with triethylamine to generate nitrile oxide in situ, which is reacted with methyl trans-3-mthoxyacrylate or methyl propiolate to give the isoxazole structure (Chemical Letters, 1, 85 (1987)).

Scheme 6
For isoxazole-linked heterocycle compounds

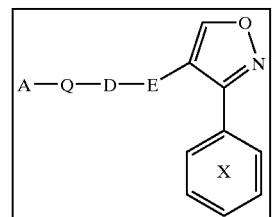

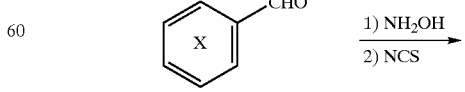

-continued

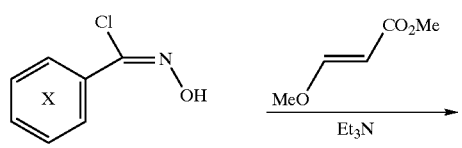

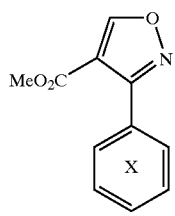

coupling

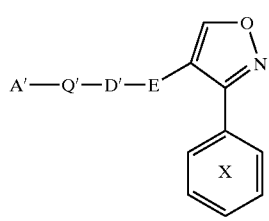

deprotection

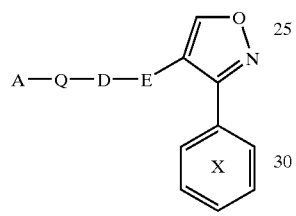

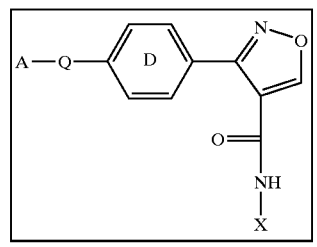

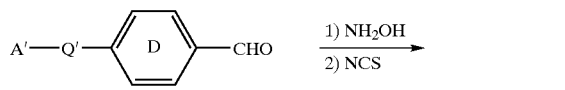

1) NH$_2$OH
2) NCS

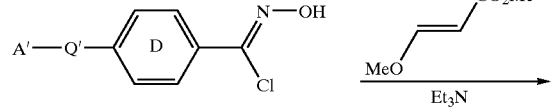

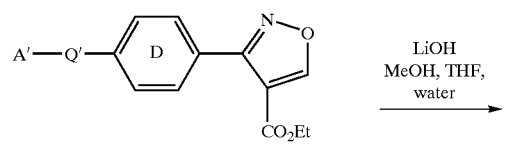

LiOH
MeOH, THF,
water

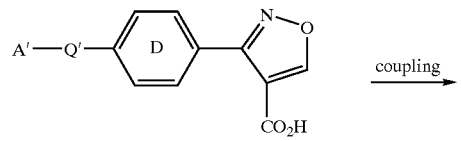

coupling

-continued

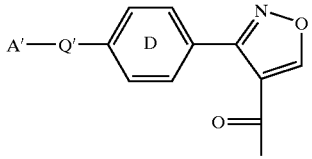

deprotection

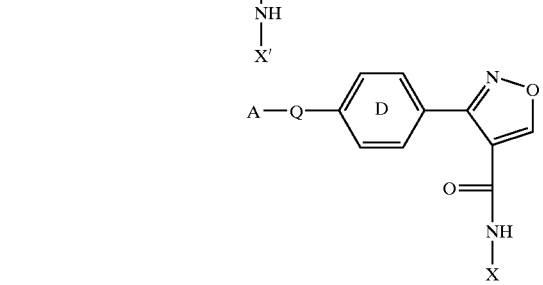

Scheme 7 shows the general synthesis of compounds with a C-linked thiozole G ring. A substituted aromatic aldehyde is reacted with ethyl diazoacetate in presence of tin(II) chloride to afford the beta-ketoester. It is then converted to thiazole.

Scheme 7

For thiazole-linked heterocycle compounds

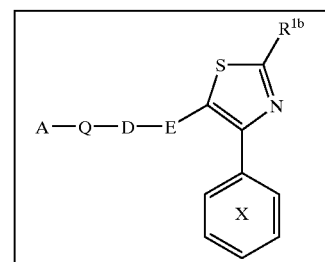

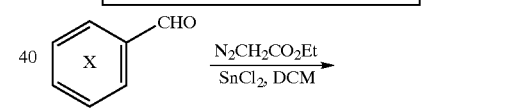

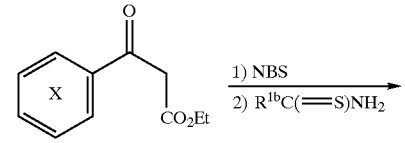

1) NBS
2) R$^{1b}$C(=S)NH$_2$

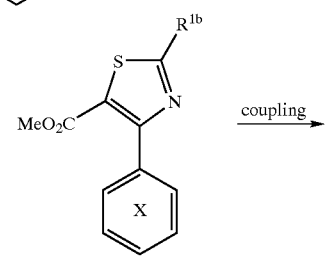

coupling

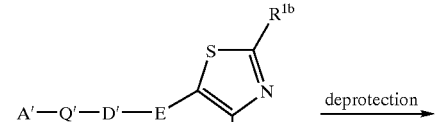

deprotection

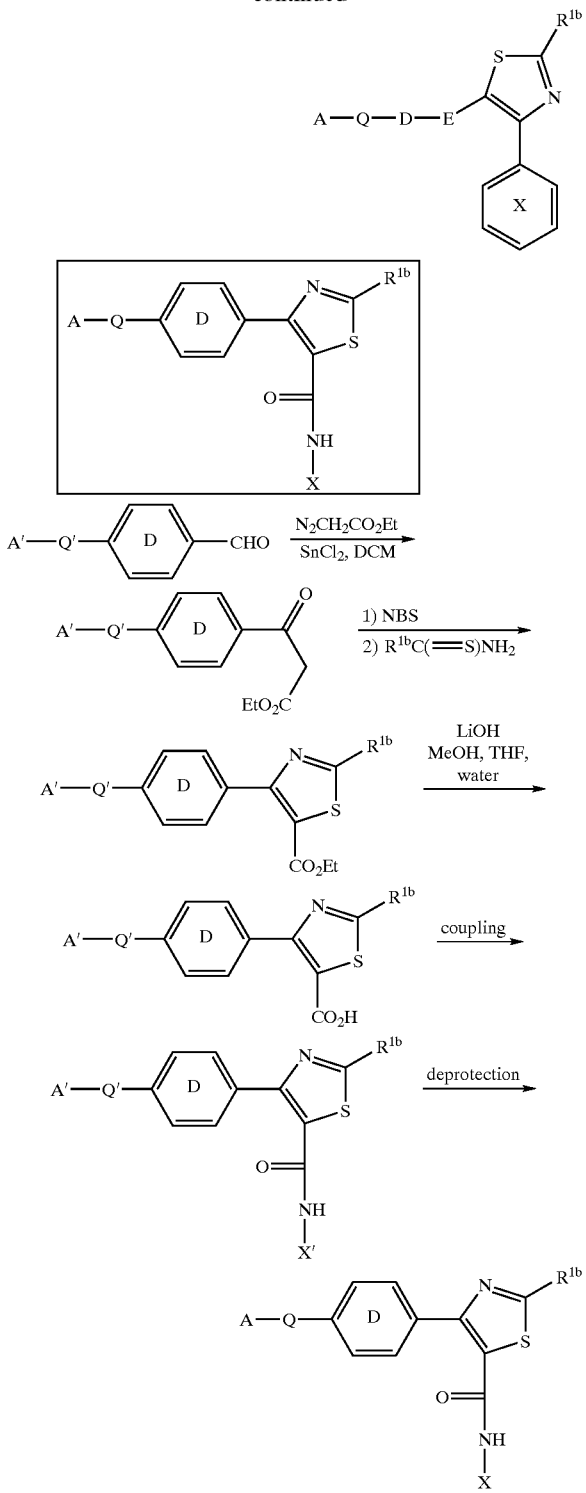

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or. administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between about 3 and about 11, more preferably from about 5 to about 9 and most preferably from about 7 to about 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to about 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated ith heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

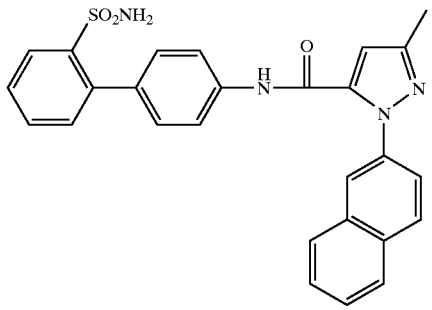

Step 1. To the solutionof 2-naphthylboronic acid (5.00 g, 29.1 mmol) and ethyl 3-methylpyrazole-5-carboxylate (4.48 g, 29.1 mmol) in 100 mL dry dichloromethane (DCM) were added pyridine (4.7 mL, 58.2 mmol) and anhydrous powder of copper(II) acetate (7.94 g, 43.7 mmol). Some activated molecular sieve powder was added afterwards. The resulting slurry was stirred for 2 days under argon. The mixture was diluted with DCM. It was filtered through a celite bed. The blue filtrate was washed with water ($\times$2), dried over $MgSO_4$, concentrated, purified by silica column to yield ethyl 3-methyl-1-(2-naphthyl)-1H-pyrazole-5-carboxylate and its regioisomer in a 1:1 ratio in 70% yield. Rf 0.59 (1:2 EtOAc:hexane), M+H 281; regioisomer, ethyl 5-methyl-1-(2-naphthyl)-1H-pyrazole-3-carboxylate, Rf 0.44 (1:2 EtOAc:hexane). ES-MS: $(M+H)^+$ 281.

Step 2. To a solution of 2'-N-tert-butylaminosulfonyl-[1,1']-biphenyl-4-ylamine (50 mg, 0.16 mmol) in 1 mL DCM was added trimethylaluminum (2.0M in hexane, 0.41 mL, 0.82 mmol) under argon at room temperature. After being stirred for 30 minutes, to the mixture was added the above-prepared ester (46 mg, 0.16 mmol) in 1 mL DCM. The resulting mixture was stirred overnight. The reaction was quenched using 5 mL saturated Rochelle salt aq solution. The mixture was extracted using DCM ($\times$3). The organic phases were combined, dried, rotovaped and subjected on flash column to give the coupled product in 52% yield (46 mg). Rf 0.46 (1:1 EtOAc:hexane). ES-MS: $(M+H)^+$ 539.

Step 3. The above-prepared compound (42 mg, 0.078 mmol) was placed in 3 mL trifluoroacetic acid (TFA). The solution was stirred in 60° C. bath for 30 minutes. TFA was removed on rotovap. The residue was dissolved in methanol and purified by preparative HPLC to afford the title compound in 95% yield. ES-MS: $(M+H)^+$ 483.

Example 2

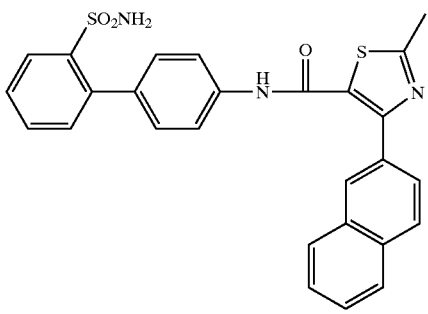

Step 1. A mixture of tin(II) chloride (2.08 g, 10.96 mmol) and ethyl diazoacetate (2.76 mL, 26.29 mmol) in 50 mL DCM was stirred for 2 hours. Naphthalene-2-carbaldehyde was added. After stirred at room temperature for 18 hours, the mixture was concentrated, dissolved in EtOAc, washed with water (×3), dried and evaporated. The crude material was purified to give product ethyl 3-(2-naphthyl)-3-oxoprppionate. Rf 0.61 (1:1 EtOAc:hexane). ES-MS: (M+H)+ 243.

Step 2. To a solution of the above-prepared ester (240 mg, 1 mmol) in 15 mL MeCN at 65° C. was added hydroxy(tosyloxy)iodobenzene (430 mg, 1.1 mmol). After stirred for 1 hour, to the mixture was added thiourea (83 mg, 1.1 mmol). The resulting mixture was stirred overnight at 65° C. The solution was cooled and concentrated. The residue was dissolved in EtOAc, washed with brine, dried over MgSO$_4$, and evaporated to give crude 2-methyl-4-(2-naphthyl)-5-(carboethoxy)thiazole. Rf 0.64 (1:3 EtOAc:hexane). ES-MS: (M+H)+ 298.

Step 3. To a solution of the above-prepared product (148 mg, 0.50 mmol) and 2'-N-tert-butylaminosulfonyl-[1,1']-biphenyl-4-ylamine (152 mg, 0.50 mmol) in 3 mL DCM was added trimethylaluminum (2.0M in hexane, 0.75 mL, 1.5 mmol), and the mixture was stirred at room temperature for 20 hours. The reaction was neutralized with 4 mL 1N HCl and extracted with EtOAc. The organic layer was washed with brine, dried over MgSO$_4$, and concentrated to give the coupling product (170 mg, 61%). Rf 0.25 (1:3 EtOAc:hexane). ES-MS: (M+H)+ 556.

Step 4. The above-prepared product (100 mg) was placed in 3 mL TFA. The solution was stirred in 80° C. bath for 60 minutes. TFA was removed on rotovap. The residue was dissolved in methanol and purified by preparative HPLC to afford the title compound in over 90% yield. ES-MS: (M+H)+ 500.

Example 3

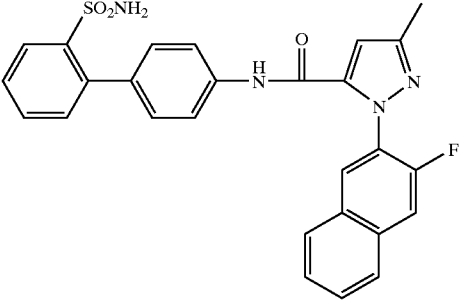

Step 1. 3-Amino-2-naphthoic acid (40.4 g, 216 mmol) was placed in 200 mL concentrated HCl. At 0° C., the slurry was stirred vigorously using a mechanical stirring blade. To it was added a cold solution of sodium nitrite (29.8 g, 432 mmol) in 70 mL water. After completion, the cold slurry was stirred for 30 minutes at 0° C. To it was added cold tetrafluoroboric acid (48 wt. % in water, 56 mL, 432 mmol). After stirred at 0° C. for 30 minutes, the solid was filtered using a Buchner funnel. The soild cake was carefully rinsed with cold water (10 mL×2), cold tetrafluoroboric acid (10 mL×2) and cold ethanol (5 mL×2). The solid was dried in vacuuo. It was then placed in 300 mL xylene and refluxed overnight. Xylene was removed on rotovap. The residue was acidified to pH1 with aq HCl and taken into EtOAc. It was washed with brine (×2), dried, evaporated to give 3-fluoro-2-naphthoic acid (32.6 g, 78%). ES-MS: (M+H)+ 191.

Step 2. The above-prepared acid (14.7 g, 77 mmol) was dissolved in 200 mL CHCl$_3$. To it was added 0.5 mL dry DMF. Then at room temperature, oxalyl chloride (20 mL, 232 mmol) was added dropwise. The reaction solution was stirred for overnight. All solvent was removed in vacuuo. The residue was pumped till dryness. It was dissolved in 150 mL dry dioxane, chilled to 0° C. and vigorously stirred. To it, at the cold tempareture, was added the cold solution of sodium azide (10 g, 155 mmol, in 30 mL water and 15 mL dioxane) in small portions. The reaction was allowed for 2 hours at 0° C. The solvent was removed in vacuuo. The residue was taken into EtOAc and washed with brine (×3). The organic phase was dried and evaporated to dryness in vacuuo to give 3-fluoro-2-naphthoyl azide. Rf 0.83 (1:1 EtOAc:hexane). It was dissolved in 80 mL DMF. To it was added 40 mL water. The milky mixture was refluxed overnight. The solvent was removed in vacuuo. The residue was taken into EtOAc, and washed with brine (×2). The organic phase was dried, concentrated and purified with flash silica column to yield 3-fluoro-2-naphthylamine (8.1 g, 65%). Rf 0.40 (1:3 EtOAc:hexane). ES-MS: (M+H)+ 162.

Step 3. The above-prepared compound (7.5 g, 46 mmol) was placed in 50 mL concentrate HCl. The mixture was vigorously stirred in ice bath. To it was dropwise added cold sodium nitrite (3.8 g, 55 mmol) solution in 10 mL water. After completion, the mixture was stirred at 0° C. for half an hour. At 0° C., to it was dropwise added cold SnCl$_2$.2H$_2$O (26.3 g, 116 mmol) solution in 20 mL concentrate HCl. The slurry was stirred for half an hour at 0° C., chilled, and filtered through a Buchner funnel to isolate the solid hydrazine. It was dried in vacuuo. The solid hydrazine was dissolved in 100 mL glacial acetic acid. To it were added ethyl 2-N-(methoxy)imino-4-oxopentanoate (10.4 g, 56 mmol, prepared from ethyl 2,4-dioxovalerate and methoxylamine hydrogen chloride in ethanol) and 50 mL THF. The mixture was refluxed for 2 hours. The solvent was removed in vacuuo. The residue was taken into EtOAc, washed with brine and water. The organic phase was dried, concentrated and purified with flash column to yield ethyl 3-methyl-1-(3-fluoro-2-naphthyl)-1H-pyrazole-5-carboxylate (9.0 g, 65%). Rf 0.52 (1:2 EtOAc:hexane). ES-MS: (M+H)+ 299.

Step 4. To a solution of 2'-N-tert-butylaminosulfonyl-[1,1']-biphenyl-4-ylamine (77 mg, 0.25 mmol) in 1 mL dry DCM was added trimethylaluminum (2.0M in hexane, 0.51 mL, 1.0 mmol). The mixture was stirred for 20 minutes. The above-prepared ester (50 mg, 0.17 mmol) was dissolved in 3 mL dry DCM and added into the aluminum mixture. The reaction was stirred at room temperature for overnight and quenched using saturated Rochelle's salt aq solution. It was extracted with CHCl$_3$ (×3). The organic phases were combined, dried, concentrated and purified with flash column to yield the coupling product (85 mg, 90%). Rf 0.45 (1:1 EtOAc:hexane). ES-MS: (M+H)+ 557.

Step 5. The above-prepared product was placed into 3 mL TFA. The mixture was stirred overnight at room temperature. It was evaporated, dissolved in methanol, purified with prep HPLC to afford the title compound in over 90% yield.). ES-MS: (M+H)+ 501.

Example 4

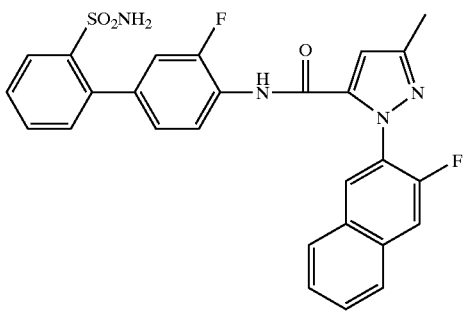

Step 1. The preparation of ethyl 3-methyl-1-(3-fluoro-2-naphthyl)-1H-pyrazole-5-carboxylate was the same as that in Step 3 for Example 3. This ester (13.2 g, 44 mmol) was dissolved in 80 mL methanol. To it were added LiOH.H$_2$O (3.7 g, 49 mmol) and 40 mL water. The mixture was stirred for overnight at room temperature. It was evaporated in vacuuo to remove methanol. The residue was acidified with 1N HCl till pH 1. The mixture was extracted with EtOAc (×4). The organic extracts were combined, dried, evaporated and pumped to dryness to afford 3-methyl-1-(3-fluoro-2-naphthyl)-1H-pyrazolecarboxylic acid in over 90% yield. ES-MS: (M+H)+ 271.

Step 2. The above-prepared acid (33 mg, 0.12 mmol), 2'-N-tert-butylaminosulfonyl-3-fluoro-[1,1']-biphenyl-4-ylamine (77 mg, 0.24 mmol) and catalytic amount of DMAP (5 mg) were dissolved in 2 mL pyridine. The solution was stirred at 0° C. To it was added POCl$_3$ (45 μL, 0.48 mmol). The mixture was stirred for 1 hour and quenched with ice chips. To it was added EtOAc. It was washed with brine (×2), dried, and concentrated. To the residue was added 3 mL TFA. The mixture was stirred at 60° C. for 1 hour, concentrated, dissolved in methanol and subjected on prep HPLC to afford the title compound in 50% yield (31 mg). ES-MS: (M+H)+ 519.

Example 5

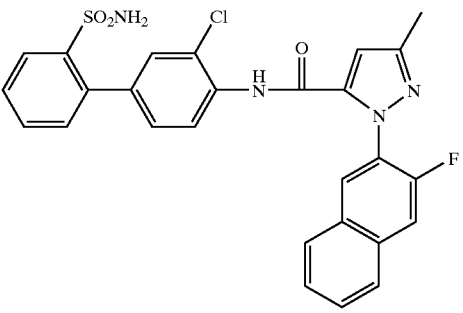

This compound was prepared by the same methodology described for Example 4 with 2'-N-tert-butylaminosulfonyl-3-chloro-[1,1']-biphenyl-4-ylamine substituted for 2'-N-tert-butylaminosulfonyl-3-fluoro-[1,1']-biphenyl-4-ylamine. ES-MS: (M+H)+ 535.

Example 6

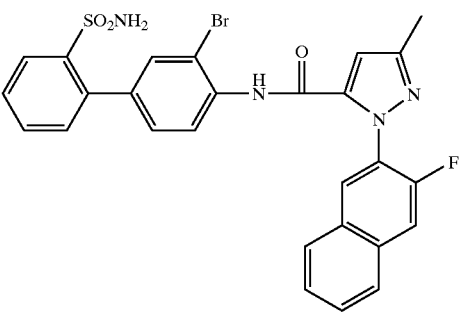

This compound was prepared by the same methodology described for Example 4 with 2'-N-tert-butylaminosulfonyl-3-bromo-[1,1']-biphenyl-4-ylamine substituted for 2'-N-tert-butylaminosulfonyl-3-fluoro-[1,1']-biphenyl-4-ylamine. ES-MS: (M+H)+ 579, 581 (Br pattern).

Example 7

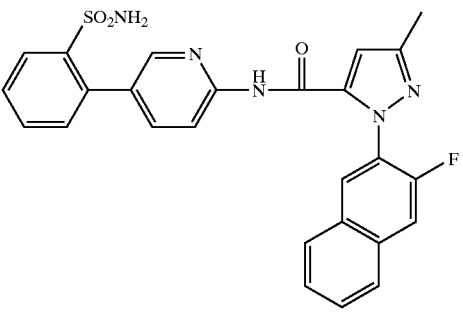

This compound was prepared by the same methodology described for Example 4 with 2-amino-5-(2-(N-tert-butylaminosulfonyl)phenyl)pyridine substituted for 2'-N-tert-butylaminosulfonyl-3-fluoro-[1,1']-biphenyl-4-ylamine. ES-MS: (M+H)+ 502.

Example 8

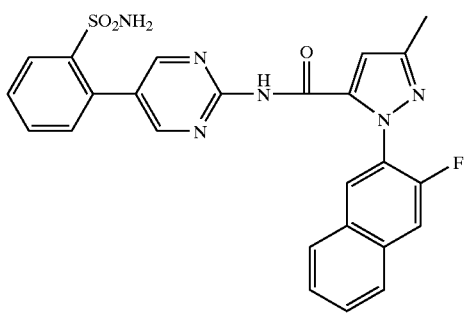

This compound was prepared by the same methodology described for Example 4 with 2-amino-5-(2-(N-tert-butylaminosulfonyl)phenyl)pyrimidine substituted for 2'-N-tert-butylaminosulfonyl-3-fluoro-[1,1']-biphenyl-4-ylamine. ES-MS: (M+H)$^+$ 503.

Example 9

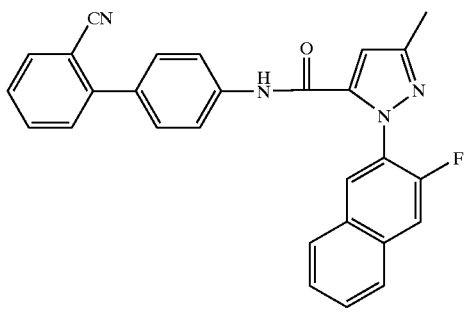

This compound was prepared by the same methodology described for Example 4 with 2'-cyano-[1,1']-biphenyl-4-ylamine substituted 2'-N-tert-butylaminosulfonyl-3-fluoro-[1,1']-biphenyl-4-ylamine, without the TFA treatment. ES-MS: (M+H)$^+$ 447.

Example 10

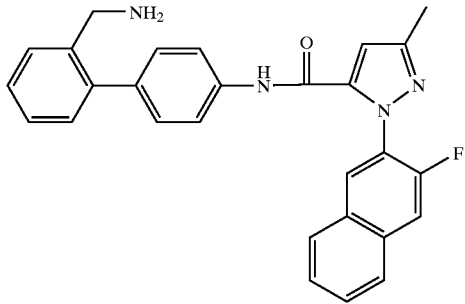

The title compound (40 mg, 0.09 mmol) of Example 9 was dissolved in 2 mL dry DMF. At 0° C., to it were added sodium borohydride (27 mg, 0.72 mmol) and anhydrous Co(II) chloride (23 mg, 0.18 mmol). The mixture was stirred for 2 hours and quenched with 1 mL acetic acid. The mixture was evaporated, dissolved in methanol, filtered, loaded on prep HPLC to afford the title compound in 60% yield. ES-MS: (M+H)$^+$ 451.

Example 11

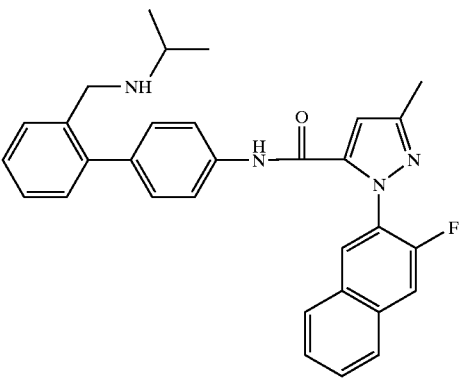

The title compound (40 mg, 0.09 mmol) of Example 9 was dissolved in 2 mL dry DMF. At 0° C., to it were added sodium borohydride (27 mg, 0.72 mmol) and anhydrous Co(II) chloride (23 mg, 0.18 mmol). The mixture was stirred for 2 hours. To it was added 10 mL acetone. The mixture was stirred for 1 hour at room temperature. The reaction was quenched with 1 mL acetic acid. The mixture was evaporated, dissolved in methanol, filtered, loaded on prep HPLC to afford the title compound in 50% yield. ES-MS: (M+H)$^+$ 493.

Example 12

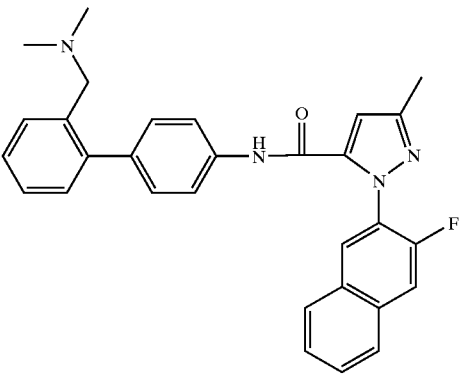

This compound was prepared by the same methodology described for Example 4 with 2'-(N-dimethylamino)methyl-[1,1']-biphenyl-4-ylamine substituted for 2'-N-tert-butylaminosulfonyl-3-fluoro-[1,1']-biphenyl-4-ylamine, without the TFA treatment. ES-MS: (M+H)$^+$ 479.

Example 13

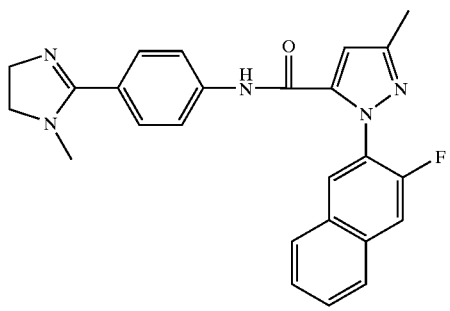

Step 1. The preparation of 3-methyl-1-(3-fluoro-2-naphthyl)-1H-pyrazolecarboxylic acid was the same as that in Step 1of Example 4.

Step 2. This acid (65 mg, 0.24 mmol), 4-aminobenzonitrile (57 mg, 0.48 mmol) and DMAP (5 mg) were dissolved in 3 mL pyridine. The solution was stirred at 0° C. To it was added POCl$_3$ (90 µL, 0.96 mmol). The mixture was stirred for 1 hour. The reaction was then quenched with ice chips. It was diluted with EtOAc. The organic phase was washed with brine (×2). It was dried, concentrated and purified with flash column to afford the coupling product (60 mg, 68%). Rf 0.40 (1:1 EtOAc:hexane). ES-MS: (M+H)$^+$ 371.

Step 3. The above-prepared nitrile was dissolved in 10 mL dry methanol. It was chilled and stirred in an ice bath. To this solution was bubbled dry HCl gas via a long needle till saturation reached (indicated by a blown-up balloon attached on the top of the reaction flask). The resulting solution was stirred overnight. ES-MS: (M+H)$^+$ 403. The solvent was removed in vacuuo. The residue was pumped to dryness. The solid was dissolved in 5 mL dry methanol. To it was added anhydrous N-methylethylenediamine (0.5 mL). The mixture was refluxed for 1 hour, concentrated and loaded on prep HPLC to afford the title compound in 80% yield. ES-MS: (M+H)$^+$ 428.

Example 14

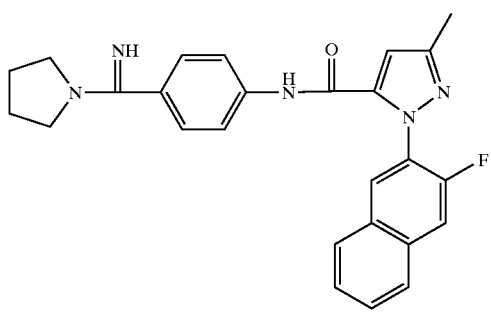

This compound was prepared by the same methodology described for Example 13 with pyrolidine substituted for N-methylethylenediamine. ES-MS: (M+H)$^+$ 442.

Example 15

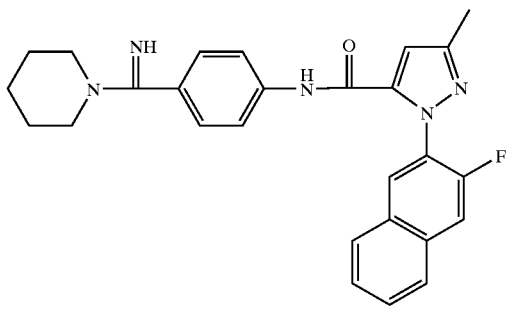

This compound was prepared by the same methodology described for Example 13 with piperidine substituted for N-methylethylenediamine. ES-MS: (M+H)$^+$ 456.

Example 16

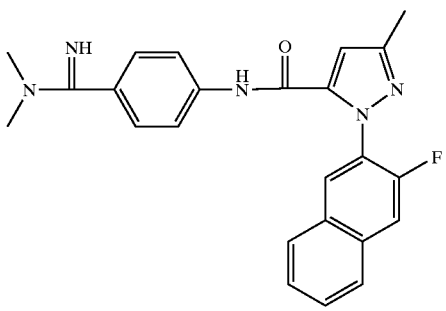

This compound was prepared by the same methodology described for Example 13 with dimethylamine (commercial 2M solution in THF) substituted for N-methylethylenediamine. ES-MS: (M+H)$^+$ 416.

Example 17

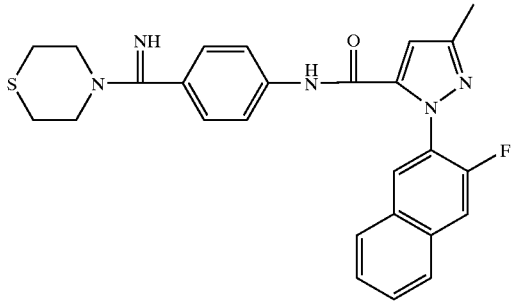

This compound was prepared by the same methodology described for Example 13 with thiomorpholine substituted for N-methylethylenediamine. ES-MS: (M+H)$^+$ 474.

Example 18

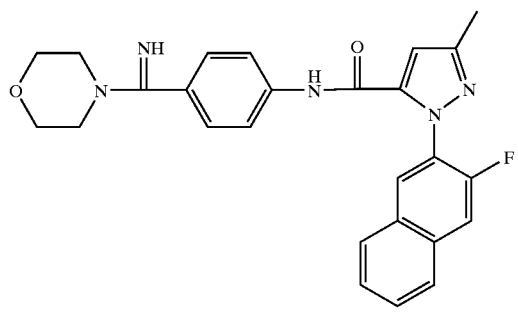

This compound was prepared by the same methodology described for Example 13 with morpholine substituted for N-methylethylenediamine. ES-MS: (M+H)+ 458.

Example 19

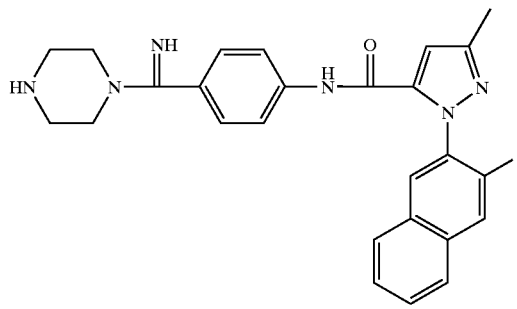

This compound was prepared by the same methodology described for Example 13 with piperazine substituted for N-methylethylenediamine. ES-MS: (M+H)+ 457.

Example 20

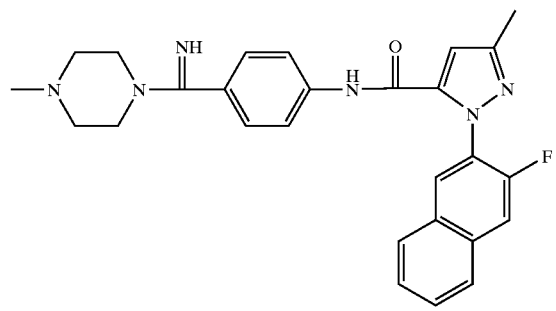

This compound was prepared by the same methodology described for Example 13 with N-methylpiperazine substituted for N-methylethylenediamine. ES-MS: (M+H)+ 471.

Example 21

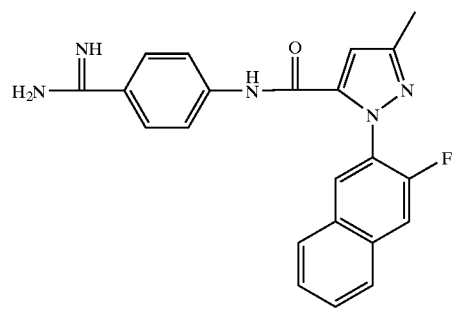

This compound was prepared by the same methodology described for Example 13 with ammonium acetate substituted for N-methylethylenediamine. ES-MS: (M+H)+ 388.

Example 22

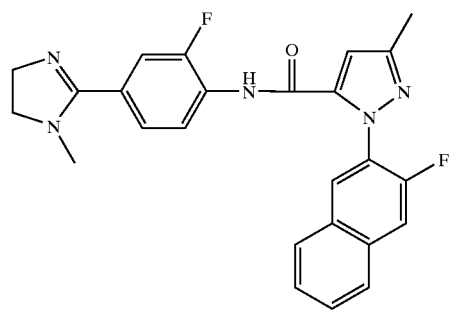

Step 1. 2-Fluoro-4-iodoaniline (5.0 g, 21 mmol) was dissolved in 20 mL dry DMF. To it were added CuCN (3.8 g, 42 mmol) and catalytic amount of CuI (200 mg). The slurry was refluxed for 1 hour. Diluted with EtOAc. Filtered through celite. Concentrated in vacuuo to yield solid 4-amino-3-fluorobenzonitrile (2.9 g, 100%). ES-MS: (M+H)+ 137.

Step 2. The preparation of 3-methyl-1-(3-fluoro-2-naphthyl)-1H-pyrazolecarboxylic acid was the same as that in Step 1 of Example 4. This acid (270 mg, 1.0 mmol), 4-amino-3-fluorobenzonitrile (272 mg, 2.0 mmol) and DMAP (10 mg) were dissolved in 15 mL pyridine. The solution was stirred at 0° C. To it was added POCl$_3$ (380 μL, 4.0 mmol). The mixture was stirred for 1 hour. The reaction was then quenched with ice chips. It was diluted with EtOAc. The organic phase was washed with brine (×2). It was dried, concentrated and purified with flash column to afford the coupling product (350 mg, 97%). Rf 0.77 (7:3 EtOAc:hexane). ES-MS: (M+H)+ 389.

Step 3. The above-prepared nitrile (30 mg, 0.077 mmol) was dissolved in 10 mL dry methanol. It was chilled and stirred in an ice bath. To this solution was bubbled dry HCl gas via a long needle till saturation reached (indicated by a blown-up balloon attached on the top of the reaction flask). The resulting solution was stirred overnight. ES-MS: (M+H)+ 421. The solvent was removed in vacuuo. The residue was pumped to dryness. The solid was dissolved in 5 mL dry methanol. To it was added anhydrous N-methylethylenediamine (0.5 mL). The mixture was refluxed for 1 hour, concentrated and loaded on prep HPLC to afford the title compound in 80% yield. ES-MS: (M+H)+ 446.

Example 23

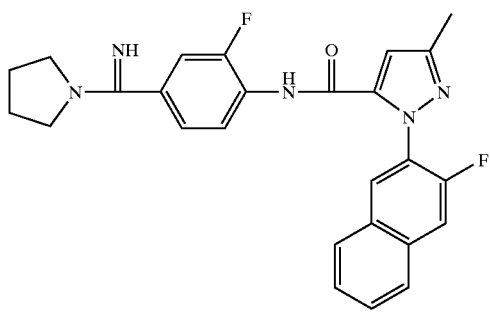

This compound was prepared by the same methodology described for Example 22 with pyrolidine substituted for N-methylethylenediamine. ES-MS: (M+H)+ 460.

Example 24

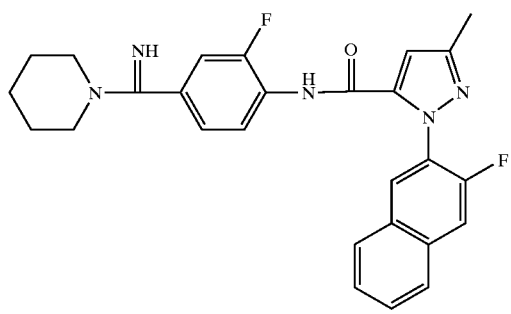

This compound was prepared by the same methodology described for Example 22 with piperidine substituted for N-methylethylenediamine. ES-MS: (M+H)+ 474.

Example 25

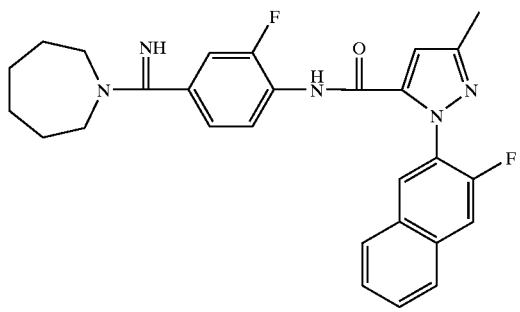

This compound was prepared by the same methodology described for Example 22 with hexamethyleneimine substituted for N-methylethylenediamine. ES-MS: (M+H)+ 488.

Example 26

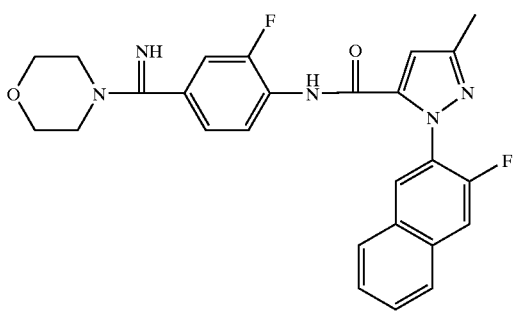

This compound was prepared by the same methodology described for Example 22 with morpholine substituted for N-methylethylenediamine. ES-MS: (M+H)+ 476.

Example 27

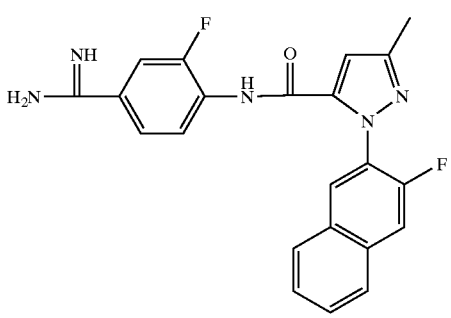

This compound was prepared by the same methodology described for Example 22 with ammonium acetate substituted for N-methylethylenediamine. ES-MS: (M+H)+ 406.

Example 28

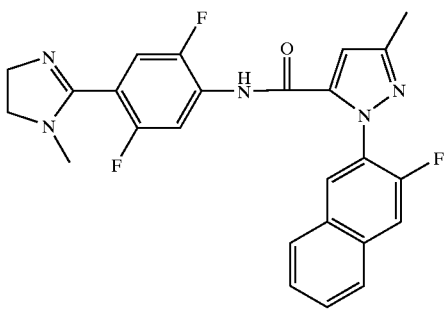

Step 1. The preparation of 3-methyl-1-(3-fluoro-2-naphthyl)-1H-pyrazolecarboxylic acid was the same as that in Step 1 of Example 4. This acid (50 mg, 0.18 mmol), 4-amino-2,5-difluorobenzonitrile (57 mg, 0.36 mmol) and DMAP (5 mg) were dissolved in 8 mL pyridine. The solution was stirred at 0° C. To it was added POCl$_3$ (70 µL, 0.74 mmol). The mixture was stirred for 1 hour. The reaction was then quenched with ice chips. It was diluted with EtOAc. The organic phase was washed with brine (×2). It was dried, concentrated and purified with flash column to afford the coupling product (70 mg, 93%). Rf 0.69 (7:3 EtOAc:hexane). ES-MS: (M+H)+ 407.

Step 2. The above-prepared nitrile (30 mg, 0.074 mmol) was dissolved in 10 mL dry methanol. It was chilled and stirred in an ice bath. To this solution was bubbled dry HCl gas via a long needle till saturation reached (indicated by a blown-up balloon attached on the top of the reaction flask). The resulting solution was stirred overnight. ES-MS: (M+H)+ 439. The solvent was removed in vacuuo. The residue was pumped to dryness.

The solid was dissolved in 5 mL dry methanol. To it was added anhydrous N-methylethylenediamine (0.5 mL). The mixture was refluxed for 1 hour, concentrated and loaded on prep HPLC to afford the title compound in 80% yield. ES-MS: (M+H)+ 464.

Example 29

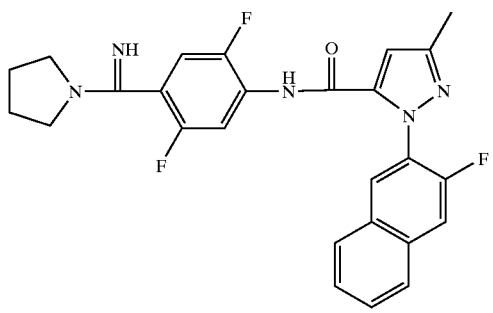

This compound was prepared by the same methodology described for Example 28 with pyrolidine substituted for N-methylethylenediamine. ES-MS: (M+H)+ 478.

Example 30

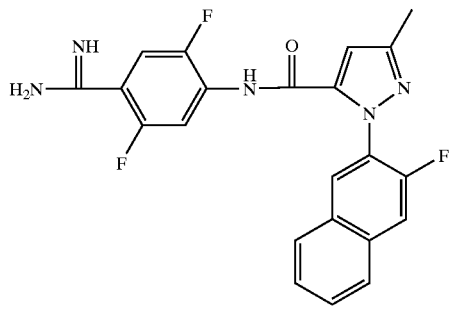

This compound was prepared by the same methodology described for Example 28 with ammonium acetate substituted for N-methylethylenediamine. ES-MS: (M+H)+ 424.

Example 31

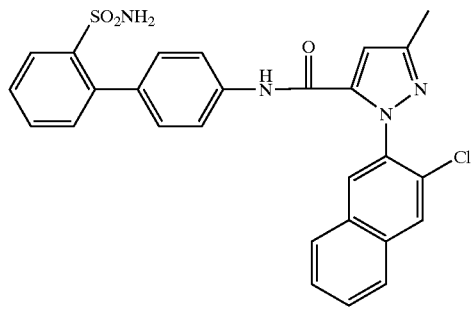

This compound was prepared by the same methodology from Step 3 to Step 5 described for Example 3 with 3-chloro-2-naphthylamine substituted for 3-fluoro-2-naphthylamine. ES-MS: (M+H)+ 517.

Example 32

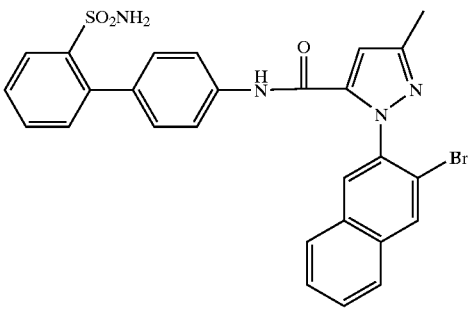

This compound was prepared by the same methodology from Step 3 to Step 5 described for Example 3 with 3-bromo-2-naphthylamine substituted for 3-fluoro-2-naphthylamine. ES-MS: (M+H)+ 561, 563 (Br pattern).

Example 33

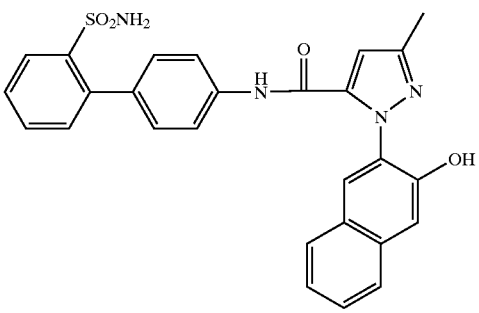

This compound was prepared by the same methodology from Step 3 to Step 5 described for Example 3 with 3-hydroxy-2-naphthylamine substituted for 3-fluoro-2-naphthylamine. ES-MS: (M+H)+ 499.

Example 34

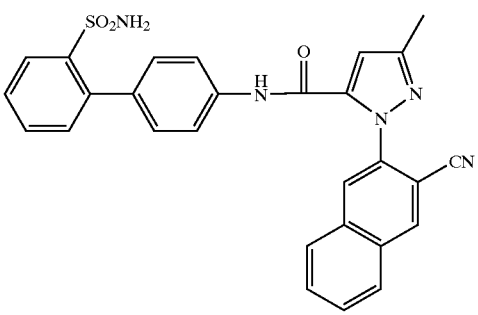

Step 1. The synthesis of ethyl 3-methyl-1-(3-bromo-2-naphthyl)-1H-pyrazole-carboxylate followed the same methodology described for Step 3 of Example 3 with commercial with 3-bromo-2-naphthylamine substituted for 3-fluoro-2-naphthylamine. Yield 60%. Rf 0.42 (1:3 EtOAc:hexane). ES-MS: (M+H)+ 359, 361 (Br pattern).

Step 2. The above-prepared bromide (370 mg, 1.0 mmol) was dissolved in 3 mL dry DMF. To it were added CuCN (180 mg, 2.0 mmol) and CuI (20 mg). The slurry mixture was refluxed for 2 hours. It was diluted with EtOAc. Filtered through celite. Concentrated and purified by flash column to yield of ethyl 3-methyl-1-(3-cyano-2-naphthyl)-1H-pyrazole-carboxylate (220 mg, 70%). Rf 0.48 (1:2 EtOAc:hexane). ). ES-MS: (M+H)+ 306.

Step 3. To a solution of 2'-N-tert-butylaminosulfonyl-[1,1']-biphenyl-4-ylamine (164 mg, 0.54 mmol) in 2 mL dry DCM was added trimethylaluminum (2.0M in hexane, 1.1 mL, 2.2 mmol). The mixture was stirred for 20 minutes. The above-prepared ester (137 mg, 0.45 mmol) was dissolved in 6 mL dry DCM and added into the aluminum mixture. The reaction was stirred at room temperature for overnight and quenched using saturated Rochelle's salt aq solution. It was extracted with CHCl₃ (×3). The organic phases were combined, dried, concentrated and purified with flash column to yield 3-methyl-1-(3-cyano-2-naphthyl)-1H-pyrazole-5-(N-(2'-N-tert-butylaminosulfonyl-[1,1']-biphen-4-yl))carboxyamide (170 mg, 67%). Rf 0.40 (1:1 EtOAc:hexane). ES-MS: (M+H)+ 564.

Step 4. The above-prepared compound (30 mg, 0.05 mmol) was dissolved in 5 mL dry DCM. At 0° C., to it was added BF₃.OEt₂ (62 μL, 0.5 mmol) dropwise. The mixture was stirred overnight. Extra 1.0 mmol BF₃.OEt₂ was added in small portions at room temperature the next day. After another overnight, deprotection was about 70% complete. The mixture was loaded on a short flash column for separation. The title product was purified using prep HPLC (55% yield). ES-MS: (M+H)+ 508.

Example 35

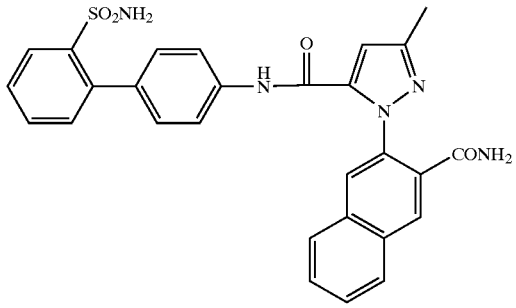

Step 1. The synthesis of 3-methyl-1-(3-cyano-2-naphthyl)-1H-pyrazole-5-(N-(2'-N-tert-butylaminosulfonyl-[1,1']-biphen-4-yl))carboxyamide followed the same procedure of Step 3 for Example 34.

Step 2. The above-prepared compound (30 mg, 0.05 mmol) was placed in 3 mL TFA and refluxed for 1 hour. After concentration, it was purified with prep HPLC to yield the title compound (85%). ES-MS: (M+H)+ 526.

Example 36

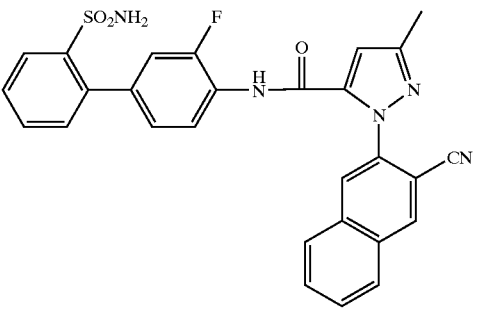

This compound was prepared by the same methodology described for Example 34 with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)+ 526.

Example 37

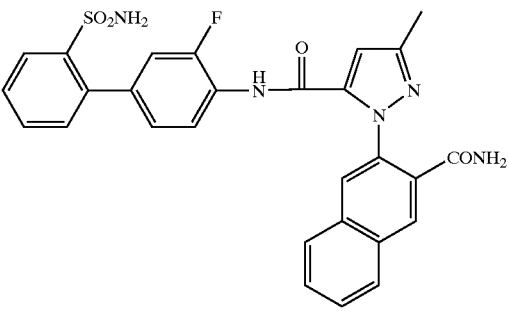

This compound was prepared by the same methodology described for Example 35 with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)+ 544.

Example 38

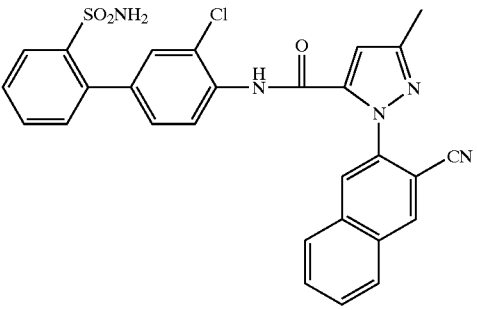

Step 1. The synthesis of ethyl 3-methyl-1-(3-cyano-2-naphthyl)-1H-pyrazole-carboxylate followed the same procedure of Step 2 for Example 34.

Step 2. The above-prepared ester (930 mg, 3.0 mmol) was dissolved in 20 mL methanol. To it were added LiOH.H₂O (256 mg, 6.0 mmol) and 10 mL water. The mixture was stirred for 3 hours at room temperature. Methanol was removed in vacuuo. The residue was carefully acidified with 1N HCl till pH 1. It was extracted with EtOAc (×4). The organic phases were combined, dried and evaporated in vacuuo till dryness to give 3-methyl-1-(3-cyano-2-naphthyl)-1H-pyrazole-5-carboxylic acid (720 mg, 85%). ES-MS: (M+H)+ 278.

Step 3. The mixture of the above-prepared acid (110 mg, 0.40 mmol), 2'-N-tert-butylaminosulfonyl-3-chloro-[1,1']-biphenyl-4-ylamine (0.21 g, 0.60 mmol), DMAP (5 mg) were dissolved in 5 mL pyridine and stirred at 0° C. To it was added POCl₃ (120 μL, 1.2 mmol). The mixture was stirred for 2.5 hours and quenched with ice chips. It was diluted with EtOAc, washed with brine (×2), dried, concentrated and purified with flash column to give 3-methyl-1-(3-cyano-2-naphthyl)-1H-pyrazole-5-(N-(2'-N-tert-butylaminosulfonyl-3-chloro-[1,1']-biphen-4-yl))carboxyamide (240 mg, 95%). Rf 0.65 (1:1 EtOAc:hexane). ES-MS: (M+H)+ 598.

Step 4. The above-prepared compound (30 mg, 0.05 mmol) was dissolved in 5 mL dry DCM. At 0° C., to it was added BF₃.OEt₂ (62 μL, 0.5 mmol) dropwise. The mixture was stirred overnight. Extra 1.0 mmol BF₃.OEt₂ was added in small portions at room temperature the next day. After another overnight, deprotection was about 70% complete. The mixture was loaded on a short flash column for separation. The title product was purified using prep HPLC (52% yield). ES-MS: (M+H)+ 542.

Example 39

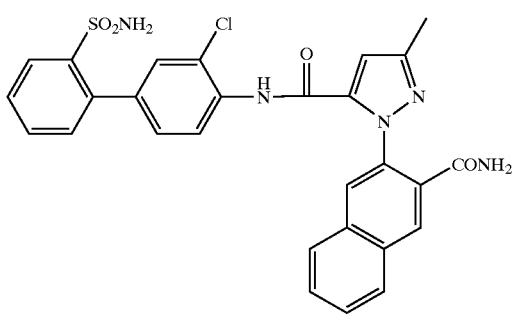

Step 1. The synthesis of 3-methyl-1-(3-cyano-2-naphthyl)-1H-pyrazole-5-(N-(2'-N-tert-butylaminosulfonyl-3-chloro-[1,1']-biphen-4-yl))carboxyamide followed the same procedure of Step 3 for Example 38.

Step 2. The above-prepared compound (30 mg, 0.05 mmol) was placed in 3 mL TFA and refluxed for 1 hour. After concentration, it was purified with prep HPLC to yield the title compound (85%). ES-MS: (M+H)+ 560.

Example 40

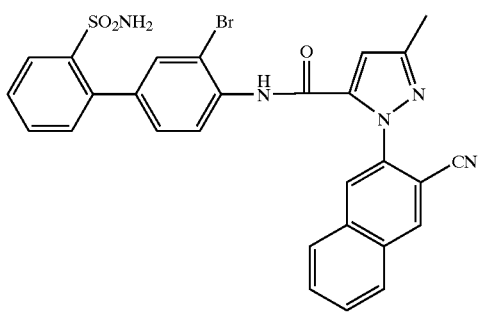

This compound was prepared by the same methodology described for Example 38 with 2'-N-tert-utylaminosulfonyl-3-bromo-[1,1']-biphenyl-4-ylarnine substituted for 2'-N-tert-butylaminosulfonyl-3-chloro-[1,1']-bipbenyl-4-ylamine. ES-MS (M+H)+ 586, 588 (Br pattern).

Example 41

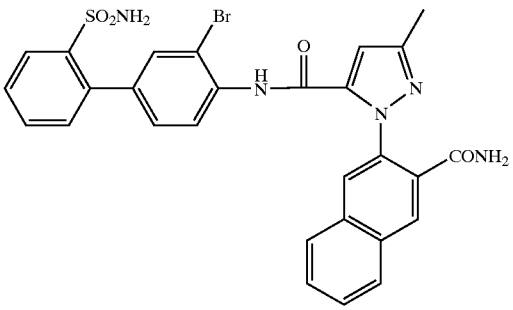

This compound was prepared by the same methodology described for Example 39 with 2'-N-tert-butylaminosulfonyl-3-bromo-[1,1']-biphenyl-4-ylamine substituted for 2'-N-tert-butylaiosulfonyl-3-chloro-[1,1']-biphenyl-4-ylamine. ES-MS: (M+H)+ 604, 606 (Br pattern).

Example 42

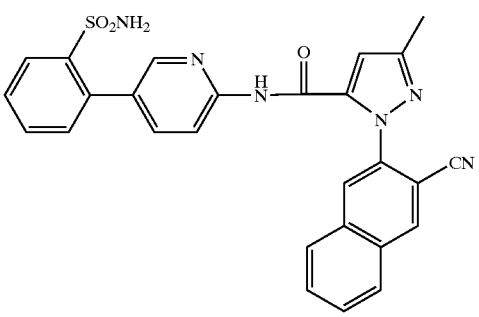

This compound was prepared by the same methodology described for Example 38 with 2-amino-5-(2-(N-tert-butylaminosul fonyl)phenyl)pyridine substituted for 2'-N-tert-butylaminosulfonyl-3-chloro-[1,1']-biphenyl-4-ylamine. ES-MS: (M+H)+ 509.

Example 43

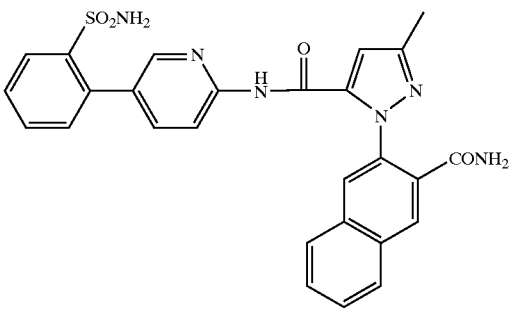

This compound was prepared by the same methodology described for Example 39 with 2-amino-5-(2-(N-tert-butylaminosulfonyl)phenyl)pyridine substituted for 2'-N-tert-butylaminosulfonyl-3-chloro-[1,1']-biphenyl-4-ylamine. ES-MS: (M+H)+ 527.

Example 44

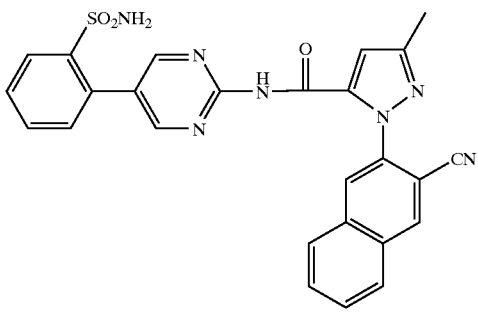

This compound was prepared by the same methodology described for Example 38 with 2-amino-5-(2-(N-tert-butylaminosulfonyl)phenyl)pyrimidine substituted for 2'-N-tert-butylaminosulfonyl-3-chloro-[1,1']-biphenyl-4-ylamine. ES-MS: (M+H)$^+$ 510.

Example 45

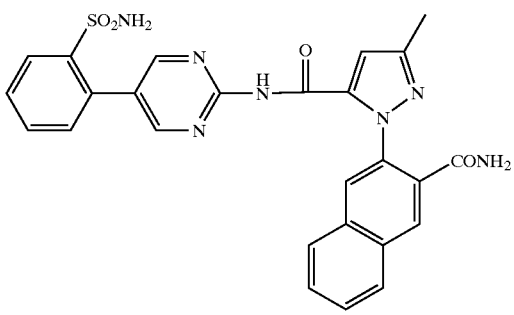

This compound was prepared by the same methodology described for Example 39 with 2-amino-5-(2-(N-tert-butylaminosulfonyl)phenyl)pyrimidine substituted for 2'-N-tert-butylaminosulfonyl-3-chloro-[1,1']-biphenyl-4-ylamine. ES-MS: (M+H)$^+$ 528.

Example 46

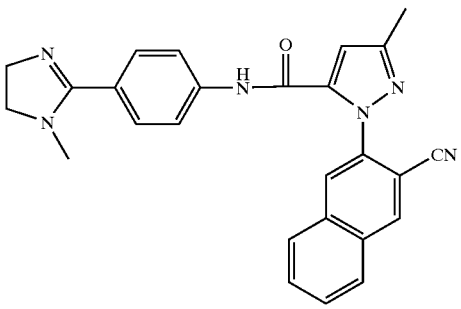

Step 1. To a solution of 4-nitroaniline (1.0 g, 6.7 mmol) in 50 mL anhydrous ethanol at 0° C. was bubbled dry HCl gas via a long needle till saturation reached. The resulting solution was stirred overnight. The solvent was removed in vacuuo. The residue was pumped to dryness. It was dissolved in 50 mL anhydrous ethanol. To it was added 2 mL N-methylethylenediamine. The mixture was refluxed for 1 hour and evaporated in vacuuo to give the 1-methyl-2-(4-nitrophenyl)-2-imidazoline HCl salt in 90% yield. ES-MS: (M+H)$^+$ 206.

Step 2. To a solution of the above-prepared nitro compound (500 mg, 2.4 mmol) in 4 mL 4N HCl and 50 mL methanol was added 10% Pd/C (50 mg). The mixture was stirred for 2 hours under a hydrogen balloon. It was filtered through celite and concentrated in vacuuo to give the 4-(1-methyl-2-imidazolin-2-yl)aniline HCl salt in 90% yield. ES-MS: (M+H)$^+$ 176.

Step 3. To a solution of the above-prepared amine (40 mg, 0.22 mmol), 3-methyl-1-(3-cyano-2-naphthyl)-1H-pyrazole-5-carboxylic acid (15 mg, 0.054 mmol, see Step 2, Example 38), DMAP (2 mg) in 2 mL pyridine at 0° C. was added POCl$_3$ (20 μL, 0.22 mmol). The mixture was stirred for 2 hours. It was concentrated in vacuuo and loaded on prep HPLC to afford the title compound in 60% yield. ES-MS: (M+H)$^+$ 435.

Example 47

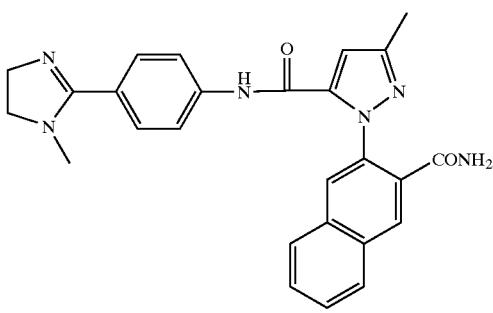

The title compound in Example 46 (10 mg) was placed in TFA. It was refluxed for 1 hour and subjected on prep HPLC purification to afford the title compound in 85% yield. ES-MS: (M+H)$^+$ 453.

Example 48

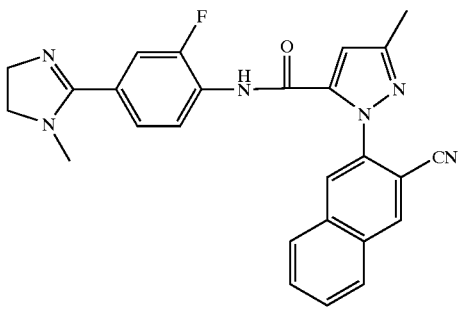

Step 1. To a solution of 2-fluoro-4-nitroaniline (300 mg, 2.2 mmol) in 20 mL anhydrous methanol at 0° C. was bubbled dry HCl gas via a long needle till saturation reached. The resulting solution was stirred overnight. The solvent was removed in vacuuo. The residue was pumped to dryness. It was dissolved in 10 mL anhydrous methanol. To it was added 1 mL N-methylethylenediamine. The mixture was refluxed for 1 hour and evaporated in vacuuo to give the 1-methyl-2-(2-fluoro-4-nitrophenyl)-2-imidazoline HCl salt in 90% yield. ES-MS: (M+H)$^+$ 224.

Step 2. To a solution of the above-prepared nitro compound in 2 mL 4N HCl and 25 mL methanol was added 10% Pd/C (20 mg). The mixture was stirred for 2 hours under a hydrogen balloon. It was filtered through celite and concentrated in vacuuo to give the 2-fluoro-4-(1-methyl-2-imidazolin-2-yl)aniline HCl salt in 90% yield. ES-MS: (M+H)$^+$ 194.

Step 3. To a solution of the above-prepared amine (100 mg, 0.51 mmol) in 2 mL DCM was added trimethylaluminum (2.0M in hexane, 2 mL, 4.0 mmol). The mixture was stirred for 20 minutes. Ethyl 3-methyl-1-(3-cyano-2-naphthyl)-1H-pyrazole-carboxylate (76 mg, 0.25 mmol, see Step 2 of Example 34) was dissolved in 2 mL DCM and added into the reaction flask. The mixture was stirred for 2 days at room temperature. It was quenched with saturated Rochelle's salt aq solution and extracted with CHCl₃ (×4). The organic phases were combined, dried, concentrated and purifed with prep HPLC to yield the title compound (55%). ES-MS: (M+H)⁺ 453.

Example 49

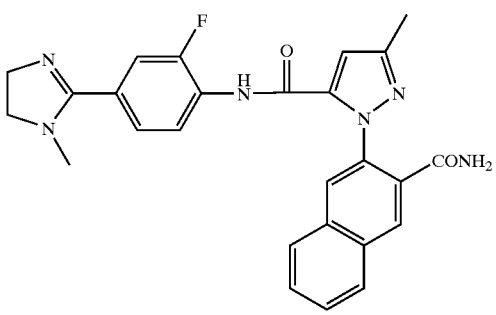

The title compound in Example 48 (10 mg) was placed in TFA. It was refluxed for 1 hour and subjected on prep HPLC purification to afford the title compound in 85% yield. ES-MS: (M+H)⁺ 471.

Example 50

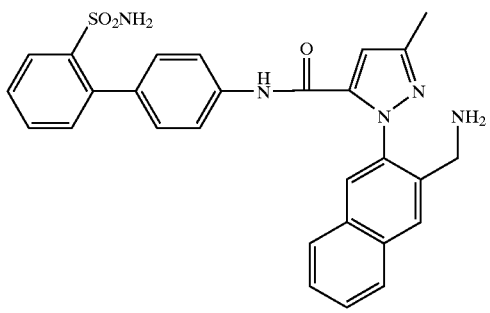

Step 1. Compound 3-methyl-1-(3-cyano-2-naphthyl)-1H-pyrazole-5-(N-(2'-N-tert-butylaminosulfonyl-[1,1']-biphen-4-yl))carboxyamide was prepared by the same procedure shown in Step 3 of Example 34.

Step 2. The above-prepared compound (70 mg, 0.12 mmol) was dissolved in 2 mL dry DMF. At 0° C., to it were added sodium borohydride (36 mg, 0.96 mmol) and CoCl₂ (32 mg, 0.24 mmol). It was stirred for 2 days. Diluted with EtOAc and stirred for 1 hour. The mixture was filtered through celite. The filtrate was evaporated to give crude 3-methyl-1-(3-aminomethyl-2-naphthyl)-1H-pyrazole-5-(N-(2'-N-tert-butylaminosulfonyl-[1,1']-biphen-4-yl))carboxyamide. ES-MS: (M+H)⁺ 568.

Step 3. The above-prepared crude compound was taken into 3 mL TFA. The mixture was stirred for 1 hour at 60° C. The mixture was evaporated and subjected on prep HPLC to isolate the title compound (35% yield). ES-MS: (M+H)⁺ 512.

Example 51

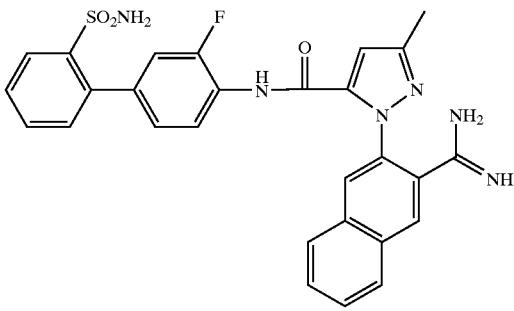

Step 1. Compound 3-methyl-1-(3-cyano-2-naphthyl)-1H-pyrazole-5-(N-(2'-N-tert-butylaminosulfonyl-3-fluoro-[1,1']-biphen-4-yl))carboxyamide was prepared by the same methodology shown in Step 3 of Example 34, with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)⁺ 582.

Step 2. To a solution of the above-prepared compound (77 mg, 0.13 mmol) in 3 mL anhydrous methanol and 3 mL anhydrous EtOAc at −20° C. was bubbled dry HCl gas via a long needle till saturation reached. The mixture was stirred for overnight. The solvent was removed in vacuuo. The dry residue was dissolved in 5 mL anhydrous methanol. To it was added 50 mg ammonium acetate. The mixture was refluxed for 2.5 hours. It was subjected on prep HPLC to isolate the title compound (55% yield). ES-MS: (M+H)⁺ 543.

Example 52

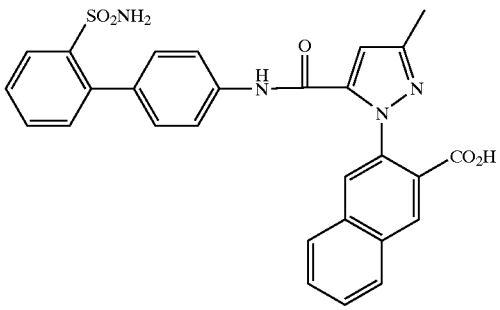

Step 1. 3-Amino-2-naphthoic acid (5.8 g, 31 mmol) was placed in 50 mL concentrate HCl. The slurry was vigorously stirred at 0° C. To it was added dropwise a cold solution of sodium nitrite (2.35 g, 34 mmol, in 14 mL water). After completion, the mixture was stirred for 40 minutes at 0° C. Under vigorously stirring, a cold solution of SnCl₂.2H₂O (21 g, 93 mmol, in 30 mL concentrate HCl) was added dropwise. The mixture was stirred for 30 minutes and chilled in ice bath. The crude 3-carboxyl-2-naphthylhydrazine was collected with a Buchner funnel and pumped to dryness in vacuuo.

Step 2. The crude hydrazine prepared above was taken into 60 mL glacial acetic acid and 30 mL THF. To it was added ethyl 2-N-(methoxy)imino-4-oxopentanoate (2.6 g, 14 mmol). The mixture was refluxed for overnight. The solvent was removed in vacuuo. The residue was dissolved in EtOAc and washed with brine (×2). The organic phase was dried, concentrated and purified with flash column to yield ethyl 3-methyl-1-(3-carboxyl-2-naphthyl)-1H-pyrazole-5-carboxylate (4.1 g, 90%). Rf 0.15 (1:1 EtOAc:hexane). ES-MS: (M+H)$^+$ 325.

Step 3. To a solution of 2'-N-tert-butylaminosulfonyl-[1,1']-biphenyl-4-ylamine (36 mg, 0.12 mmol) in 1 mL dry DCM was added trimethylaluminum (2.0M in hexane, 0.5 mL, 1.0 mmol). The mixture was stirred for 20 minutes. The above-prepared ester (38 mg, 0.12 mmol) was dissolved in 3 mL dry DCM and added into the aluminum mixture. The reaction was stirred at room temperature for overnight and quenched using saturated Rochelle's salt aq solution. It was extracted with CHCl$_3$ (×3). The organic phases were combined, dried, concentrated and purified with flash column to yield the coupling product (60%). ES-MS: (M+H)$^+$ 583.

Step 4. The above-prepared compound (15 mg) was placed in 3 mL TFA and stirred overnight. It was concentrated and purified with prep HPLC to afford the title compound in 90% yield. ES-MS: (M+H)$^+$ 527.

Example 53

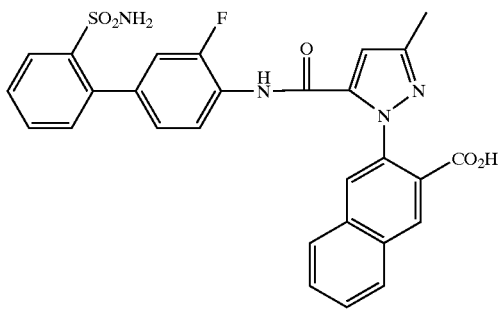

This compound was prepared by the same methodology described for Example 52 with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)$^+$ 545.

Step 1. The above-prepared crude acid was dissolved in 150 mL anhydrous ethanol. To it was added pTSA (3.3 g). The mixture was refluxed for 4 days till the esterification was over 95% complete. The solvent was removed in vacuuo. The residue was dissolved in EtOAc, washed with brine (×3), dried and purified by a short silica column to afford ethyl 3-methyl-1-(3-methylthio-2-naphthyl)-1H-pyrazole-5-carboxylate in over 80% yield. ES-MS: (M+H)$^+$ 327.

Step 2. The above-prepared ester (4.95 g, 15 mmol) was dissolved in 150 mL DCM. At 0° C., to the vigorously stirred solution was added MCPBA (11 g, 38 mmol) in small portions over 20 minutes. The reaction was allowed for 1 hour and diluted with CHCl$_3$. It was washed with NaHCO$_3$ saturated aq solution (×3), dried, concentrated and purified with flash column to give ethyl 3-methyl-1-(3-methylsulfonyl-2-naphthyl)-1H-pyrazole-5-carboxylate (3.49 g, 65%). Rf 0.52 (1:1 EtOAc:hexane). ES-MS: (M+H)$^+$ 359.

Step 3. To a solution of 2'-N-tert-butylaminosulfonyl-[1,1']-biphenyl-4-ylamine (21 mg, 0.068 mmol) in 1 mL dry DCM was added trimethylaluminum (2.0M in hexane, 0.14 mL, 0.28 mmol). The mixture was stirred for 20 minutes. The above-prepared ester (16 mg, 0.045 mmol) in Step 4 was dissolved in 4 mL dry DCM and added into the aluminum mixture. The reaction was stirred at room temperature for overnight and quenched using saturated Rochelle's salt aq solution. It was extracted with CHCl$_3$ (×3). The organic phases were combined, dried, concentrated and purified with flash column to yield the coupling product (52%). Rf 0.17 (1:1 EtOAc:Hexane). ES-MS: (M+H)$^+$ 617.

Step 4. The above-prepared compound was dissolved in 2 mL acetonitrile and 2 mL TFA. The mixture was stirred for 1 hour at 70° C. The mixture was evaporated and purified with prep HPLC to afford the title compound in 90% yield. ES-MS: (M+H)$^+$ 561.

Example 54

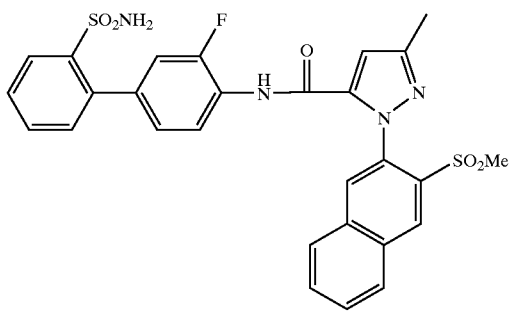

Step 1. The synthesis of ethyl 3-methyl-1-(3-methylsulfonyl-2-naphthyl)-1H-pyrazole-5-carboxylate was the same as that described in Step 4 of Example 53.

Step 2. The above-prepared ester (3.4 g, 9.7 mmol) was dissolved in 20 mL methanol. To it were added LiOH.H$_2$O (0.82 g, 19.5 mmol) and 10 mL water. The mixture was stirred at room temperature for overnight. The solvent was evaporated. The residue was acidified with 1N HCl till pH 1. The mixture was extracted with EtOAc (×4). The organic phases were combined, dried, evaporated to dryness to afford 3-methyl-1-(3-methylsulfonyl-2-naphthyl)-1H-pyrazole-5-carboxylic acid (3.24 g, 99%). ES-MS: (M+H)$^+$ 331.

Step 3. The above-prepared acid (102 mg, 0.31 mmol), 2'-N-tert-butylaminosulfonyl-3-fluoro-[1,1']-biphenyl-4-ylamine (150 mg, 0.46 mmol), DMAP (10 mg) were dissolved in 3 mL pyridine. To this stirred solution at 0° C. was added POCl$_3$ (87 μL, 0.93 mmol). The mixture was stirred for 2 hours and quenched with ice chips. It was diluted with EtOAc, washed with brine (×2), dried, concentrated and purified with flash column to give the coupling product (130 mg, 66%). Rf 0.29 (1:1 EtOAc:hexane). MS: (M+H)$^+$ 635.

Step 4. The above-prepared compound (100 mg) was taken into 5 mL TFA and stirred at room temperature for overnight. After evaporation, the mixture was subjected on prep HPLC to isolate the title compound (90%). MS: (M+H)$^+$ 579.

Example 55

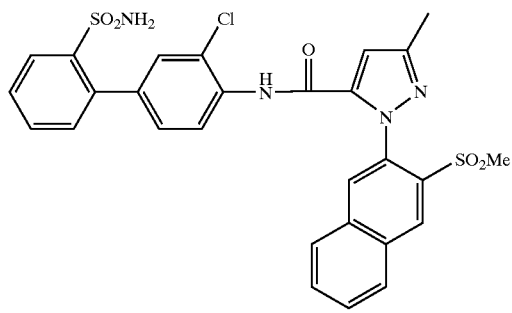

This compound was prepared by the same methodology described for Example 54 with 2'-N-tert-butylaminosulfonyl-3-chloro-[1,1']-biphenyl-4-ylamine substituted for 2'-N-tert-butylaminosulfonyl-3-fluoro-[1,1']-biphenyl-4-ylamine. ES-MS: (M+H)$^+$ 595.

Example 56

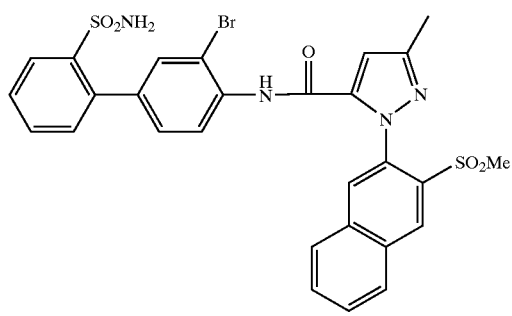

This compound was prepared by the same methodology described for Example 54 with 2'-N-tert-butylaminosulfonyl-3-bromo-[1,1']-biphenyl-4-ylamine substituted for 2'-N-tert-butylaminosulfonyl-3-fluoro-[1,1']-biphenyl-4-ylamine. ES-MS: (M+H)$^+$ 639, 641 (Br pattern).

Example 57

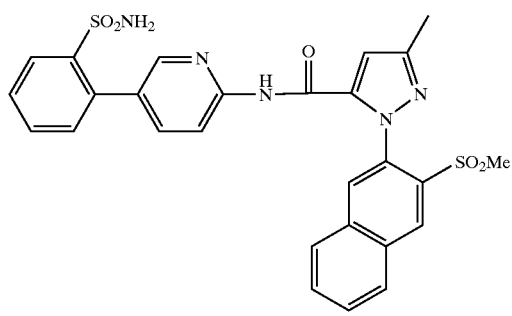

This compound was prepared by the same methodology described for Example 54 with 2-amino-5-(2-(N-tert-butylaminosulfonyl)phenyl)pyridine substituted for 2'-N-tert-butylaminosulfonyl-3-fluoro-[1,1']-biphenyl-4-ylamine. ES-MS: (M+H)$^+$ 562.

Example 58

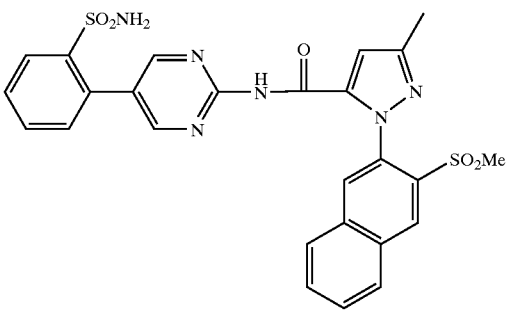

This compound was prepared by the same methodology described for Example 54 with 2-amino-5-(2-(N-tert-butylaminosulfonyl)phenyl)pyrimidine substituted for 2'-N-tert-butylaminosulfonyl-3-fluoro-[1,1']-biphenyl-4-ylamine. ES-MS: (M+H)$^+$ 563.

Example 59

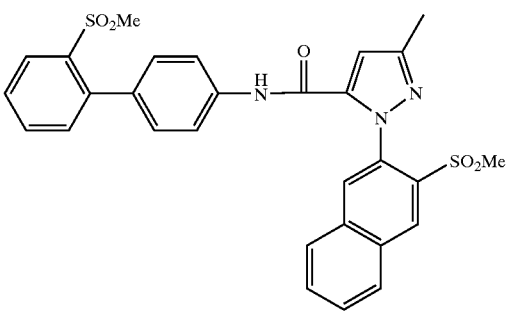

This compound was prepared by the same methodology described for Example 54 with for 2'-methylsulfonyl-[1,1']-biphenyl-4-ylamine substituted for 2'-N-tert-butylaminosulfonyl-3-fluoro-[1,1']-biphenyl-4-ylamine, without the final TFA treatment. ES-MS: (M+H)$^+$ 560.

Example 60

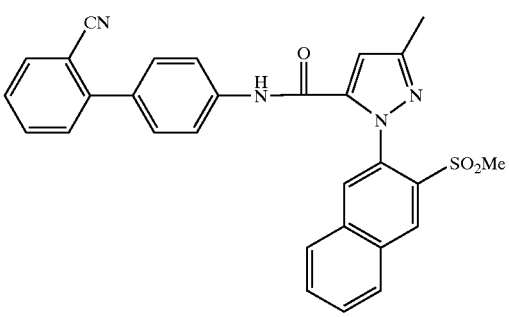

This compound was prepared by the same methodology described for Example 54 with for 2'-cyano-[1,1']-biphenyl-4-ylamine substituted for 2'-N-tert-butylaminosulfonyl-3-fluoro-[1,1']-biphenyl-4-ylamine, without the final TFA treatment. ES-MS: (M+H)$^+$ 507.

Example 61

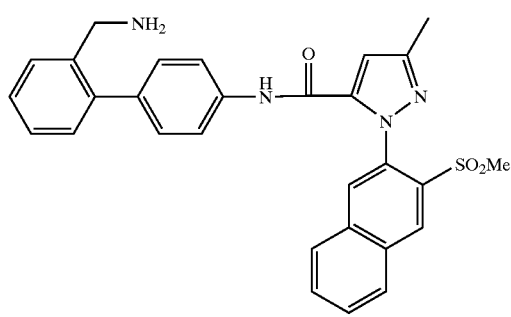

The title compound of Example 60 (55 mg, 0.11 mmol) was dissolved in 2 mL anhydrous DMF. To this stirred solution at 0° C. were added sodium borohydride (33 mg, 0.88 mmol) and $CoCl_2$ (30 mg, 0.22 mmol). The reaction was allowed for 2 hours and quenched with acetic acid. The mixture was evaporated, diluted with EtOAc, and washed with $NaHCO_3$ aq solution. The organic phase was dried, evaporated and purified with prep HPLC to afford the title compound in 55% yield. ES-MS: $(M+H)^+$ 511.

Example 62

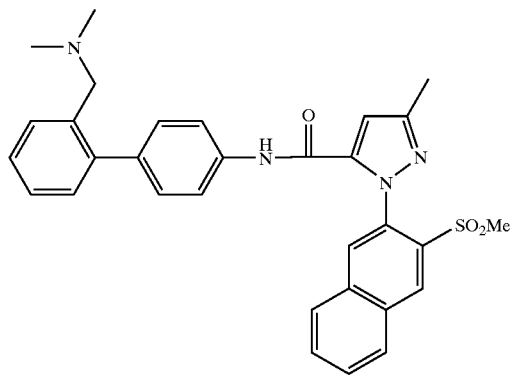

This compound was prepared by the same methodology described for Example 54 with for 2'-(N-dimethylaminomethyl)-[1,1']-biphenyl-4-ylamine substituted for 2'-N-tert-butylaminosulfonyl-3-fluoro-[1,1']-biphenyl-4-ylamine, without the final TFA treatment. ES-MS: $(M+H)^+$ 539.

Example 63

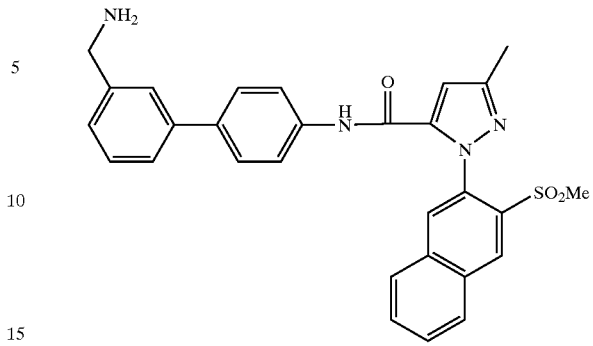

This compound was prepared by the same methodology described for Example 54 with for 3'-(N-tert-Boc-aminomethyl)-[1,1']-biphenyl-4-ylamine substituted for 2'-N-tert-butylaminosulfonyl-3-fluoro-[1,1']-biphenyl-4-ylamine. ES-MS: $(M+H)^+$ 511.

Example 64

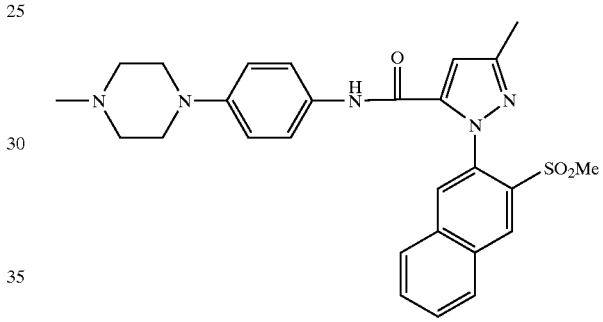

This compound was prepared by the same methodology described for Example 54 with for 1-(4-Aminophenyl)-4-methylpiperazine hydrochloride substituted for 2'-N-tert-butylaminosulfonyl-3-fluoro-[1,1']-biphenyl-4-ylamine, without the final TFA treatment. ES-MS: $(M+H)^+$ 504.

Example 65

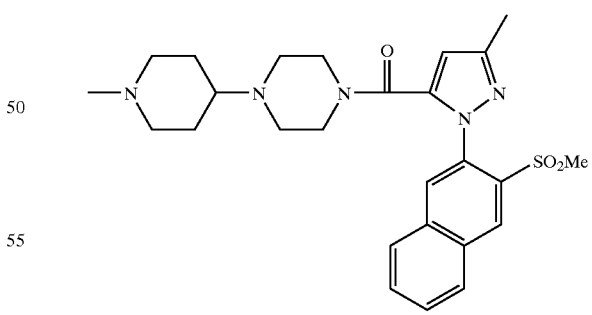

This compound was prepared by the same methodology described for Example 54 with for 1-(N-methylpiperidin-4-yl)-piperazine substituted for 2'-N-tert-butylaminosulfonyl-3-fluoro-[1,1']-biphenyl-4-ylamine, without the final TFA treatment. ES-MS: (M+H)$^+$ 496.

Example 66

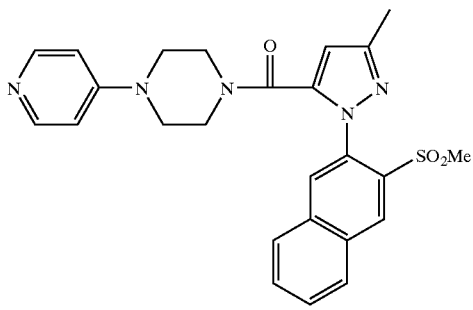

This compound was prepared by the same methodology described for Example 54 with for 1-(4-pyridyl)-piperazine substituted for 2'-N-tert-butylaminosulfonyl-3-fluoro-[1,1']-biphenyl-4-ylamine, without the final TFA treatment. ES-MS: (M+H)$^+$ 476.

Example 67

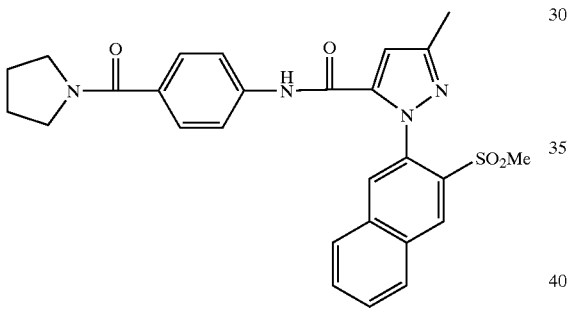

This compound was prepared by the same methodology described for Example 54 with for 4-(N-pyrrolidinylcarbonyl)-aniline substituted for 2'-N-tert-butylaminosulfonyl-3-fluoro-[1,1']-biphenyl-4-ylamine, without the final TFA treatment. ES-MS: (M+H)$^+$ 503.

Example 68

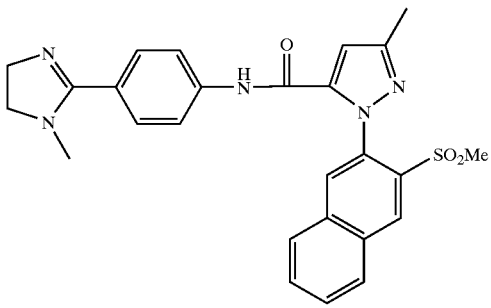

Step 1. The synthesis of 3-methyl-1-(3-methylsulfonyl-2-naphthyl)-1H-pyrazole-5-carboxylic acid was the same as that described in Step 2 of Example 54.

Step 2. The above-prepared acid (200 mg, 0.61 mmol), 4-aminobenzonitrile (108 mg, 0.91 mmol) and DMAP (10 mg) were dissolved in 6 mL pyridine. The solution was stirred at 0° C. To it was added POCl$_3$ (170 μL, 1.8 mmol). The mixture was stirred for 1 hour. The reaction was then quenched with ice chips. It was diluted with EtOAc. The organic phase was washed with brine (×2). It was dried, concentrated and purified with flash column to afford the coupling product (250 mg, 95%). Rf 0.20 (1:1 EtOAc:hexane). ES-MS: (M+H)$^+$ 431.

Step 3. The above-prepared nitrile (70 mg, 0.16 mmol) was dissolved in 6 mL dry methanol. It was chilled and stirred in an ice bath. To this solution was bubbled dry HCl gas via a long needle till saturation reached (indicated by a blown-up balloon attached on the top of the reaction flask). The resulting solution was stirred overnight. ES-MS: (M+H)$^+$ 463. The solvent was removed in vacuuo. The residue was pumped to dryness. The solid was dissolved in 6 mL dry methanol. To it was added anhydrous N-methylethylenediamine (0.5 mL). The mixture was refluxed for 1 hour, concentrated and loaded on prep HPLC to afford the title compound in 80% yield. ES-MS: (M+H)$^+$ 488.

Example 69

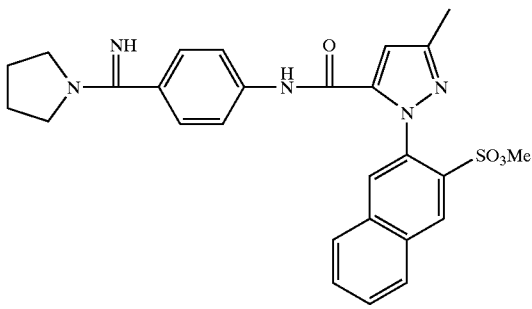

This compound was prepared by the same methodology described for Example 68 with pyrolidine substituted for N-methylethylenediamine. ES-MS: (M+H)$^+$ 502.

Example 70

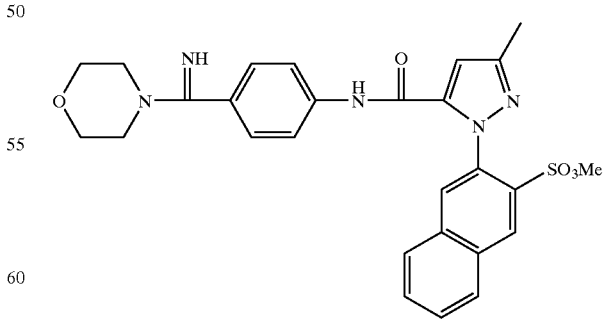

This compound was prepared by the same methodology described for Example 68 with morpholine substituted for N-methylethylenediamine. ES-MS: (M+H)$^+$ 518.

Example 71

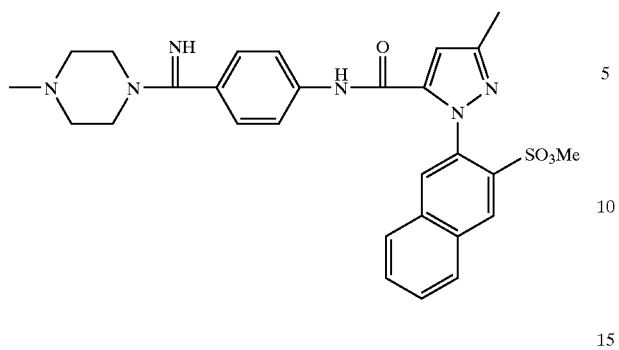

This compound was prepared by the same methodology described for Example 68 with N-methylpiperazine substituted for N-methylethylenediamine. ES-MS: (M+H)+ 531.

Example 72

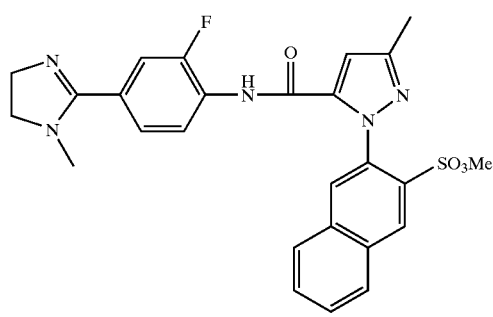

This compound was prepared by the same methodology described for Example 68 with 4-amino-3-fluorobenzonitrile (preparation described in Step 1 of Example 22) substituted for 4-aminobenzonitrile. ES-MS: (M+H)+ 506.

Example 73

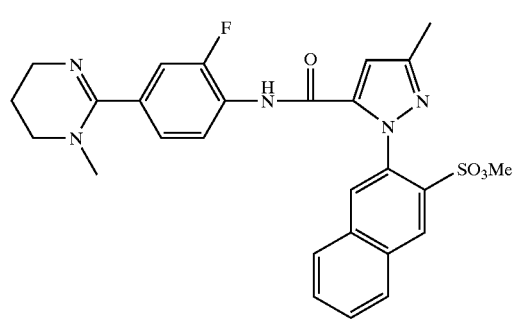

This compound was prepared by the same methodology described for Example 68 with 4-amino-3-fluorobenzonitrile substituted for 4-aminobenzonitrile, and with N-methyl-1,3-propanediamine substituted for N-methylethylenediamine. ES-MS: (M+H)+ 520.

Example 74

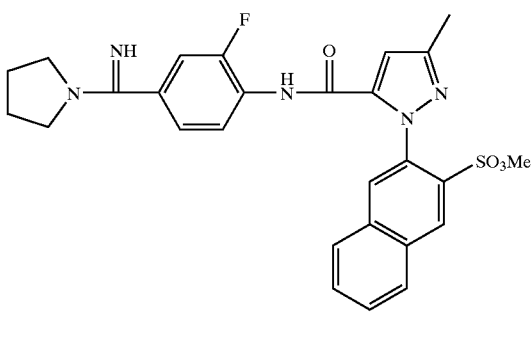

This compound was prepared by the same methodology described for Example 68 with 4-amino-3-fluorobenzonitrile substituted for 4-aminobenzonitrile, and with pyrrolidine substituted for N-methylethylenediamine. ES-MS: (M+H)+ 520.

Example 75

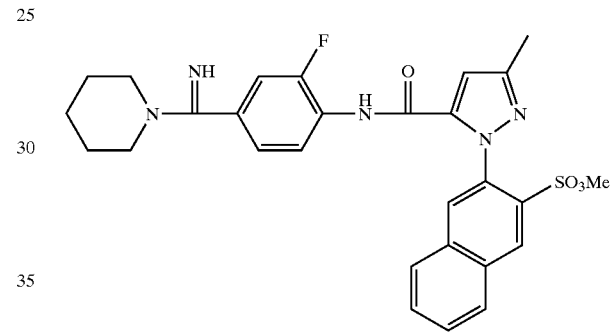

This compound was prepared by the same methodology described for Example 68 with 4-amino-3-fluorobenzonitrile substituted for 4-aminobenzonitrile, and with piperidine substituted for N-methylethylenediamine. ES-MS: (M+H)+ 534.

Example 76

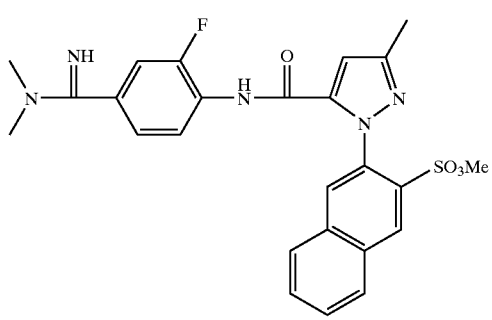

This compound was prepared by the same methodology described for Example 68 with 4-amino-3-fluorobenzonitrile substituted for 4-aminobenzonitrile, and with dimethylamine (2M solution in THF) substituted for N-methylethylenediamine. ES-MS: (M+H)+ 494.

Example 77

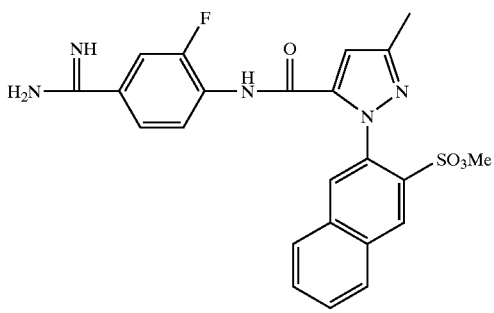

This compound was prepared by the same methodology described for Example 68 with 4-amino-3-fluorobenzonitrile substituted for 4-aminobenzonitrile, and with ammonium acetate substituted for N-methylethylenediamine. ES-MS: (M+H)+ 466.

Example 78

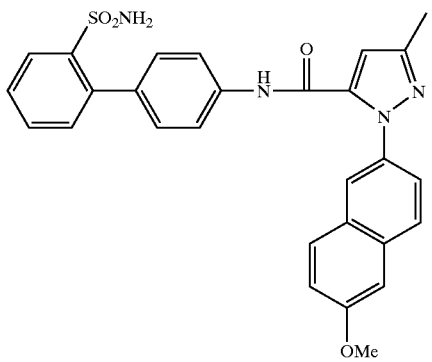

Step 1. To a solution of 2-bromo-6-methoxynaphthalene (2.0 g, 8.4 mmol) in 20 mL anhydrous THF at −78° C. was added BuLi (1.6M, 7.9 mL, 12.6 mmol) dropwise with a syringe. The mixture was stirred for 30 minutes, then to it was added triisopropyl borane (2.34 mL, 10.1 mmol) dropwise. The dry ice bath was removed. The reaction mixture was allowed to warm up to room temperature. After 15 hours, THF was mostly removed in vacuuo. To the residue was added 40 mL 3M HCl. The mixture was stirred at room temperature for 8 hours. Ether was used to extract the product (×3). The organic phases were combined, dried, concentrated in vacuuo and pumped to dryness to afford 6-methoxy-2-naphthylboronic acid (75% yield) as a white solid. Rf 0.34 (1:1 EtOAc:hexane).

Step 2. To a solution of the above-prepared boronic acid (0.84 g, 3.2 mmol) and ethyl 3-methylpyrazole-5-carboxylate (0.49 g, 3.2 mmol) in 20 mL dry DCM were added pyridine (0.77 mL, 9.5 mmol) and anhydrous powder of copper(II) acetate (1.15 g, 6.3 mmol). Some activated molecular sieve powder was added afterwards. The resulting slurry was stirred for 4 days under argon. The mixture was diluted with DCM. It was filtered through celite. The blue filtrate was washed with water (×2), dried, concentrated and purified by flash column to separately afford ethyl 3-methyl-1-(6-methoxy-2-naphthyl)-1H-pyrazole-5-carboxylate [37% yield. Rf 0.80 (1:1 EtOAc:hexane). ES-MS: (M+H)+ 311] and ethyl 5-methyl-1-(6-methoxy-2-naphthyl)-1H-pyrazole-3-carboxylate [25% yield. Rf 0.69 (1:1 EtOAc:hexane). ES-MS: (M+H)+ 311] in a 1.5:1 ratio.

Step 3. To a solution of 2'-N-tert-butylaminosulfonyl-[1,1']-biphenyl-4-ylamine (44 mg, 0.14 mmol) in 1 mL DCM was added trimethylaluminum (2.0M in hexane, 0.35 mL, 0.70 mmol) at room temperature. The mixture was stirred for 30 minutes, and to it was added the above-prepared ethyl 3-methyl-1-(6-methoxy-2-naphthyl)-1H-pyrazole-5-carboxylate (44 mg, 0.14 mmol) in 2 mL DCM. The resulting mixture was stirred overnight. The reaction was quenched using 5 mL saturated Rochelle salt aq solution. The mixture was extracted using DCM (×3). The organic phases were combined, dried, concentrated and subjected on flash column to afford the coupling product in 84% yield (67 mg). Rf 0.41 (1:1 EtOAc:hexane). ES-MS: (M+H)+ 569.

Step 4. The above-prepared compound was placed in 3 mL TFA and stirred at 65° C. for 30 minutes. After evaporation, the residue was dissolved in methanol and purified with prep HPLC to afford the title compound in 95% yield. ES-MS: (M+H)+ 513.

Example 79

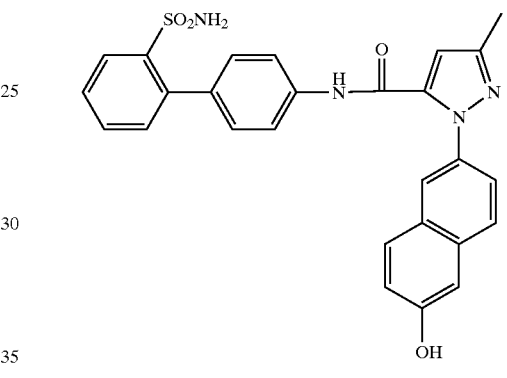

Step 1. The preparation of ethyl 3-methyl-1-(6-methoxy-2-naphthyl)-1H-pyrazole-5-carboxylate was the same as described in Step 2 of Example 83.

Step 2. The above-prepared compound (150 mg, 0.48 mmol) was dissolved in 2 mL DCM. At 0° C., to the stirred solution was added boron tribromide (1.0M in DCM, 0.72 mL, 0.72 mmol). The mixture was stirred overnight at room temperature. It was directly subjected to flash column to afford ethyl 3-methyl-1-(6-hydroxy-2-naphthyl)-1H-pyrazole-5-carboxylate (78 mg, 55%). Rf 0.73 (2:1 EtOAc:hexane). ES-MS: (M+H)+ 297.

Step 3. To a stirred solution of 2'-N-tert-butylaminosulfonyl-[1,1']-biphenyl-4-ylamine (80 mg, 0.26 mmol) in 1 mL DCM was added trimethylaluminum (2.0M in hexane, 0.65 mL, 1.3 mmol) at room temperature. After 30 minutes, to the mixture was added ethyl 3-methyl-1-(6-hydroxy-2-naphthyl)-1H-pyrazole-5-carboxylate (78 mg, 0.26 mmol) in 3 mL DCM. The resulting mixture was stirred 4 hours. The reaction was quenched using 5 mL saturated Rochelle salt aq solution. The mixture was extracted using DCM (×3). The organic phases were combined, dried, concentrated and purified with flash column to afford the coupling product in 65% yield. Rf 0.32 (1:1 EtOAc:hexane). ES-MS: (M+H)+ 555.

Step 4. The above-prepared compound was placed in 3 mL TFA and stirred at 70° C. for 30 minutes. After evaporation, the residue was dissolved in methanol and purified with prep HPLC to afford the title compound in 95% yield. ES-MS: (M+H)+ 499.

Example 80

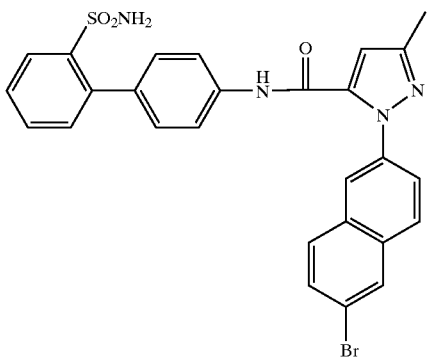

Step 1. A mixture of 6-bromo-2-naphthoic acid (1.11 g, 4.4 mmol) and 2 mL thionyl chloride was refluxed for overnight. Thionyl chloride was removed in vacuuo. The dry acid chloride was dissolved in 5 mL dioxane. At 0° C. to it was added a solution of sodium azide (0.52 g, 8.0 mmol) in 2.5 mL water and 2.5 mL dioxane dropwise. The mixture was stirred for 2 hours. After evaporation in vacuuo to remove the solvent, the residue was dissolved in EtOAc, washed with brine, dried, concentrated in vacuuo to give the azidoketone (1.22 g, 99%). Rf 0.88 (1:1 EtOAc:hexane).

Step 2. The above-prepared compound was dissolved in 20 mL DMF. To it was added 10 mL water. The mixture was refluxed overnight. It was diluted with 500 mL EtOAc, washed with brine (×2), dried, concentrated in vacuuo to afford 6-bromo-2-naphthylamine (1.2 g, 99%). Rf 0.73 (1:1 EtOAc:hexane), ES-MS: (M+H)$^+$ 222, 224 (Br pattern).

Step 3. The above-prepared compound (1.2 g, 5.4 mmol) was placed in 6 mL concentrate HCl. At 0° C. to it was added a solution of sodium nitrite (0.37 g, 5.4 mmol) in 2 mL water dropwise. The mixture was stirred for 30 minutes. At 0° C. to the mixture was added a solution of SnCl$_2$.2H$_2$O (3.66 g, 16.2 mmol) in 6 mL concentrate HCl dropwise. After stirring for 10 minutes, the mixture was placed in a freezer for overnight. The solid was collected on a cold Buchner funnel. It was washed by ice-cold brine (7 mL) and ice-cold hexane (7 mL). The solid cake was transferred into a flask and pumped to dryness. To it were added 30 mL acetic acid, 15 mL THF, and ethyl 2-N-(methoxy)imino-4-oxopentanoate (1.3 g, 7.0 mmol). The resulting mixture was refluxed for overnight. The solvent was removed in vacuuo. The residue was dissolved in EtOAc, washed with brine (×2), dried, concentrated and purified by flash column to yield ethyl 3-methyl-1-(6-bromo-2-naphthyl)-1H-pyrazole-5-carboxylate (0.64 g, 33%). Rf 0.71 (1:2 EtOAc: hexane). ES-MS: (M+H)$^+$ 359, 361 (Br pattern).

Step 4. To a stirred solution of 2'-N-tert-butylaminosulfonyl-[1,1']-biphenyl-4-ylamine (93 mg, 0.31 mmol) in 1 mL DCM was added trimethylaluminum (2.0M in hexane, 0.70 mL, 1.4 mmol) at room temperature. After 30 minutes, to the mixture was added the above-prepared ethyl ester (100 mg, 0.28 mmol) in 3 mL DCM. The resulting mixture was stirred overnight. The reaction was quenched using 5 mL saturated Rochelle's salt aq solution. The mixture was extracted using DCM (×3). The organic phases were combined, dried, evaporated and purified with flash column to yield the coupling product (146 mg, 85%). Rf 0.44 (1:1 EtOAc:hexane). ES-MS: (M+H)$^+$ 617, 619 (Br pattern).

Step 5. The above-prepared compound was placed in 3 mL TFA and stirred at 65° C. for 40 minutes. After evaporation, the residue was dissolved in methanol and purified with prep HPLC to afford the title compound in 95% yield. ES-MS: (M+H)$^+$ 561, 563 (Br pattern).

Example 81

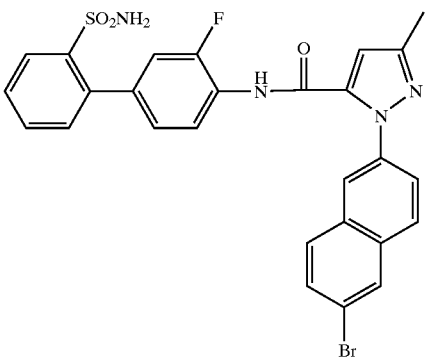

This compound was prepared by the same methodology described for Example 80 with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)$^+$ 579, 581 (Br. pattern).

Example 82

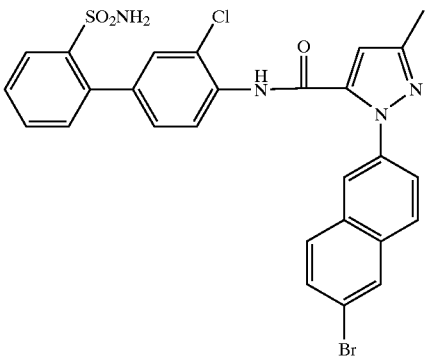

This compound was prepared by the same methodology described for Example 80 with 2'-N-tert-butylaminosulfonyl-3-chloro-[1,1']-biphenyl-4-ylamine substituted for 2'-N-tert-butylaminosulfonyl-[1,1']-biphenyl-4-ylamine. ES-MS: (M+H)$^+$ 595, 597 (BrCl pattern).

Example 83

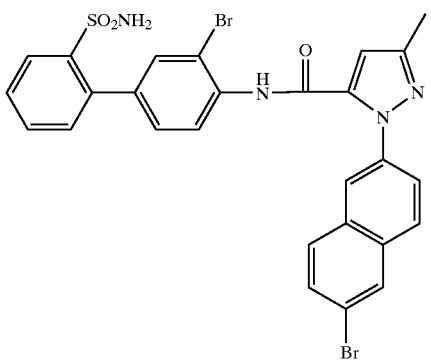

This compound was prepared by the same methodology described for Example 80 with 2'-N-tert-butylaminosulfonyl-3-bromo-[1,1']-biphenyl-4-ylamine substituted for 2'-N-tert-butylaminosulfonyl-[1,1']-biphenyl-4-ylamine. ES-MS: (M+H)+ 640, 642, 644 (Br$_2$ pattern).

Example 84

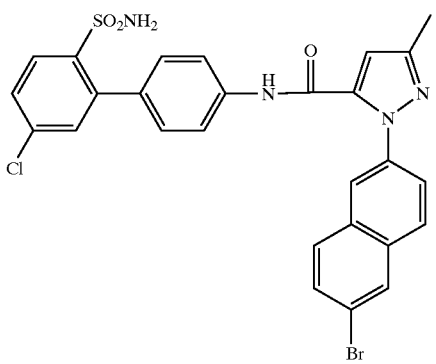

This compound was prepared by the same methodology described for Example 80 with 2'-N-tert-butylaminosulfonyl-5'-chloro-[1,1']-biphenyl-4-ylamine substituted for 2'-N-tert-butylaminosulfonyl-[1,1']-biphenyl-4-ylamine. ES-MS: (M+H)+ 595, 597 (BrCl pattern).

Example 85

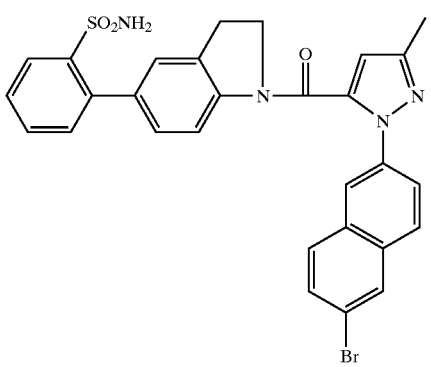

This compound was prepared by the same methodology described for Example 80 with 5-(2-N-tert-butylaminosulfonyl-1-phenyl)-2,3-dihydroindole substituted for 2'-N-tert-butylaminosulfonyl-[1,1']-biphenyl-4-ylamine. ES-MS: (M+H)+ 587, 589 (Br pattern).

Example 86

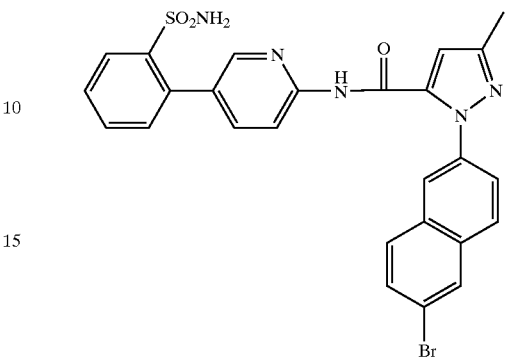

Step 1. The synthesis of ethyl 3-methyl-1-(6-bromo-2-naphthyl)-1H-pyrazole-5-carboxylate was the same as Step 3 of Example 80.

Step 2. The above-prepared ethyl ester (1.0 g, 2.8 mmol) was dissolved in 20 mL methanol. To the solution were added LiOH.H$_2$O (350 mg, 8.3 mmol) and 10 mL water. The mixture was stirred for overnight and evaporated in vacuuo. The residue was acidified with 1N HCl. It was extracted with EtOAc (×4). The organic phases were combined, dried and concentrated in vacuuo to give 3-methyl-1-(6-bromo-2-naphthyl)-1H-pyrazole-5-carboxylic acid (0.97 g, 100%). ES-MS: (M+H)+ 331, 333 (Br pattern).

Step 3. A mixture of the above-prepared acid (33 mg, 0.10 mmol), 2-amino-5-(2-(N-tert-butylaminosulfonyl)phenyl)pyridine (61 mg, 0.20 mmol), DMAP (5 mg) were dissolved in 3 mL pyridine and stirred at 0° C. To it was added POCl$_3$ (55 µL, 0.6 mmol). The mixture was stirred for 2 hours and quenched with ice chips. It was diluted with EtOAc, washed with brine (×2), dried, concentrated and purified with flash column to give the coupling product (34 mg, 55%). Rf 0.35 (1:1 EtOAc:hexane). ES-MS: (M+H)+ 618, 620 (Br pattern).

Step 4. The above-prepared compound was placed in 3 mL TFA and stirred at 65° C. for 40 minutes. After evaporation, the residue was dissolved in methanol and purified with prep HPLC to afford the title compound in 95% yield. ES-MS: (M+H)+ 562, 564 (Br pattern).

Example 87

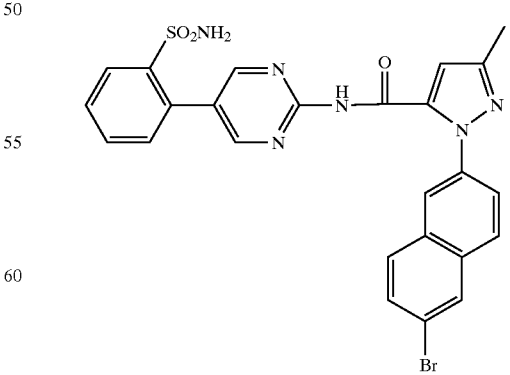

This compound was prepared by the same methodology described for Example 86 with 2-amino-5-(2-(N-tertbutylaminosulfonyl)phenyl)pyrimidine substituted for 2-amino-5-(2-(N-tert-butylaminosulfonyl)phenyl)pyridine. ES-MS: (M+H)+ 563, 565 (Br pattern).

Example 88

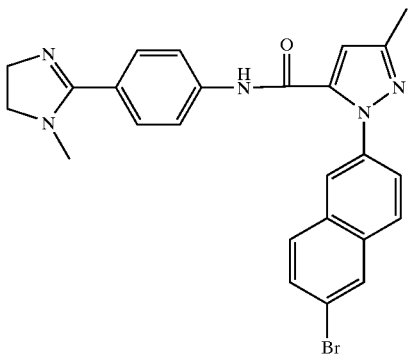

Step 1. The synthesis of 3-methyl-1-(6-bromo-2-naphthyl)-1H-pyrazole-5-carboxylic acid was the same as Step 2 of Example 86.

Step 2. A mixture of the above-prepared acid (970 mg, 2.9 mmol), 4-aminobenzonitrile (700 mg, 5.8 mmol), DMAP (40 mg) were dissolved in 15 mL pyridine and stirred at 0° C. To it was added POCl$_3$ (1.1 mL, 12 mmol). The mixture was stirred for 1 hour and quenched with ice chips. It was diluted with EtOAc, washed with brine (×2), dried, concentrated and purified with flash column to give the coupling product (720 mg, 58%). Rf 0.30 (1:1 EtOAc:hexane). ES-MS: (M+H)+ 431, 433 (Br pattern).

Step 3. The above-prepared nitrile (40 mg, 0.09 mmol) was dissolved in 6 mL dry methanol. It was chilled and stirred in an ice bath. To this solution was bubbled dry HCl gas via a long needle till saturation reached. The resulting solution was stirred overnight. ES-MS: (M+H)+ 463, 465 (Br pattern). The solvent was removed in vacuuo. The residue was pumped to dryness. The solid was dissolved in 6 mL dry methanol. To it was added anhydrous N-methylethylenediamine (0.5 mL). The mixture was refluxed for 1 hour, concentrated and loaded on prep HPLC to afford the title compound in 85% yield. ES-MS: (M+H)+ 488, 490 (Br pattern).

Example 89

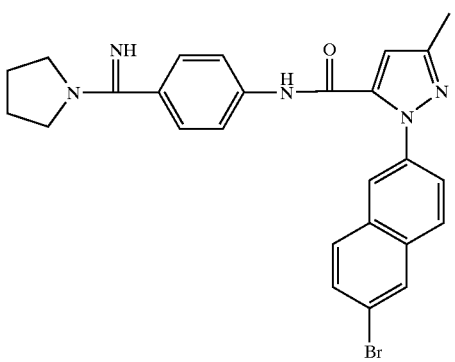

This compound was prepared by the same methodology described for Example 88 with pyrrolidine substituted for N-methylethylenediamine. ES-MS: (M+H)+ 502, 504 (Br pattern).

Example 90

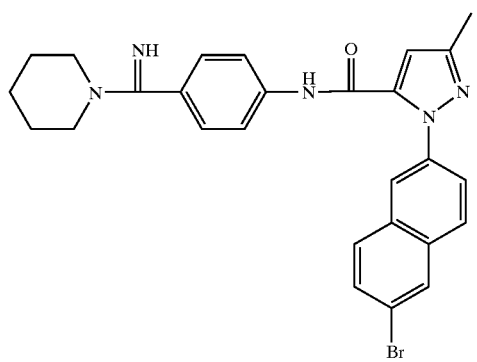

This compound was prepared by the same methodology described for Example 88 with piperidine substituted for N-methylethylenediamine. ES-MS: (M+H)+ 516, 518 (Br pattern).

Example 91

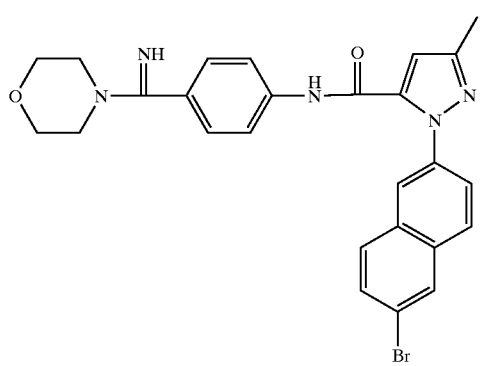

This compound was prepared by the same methodology described for Example 88 with morpholine substituted for N-methylethylenediamine. ES-MS: (M+H)+ 518, 520 (Br pattern).

Example 92

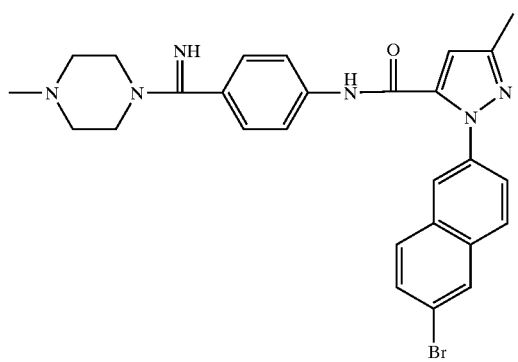

This compound was prepared by the same methodology described for Example 88 with N-methylpiperazine substituted for N-methylethylenediamine. ES-MS: (M+H)+ 531, 533 (Br pattern).

Example 93

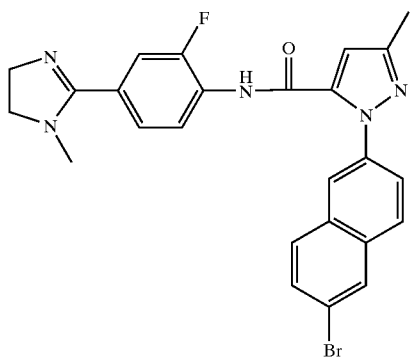

This compound was prepared by the same methodology described for Example 88 with 4-amino-3-fluorobenzonitrile substituted for 4-aminobenzonitrile. ES-MS: (M+H)+ 506, 508 (Br pattern).

Example 94

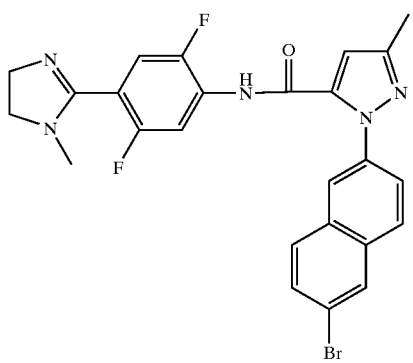

This compound was prepared by the same methodology described for Example 88 with 4-amino-2,5-difluorobenzonitrile substituted for 4-aminobenzonitrile. ES-MS: (M+H)+ 524, 526 (Br pattern).

Example 95

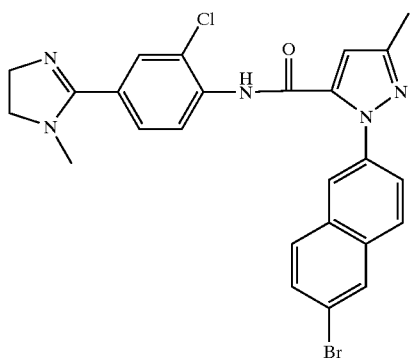

This compound was prepared by the same methodology described for Example 88 with 4-amino-3-chlorobenzonitrile substituted for 4-aminobenzonitrile. ES-MS: (M+H)+ 522, 524 (BrCl pattern).

Example 96

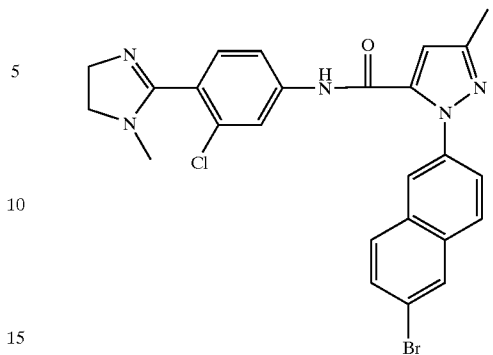

This compound was prepared by the same methodology described for Example 88 with 4-amino-2-chlorobenzonitrile substituted for 4-aminobenzonitrile. ES-MS: (M+H)+ 522, 524 (BrCl pattern).

Example 97

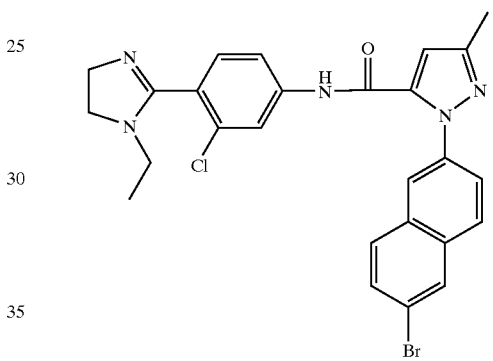

This compound was prepared by the same methodology described for Example 88 with 4-amino-2-chlorobenzonitrile substituted for 4-aminobenzonitrile, and with N-ethyl ethylenediamine substituted for N-methylethylenediamine. ES-MS: (M+H)+ 536, 538 (BrCl pattern).

Example 98

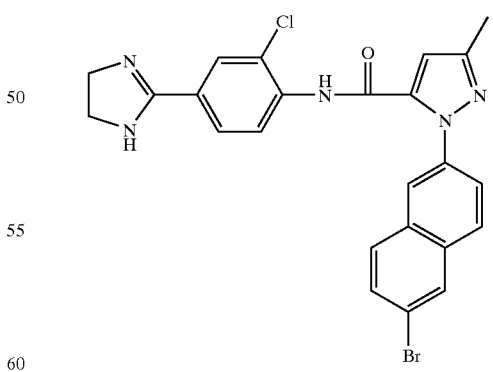

This compound was prepared by the same methodology described for Example 88 with 4-amino-3-chlorobenzonitrile substituted for 4-aminobenzonitrile, and with ethylenediamine substituted for N-methylethylenediamine. ES-MS: (M+H)+ 508, 510 (BrCl pattern).

Example 99

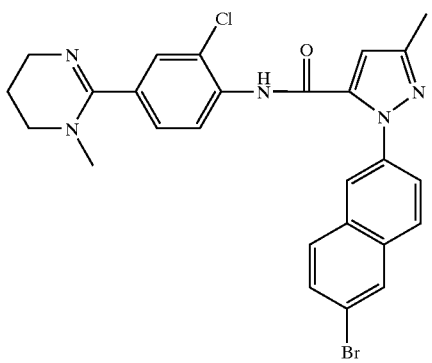

This compound was prepared by the same methodology described for Example 88 with 4-amino-3-chlorobenzonitrile substituted for 4-aminobenzonitrile, and with N-methyl-1,3-propanediamine substituted for N-methylethylenediamine. ES-MS: (M+H)+ 536, 538 (BrCl pattern).

Example 100

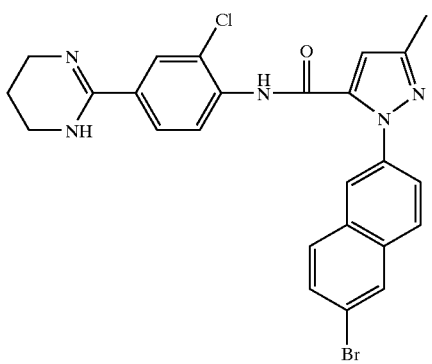

This compound was prepared by the same methodology described for Example 88 with 4-amino-3-chlorobenzonitrile substituted for 4-aminobenzonitrile, and with 1,3-propanediamine substituted for N-methylethylenediamine. ES-MS: (M+H)+ 522, 524 (BrCl pattern).

Example 101

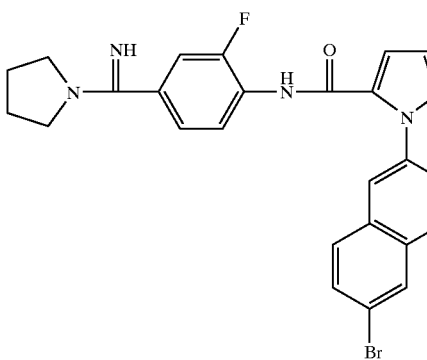

This compound was prepared by the same methodology described for Example 88 with 4-amino-3-fluorobenzonitrile substituted for 4-aminobenzonitrile, and with pyrrolidine substituted for N-methylethylenediamine. ES-MS: (M+H)+ 520, 522 (Br pattern).

Example 102

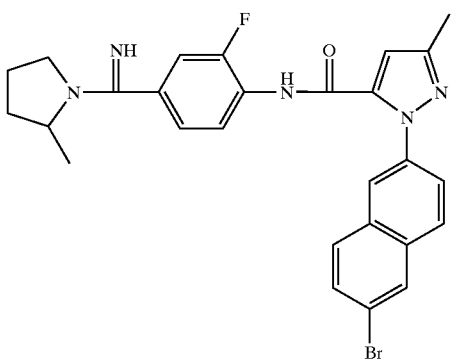

This compound was prepared by the same methodology described for Example 88 with 4-amino-3-fluorobenzonitrile substituted for 4-aminobenzonitrile, and with 2-methylpyrrolidine substituted for N-methylethylenediamine. ES-MS: (M+H)+ 534, 536 (Br pattern).

Example 103

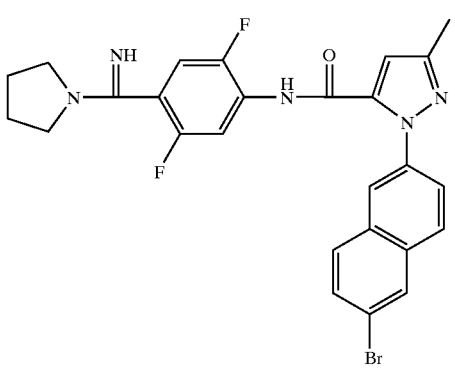

This compound was prepared by the same methodology described for Example 88 with 4-amino-2,5-difluorobenzonitrile substituted for 4-aminobenzonitrile, and with pyrrolidine substituted for N-methylethylenediamine. ES-MS: (M+H)+ 538, 540 (Br pattern).

Example 104

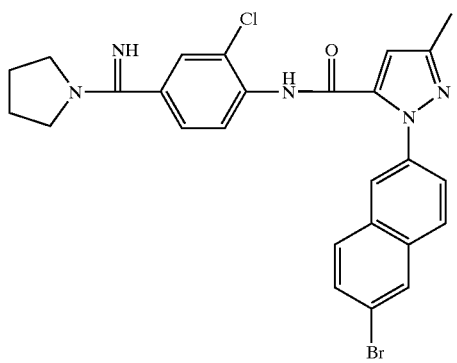

This compound was prepared by the same methodology described for Example 88 with 4-amino-3-chlorobenzonitrile substituted for 4-aminobenzonitrile, and with pyrrolidine substituted for N-methylethylenediamine. ES-MS: (M+H)$^+$ 536, 538 (BrCl pattern).

Example 105

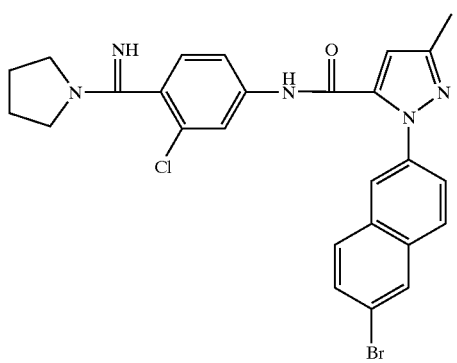

This compound was prepared by the same methodology described for Example 88 with 4-amino-2-chlorobenzonitrile substituted for 4-aminobenzonitrile, and with pyrrolidine substituted for N-methylethylenediamine. ES-MS: (M+H)$^+$ 536, 538 (BrCl pattern).

Example 106

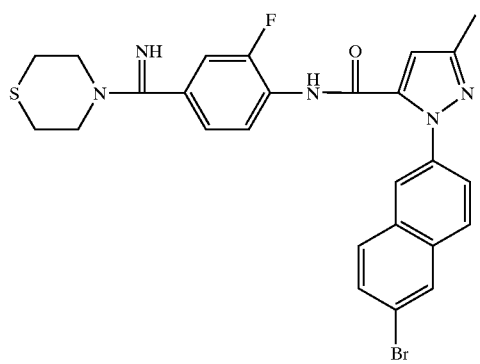

This compound was prepared by the same methodology described for Example 88 with 4-amino-3-fluorobenzonitrile substituted for 4-aminobenzonitrile, and with thiomorpholine substituted for N-methylethylenediamine. ES-MS: (M+H)$^+$ 552, 554 (Br pattern).

Example 107

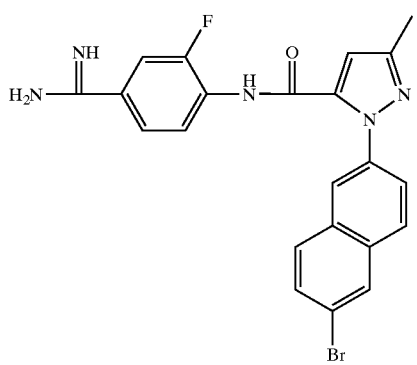

This compound was prepared by the same methodology described for Example 88 with 4-amino-3-fluorobenzonitrile substituted for 4-aminobenzonitrile, and with ammonium acetate substituted for N-methylethylenediamine. ES-MS: (M+H)$^+$ 466, 468 (Br pattern).

Example 108

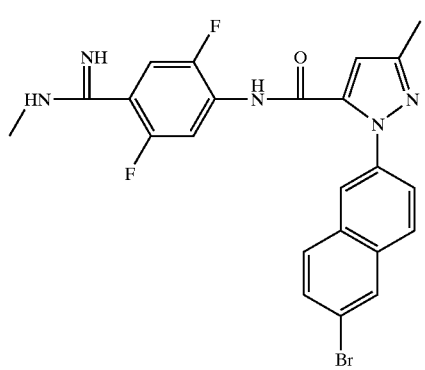

This compound was prepared by the same methodology described for Example 88 with 4-amino-2,5-difluorobenzonitrile substituted for 4-aminobenzonitrile, and with methylamine (2M in methanol) substituted for N-methylethylenediamine. ES-MS: (M+H)$^+$ 498, 500 (Br pattern).

Example 109

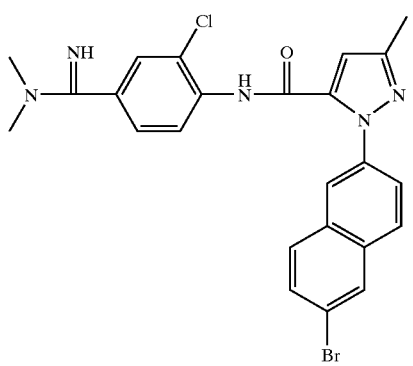

This compound was prepared by the same methodology described for Example 88 with 4-amino-3-chlorobenzonitrile substituted for 4-aminobenzonitrile, and with dimethylamine (2M in THF) substituted for N-methylethylenediamine. ES-MS: (M+H)$^+$ 510, 512 (BrCl pattern).

Example 110

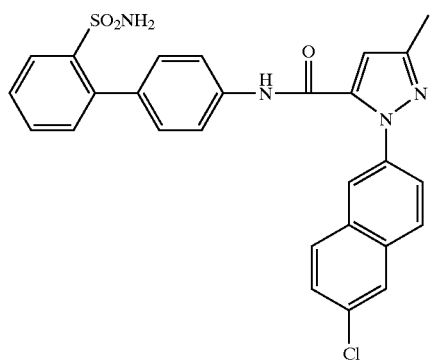

Step 1. To a solution of 6-bromo-2-naphthoic acid (4.4 g, 17.5 mmol) in 50 mL anhydrous DMF were added CuCl (8.7 g, 87.5 mmol) and CuI (0.2 g). The slurry was refluxed for 1 hour. At room temperature it was diluted with 300 mL EtOAc and stirred for 2 hours. It was filtered through celite. The filtrate was evaporated in vacuuo to afford 6-chloro-2-naphthoic acid (2.7 g, 75%). ES-MS: (M+H)$^+$ 207.

Step 2. The title compound was prepared using the same methodology shown for Example 80, with 6-chloro-2-naphthoic acid substituted for 6-bromo-2-naphthoic acid. ES-MS: (M+H)$^+$ 517.

Example 111

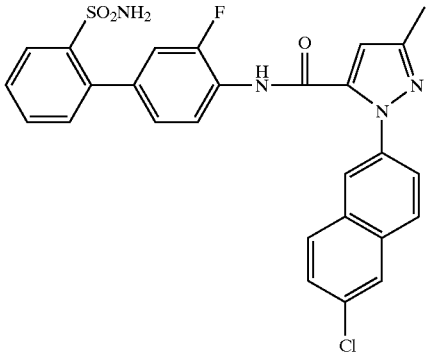

The title compound was prepared using the same methodology shown for Example 1 10, with 2'-N-tert-butylaminosulfonyl-3-fluoro-[1,1']-biphenyl-4-ylamine substituted for 2'-N-tert-butylaminosulfonyl-[1,1']-biphenyl-4-ylamine. ES-MS: (M+H)$^+$ 535.

Example 112

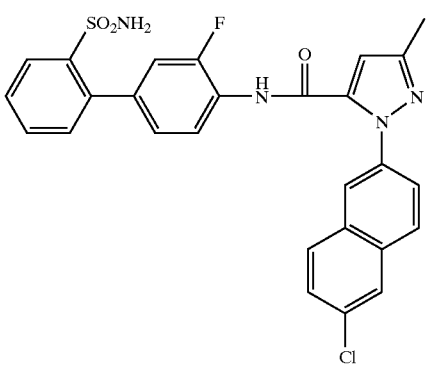

The title compound was prepared using the same methodology shown for Example 110, with 2'-methylsulfonyl-3-fluoro-[1,1']-biphenyl-4-ylamine substituted for 2'-N-tert-butylaminosulfonyl-[1,1']-biphenyl-4-ylamine. ES-MS: (M+H)$^+$ 534.

Example 113

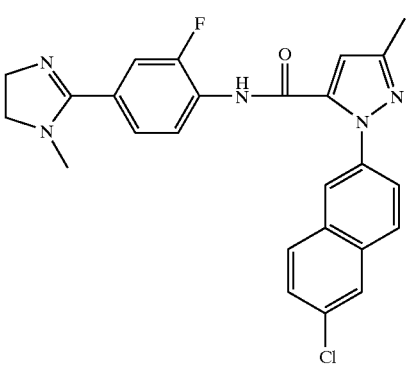

The title compound was prepared using the same methodology shown for Example 93, with 6-chloro-2-naphthoic acid substituted for 6-bromo-2-naphthoic acid. ES-MS: (M+H)$^+$ 462.

Example 114

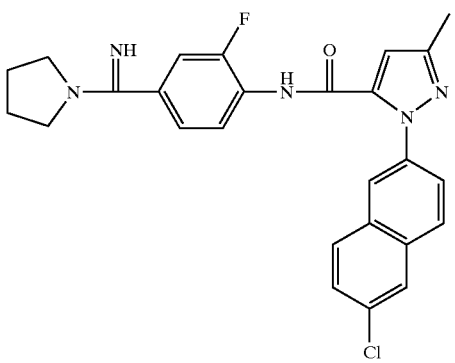

The title compound was prepared using the same methodology shown for Example 101, with 6-chloro-2-naphthoic acid substituted for 6-bromo-2-naphthoic acid. ES-MS: (M+H)+ 476.

Example 115

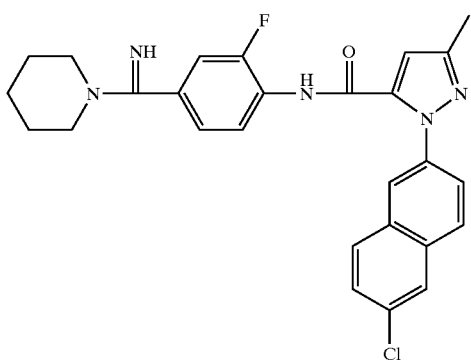

The title compound was prepared using the same methodology shown for Example 114, with piperidine substituted for N-methylethylenediamine. ES-MS: (M+H)+ 490.

Example 116

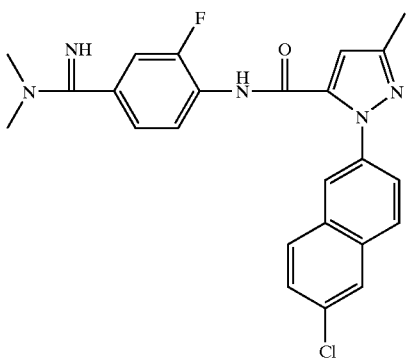

The title compound was prepared using the same methodology shown for Example 114, with dimethylamine (2M in THF) substituted for N-methylethylenediamine. ES-MS: (M+H)+ 450.

Example 117

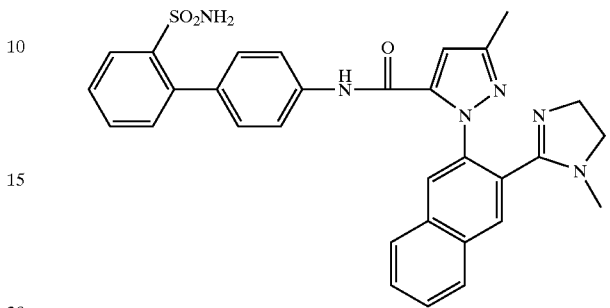

Step 1. The synthesis of 3-methyl-1-(3-cyano-2-naphthyl)-1H-pyrazole-5-(N-(2'-N-tert-butylaminosulfonyl-[1,1']-biphen-4-yl))carboxyamide followed the same procedure shown in Step 3 of Example 34.

Step 2. To a solution of the above-prepared compound (30 mg) in 10 mL anhydrous ethanol at 0° C. was bubbled dry HCl gas via a long needle till saturation reached. The mixture was stirred for overnight. The solvent was removed in vacuuo. The dry residue was dissolved in 5 mL anhydrous methanol. To it was added 0.5 mL N-methylethylenediamine. The mixture was refluxed for 2 hours. ES-MS: (M+H)+ 621. It was concentrated in vacuuo. To the residue was added 3 mL TFA and the mixture was stirred at 70° C. for 1 hour. After evaporation, the reaction mixture was subjected on prep HPLC to isolate the title compound (20% yield). ES-MS: (M+H)+ 565.

Example 118

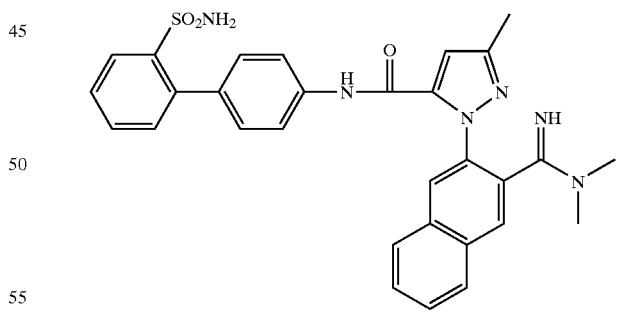

The title compound was prepared using the same methodology shown for Example 117, with dimethylamine (2M in THF) substituted for N-methylethylenediamine. ES-MS: (M+H)+ 553.

Example 119

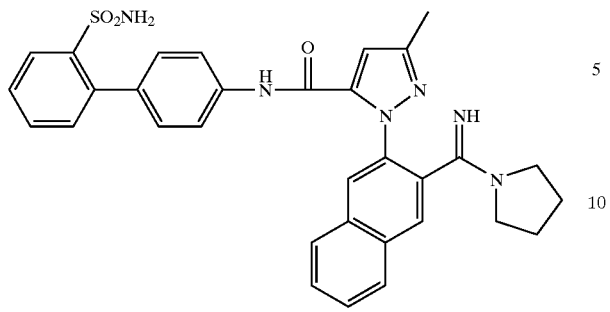

The title compound was prepared using the same methodology shown for Example 1I17, with pyrrolidine substituted for N-methylethylenediamine. ES-MS: (M+H)+ 579.

Example 120

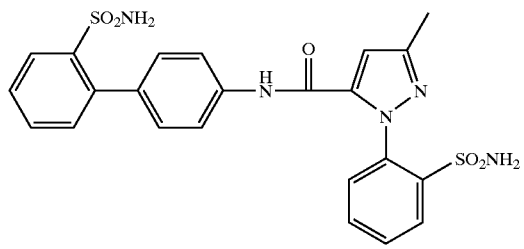

The title compound was prepared using the same methodology shown for Example 1, with 2-N-tert-butylaminosulfonylphenylboronic acid substituted for 2-naphthylboronic acid. ES-MS: (M+H)+ 512.

Example 121

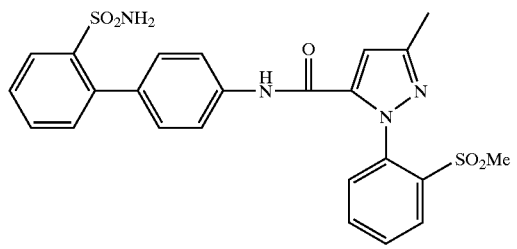

The title compound was prepared using the same methodology shown for Example 1, with 2-methylsulfonylphenylboronic acid substituted for 2-naphthylboronic acid. ES-MS: (M+H)+ 511.

Example 122

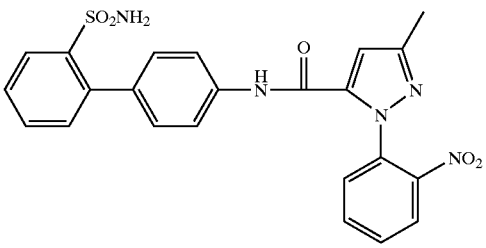

The title compound was prepared using the same methodology shown for Example 52, with commercial 2-nitrophenylhydrazine substituted for 3-carboxyl-2-naphthylhydrazine. ES-MS: (M+H)+ 478.

Example 123

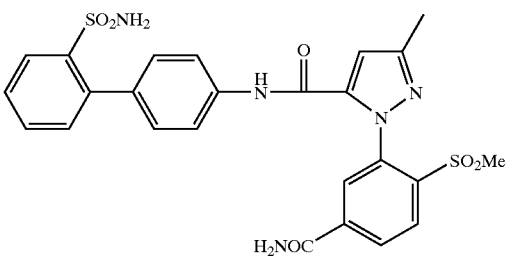

Step 1. 4-methylsulfonyl-3-nitrobenzoic acid (0.90 g, 3.7 mmol) was dissolved in 10 mL ethanol. To it were added hydrazine monohydrate (0.46 mL, 15 mmol) and catalytic amount of 10% Pd/C. The mixture was refluxed for 1.5 hour, diluted with methanol, filtered through celite and concentrated in vacuuo to afford 3-amino-4-methylsulfonylbenzoic acid (>70%). ES-MS: (M+H)+ 216.

Step 2. The above-prepared aniline (2.2 g, 10 mmol) was stirred in 16 mL concentrate HCl in ice bath. To it was dropwise added a cold solution of sodium nitrite (1.1 g, 15 mmol, in 7 mL water). After completion, the mixture was stirred for 30 minutes at 0° C.

To it was added dropwise a cold solution of SnCl$_2$.2H$_2$O (9.2 g, 40 mmol, in 14 mL concentrate HCl). The mixture was stirred for 30 minutes and filtered through a Buchner funnel. The solid crude hydrazine was collected and dried.

Step 3. The crude hydrazine was dissolved in 40 mL acetic acid. To it were added 20 mL THF and ethyl 2-N-(methoxy)imino-4-oxopentanoate (2.8 g, 15 mmol). The mixture was refluxed for overnight. After removal of the solvent in vacuuo, the reaction mixture residue was dissolved in 800 mL ether. The organic solution was washed with brine (×2), dried, concentrated and purified with flash column to afford ethyl 3-methyl-1-(5-carboxyl-2-methylsulfonylphenyl)-1H-pyrazole-5-carboxylate (2.1 g, 60%). Rf 0.17 (pure EtOAc). ES-MS: (M+H)+ 353.

Step 4. The above-prepared acid (2.1 g, 6.5 mmol) was dissolved in 50 mL dry DMF. To it were added tert-butylamine (1.4 mL, 13 mmol), DIEA (9.2 mL, 52 mmol) and PyBOP (13 g, 26 mmol) in order. The resulting mixture was stirred for overnight at room temperature. DMF was removed in vacuuo. The residue was taken into EtOAc and washed with brine (×2). The organic phase was dried, concentrated and subjected on flash column to isolate ethyl 3-methyl-1-(5-N-tert-butylaminocarbonyl-2- methylsulfonylphenyl)-1H-pyrazole-5-carboxylate (0.74 g, 30%). Rf 0.70 (pure EtOAc). ES-MS: (M+H)+ 408.

Step 5. To a solution of 2'-N-tert-butylaminosulfonyl-[1, 1']-biphenyl-4-ylamine (100 mg, 0.33 mmol) in 2 mL DCM was added trimethylaluminum (2.0M in hexane, 0.66 mL, 1.3 mmol) under argon at room temperature. After being stirred for 30 minutes, to the mixture was added the above-prepared ester (90 mg, 0.22 mmol) in 10 mL DCM. The resulting mixture was stirred overnight. The reaction was quenched using 10 mL saturated Rochelle's salt aq solution. The mixture was extracted using DCM (×3). The organic phases were combined, dried, rotovaped and subjected on flash chromatography column to give the coupled product in 62% yield (90 mg). Rf 0.10 (1:1 EtOAc:hexane). ES-MS: (M+H)+ 666.

Step 6. The above-prepared compound (20 mg) was placed in 5 mL TFA. It was stirred at 70° C. for 1 hour and subjected on prep HPLC to isolate the title compound (90%) after evaporation. ES-MS: (M+H)+ 554.

Example 124

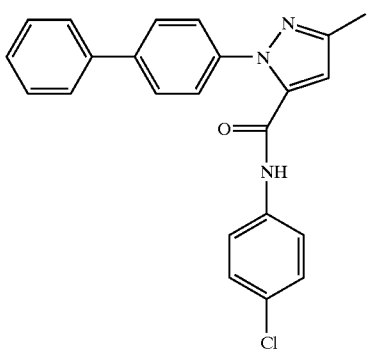

Step 1. To a solution of 4-biphenylboronic acid (1.0 g, 5.1 mmol) and ethyl 3-methylpyrazole-5-carboxylate (0.78 g, 5.1 mmol) in 25 mL dry DCM were added pyridine (1.2 mL, 15 mmol) and anhydrous powder of copper(II) acetate (1.84 g, 10 mmol). Some activated molecular sieve powder was added afterwards. The resulting slurry was refluxed for 2 days under argon. The mixture was diluted with DCM, filtered through celite. The blue filtrate was washed with water (×2), dried, concentrated, purified with flush column to yield ethyl 3-methyl-1-(4-phenylphenyl)-1H-pyrazole-5-carboxylate (26%), Rf 0.67 (1:2 EtOAc:hexane), ES-MS: (M+H)+ 307; and its regioisomer, ethyl 5-methyl-1-(4-phenylphenyl)-1H-pyrazole-3-carboxylate (31%), Rf 0.50 (1:2 EtOAc:hexane), ES-MS: (M+H)+ 307.

Step 2. To a stirred solution of 4-chloroaniline (24 mg, 0.18 mmol) in 1 mL DCM was added trimethylaluminum (2.0M, 0.43 mL, 0.86 mmol) at room temperature. After 30 minutes, to the mixture was added ethyl 3-methyl-1-(4-phenylphenyl)-1H-pyrazole-5-carboxylate (52 mg, 0.17 mmol) in 3 mL DCM. The resulting mixture was stirred for overnight. It was quenched using 5 mL saturated Rochelle's salt aq solution. The mixture was extracted using DCM (×3). The organic phases were combined, dried, concentrated and subjected on flash column to afford the title compound (46 mg, 70%). Rf 0.46 (1:1 EtOAc:hexane). ES-MS: (M+H)+ 388.

Example 125

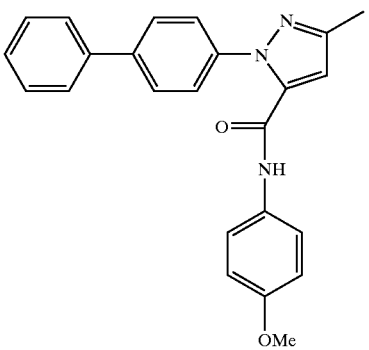

The title compound was prepared using the same methodology shown for Example 124, with 4-methoxyaniline substituted for 4-chloroaniline. ES-MS: (M+H)+ 384.

Example 126

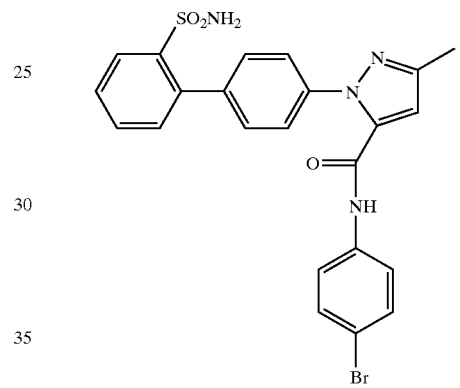

Step 1. 2'-N-tert-butylaminosulfonyl-[1,1']-biphenyl-4-ylamine (1.9 g, 6.2 mmol) was placed in 8 mL concentrate HCl. At 0° C. to this stirred mixture was added a cold solution of sodium nitrite (0.43 g, 6.2 mmol in 2 mL water) dropwise. After 30 minutes, to it was added a cold solution of SnCl$_2$.2H$_2$O (4.2 g, 18.4 mmol in 8 mL concentrate HCl). The mixture was stirred at 0° C. for 1 hour and the solid was collected with a Buchner funnel. The crude solid hydrazine was dried.

Step 2. The above-prepared crude hydrazine was dissolved in 20 mL acetic acid. To it was added 10 mL THF and ethyl 2-N-(methoxy)imino-4-oxopentanoate (0.93 g, 5.0 mmol). The mixture was refluxed for 3 hours. The solvent was removed in vacuuo. The residue was taken into EtOAc, washed with brine, dried, concentrated and purified with flash column to yield ethyl 3-methyl-1-(4-(2-aminosulfonylphenyl)-phenyl)-1H-pyrazole-5-carboxylate (0.95 g, 40%). Rf 0.51 (1:1 EtOAc:hexane). ES-MS: (M+H)+ 386.

Step 3. The above-prepared ethyl ester was dissolved in 20 mL methanol. To it were added LiOH.H$_2$O (0.31 g, 7.4 mol) and 10 mL water. The mixture was stirred for 3 hours, acidifed till pH 5 with acetic acid, and evaporated in vacuuo. The residue was soaked with acetonitrile and decanted for several times to extract out the organic product. The acetonitrile solutions were combined and evaporated in vacuuo to give yield 3-methyl-1-(4-(2-aminosulfonylphenyl)-phenyl)-1H-pyrazole-5-carboxylic acid (0.81 g, 92%). ES-MS: (M+H)+ 358. It was further purified using prep HPLC.

Step 4. The above-prepared acid (20 mg, 0.056 mmol) was dissolved in 1 mL dry DMF. To it were added 4-bromoaniline (10 mg, 0.056 mmol), DIEA (30 μL, 0.17 mmol) and PyBOP (58 mg, 0.12 mmol) in order. The reaction mixture was directly loaded on prep HPLC to yield the title compound in 45% yield. ES-MS: (M+H)$^+$ 511, 513 (Br pattern).

Example 127

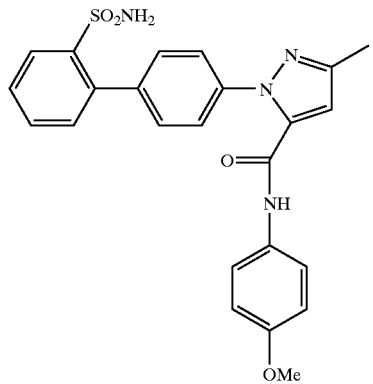

The title compound was prepared using the same methodology shown for Example 126, with 4-methoxyaniline substituted for 4-bromoaniline. ES-MS: (M+H)$^+$ 463.

Example 128

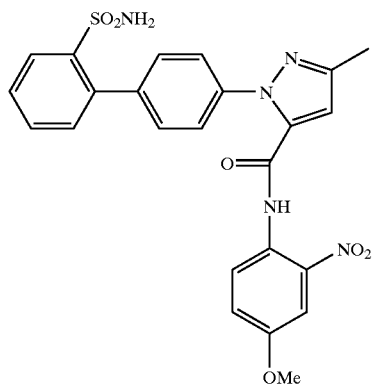

The title compound was prepared using the same methodology shown for Example 126, with 4-methoxy-2-nitroaniline substituted for 4-bromoaniline. ES-MS: (M+H)$^+$ 508.

Example 129

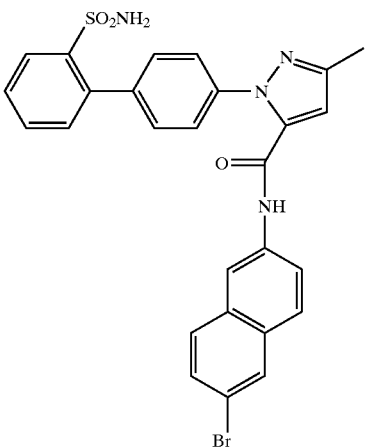

The title compound was prepared using the same methodology shown for Example 126, with 6-bromo-2-naphthylamine substituted for 4-bromoaniline. ES-MS: (M+H)$^+$ 562, 564 (Br pattern).

Example 130

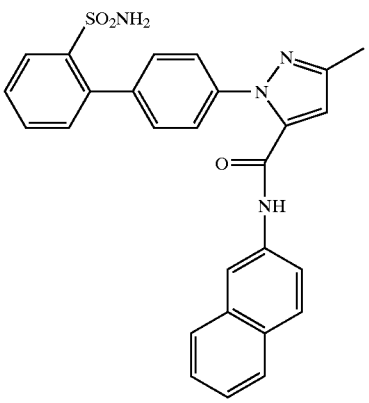

The title compound was prepared using the same methodology shown for Example 126, with 2-naphthylamine substituted for 4-bromoaniline. ES-MS: (M+H)$^+$ 483.

Example 131

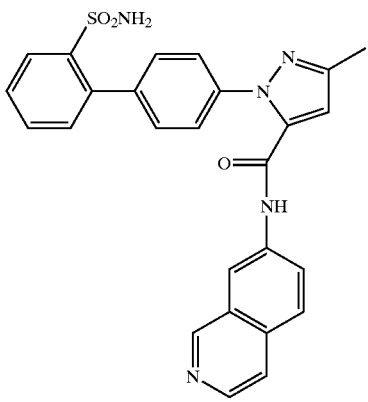

The title compound was prepared using the same methodology shown for Example 126, with 7-aminoisoquinoline substituted for 4-bromoaniline. ES-MS: (M+H)+ 484.

Example 132

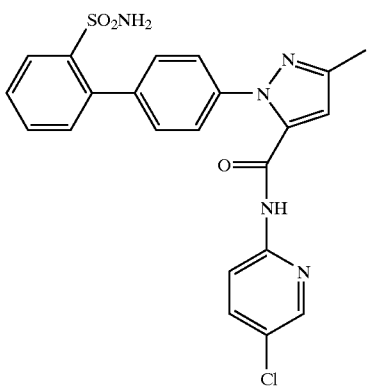

The title compound was prepared using the same methodology shown for Example 126, with 2-amino-5-chloropyridine substituted for 4-bromoaniline. ES-MS: (M+H)+ 468.

Example 133

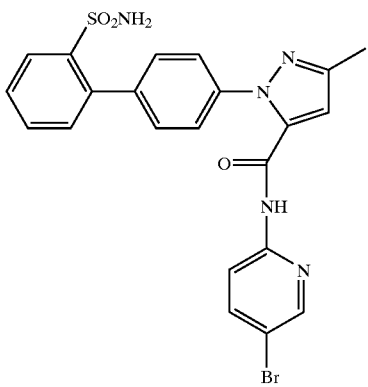

The title compound was prepared using the same methodology shown for Example 126, with 2-amino-5-bromopyridine substituted for 4-bromoaniline. ES-MS: (M+H)+ 512, 154 (Br pattern).

Example 134

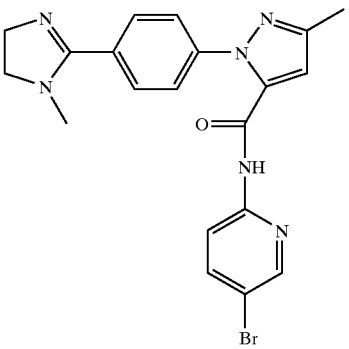

Step 1. A mixture of 4-cyanophenylhydrazine hydrochloride (5.7 g, 33 mmol), ethyl 2-N-(methoxy)imino-4-oxopentanoate (7.5 g, 40 mmol), 100 mL acetic acid and 50 mL THF was refluxed for 2 hours. The solvent was removed in vacuuo. The residue was taken into 500 mL EtOAc, which was washed with brine, dried and evaporated in vacuuo to afford ethyl 3-methyl-1-(4-cyanophenyl)-1H-pyrazole-5-carboxylate (10 g, 99%). ES-MS: (M+H)+ 256.

Step 2. The above-prepared ester (10 g) was dissolved in 100 mL THF. To it were added LiOH.H$_2$O (4.2 g, 100 mmol), 100 mL methanol and 50 mL water. The mixture was stirred for 1 hour. It was acidified to pH 1 with 1N HCl. It was evaporated to remove organic solvent. The residue was extracted with EtOAc (×4). The organic phases were combined, dried and evaporated to dryness to afford 3-methyl-1-(4-cyanophenyl)-1H-pyrazole-5-carboxylatic acid (95%). ES-MS: (M+H)+ 228.

Step 3. The above-prepared acid (1.4 g, 6.2 mmol) was dissolved in 20 mL pyridine. To it were added 2-amino-5-bromopyridine (2.2 g, 13 mmol) and DMAP (100 mg). At 0° C. to this mixture was added POCl$_3$ (2.3 mL, 25 mmol). The reaction was allowed for 1.5 hour and quenched with ice chips. After evaporation in vacuuo, the residue was taken into 300 mL EtOAc, which was washed with brine, dried, evaporated and purified with flash column to yield the coupling product (45%). Rf 0.52 (1:1 EtOAc:hexane). ES-MS: (M+H)+ 382, 384 (Br pattern).

Step 4. To a solution of the above-prepared nitrile (30 mg) in 10 mL anhydrous methanol at 0° C. was bubbled dry HCl gas via a long needle till saturation reached. The mixture was stirred for overnight. The solvent was removed in vacuuo. The dry residue was dissolved in 5 mL anhydrous methanol. To it was added 0.5 mL N-methylethylenediamine. The mixture was refluxed for 1 hour. After evaporation, the reaction mixture was subjected on prep HPLC to isolate the title compound (80% yield). ES-MS: (M+H)+ 439, 441 (Br pattern).

Example 135

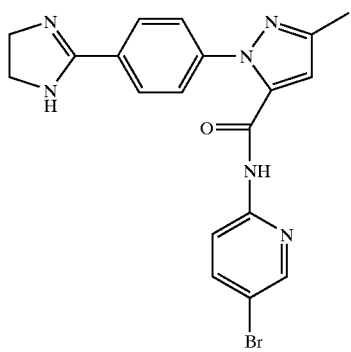

The title compound was prepared using the same methodology shown for Example 134, with ethylenediamine substituted for N-methylethylenediamine. ES-MS: (M+H)$^+$ 425, 427 (Br pattern).

Example 136

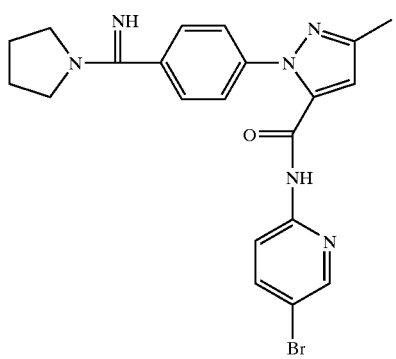

The title compound was prepared using the same methodology shown for Example 134, with pyrrolidine substituted for N-methylethylenediamine. ES-MS: (M+H)$^+$ 453, 455 (Br pattern).

Example 137

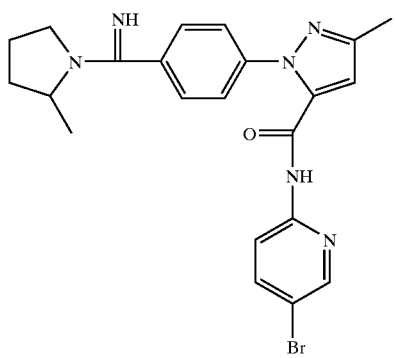

The title compound was prepared using the same methodology shown for Example 134, with 2-methylpyrrolidine substituted for N-methylethylenediamine. ES-MS: (M+H)$^+$ 467, 469 (Br pattern).

Example 138

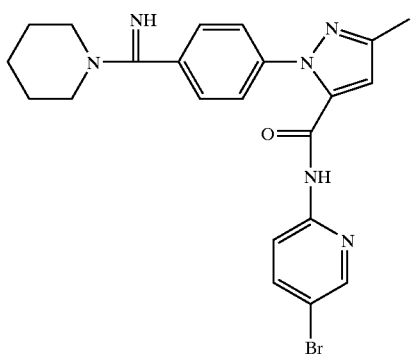

The title compound was prepared using the same methodology shown for Example 134, with piperidine substituted for N-methylethylenediamine. ES-MS: (M+H)$^+$ 467, 469 (Br pattern).

Example 139

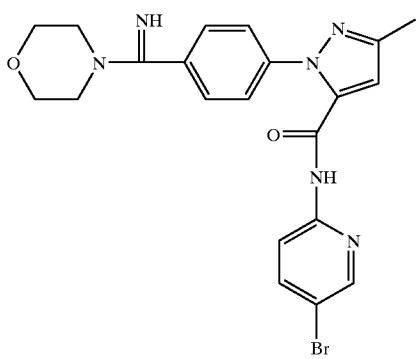

The title compound was prepared using the same methodology shown for Example 134, with morpholine substituted for N-methylethylenediamine. ES-MS: (M+H)$^+$ 469, 471 (Br pattern).

Example 140

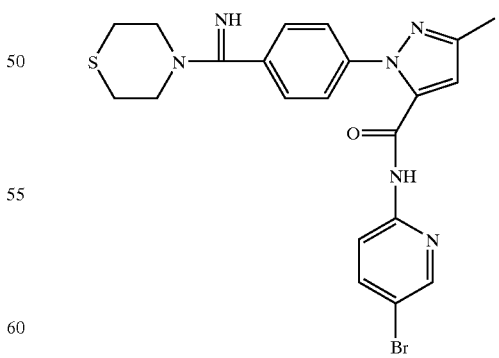

The title compound was prepared using the same methodology shown for Example 134, with thiomorpholine substituted for N-methylethylenediamine. ES-MS: (M+H)$^+$ 485, 487 (Br pattern).

Example 141

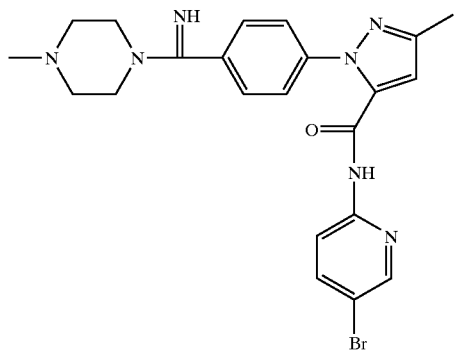

The title compound was prepared using the same methodology shown for Example 134, with N-methylpiperazine substituted for N-methylethylenediamine. ES-MS: (M+H)$^+$ 482, 484 (Br pattern).

Example 142

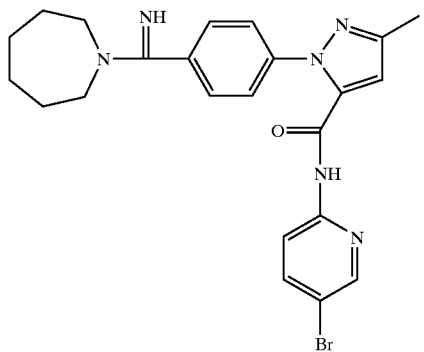

The title compound was prepared using the same methodology shown for Example 134, with hexamethyleneimine substituted for N-methylethylenediamine. ES-MS: (M+H)$^+$ 481, 483 (Br pattern).

Example 143

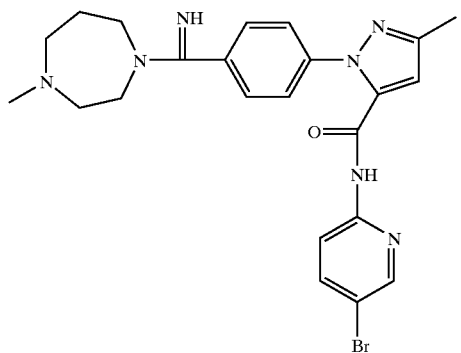

The title compound was prepared using the same methodology shown for Example 134, with 1-methylhomopiperazine substituted for N-methylethylenediamine. ES-MS: (M+H)$^+$ 496, 498 (Br pattern).

Example 144

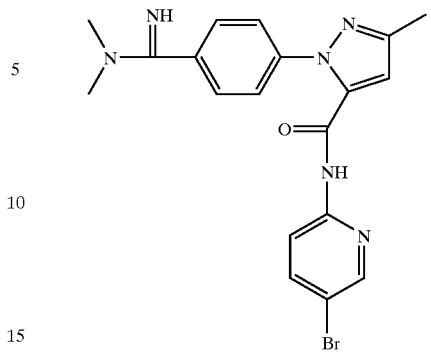

The title compound was prepared using the same methodology shown for Example 134, with dimethylamine (2M in THF) substituted for N-methylethylenediamine. ES-MS: (M+H)$^+$ 427, 429 (Br pattern).

Example 145

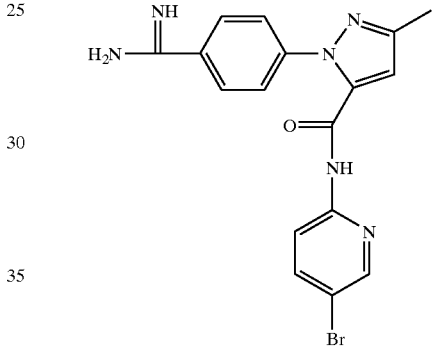

The title compound was prepared using the same methodology shown for Example 134, with ammonium acetate substituted for N-methylethylenediamine. ES-MS: (M+H)$^+$ 399, 401 (Br pattern).

Example 146

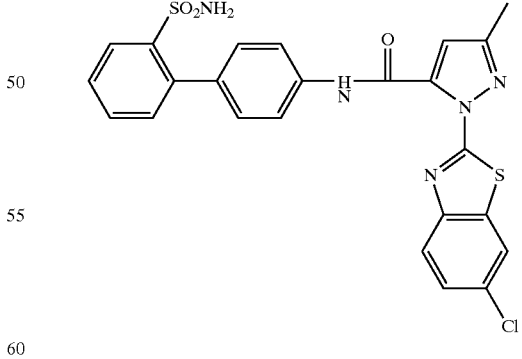

2'-N-tert-butylaminosulfonyl-[1,1']-biphenyl-4-ylamine (50 mg, 0.16 mmol) was dissolved in 1 mL dry DCM. To this stirred solution was added Me$_3$Al (2.0M, 0.4 mL, 0.8 mmol). The mixture was stirred for 30 minutes. To it was added a solution of commercial ethyl 1-(6-chloro-1,3-benzothiazol-2-yl)-3-methyl-1H-pyrazole-5-carboxylate (50 mg, 0.16 mmol) in 2 mL DCM. The resulting mixture was stirred for 4 hours. After quenched with saturated Rochelle's salt aq solution, this reaction was diluted with DCM. The mixture was washed with brine (×2), dried, evaporated in vacuuo and exposed to 3 mL TFA. After stirring overnight, the reaction mixture was evaporated and purified with reverse-phase prep HPLC to afford the title compound in 55% yield. ES-MS: (M+H)$^+$ 524 (Cl pattern).

BIOLOGICAL ACTIVITY EXAMPLES

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 μM. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 μM in the prothrombinase assay, preferably less than 200 nM, and more preferred compounds have an $IC_{50}$ of about 10 nM or less in the prothrombinase assay. The compounds of the present invention desirably have an $IC_{50}$ of greater than 1.0 μM in the thrombin assay, preferably greater than 10.0 μM, and more preferred compounds have an $IC_{50}$ of greater than 100.0 μM in the thrombin assay.

Amidolytic Assays for Determining Protease Inhibition Activity

The factor Xa and thrombin assays are performed at room temperature, in 0.02 M Tris HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 25, 427–436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 μM) in 20 mM TrisHCl buffer, pH 7.5, containing 0.15 M NaCl, 5 mM $CaCl_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 μg/kg+2.57 μg/kg/min). Compounds have no significant effects on hematological parameters as compared to saline controls. All measurements are an average of all samples after steady state administration of vehicle or (D)-Arg-Gly-Arg-thiazole. Values are expressed as mean±SD.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the formula (I):

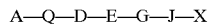

wherein:

A is phenyl, which is independently substituted with 0–2 $R^1$ substituents;

$R^1$ is selected from halo, —CN, —C(=O)—N($R^2$, $R^3$), —$NO_2$, —$SO_2$N($R^2$, $R^3$), —$SO_2R^2$, —$(CH_2)_m NR^2 R^3$, —$(CH_2)_m$—C(=$NR^3$)—$R^2$, —$(CH_2)_m$—C(=$NR^2$)—N($R^2$,$R^3$), —$(CH_2)_m$—N($R^2$)—C(=$NR^2$)—N($R^2$,$R^3$), —$(CH_2)_m NR^2$—$C_{3-6}$heterocyclics, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CF$_3$, —OR$^2$, and a 5–6 membered heterocyclic system having from 1–4 heteroatoms each independently a member selected from the group consisting of N, O and S, wherein from 1–4 hydrogen atoms on the heterocyclic system may be independently replaced with a member selected from the group consisting of halo, $C_{1-4}$alkyl-CN, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl and —NO$_2$;

each of R$^2$ and R$^3$ is independently a member selected from the group consisting of —H, —OR$^a$, —N(—R$^a$, —R$^b$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl-CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN and —NO$_2$;

or R$^2$ and R$^3$ are taken together to form a 3–8 membered cycloalkyl or a heterocyclic ring system, wherein the heterocyclic ring system may have from 3 to 10 ring atoms, with 1 to 2 rings being in the ring system and having from 1–4 heteroatoms each independently a member selected from the group consisting of N, O and S, wherein from 1–4 hydrogen atoms on the heterocyclic ring system may be independently replaced with a member selected from the group consisting of halo, $C_{1-4}$alkyl-CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

each of R$^a$ and R$^b$ is independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl can be taken together with a nitrogen atom to which they are attached to form a 3–8 heterocyclic ring system having 1–4 heteroatoms each independently a member selected from the group consisting of N, O and S, wherein from 1–4 hydrogen atoms on the heterocyclic ring system may be independently replaced with a member selected from the group consisting of halo, —CN, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

m is an integer of 0–2;

Q is a direct link;

D is a monocyclic heterocyclic ring system having from 5 to 6 ring atoms, wherein 1–3 ring atoms of the ring system are N, and wherein the ring system may be substituted from 0–2 R$^{1a}$ substituents;

each R$^{1a}$ is independently a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN, —NO$_2$, (CH$_2$)$_n$NR$^{2a}$R$^{3a}$, SO$_2$NR$^{2a}$R$^{3a}$, SO$_2$R$^{2a}$, CF$_3$, OR$^{2a}$, and a 5–6 membered aromatic heterocycl system having from 1–4 heteroatoms each independently a member selected from the group consisting of N, O and S, wherein from 1–4 hydrogen atoms on the aromatic heterocyclic system may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

each of R$^{2a}$ and R$^{3a}$ is independently a member selected from the group consisting of —H, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, C$_{0-4}$alkylphenyl and C$_{0-4}$alkylnaphthyl, wherein from 1–4 hydrogen atoms on the ring atoms of the phenyl and naphthyl moieties may be independently replaced with a member selected from the group consisting of halo, C$_{1-4}$alkyl, C$_{2-6}$alkenyl, C$_{2-6}$alkynyl, C$_{3-8}$cycloalkyl, C$_{0-4}$alkylC$_{3-8}$cycloalkyl, —CN and —NO$_2$;

n is an integer of 0–2;

E is —N(—R$^5$)—C(=O)—;

R$^5$ is a member selected from the group consisting of H, —C$_{1-6}$alkyl, —C$_{1-6}$alkyloxy, —C$_{2-6}$alkenyl, —C$_{2-6}$alkynyl, —C$_{3-8}$cycloalkyl, —C$_{0-6}$alkylC$_{3-8}$cycloalkyl, —C$_{1-4}$alkyl-C(=O)—OH, —C$_{0-6}$alkyl-(carbocyclic aryl), —C$_{0-4}$alkyl-(monocyclic heteroaryl) and —C$_{1-4}$alkyl-C(=O)—O—C$_{1-4}$alkyl, wherein from 0–4 hydrogen atoms on the ring atoms of the carbocyclic aryl moiety and the monocyclic heteroaryl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —S(=O)$_2$—OH, —CN, —CF$_3$ and —NO$_2$;

G is a pyrazolyl substituted with 0–2 R$^{1b}$ groups;

each R$^{1b}$ is independently a member selected from the group consisting of halo, —C$_{1-6}$alkyl, —C$_{2-6}$alkenyl, —C$_{2-6}$alkynyl, —C$_{3-8}$cycloalkyl, —C$_{0-6}$alkylC$_{3-8}$cycloalkyl, —C$_{1-4}$alkyl-C(=O)—OH, —CN, —COOR$^{2b}$, —CONR$^{2b}$R$^{3b}$, —NO$_2$, —S(=O)$_2$—OH, —N(—R$^{2b}$, —R$^{3b}$), —C(=O)—N(—R$^{2b}$, —R$^{3b}$), —S(=O)$_2$—N(—R$^{2b}$, —R$^{3b}$), —S(=O)$_2$—R$^{2b}$, —CF$_3$, —O—R$^{2b}$, —O—CH$_2$—CH$_2$—O—R$^{2b}$, —O—CH$_2$—C(=O)—O—R$^{2b}$, —N(—R$^{2b}$)CH$_2$—CH$_2$—O—R$^{2b}$, —N(—CH$_2$—CH$_2$—O—R$^{2b}$)$_2$, —N(—R$^{2b}$)—C(=O)—R$^{3b}$, —N(—R$^{2b}$)—S(=O)$_2$—R$^{3b}$, and a 5–6 membered heterocyclic ring having 1–4 heteroatoms each independently a member selected from the group consisting of N, O and S, wherein said heterocyclic ring is substituted with 0–4 R$^{1b'}$ groups;

alternatively, two R$^{1b}$ may be present on adjacent ring atoms of G and combine to form a benzene ring substituted with 0–4 R$^{1b'}$ groups or a 5–6 membered aromatic or non-aromatic heterocyclic ring having 1–3 heteroatoms each independently a member selected from the group consisting of N, O and S, and substituted with 0–4 R$^{1b'}$ groups;

each of R$^{2b}$ and R$^{3b}$ is independently a member selected from the group consisting of —H, —C$_{1-6}$alkyl, —C$_{1-6}$alkyloxy, —C$_{2-6}$alkenyl, —C$_{2-6}$alkynyl, —C$_{3-8}$cycloalkyl, —C$_{0-6}$alkylC$_{3-8}$cycloalkyl and —C$_{0-6}$alkyl-(carbocyclic aryl), wherein from 0–4 hydrogen atoms on the ring atoms of the carbocyclic aryl moiety may be independently replaced with a member selected from the group consisting of halo, —C$_{1-4}$alkyl, —C$_{2-6}$alkenyl, —C$_{2-6}$alkynyl, —C$_{3-8}$cycloalky —C$_{0-4}$alkylC$_{3-8}$cycloalkyl, —S(=O)$_2$—OH, —CN, —CF$_3$ and —NO$_2$;

each R$^{1b'}$ is independently a member selected from the group consisting of halo, —C$_{1-6}$alkyl, —C$_{2-6}$alkenyl, —C$_{2-6}$alkynyl, —C$_{3-8}$cycloalkyl, —C$_{0-6}$alkylC$_{3-8}$cycloalkyl, —C$_{1-4}$alkyl-C(=O)—OH, —CN, —NO$_2$, —S(=O)$_2$—OH, —N(—R$^{2b'}$, —R$^{3b'}$), —C(=O)—N (—R$^{2b'}$, —R$^{3b'}$), —S(=O)$_2$—N(—R$^{2b'}$, —R$^{3b'}$), —S(=O)$_2$—R$^{2b'}$, —CF$_3$, —O—R$^{2b'}$, —O—CH$_2$—CH$_2$—R$^{2b'}$, —O—CH$_2$—C(=O)—O—R$^{2b'}$, —N(—R$^{2b'}$)—CH$_2$—CH$_2$—O—R$^{2b'}$, —N(—CH$_2$—CH$_2$—

O—$R^{2b'}$)$_2$, —N(—$R^{2b'}$)—C(=O)—$R^{3b'}$ and —N(—$R^{2b'}$)—S(=O)$_2$—$R^{3b'}$;

each of $R^{2b'}$ and $R^{3b'}$ is independently a member selected from the group consisting of —H, —$C_{1-6}$alkyl, —$C_{1-6}$alkoxy, —$C_{2-6}$alkenyl, —$C_{2-6}$alkynyl, —$C_{3-8}$cycloalkyl, —$C_{0-6}$alkyl$C_{3-8}$cycloalkyl and —$C_{0-6}$alkyl-(carbocyclic aryl), wherein from 0–4 hydrogen atoms on the ring atoms of the carbocyclic aryl moiety may be independently replaced with a member selected from the group consisting of halo, —$C_{1-4}$alkyl, —$C_{2-6}$alkenyl, —$C_{2-6}$alkynyl, —$C_{3-8}$cycloakyl, —$C_{0-4}$alkyl$C_{3-8}$cycloalkyl, —S(=O)$_2$—OH, —CN, —$CF_3$ and —$NO_2$;

J is a direct link;

X is naphthyl, which is substituted with 0–3 $R^{1c}$ groups;

each $R^{1c}$ is independently a member selected from the group consisting of halo, —$CF_3$, —$C_{1-6}$alkyl, —$C_{2-6}$alkenyl, —$C_{2-6}$alkynyl, —$C_{3-8}$cycloalkyl, —$C_{0-6}$alkyl$C_{3-8}$cycloalkyl, —$C_{1-4}$alkyl-C(=O)—OH, —$CF_3$, —CN, —$NO_2$, —(CH$_2$)$_z$—N(—$R^{2c}$, —$R^{3c}$), —C(=O)—N(—$R^{2c}$, —$R^{3c}$), —C(=NH)—N(—$R^{2c}$, —$R^{3c}$), —C(=NMe)—N(—$R^{2c}$, —$R^{3c}$), —S(=O)$_2$—N(—$R^{2c}$, —$R^{3c}$), —S(=O)$_2$—$R^{2c}$, —S(=O)$_2$—OH, —$CF_3$, —O—$R^{2c}$, —O(—CH$_2$)$_z$—O—$R^{2c}$, —O(—CH$_2$)$_z$—C(=O)—O—$R^{2c}$, —N(—$R^{2c}$), —O(—CH$_2$)$_z$—O—$R^{2c}$, —N[(—CH$_2$)$_z$—OR$^{2c}$]$_2$, —(CH$_2$)$_z$—N(—$R^{2c}$)—C(=O)—$R^{3c}$, —(CH$_2$)$_z$—N(—$R^{2c}$)—S(=O)$_2$—$R^{3c}$, and a 5–6 membered heterocyclic ring having 1–4 heteroatoms each independently a member selected from the group consisting of N, O and S;

z is an integer of 0–4;

each of $R^{2c}$ and $R^{3c}$ is independently a member selected from the group consisting of —H, —$C_{1-6}$alkyl, —$C_{1-6}$alkyloxy, —$C_{2-6}$alkenyl, —$C_{2-6}$alkynyl, —$C_{3-8}$cycloalkyl, —$C_{0-6}$alkyl$C_{3-8}$cycloalkyl and —$C_{0-6}$alkyl-(carbocyclic aryl), wherein from 0–4 hydrogen atoms on the ring atoms of the carbocyclic aryl moiety may be independently replaced with a member selected from the group consisting of halo, —$C_{1-4}$alkyl, —$C_{2-6}$alkenyl, —$C_{2-6}$alkynyl, —$C_{3-8}$cycloalky —$C_{0-4}$alkyl$C_{3-8}$cycloalkyl, —S(=O)$_2$—OH, —CN, —$CF_3$ and —$NO_2$;

or all pharmaceutically acceptable diastereoisomers, enantiomers or mixtures thereof, salts, hydrates or solvates thereof.

2. The compound of claim 1, wherein:

A is phenyl, which is substituted with 0–2 $R^1$ groups;

each $R^1$ is independently a member selected from the group consisting of halo, —$C_{1-4}$alkyl, —CN, —$NO_2$, —(CH$_2$)$_m$—N(—$R^2$, —$R^3$), —C(=O)—N(—$R^2$, —$R^3$), —S(=O)$_2$—N(—$R^2$, —$R^3$), —S(=O)$_2$—$R^2$, —(CH$_2$)$_m$—C(=NR$^3$)—$R^2$, —(CH$_2$)$_m$—C(=NR$^2$)—N(R$^2$, R$^3$), —(CH$_2$)$_m$—N(R$^2$)—C(=NR$^2$)—N(R$^2$, R$^3$), —$CF_3$, —(CH$_2$)$_m$—O—$R^2$ and a 5–6 membered aromatic heterocyclic ring having 1–4 heteroatoms each independently a member selected from the group consisting of N, O and S;

each of $R^2$ and $R^3$ is independently a member selected from the group consisting of —H and —$C_{1-4}$alkyl;

or $R^2$ and $R^3$ are taken together to form a 3–8 membered cycloalkyl or a heterocyclic ring system, wherein the heterocyclic ring system may have from 3 to 10 ring atoms, with 1 to 2 rings being in the ring system and having from 1–4 heteroatoms each independently a member selected from the group consisting of N, O and S, wherein from 1–4 hydrogen atoms on the heterocyclic ring system may be independently replaced with a member selected from the group consisting of halo, $C_1$-$C_4$-alkyl-CN, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0–2;

Q is a direct link;

D is a 6 membered aromatic heterocyclic ring system, wherein the heterocyclic ring system has 1–2 N heteroatoms, substituted with 0–2 $R^{1a}$ groups;

each $R^{1a}$ is independently a member selected from the group consisting of halo, —$C_{1-4}$alkyl, —CN, —$NO_2$, —(CH$_2$)$_n$—N(—$R^{2a}$, —$R^{3a}$), —S(=O)$_2$—N(R$^{2a}$, —$R^{3a}$), —S(=O)$_2$—$R^{2a}$, —$CF_3$, —(CH$_2$)$_n$—OR$^{2a}$, —C(=O)—O—$R^{2a}$, —C(=O)—N(—$R^{2a}$, —$R^{3a}$) and a 5–6 membered aromatic heterocyclic ring having 1–4 heteroatoms each independently a member selected from the group consisting of N, O and S;

n is an integer of 0–2;

each of $R^{2a}$ and $R^{3a}$ is independently a member selected from the group consisting of —H, —$CF_3$ and —$C_{1-4}$alkyl;

E is —N(—$R^5$)—C(=O)—;

$R^5$ is a member selected from the group consisting of H, —$C_{1-4}$alkyl, —$C_{2-6}$alkenyl, —$C_{2-6}$alkynyl, —$C_{3-8}$cycloalkyl and —$C_{0-4}$alkyl$C_{3-8}$cycloalkyl;

G is a pyrazolyl substituted with 0–2 $R^{1b}$ groups;

each $R^{1b}$ is independently a member selected from the group consisting of halo, —$C_{1-4}$alkyl, —CN, —$NO_2$, —N(R$^{2b}$, R$^{3b}$), —C(=O)—N(—$R^{2b}$, —$R^{3b}$), —S(=O)$_2$—N(—$R^{2b}$, —$R^{3b}$), —S(=O)$_2$—$R^{2b}$, —$CF_3$, —O—$R^{2b}$, —O—CH$_2$—CH$_2$—O—$R^{2b}$, —O—CH$_2$—C(=O)—O—$R^{2b}$, —N(—$R^{2b}$)—CH$_2$—CH$_2$—O—$R^{2b}$, —N(—CH$_2$—CH$_2$—O—$R^{2b}$)$_2$, —N(—$R^{2b}$)—C(=O)—$R^{3b}$, —N(—$R^{2b}$)—S(=O)$_2$—$R^{3b}$ and a 5–6 membered heterocyclic ring having 1–4 heteroatoms each independently a member selected from the group consisting of N, O and S;

alternatively, two $R^{1b}$ may be present on adjacent ring atoms of G and combine to form a benzene ring substituted with 0–4 $R^{1b'}$ groups or a 5–6 membered aromatic or non-aromatic heterocyclic ring having 1–3 heteroatoms each independently a member selected from the group consisting of N, O and S substituted with 0–4 $R^{1b'}$ groups; each of $R^{2b}$ and $R^{3b}$ is independently a member selected from the group consisting of —H, —$CF_3$, —$C_{1-4}$alkyl and —$C_{1-4}$alkyl-(carbocyclic aryl);

each $R^{1b'}$ is independently a member selected from the group consisting of halo, —$C_{1-4}$alkyl, —CN, —$NO_2$, —N(—$R^{2b'}$, —$R^{3b'}$), —C(=O)—N(—$R^{2b'}$, R$^{3b'}$), —S(=O)$_2$—N(—$R^{2b'}$, —$R^{3b'}$), —S(=O)$_2$—$R^{2b'}$, —$CF_3$, —O—$R^{2b'}$, —O—CH$_2$—CH$_2$—O—$R^{2b'}$, —O—CH$_2$—C(=O)—O—$R^{2b'}$, —N(—$R^{2b'}$)—CH$_2$—CH$_2$—O—$R^{2b'}$, —N(—CH$_2$—CH$_2$—O—$R^{2b'}$)$_2$, —N(—$R^{2b'}$)—C(=O)—$R^{3b'}$ and —N(—$R^{2b'}$)—S(=O)$_2$R$^{3b'}$;

each of $R^{2b'}$ and $R^{3b'}$ is independently a member selected from the group consisting of —H, —$C_{1-4}$alkyl and —$C_{1-4}$alkyl-(carbocyclic aryl);

J is a direct link;

X is naphthyl, which is substituted with 0–3 $R^{1c}$ groups;

each $R^{1c}$ is independently a member selected from the group consisting of halo, —$C_{1-4}$alkyl, —CN, —$NO_2$, —(CH$_2$), —N(—R$^{2c}$, —R$^{3c}$), —C(=O)—N(R$^{2c}$, R$^{3c}$), C(=NH)—N(—R$^{2c}$, —R$^{3c}$), —C(=NMe)—N(—R$^{2c}$, —R$^{3c}$), —S(=O)$_2$—N(—R$^{2c}$, R$^{3c}$), —S(=O)$_2$—R$^{2c}$, —S(=O)$_2$—O$^-$, —CF$_3$, —O—R$^{2c}$, —O—CH$_2$—CH$_2$—O—R$^{2c}$, —O—CH$_2$—C(=O)—O—R$^{2c}$, —N(—R$^{2c}$)—CH$_2$—CH$_2$—O—R$^{2c}$, —N(—CH$_2$—CH$_2$—O—R$^{2c}$)$_2$, —(—CH$_2$)$_z$—N(—R$^{2c}$)—C(=O)R$^{3c}$, —(CH$_2$)$_z$—N(—R$^{2c}$)—S(=O)$_2$R$^{3c}$, and a 5–6 membered heterocyclic ring having 1–4 heteroatoms each independently a member selected from the group consisting of N, O and S;

z is an integer of 0–2;

each of R$^{2c}$ and R$^{3c}$ is independently a member selected from the group consisting of —H, —C$_{1-4}$alkyl and —C$_{1-4}$alkyl-(carbocyclic aryl);

or all pharmaceutically acceptable diastereoisomers, enantiomers or mixtures thereof, salts, hydrates or solvates thereof.

3. The compound of claim 1, wherein:

A is a member selected from the group consisting of:

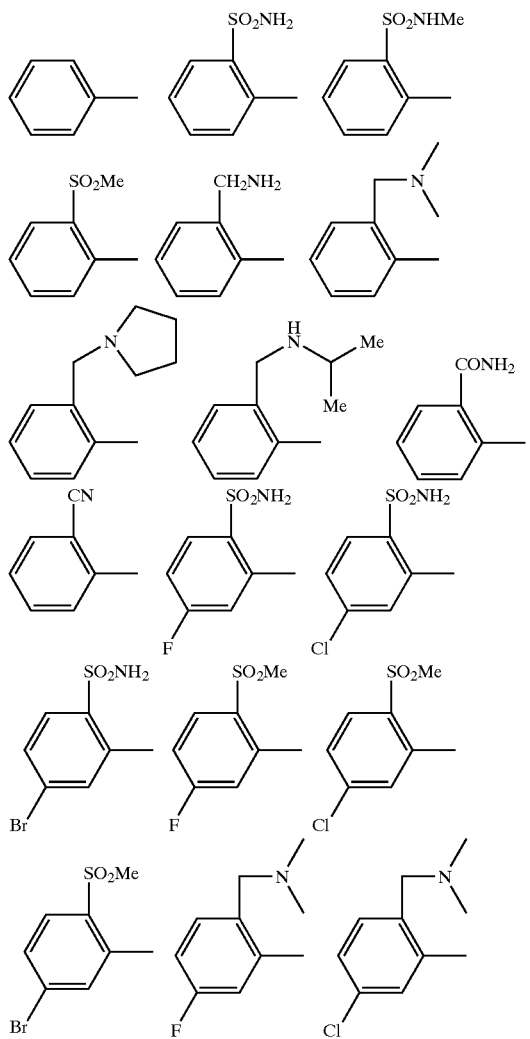

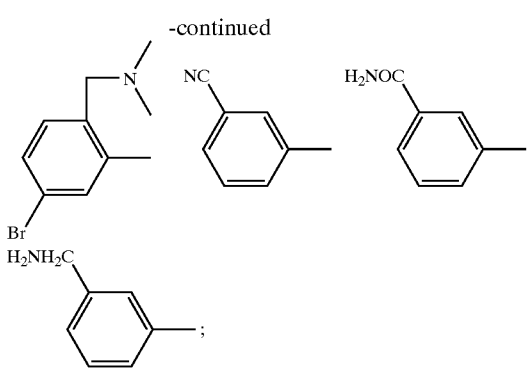

Q is a direct link;
D is a member selected from the group consisting of:

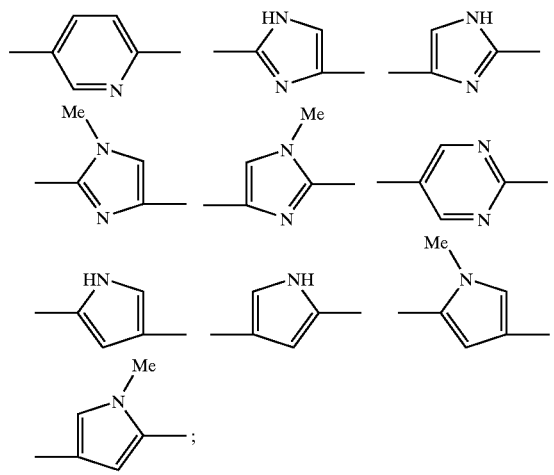

E is —NH—C(=O)—;
G is a member selected from the group consisting of:

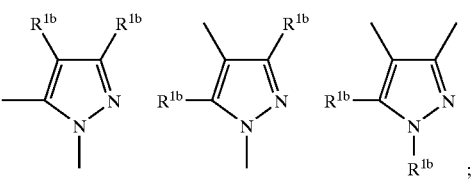

each R$^{1b}$ is independently a member selected from the group consisting of —H, -Me, —CF$_3$, —F, —Cl, —Br, —SO$_2$Me, —CN, —CONH$_2$, —CONMe$_2$, —NH$_2$, —NO$_2$, —NHCOMe, —NHSO$_2$Me, —CH$_2$NH$_2$ and —CO$_2$H;
J is a direct link;
X is a member selected from the group consisting of:

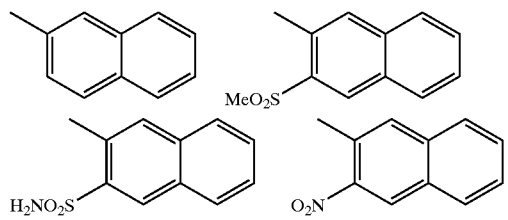

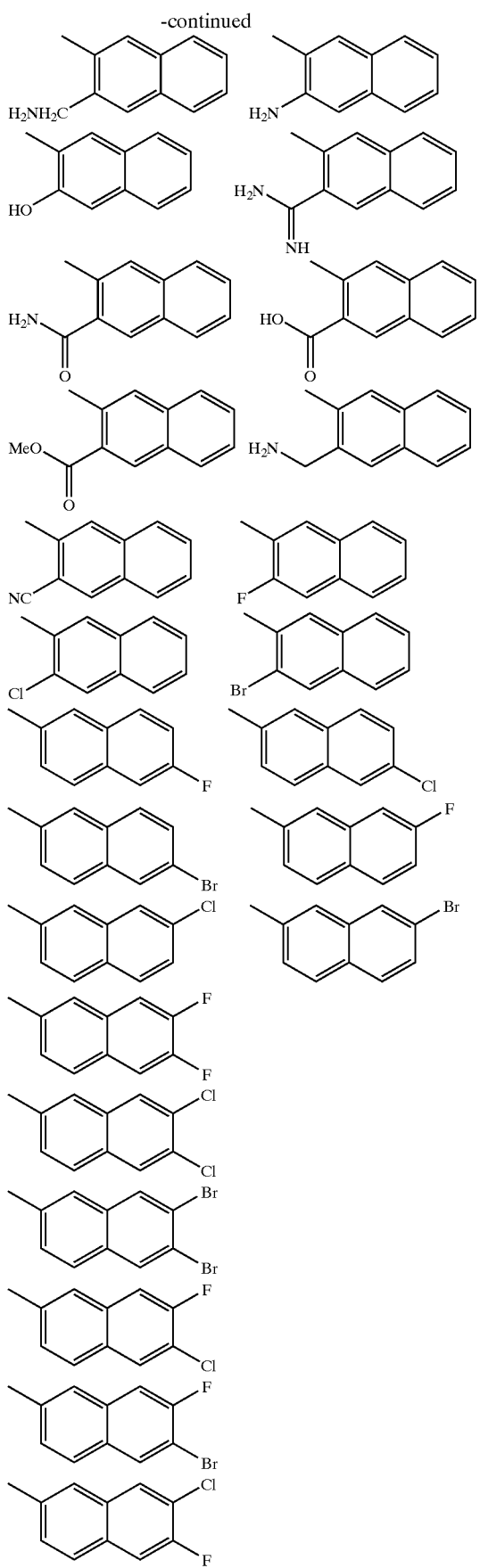
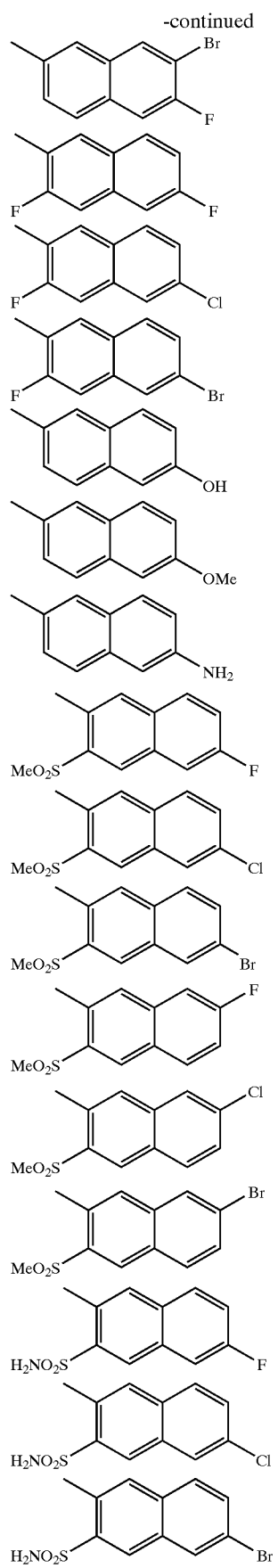

-continued
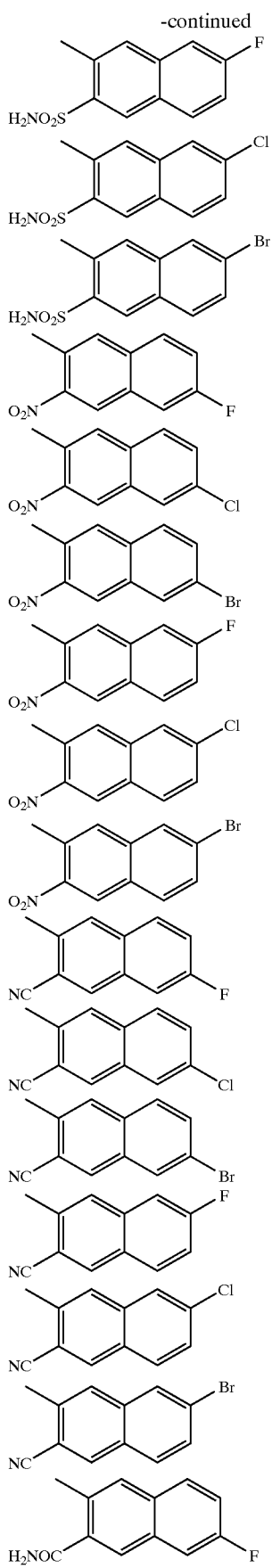
-continued
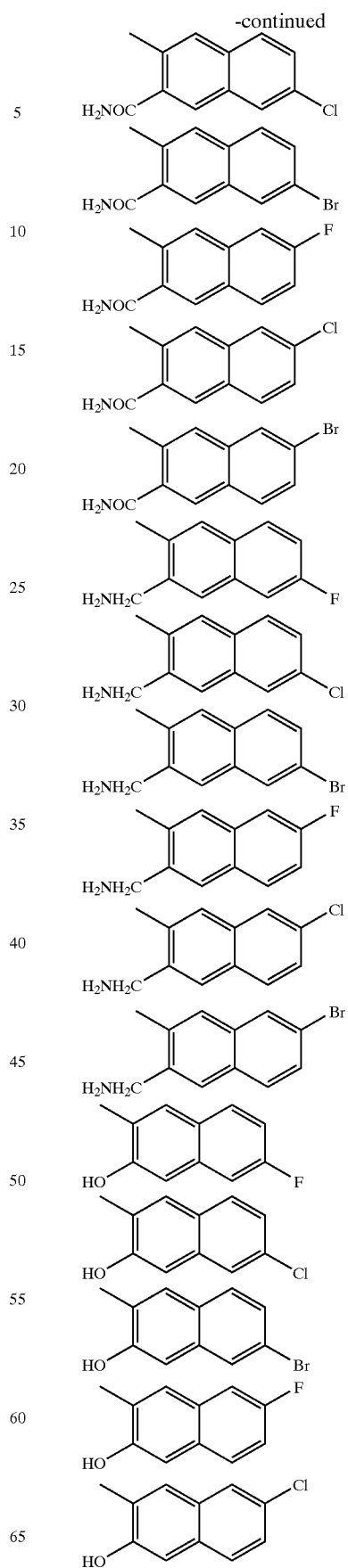

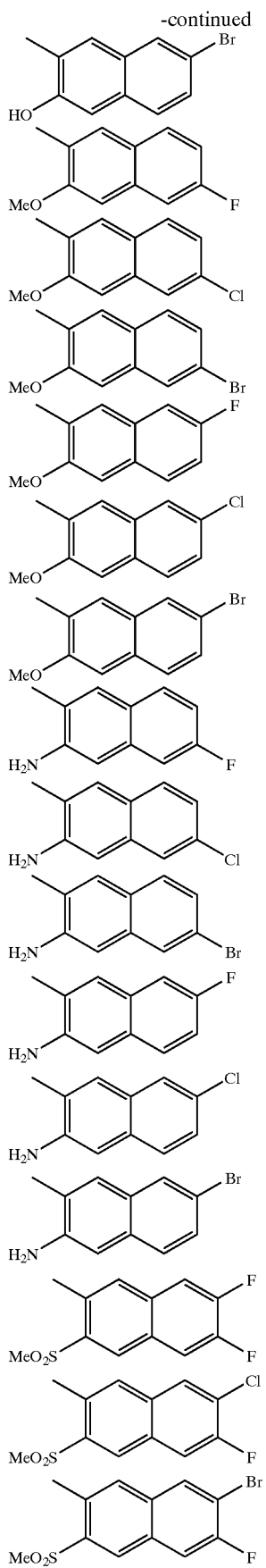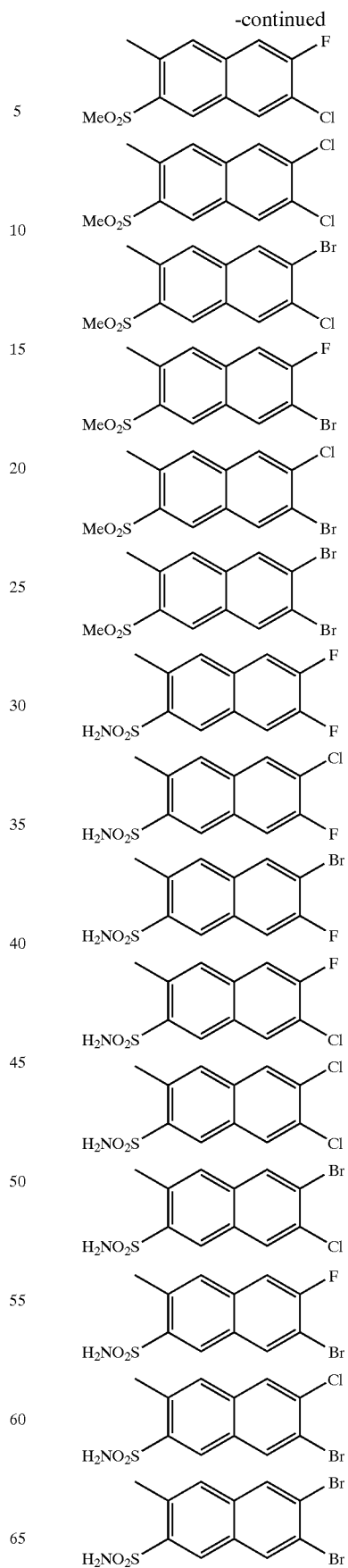

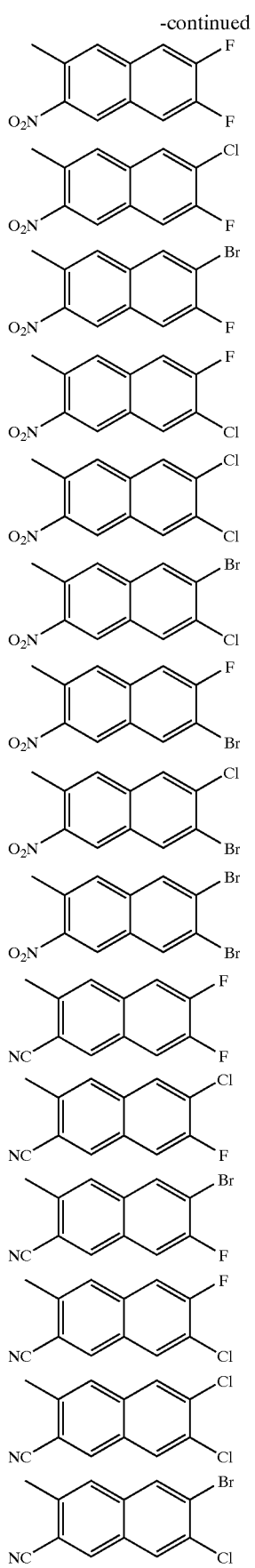
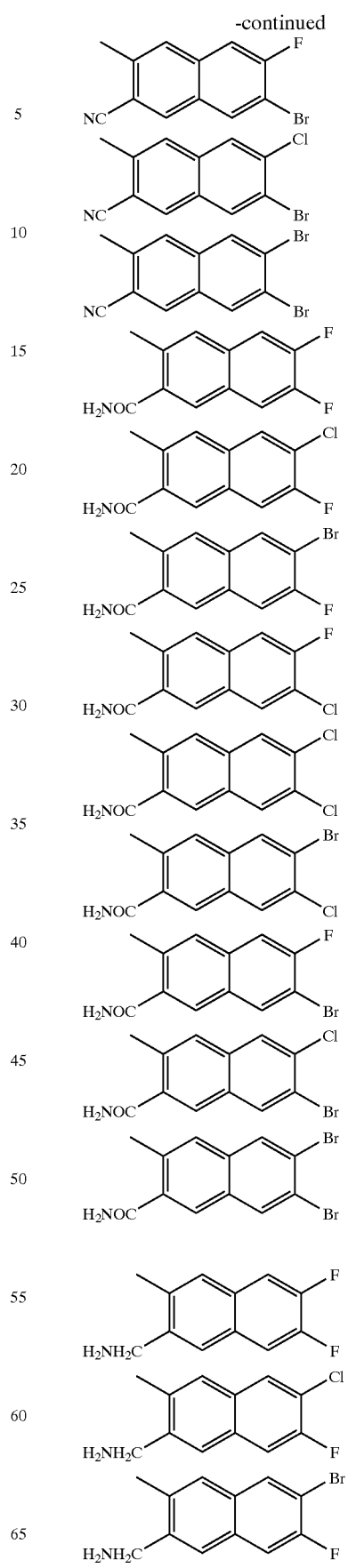

-continued

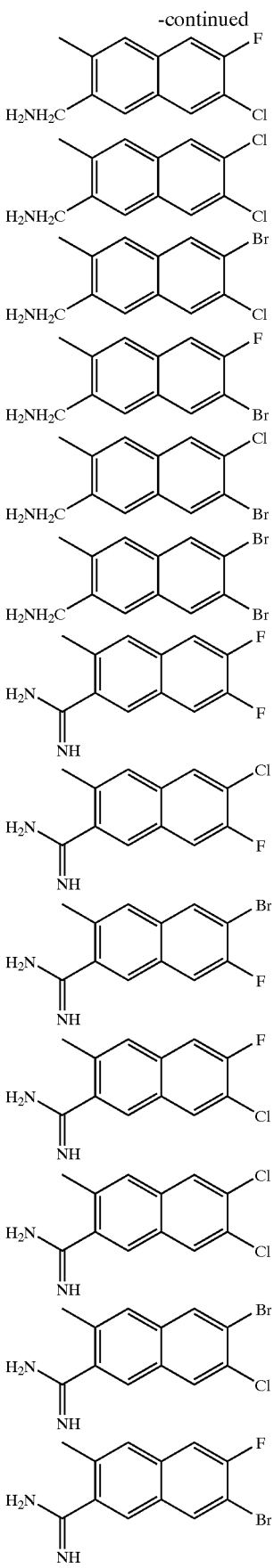

-continued

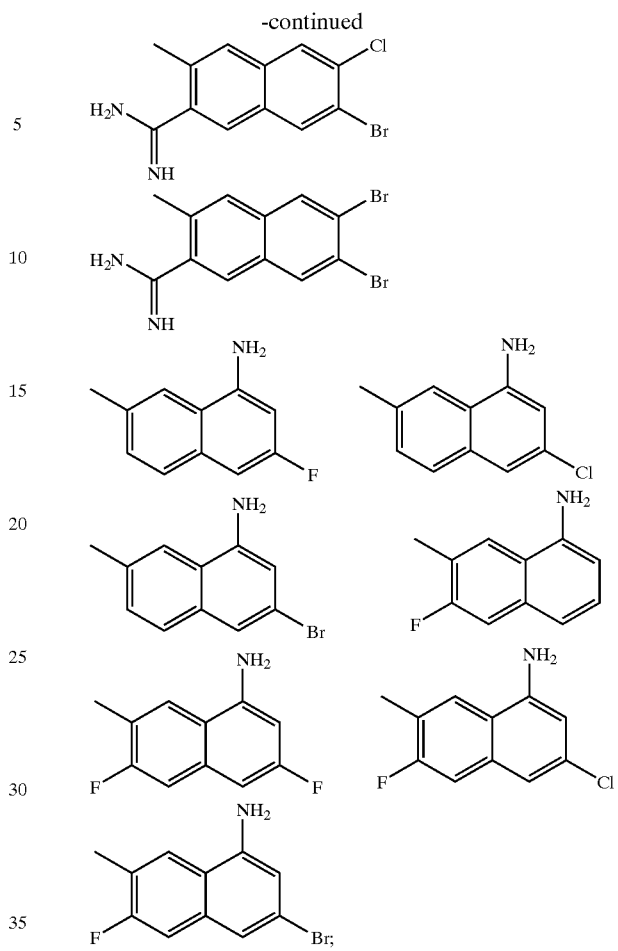

or all pharmaceutically acceptable diastereoisomers, enantiomers or mixtures thereof, salts, hydrates or solvates thereof.

4. The compound of claim 1, wherein:

A is phenyl, which is substituted with 0–2 $R^1$ groups;

each $R^1$ is independently a member selected from the group consisting of —S(=O)$_2$—N(—$R^2$, —$R^3$), —S(=O)$_2$—$R^2$, —CH$_2$N(—$R^2$, —$R^3$), —CN and halo;

each of $R^2$ and $R^3$ is independently a member selected from the group consisting of —H and —C$_{1-4}$alkyl;

Q is a direct link;

D is a member selected from the group consisting of pyridinyl, pyrimidinyl, pyrazinyl and pyridazinyl, each substituted with 0–1 $R^{1a}$ groups;

$R^{1a}$ is a member selected from the group consisting of —H and halo;

E is —NH—C(=O)—;

G is pyrazole, substituted with 0–2 $R^{1b}$ groups;

each $R^{1b}$ is independently a member selected from the group consisting of -Me, —Et, —CF$_3$, —C(=O)—NH$_2$, —NH$_2$, —NH—C(=O)-Me, —NH—S(=O)$_2$-Me, —SMe, —S(=O)$_2$-Me and halo;

alternatively, when two $R^{1b}$ groups may be present on adjacent ring atoms of G and combine to form a benzene ring;

J is a direct link;

X is naphthyl, which is substituted with 0–3 $R^{1c}$ groups;

each $R^{1c}$ is independently a member selected from the group consisting of —H, halo, -Me, —CF$_3$, —OH, —OMe, —NH$_2$, —CN, —NO$_2$, —CH$_2$—R$^{2c}$, —C(=O)—N(—R$^{2c}$, —R$^{3c}$), —S(=O)$_2$—R$^{2c}$, —S(=O)$_2$—N(—R$^{2c}$, —R$^{3c}$), —S(=O)$_2$—OH, —C(=NH)—N(—R$^{2c}$, —R$^{3c}$), 2-imidazolin-2-yl and 1-methyl-2-imidazolin-2-yl;

each of $R^{2c}$ and $R^{3c}$ is independently a member selected from the group consisting of —H, —OH, —NH$_2$ and —C$_{1-4}$alkyl;

or all pharmaceutically acceptable diastereoisomers, enantiomers or mixtures thereof, salts, hydrates or solvates thereof.

5. A compound selected from the group consisting of:

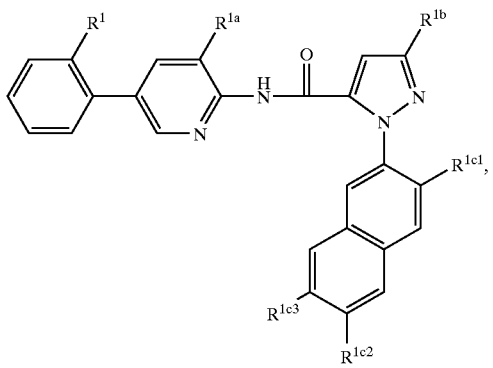

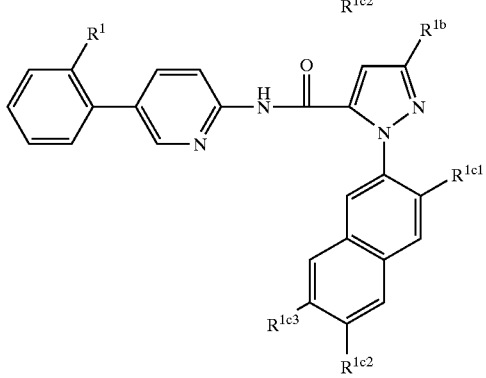

and

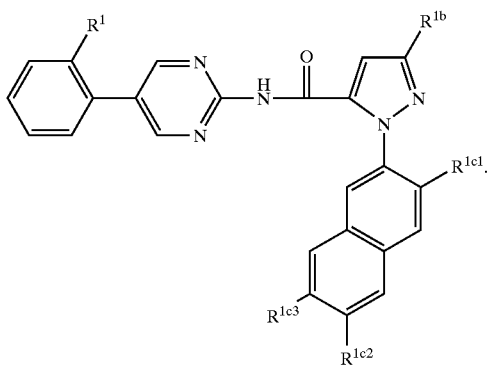

wherein
$R^1$ is a member selected from the group consisting of —SO$_2$NH$_2$, —SO$_2$Me, —CH$_2$NH$_2$ and —CH$_2$NMe$_2$;
$R^{1a}$ is a member selected from the group consisting of —H, —F, —Cl and —Br;
$R^{1b}$ is a member selected from the group consisting of —CH$_3$, —CF$_3$, —CH$_2$CH$_3$, —SO$_2$Me, —CONH$_2$ and —NHSO$_2$Me;

$R^{1c1}$ is a member selected from the group consisting of —H, —F, —Cl, —Br, —NH$_2$, —OH, —SO$_2$Me, —SO$_2$Et, —SO$_2$NH$_2$, —NO$_2$, —CH$_2$NH$_2$, —CN, —CONH$_2$ and —CH$_2$OH;
$R^{1c2}$ is a member selected from the group consisting of —H, —F, —Cl and —Br;
$R^{1c3}$ is a member selected from the group consisting of —H, —F, —Cl and —Br;

or all pharmaceutically acceptable diastereoisomers, enantiomers or mixtures thereof, salts, hydrates or solvates thereof.

6. A compound selected from the group consisting of:

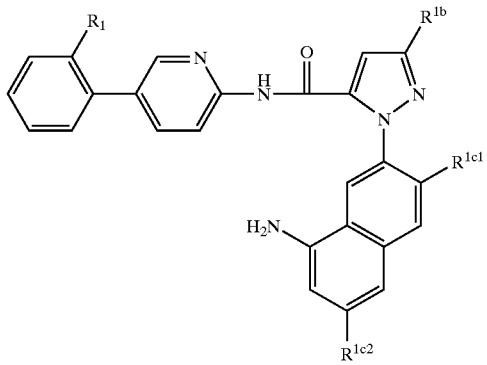

and

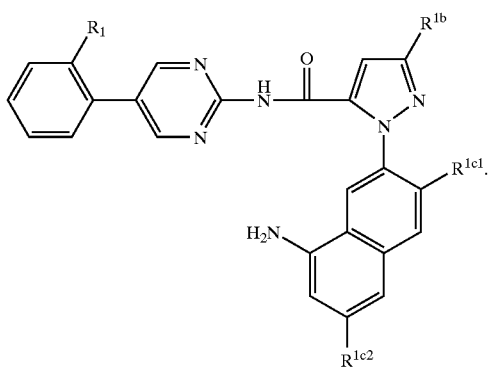

wherein
$R^1$ is a member selected from the group consisting of —SO$_2$NH$_2$, —SO$_2$Me, —CH$_2$NH$_2$ and —CH$_2$NMe$_2$;
$R^{1b}$ is a member selected from the group consisting of —CH$_3$, —CF$_3$, —CH$_2$CH$_3$, —SO$_2$Me, —CONH$_2$ and —NHSO$_2$Me;
$R^{1c1}$ is a member selected from the group consisting of —H, —F, —Cl, —Br, —NH$_2$, —OH, —SO$_2$Me, —SO$_2$Et, —SO$_2$NH$_2$, —NO$_2$, —CH$_2$NH$_2$, —CN, —CONH$_2$ and —CH$_2$OH;
$R^{1c2}$ is a member selected from the group consisting of —H, —F, —Cl and —Br;

or all pharmaceutically acceptable diastereoisomers, enantiomers or mixtures thereof, salts, hydrates or solvates thereof.

7. A pharmaceutical composition for treating a condition in a mammal characterized by undesired thrombosis comprising a pharmaceutically acceptable carrier and a pharmaceutically effective amount of a compound of claim 1.

8. A method for treating a condition in a mammal characterized by undesired thrombosis comprising administering to said mammal a therapeutically effective amount of a compound of claim 1.

9. The method of claim 8, wherein the condition is a member selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

10. A method for inhibiting the coagulation of biological samples, comprising the step of administering a compound of claim 1.

11. A method for treating a condition in a mammal characterized by undesired thrombosis comprising administering to said mammal a therapeutically effective amount of a compound of claim 4.

12. The method of claim 11, wherein the condition is a member selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

13. A method for inhibiting the coagulation of biological samples, comprising the step of administering a compound of claim 4.

14. A method for treating a condition in a mammal characterized by undesired thrombosis comprising administering to said mammal a therapeutically effective amount of a compound of claim 5.

15. The method of claim 14, wherein the condition is a member selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

16. A method for inhibiting the coagulation of biological samples, comprising the step of administering a compound of claim 5.

17. A method for treating a condition in a mammal characterized by undesired thrombosis comprising administering to said mammal a therapeutically effective amount of a compound of claim 6.

18. The method of claim 17, wherein the condition is a member selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

19. A method for inhibiting the coagulation of biological samples, comprising the step of administering a compound of claim 6.

* * * * *